US007858632B2

(12) United States Patent
Broka et al.

(10) Patent No.: US 7,858,632 B2
(45) Date of Patent: Dec. 28, 2010

(54) DIAMINOPYRIMIDINES AS $P2X_3$ AND $P2X_{2/3}$ ANTAGONISTS

(75) Inventors: Chris Allen Broka, Foster City, CA (US); David Scott Carter, Sunnyvale, CA (US); Michael Patrick Dillon, San Carlos, CA (US); Ronald Charles Hawley, Mountain View, CA (US); Alam Jahangir, San Jose, CA (US); Clara Jeou Jen Lin, Palo Alto, CA (US); Daniel Warren Parish, Sunnyvale, CA (US)

(73) Assignee: Roche Palo Alto LLC, Palo Alto, CA (US)

(*) Notice: Subject to any disclaimer, the term of this patent is extended or adjusted under 35 U.S.C. 154(b) by 864 days.

(21) Appl. No.: 11/071,555

(22) Filed: Mar. 3, 2005

(65) Prior Publication Data

US 2005/0209260 A1 Sep. 22, 2005

Related U.S. Application Data

(60) Provisional application No. 60/550,499, filed on Mar. 5, 2004.

(51) Int. Cl.
C07D 239/48 (2006.01)
C07D 403/12 (2006.01)
A61K 31/505 (2006.01)

(52) U.S. Cl. .................. 514/269; 514/275; 544/298; 544/325

(58) Field of Classification Search .................. 544/325, 544/298; 514/275, 269
See application file for complete search history.

(56) References Cited

U.S. PATENT DOCUMENTS

| 2,657,206 | A | * | 10/1953 | Hitchings et. al. | .......... 544/298 |
|---|---|---|---|---|---|
| 2,953,567 | A | | 9/1960 | Burroughs | |
| 3,715,357 | A | | 2/1973 | Rey-Bellet et al. | |
| 3,849,470 | A | | 11/1974 | Cresswell et al. | |
| 3,850,927 | A | | 11/1974 | Cresswell et al. | |
| 3,852,276 | A | | 12/1974 | Cresswell et al. | |
| 3,855,265 | A | | 12/1974 | Cresswell et al. | |
| 3,878,252 | A | * | 4/1975 | Cresswell et al. | ............. 568/33 |
| 3,931,181 | A | | 1/1976 | Kompis et al. | |
| 3,940,393 | A | | 2/1976 | Greenspan et al. | |
| 3,991,050 | A | | 11/1976 | Cresswell et al. | |
| 4,024,145 | A | | 5/1977 | Kompis | |
| 4,033,962 | A | | 7/1977 | Rosen | |
| 4,039,543 | A | | 8/1977 | Kompis et al. | |
| 4,052,553 | A | | 10/1977 | Cresswell et al. | |
| 4,075,209 | A | | 2/1978 | Jernow et al. | |
| 4,108,888 | A | | 8/1978 | Rosen | |
| 4,115,650 | A | | 9/1978 | Manchand | |
| 4,143,227 | A | | 3/1979 | Rosen | |
| 4,144,263 | A | | 3/1979 | Yeowell et al. | |
| 4,151,196 | A | | 4/1979 | Rosen | |
| 4,216,319 | A | | 8/1980 | Yeowell et al. | |
| 4,232,023 | A | | 11/1980 | Dick et al. | |
| 4,255,574 | A | | 3/1981 | Rosen | |
| 4,258,045 | A | | 3/1981 | Poe et al. | |
| 4,386,084 | A | | 5/1983 | Scharwaechter et al. | |
| 4,415,574 | A | | 11/1983 | Laruelle et al. | |
| 4,485,248 | A | | 11/1984 | Dall'Asta | |
| 4,515,948 | A | | 5/1985 | Kompis et al. | |
| 4,587,341 | A | | 5/1986 | Roth et al. | |
| 4,590,271 | A | | 5/1986 | Daluge et al. | |
| 4,883,798 | A | | 11/1989 | Petöcz et al. | |
| 4,912,112 | A | | 3/1990 | Seydel et al. | |
| 4,996,198 | A | | 2/1991 | Schildknecht et al. | |
| 5,063,219 | A | | 11/1991 | Schildknecht et al. | |
| 5,240,640 | A | | 8/1993 | Siiman et al. | |
| 5,258,373 | A | | 11/1993 | Schildknecht et al. | |
| 5,541,186 | A | | 7/1996 | Breu et al. | |
| 6,136,971 | A | | 10/2000 | Harrington et al. | |
| 6,211,185 | B1 | | 4/2001 | Strobel et al. | |
| 6,410,543 | B1 | | 6/2002 | Strobel et al. | |
| 6,423,720 | B1 | | 7/2002 | Gangjee | |
| 6,440,965 | B1 | | 8/2002 | Kelley et al. | |
| 6,583,148 | B1 | | 6/2003 | Kelley et al. | |
| 6,916,820 | B1 | | 7/2005 | Kelley et al. | |

(Continued)

FOREIGN PATENT DOCUMENTS

EP 0 237 516 A1 9/1987

(Continued)

OTHER PUBLICATIONS

Caplus Abstract 98:179315 Michele Casas, et al., *Synthesis of new trimethoprim analogs. Antibacterial structure-activity relationship*, Eur. J. Med. Chem, (1982), pp. 497-504, vol. 17(6).

(Continued)

*Primary Examiner*—Deepak Rao
(74) *Attorney, Agent, or Firm*—Robert C. Hall

(57) ABSTRACT

Compounds and methods for treating diseases mediated by a $P2X_3$ and/or a $P2X_{2/3}$ receptor antagonist, the methods comprising administering to a subject in need thereof an effective amount of a compound of formula (I):

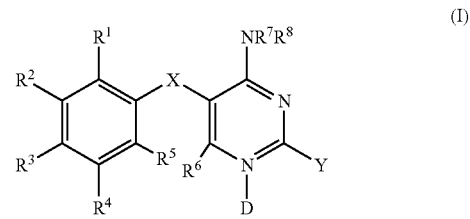

or a pharmaceutically acceptable salt, solvate or prodrug thereof,
wherein D, X, Y, $R^1$, $R^2$, $R^3$, $R^4$, $R^5$, $R^6$, $R^7$ and $R^8$ are as defined herein.

30 Claims, No Drawings

U.S. PATENT DOCUMENTS

2003/0040513 A1 2/2003 Baxter et al.

FOREIGN PATENT DOCUMENTS

| EP | 0 658 548 B1 | 11/1997 |
| EP | 0 959 073 A1 | 11/1999 |
| EP | 0 743 307 B1 | 9/2001 |
| EP | 0 959 072 B1 | 9/2002 |
| EP | 1 310 493 A1 | 5/2003 |
| WO | 9616963 A1 | 6/1996 |
| WO | WO 01/17976 A1 | 3/2001 |
| WO | WO 01/22938 A1 | 4/2001 |
| WO | WO 01/81335 A1 | 11/2001 |
| WO | WO 01/81338 A1 | 11/2001 |
| WO | WO 02/08200 A2 | 1/2002 |
| WO | WO 02/24665 A1 | 3/2002 |
| WO | WO 02/053557 A1 | 7/2002 |
| WO | WO 02/083650 A1 | 10/2002 |
| WO | WO 02/094767 A2 | 11/2002 |

OTHER PUBLICATIONS

Calas, M., et al, "Synthèses d-analogues nouveaus de la triméthoprime etude de relation structure-activité antibactérienne", European Journal of Medicinal Chemistry, 1982, 17(6):497-504.

Dias Selassie, C., et al, "Quantitative structure-activity relationships of 2,4-diamino-5-(2-x-benzyl)pyrimidines versus bacterial and avian dihydrofolate reductase", Journal of Medicinal Chemistry, 1998, 41:4261-4272.

Dunn, SMJ, et al, "Kinetics of ternary complex formation between dihydrofolate reductase, coenzyme, and inhibitors", *Biochemistry*, 1980, 19:766-773.

Falco, Ea, et al, "5-Arylthiopyrimidines. I. 2,4-diamino derivatives", *Journal of Organic Chemistry*, 1961, 26:1143-1146.

Seiler, P., et al "Partition coefficients of 5-(substituted benzyl)-2,4-diaminopyrimidines", *Arnzeim.-Forsch*, 1982, 32(7):711-714.

Calas, M., et. al. "Synthese et antibacterienne de nouveaux analogues de la trimethoprime," Annales Pharmaceutiques Francaises, 1985, vol. 43, No. 6, pp. 585-593.

Falco, E.A., et. al. "2,4-Diaminopyrimidines as Antimalarials. I. 5-Aryloxl and 5-Alkoxyl Derivatives," Journal of the American Society, 1951, vol. 73, pp. 3753-3758.

Wei-Zhang Zhao, et. al., "Synthesis and Antibacterial Activity of 2,4-Diamino-5-(Substituted Anilino) Pyrimidines" Acta Pharmaceutica Sinica, 1987, vol. 22, No. 7, pp. 541-544.

* cited by examiner

DIAMINOPYRIMIDINES AS P2X$_3$ AND P2X$_{2/3}$ ANTAGONISTS

CROSS REFERENCE TO RELATED APPLICATIONS

This application claims benefit under 35 U.S.C. 119(e) of U.S. Provisional Application No. 60/550,499 filed Mar. 5, 2004, which is hereby incorporated by reference in its entirety

FIELD OF THE INVENTION

This invention pertains to compounds useful for treatment of diseases associated with P2X purinergic receptors, and more particularly to P2X$_3$ and/or P2X$_{2/3}$ antagonists usable for treatment of genitourinary and pain-related diseases, conditions and disorders.

BACKGROUND OF THE INVENTION

The urinary bladder is responsible for two important physiological functions: urine storage and urine emptying. This process involves two main steps: (1) the bladder fills progressively until the tension in its walls rises above a threshold level; and (2) a nervous reflex, called the micturition reflex, occurs that empties the bladder or, if this fails, at least causes a conscious desire to urinate. Although the micturition reflex is an autonomic spinal cord reflex, it can also be inhibited or mediated by centers in the cerebral cortex or brain.

Purines, acting via extracellular purinoreceptors, have been implicated as having a variety of physiological and pathological roles. (See, Burnstock (1993) Drug Dev. Res. 28:195-206.) ATP, and to a lesser extent, adenosine, can stimulate sensory nerve endings resulting in intense pain and a pronounced increase in sensory nerve discharge. ATP receptors have been classified into two major families, the P2Y- and P2X-purinoreceptors, on the basis of molecular structure, transduction mechanisms, and pharmacological characterization. The P2Y-purinoreceptors are G-protein coupled receptors, while the P2X-purinoreceptors are a family of ATP-gated cation channels. Purinergic receptors, in particular, P2X receptors, are known to form homomultimers or heteromultimers. To date, cDNAs for several P2X receptors subtypes have been cloned, including: six homomeric receptors, P2X$_1$; P2X$_2$; P2X$_3$; P2X$_4$; P2X$_5$; and P2X$_7$; and three heteromeric receptors P2X$_{2/3}$, P2X$_{4/6}$, P2X$_{1/5}$ (See, e.g., Chen, et al. (1995) Nature 377:428-431; Lewis, et al. (1995) Nature 377:432-435; and Burnstock (1997) Neurophamacol. 36:1127-1139). The structure and chromosomal mapping of mouse genomic P2X$_3$ receptor subunit has also been described (Souslova, et al. (1997) Gene 195:101-111). In vitro, co-expression of P2X$_2$ and P2X$_3$ receptor subunits is necessary to produce ATP-gated currents with the properties seen in some sensory neurons (Lewis, et al. (1995) Nature 377:432435).

P2X receptor subunits are found on afferents in rodent and human bladder urothelium. Data exists suggesting that ATP may be released from epithelial/endothelial cells of the urinary bladder or other hollow organs as a result of distention (Burnstock (1999) J. Anatomy 194:335-342; and Ferguson et al. (1997) J. Physiol. 505:503-511). ATP released in this manner may serve a role in conveying information to sensory neurons located in subepithelial components, e.g., suburothelial lamina propria (Namasivayam, et al. (1999) BJU Intl. 84:854-860). The P2X receptors have been studied in a number of neurons, including sensory, sympathetic, parasympathetic, mesenteric, and central neurons (Zhong, et al. (1998) Br. J. Pharmacol. 125:771-781). These studies indicate that purinergic receptors play a role in afferent neurotransmission from the bladder, and that modulators of P2X receptors are potentially useful in the treatment of bladder disorders and other genitourinary diseases or conditions.

Recent evidence also suggests a role of endogenous ATP and purinergic receptors in nociceptive responses in mice (Tsuda, et al. (1999) Br. J. Pharmacol. 128:1497-1504). ATP-induced activation of P2X receptors on dorsal root ganglion nerve terminals in the spinal cord has been shown to stimulate release of glutamate, a key neurotransmitter involved in nociceptive signaling (Gu and MacDermott, Nature 389:749-753 (1997)). P2X$_3$ receptors have been identified on nociceptive neurons in the tooth pulp (Cook et al., Nature 387:505-508 (1997)). ATP released from damaged cells may thus lead to pain by activating P2X$_3$ and/or P2X$_{2/3}$ containing receptors on nociceptive sensory nerve endings. This is consistent with the induction of pain by intradermally applied ATP in the human blister-base model (Bleehen, Br J Pharmacol 62:573-577 (1978)). P2X antagonists have been shown to be analgesic in animal models (Driessen and Starke, Naunyn Schmiedebergs Arch Pharmacol 350:618-625 (1994)). This evidence suggests that P2X$_2$ and P2X$_3$ are involved in nociception, and that modulators of P2X receptors are potentially useful as analgesics.

There is accordingly a need for methods of treating diseases, conditions and disorders mediated by P2X$_3$ and/or P2X$_{2/3}$ receptors, as well as a need for compounds that act as modulators of P2X receptors, including antagonists of P2X$_3$ and P2X$_{2/3}$ receptors. The present invention satisfies these needs as well as others.

Many diaminopyrimidine compounds, such as "ormetoprim" (U.S. Pat. No. 2,658,897) and "trimetoprim" (U.S. Pat. No. 2,909,522), have previously been made and identified as antibacterial agents. However, no diaminopyrimidines have heretofore been identified as modulators of P2X receptors.

SUMMARY OF THE INVENTION

The invention provides compound of formula (I):

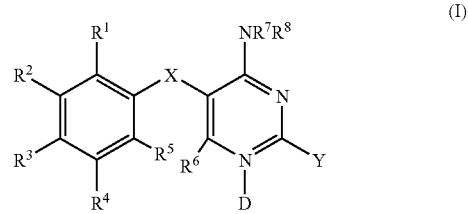

or pharmaceutically acceptable salts thereof, wherein:
X is: —CH$_2$—; —O—; —S(O)$_n$—; or —NR$^c$— wherein n is from 0 to 2 and R$^c$ is hydrogen or alkyl;
Y is: hydrogen; or —NR$^d$R$^e$ wherein one of R$^d$ and R$^e$ is hydrogen, and the other is: hydrogen; alkyl; cycloalkyl; cycloalkylalkyl; haloalkyl; haloalkoxy; hydroxyalkyl; alkoxyalkyl; acetyl; alkylsulfonyl; alkylsulfonylalkyl; aminocarbonyloxyalkyl; hydroxycarbonylalkyl; hydroxyalkyloxycarbonylalkyl; aryl; aralkyl; arylsulfonyl; heteroaryl; heteroarylalkyl; heteroarylsulfonyl; heterocyclyl; or heterocyclylalkyl;

D is an optional oxygen;

$R^1$ is: alkyl; alkenyl; cycloalkyl; cycloalkenyl; halo; haloalkyl; or hydroxyalkyl;

$R^2$, $R^3$, $R^4$ and $R^5$ each independently is: hydrogen; alkyl; alkenyl; amino; halo; amido; haloalkyl; alkoxy; hydroxy; haloalkoxy; nitro; amino; hydroxyalkyl; alkoxyalkyl; hydroxyalkoxy; alkynylalkoxy; alkylsulfonyl; arylsulfonyl; cyano; aryl; heteroaryl; heterocyclyl; heterocyclylalkoxy; aryloxy; heteroaryloxy; aralkyloxy; heteroaralkyloxy; optionally substituted phenoxy; —$(CH_2)_m$-$(Z)_n$-(CO)—$R^f$ or —$(CH_2)_n$-$(Z)_n$-$SO_2$—$(NR_g)_n$—$R^f$ where m and n each independently is 0 or 1, Z is 0 or $NR^g$, $R^f$ is hydrogen, alkyl, hydroxy, alkoxy, amino, hydroxyalkyl or alkoxyalkyl, and each $R^g$ is independently hydrogen or alkyl; or $R^3$ and $R^4$ may together form an alkylene dioxy; or $R^3$ and $R^4$ together with the atoms to which they are attached may form a five or six-membered ring that optionally includes one or two heteroatoms selected from O, S and N; or $R^2$ and $R^3$ may together form an alkylene dioxy; or $R^2$ and $R^3$ together with the atoms to which they are attached may form a five or six-membered ring that optionally includes one or two heteroatoms selected from O, S and N;

$R^6$ is: hydrogen; alkyl; halo; haloalkyl; amino; or alkoxy; and one of $R^7$ and $R^8$ is hydrogen, and the other is: hydrogen; alkyl; cycloalkyl; cycloalkylalkyl; haloalkyl; haloalkoxy; hydroxyalky; alkoxyalkyl; acetyl; alkylsulfonyl; alkylsulfonylalkyl; aminocarbonyloxyalkyl; hydroxycarbonylalkyl; hydroxyalkyloxycarbonylalkyl; aryl; aralkyl; arylsulfonyl; heteroaryl; heteroarylalkyl; heteroarylsulfonyl; heterocyclyl; or heterocyclylalkyl; provided that when X is —$CH_2$—, $R^1$ is isopropyl.

The invention also provides and pharmaceutical compositions comprising the compounds, methods of using the compounds, and methods of preparing the compounds.

DETAILED DESCRIPTION OF THE INVENTION

Definitions

Unless otherwise stated, the following terms used in this Application, including the specification and claims, have the definitions given below. It must be noted that, as used in the specification and the appended claims, the singular forms "a", "an," and "the" include plural referents unless the context clearly dictates otherwise.

"Agonist" refers to a compound that enhances the activity of another compound or receptor site.

"Alkyl" means the monovalent linear or branched saturated hydrocarbon moiety, consisting solely of carbon and hydrogen atoms, having from one to twelve carbon atoms. "Lower alkyl" refers to an alkyl group of one to six carbon atoms, i.e. $C_1$-$C_6$alkyl. Examples of alkyl groups include, but are not limited to, methyl, ethyl, propyl, isopropyl, isobutyl, sec-butyl, tert-butyl, pentyl, n-hexyl, octyl, dodecyl, and the like.

"Alkenyl" means a linear monovalent hydrocarbon radical of two to six carbon atoms or a branched monovalent hydrocarbon radical of three to six carbon atoms, containing at least one double bond, e.g. ethenyl, propenyl, and the like.

"Alkynyl" means a linear monovalent hydrocarbon radical of two to six carbon atoms or a branched monovalent hydrocarbon radical of three to six carbon atoms, containing at least one triple bond, e.g., ethynyl, propynyl, and the like.

"Alkylene" means a linear saturated divalent hydrocarbon radical of one to six carbon atoms or a branched saturated divalent hydrocarbon radical of three to six carbon atoms, e.g., methylene, ethylene, 2,2-dimethylethylene, propylene, 2-methylpropylene, butylene, pentylene, and the like.

"Alkoxy" means a moiety of the formula —OR, wherein R is an alkyl moiety as defined herein. Examples of alkoxy moieties include, but are not limited to, methoxy, ethoxy, isopropoxy, and the like.

"Alkoxyalkyl" means a moiety of the formula $R^a$—O—$R^b$—, where $R^a$ is alkyl and $R^b$ is alkylene as defined herein. Exemplary alkoxyalkyl groups include, by way of example, 2-methoxyethy, 3-methoxypropyl, 1-methyl-2-methoxyethyl, 1-(2-methoxyethyl)-3-methoxypropyl, and 1-(2-methoxyethyl)-3-methoxypropyl.

"Alkylcarbonyl" means a moiety of the formula —R'—R", where R' is oxo and R" is alkyl as defined herein.

"Alkylsulfonyl" means a moiety of the formula —R'—R", where R' is —$SO_2$— and R" is alkyl as defined herein.

"Alkylsulfonylalkyl means a moiety of the formula —R'—R"—R''' where where R' is alkylene, R" is —$SO_2$— and R''' is alkyl as defined herein.

"Alkylamino means a moiety of the formula —NR—R' wherein R is hyrdogen or alkyl and R' is alkyl as defined herein.

"Alkoxyamino" means a moiety of the formula —NR—OR' wherein R is hydrogen or alkyl and R' is alkyl as defined herein.

"Alkylsulfanyl" means a moiety of the formula —SR wherein R is alkyl as defined herein.

"Aminoalkyl" means a group —R—R' wherein R' is amino and R is alkylene as defined herein. "Aminoalkyl" includes aminomethyl, aminoethyl, 1-aminopropyl, 2-aminopropyl, and the like. The amino moiety of "aminoalkyl" may be substituted once or twice with alkyl to provide "alkylaminoalkyl" and "dialkylaminoalkyl" respectively. "Alkylaminoalkyl" includes methylaminomethyl, methylaminoethyl, methylaminopropyl, ethylaminoethyl and the like. "Dialkylaminoalkyl" includes dimethylaminomethyl, dimethylaminoethyl, dimethylaminopropyl, N-methyl-N-ethylaminoethyl, and the like.

"Aminoalkoxy" means a group —OR—R' wherein R' is amino and R is alkylene as defined herein.

"Alkylsulfonylamido" means a moiety of the formula —NR'$SO_2$—R wherein R is alkyl and R' is hydrogen or alkyl.

"Aminocarbonyloxyalkyl" or "carbamylalkyl" means a group of the formula —R—O—C(O)—NR'R" wherein R is alkylene and R', R" each independently is hydrogen or alkyl as defined herein.

"Alkynylalkoxy" means a group of the formula —O—R—R' wherein R is alkylene and R' is alkynyl as defined herein.

"Antagonist" refers to a compound that diminishes or prevents the action of another compound or receptor site.

"Aryl" means a monovalent cyclic aromatic hydrocarbon moiety consisting of a mono-, bi- or tricyclic aromatic ring. The aryl group can be optionally substituted as defined herein. Examples of aryl moieties include, but are not limited to, optionally substituted phenyl, naphthyl, phenanthryl, fluorenyl, indenyl, pentalenyl, azulenyl, oxydiphenyl, biphenyl, methylenediphenyl, aminodiphenyl, diphenylsulfidyl, diphenylsulfonyl, diphenylisopropylidenyl, benzodioxanyl, benzofuranyl, benzodioxylyl, benzopyranyl, benzoxazinyl, benzoxazinonyl, benzopiperadinyl, benzopiperazinyl, benzopyrrolidinyl, benzomorpholinyl, methylenedioxyphenyl, ethylenedioxyphenyl, and the like, including partially hydrogenated derivatives thereof.

"Arylalkyl" and "Aralkyl", which may be used interchangeably, mean a radical-$R^aR^b$ where $R^a$ is an alkylene group and $R^b$ is an aryl group as defined herein; e.g., phenylalkyls such as benzyl, phenylethyl, 3-(3-chlorophenyl)-2-methylpentyl, and the like are examples of arylalkyl.

"Arylalkyl" means a group of the formula —R—R' wherein R is alkylene and R' is aryl as defined herein.

"Arylsulfonyl means a group of the formula —SO$_2$—R wherein R is aryl as defined herein.

"Aryloxy" means a group of the formula —O—R wherein R is aryl as defined herein.

"Aralkyloxy" means a group of the formula —O—R—R" wherein R is alkylene and R' is aryl as defined herein.

"Cyanoalkyl"" means a moiety of the formula —R'—R", where R' is alkylene as defined herein and R" is cyano or nitrile.

"Cycloalkyl" means a monovalent saturated carbocyclic moiety consisting of mono- or bicyclic rings. Cycloalkyl can optionally be substituted with one or more substituents, wherein each substituent is independently hydroxy, alkyl, alkoxy, halo, haloalkyl, amino, monoalkylamino, or dialkylamino, unless otherwise specifically indicated. Examples of cycloalkyl moieties include, but are not limited to, cyclopropyl, cyclobutyl, cyclopentyl, cyclohexyl, cycloheptyl, and the like, including partially unsaturated derivatives thereof.

"Cycloalkylalkyl" means a moiety of the formula —R'—R", where R' is alkylene and R" is cycloalkyl as defined herein.

"Heteroalkyl" means an alkyl radical as defined herein wherein one, two or three hydrogen atoms have been replaced with a substituent independently selected from the group consisting of —OR$^a$, —NR$^b$R$^c$, and —S(O)$_n$R$^d$ (where n is an integer from 0 to 2), with the understanding that the point of attachment of the heteroalkyl radical is through a carbon atom, wherein R$^a$ is hydrogen, acyl, alkyl, cycloalkyl, or cycloalkylalkyl; R$^b$ and R$^c$ are independently of each other hydrogen, acyl, alkyl, cycloalkyl, or cycloalkylalkyl; and when n is 0, R$^d$ is hydrogen, alkyl, cycloalkyl, or cycloalkylalkyl, and when n is 1 or 2, R$^d$ is alkyl, cycloalkyl, cycloalkylalkyl, amino, acylamino, monoalkylamino, or dialkylamino. Representative examples include, but are not limited to, 2-hydroxyethyl, 3-hydroxypropyl, 2-hydroxy-1-hydroxymethylethyl, 2,3-dihydroxypropyl, 1-hydroxymethylethyl, 3-hydroxybutyl, 2,3-dihydroxybutyl, 2-hydroxy-1-methylpropyl, 2-aminoethyl, 3-aminopropyl, 2-methylsulfonylethyl, aminosulfonylmethyl, aminosulfonylethyl, aminosulfonylpropyl, methylaminosulfonylmethyl, methylaminosulfonylethyl, methylaminosulfonylpropyl, and the like.

"Heteroaryl" means a monocyclic or bicyclic radical of 5 to 12 ring atoms having at least one aromatic ring containing one, two, or three ring heteroatoms selected from N, O, or S, the remaining ring atoms being C, with the understanding that the attachment point of the heteroaryl radical will be on an aromatic ring. The heteroaryl ring may be optionally substituted as defined herein. Examples of heteroaryl moieties include, but are not limited to, optionally substituted imidazolyl, oxazolyl, isoxazolyl, thiazolyl, isothiazolyl, oxadiazolyl, thiadiazolyl, pyrazinyl, thienyl, benzothienyl, thiophenyl, furanyl, pyranyl, pyridyl, pyrrolyl, pyrazolyl, pyrimidyl, quinolinyl, isoquinolinyl, benzofuryl, benzothiophenyl, benzothiopyranyl, benzimidazolyl, benzooxazolyl, benzooxadiazolyl, benzothiazolyl, benzothiadiazolyl, benzopyranyl, indolyl, isoindolyl, triazolyl, triazinyl, quinoxalinyl, purinyl, quinazolinyl, quinolizinyl, naphthyridinyl, pteridinyl, carbazolyl, azepinyl, diazepinyl, acridinyl and the like, including partially hydrogenated derivatives thereof.

Heteroarylalkyl" or "heteroaralkyl" means a group of the formula —R—R' wherein R is alkylene and R' is heteroaryl as defined herein.

"Heteroarylsulfonyl means a group of the formula —SO$_2$—R wherein R is heteroaryl as defined herein.

"Heteroaryloxy" means a group of the formula —O—R wherein R is heteroaryl as defined herein.

"Heteroaralkyloxy" means a group of the formula —O—R—R" wherein R is alkylene and R' is heteroaryl as defined herein.

The terms "halo", "halogen" and "halide", which may be used interchangeably, refer to a substituent fluoro, chloro, bromo, or iodo.

"Haloalkyl" means alkyl as defined herein in which one or more hydrogen has been replaced with same or different halogen. Exemplary haloalkyls include —CH$_2$Cl, —CH$_2$CF$_3$, —CH$_2$CCl$_3$, perfluoroalkyl (e.g., —CF$_3$), and the like.

"Haloalkoxy" means a moiety of the formula —OR, wherein R is a haloalkyl moiety as defined herein. An exemplary haloalkoxy is difluoromethoxy.

"Heterocycloamino" means a saturated ring wherein at least one ring atom is N, NH or N-alkyl and the remaining ring atoms form an alkylene group.

"Heterocyclyl" means a monovalent saturated moiety, consisting of one to three rings, incorporating one, two, or three or four heteroatoms (chosen from nitrogen, oxygen or sulfur). The heterocyclyl ring may be optionally substituted as defined herein. Examples of heterocyclyl moieties include, but are not limited to, optionally substituted piperidinyl, piperazinyl, homopiperazinyl, azepinyl, pyrrolidinyl, pyrazolidinyl, imidazolinyl, imidazolidinyl, pyridinyl, pyridazinyl, pyrimidinyl, oxazolidinyl, isoxazolidinyl, morpholinyl, thiazolidinyl, isothiazolidinyl, quinuclidinyl, quinolinyl, isoquinolinyl, benzimidazolyl, thiadiazolylidinyl, benzothiazolidinyl, benzoazolylidinyl, dihydrofuryl, tetrahydrofuryl, dihydropyranyl, tetrahydropyranyl, thiamorpholinyl, thiamorpholinylsulfoxide, thiamorpholinylsulfone, dihydroquinolinyl, dihydrisoquinolinyl, tetrahydroquinolinyl, tetrahydrisoquinolinyl, and the like.

"Heterocyclylalkyl" means a moiety of the formula —R—R' wherein R is alkylene and R' is heterocyclyl as defined herein.

"Heterocyclyloxy" means a moiety of the formula —OR wherein R is heterocyclyl as defined herein.

"Heterocyclylalkoxy" means a moiety of the formula —OR—R' wherein R is alkylene and R' is heterocyclyl as defined herein.

"Hydroxyalkoxy" means a moiety of the formula —OR wherein R is hydroxyalkyl as defined herein.

"Hydroxyalkylamino" means a moiety of the formula —NR—R' wherein R is hydrogen or alkyl and R' is hydroxyalkyl as defined herein.

"Hydroxyalkylaminoalkyl" means a moiety of the formula —R—NR'—R" wherein R is alkylene, R' is hydrogen or alkyl, and R" is hydroxyalkyl as defined herein.

"Hydroxycarbonylalkyl" or "carboxyalkyl" means a group of the formula —R—(CO)—OH where R is alkylene as defined herein.

"Hydroxyalkyloxycarbonylalkyl" or "hydroxyalkoxycarbonylalkyl" means a group of the formula —R—C(O)—O—R—OH wherein each R is alkylene and may be the same or different.

"Hydroxyalkyl" means an alkyl moiety as defined herein, substituted with one or more, preferably one, two or three hydroxy groups, provided that the same carbon atom does not carry more than one hydroxy group. Representative examples include, but are not limited to, hydroxymethyl, 2-hydroxyethyl, 2-hydroxypropyl, 3-hydroxypropyl, 1-(hydroxymethyl)-2-methylpropyl, 2-hydroxybutyl, 3-hydroxybutyl, 4-hydroxybutyl, 2,3-dihydroxypropyl, 2-hydroxy-1-hydroxymethylethyl, 2,3-dihydroxybutyl, 3,4-dihydroxybutyl and 2-(hydroxymethyl)-3-hydroxypropyl "Hydroxycycloalkyl" means a cycloalkyl moiety as defined herein wherein one, two or three hydrogen atoms in the cycloalkyl radical have been replaced with a hydroxy substituent. Representative examples include, but are not limited to, 2-, 3-, or 4-hydroxycyclohexyl, and the like.

"Urea" or "ureido" means a group of the formula —NR'—C(O)—NR"R''' wherein R', R" and R''' each independently is hydrogen or alkyl.

"Carbamate" means a group of the formula —O—C(O)—NR'R" wherein R' and R" each independently is hydrogen or alkyl.

"Carboxy" means a group of the formula —O—C(O)—OH.

"Sulfonamido" means a group of the formula —SO$_2$—NR'R" wherein R', R" and R''' each independently is hydrogen or alkyl.

"Optionally substituted", when used in association with "aryl", phenyl", "heteroaryl" "cycloalkyl" or "heterocyclyl", means an aryl, phenyl, heteroaryl, cyclohexyl or heterocyclyl which is optionally substituted independently with one to four substituents, preferably one or two substituents selected from alkyl, cycloalkyl, cycloalkylalkyl, heteroalkyl, hydroxyalkyl, halo, nitro, cyano, hydroxy, alkoxy, amino, acylamino, mono-alkylamino, di-alkylamino, haloalkyl, haloalkoxy, heteroalkyl, —COR (where R is hydrogen, alkyl, phenyl or phenylalkyl), —(CR'R")$_n$—COOR (where n is an integer from 0 to 5, R' and R" are independently hydrogen or alkyl, and R is hydrogen, alkyl, cycloalkyl, cycloalkylalkyl, phenyl or phenylalkyl), or —(CR'R")$_n$—CONR$^a$R$^b$ (where n is an integer from 0 to 5, R' and R" are independently hydrogen or alkyl, and R$^a$ and R$^b$ are, independently of each other, hydrogen, alkyl, cycloalkyl, cycloalkylalkyl, phenyl or phenylalkyl).

"Leaving group" means the group with the meaning conventionally associated with it in synthetic organic chemistry, i.e., an atom or group displaceable under substitution reaction conditions. Examples of leaving groups include, but are not limited to, halogen, alkane- or arylenesulfonyloxy, such as methanesulfonyloxy, ethanesulfonyloxy, thiomethyl, benzenesulfonyloxy, tosyloxy, and thienyloxy, dihalophosphinoyloxy, optionally substituted benzyloxy, isopropyloxy, acyloxy, and the like.

"Modulator" means a molecule that interacts with a target. The interactions include, but are not limited to, agonist, antagonist, and the like, as defined herein.

"Optional" or "optionally" means that the subsequently described event or circumstance may but need not occur, and that the description includes instances where the event or circumstance occurs and instances in which it does not.

"Disease" and "Disease state" means any disease, condition, symptom, disorder or indication.

"Inert organic solvent" or "inert solvent" means the solvent is inert under the conditions of the reaction being described in conjunction therewith, including for example, benzene, toluene, acetonitrile, tetrahydrofuran, N,N-dimethylformamide, chloroform, methylene chloride or dichloromethane, dichloroethane, diethyl ether, ethyl acetate, acetone, methyl ethyl ketone, methanol, ethanol, propanol, isopropanol, tert-butanol, dioxane, pyridine, and the like. Unless specified to the contrary, the solvents used in the reactions of the present invention are inert solvents.

"Pharmaceutically acceptable" means that which is useful in preparing a pharmaceutical composition that is generally safe, non-toxic, and neither biologically nor otherwise undesirable and includes that which is acceptable for veterinary as well as human pharmaceutical use.

"Pharmaceutically acceptable salts" of a compound means salts that are pharmaceutically acceptable, as defined herein, and that possess the desired pharmacological activity of the parent compound. Such salts include:

acid addition salts formed with inorganic acids such as hydrochloric acid, hydrobromic acid, sulfuric acid, nitric acid, phosphoric acid, and the like; or formed with organic acids such as acetic acid, benzenesulfonic acid, benzoic, camphorsulfonic acid, citric acid, ethanesulfonic acid, fumaric acid, glucoheptonic acid, gluconic acid, glutamic acid, glycolic acid, hydroxynaphtoic acid, 2-hydroxyethanesulfonic acid, lactic acid, maleic acid, malic acid, malonic acid, mandelic acid, methanesulfonic acid, muconic acid, 2-naphthalenesulfonic acid, propionic acid, salicylic acid, succinic acid, tartaric acid, p-toluenesulfonic acid, trimethylacetic acid, and the like; or salts formed when an acidic proton present in the parent compound either is replaced by a metal ion, e.g., an alkali metal ion, an alkaline earth ion, or an aluminum ion; or coordinates with an organic or inorganic base. Acceptable organic bases include diethanolamine, ethanolamine, N-methylglucamine, triethanolamine, tromethamine, and the like. Acceptable inorganic bases include aluminum hydroxide, calcium hydroxide, potassium hydroxide, sodium carbonate and sodium hydroxide.

The preferred pharmaceutically acceptable salts are the salts formed from acetic acid, hydrochloric acid, sulphuric acid, methanesulfonic acid, maleic acid, phosphoric acid, tartaric acid, citric acid, sodium, potassium, calcium, zinc, and magnesium.

It should be understood that all references to pharmaceutically acceptable salts include solvent addition forms (solvates) or crystal forms (polymorphs) as defined herein, of the same acid addition salt.

The terms "pro-drug" and "prodrug", which may be used interchangeably herein, refer to any compound which releases an active parent drug according to formula I in vivo when such prodrug is administered to a mammalian subject. Prodrugs of a compound of formula I are prepared by modifying one or more functional group(s) present in the compound of formula I in such a way that the modification(s) may be cleaved in vivo to release the parent compound. Prodrugs include compounds of formula I wherein a hydroxy, amino, or sulfhydryl group in a compound of Formula I is bonded to any group that may be cleaved in vivo to regenerate the free hydroxyl, amino, or sulfhydryl group, respectively. Examples of prodrugs include, but are not limited to, esters (e.g., acetate, formate, and benzoate derivatives), carbamates (e.g., N,N-dimethylaminocarbonyl) of hydroxy functional groups in compounds of formula I, N-acyl derivatives (e.g. N-acetyl) N-Mannich bases, Schiff bases and enaminones of amino functional groups, oximes, acetals, ketals and enol esters of ketone and aldehyde functional groups in compounds of Formula I, and the like, see Bundegaard, H. "Design of Prodrugs" p1-92, Elsevier, New York-Oxford (1985), and the like.

"Protective group" or "protecting group" means the group which selectively blocks one reactive site in a multifunctional compound such that a chemical reaction can be carried out selectively at another unprotected reactive site in the meaning conventionally associated with it in synthetic chemistry. Certain processes of this invention rely upon the protective groups to block reactive nitrogen and/or oxygen atoms present in the reactants. For example, the terms "amino-protecting group" and "nitrogen protecting group" are used interchangeably herein and refer to those organic groups intended to protect the nitrogen atom against undesirable reactions during synthetic procedures. Exemplary nitrogen protecting groups include, but are not limited to, trifluoroacetyl, acetamido, benzyl (Bn), benzyloxycarbonyl (carbobenzyloxy, CBZ), p-methoxybenzyloxycarbonyl, p-nitrobenzyloxycarbonyl, tert-butoxycarbonyl (BOC), and the like. The artisan in the art will know how to chose a group for the ease of removal and for the ability to withstand the following reactions.

"Solvates" means solvent additions forms that contain either stoichiometric or non stoichiometric amounts of solvent. Some compounds have a tendency to trap a fixed molar ratio of solvent molecules in the crystalline solid state, thus forming a solvate. If the solvent is water the solvate formed is a hydrate, when the solvent is alcohol, the solvate formed is an alcoholate. Hydrates are formed by the combination of one or more molecules of water with one of the substances in which the water retains its molecular state as $H_2O$, such combination being able to form one or more hydrate.

"Subject" means mammals and non-mammals. Mammals means any member of the mammalia class including, but not limited to, humans; non-human primates such as chimpanzees and other apes and monkey species; farm animals such as cattle, horses, sheep, goats, and swine; domestic animals such as rabbits, dogs, and cats; laboratory animals including rodents, such as rats, mice, and guinea pigs; and the like. Examples of non-mammals include, but are not limited to, birds, and the like. The term "subject" does not denote a particular age or sex.

"Disorders of the urinary tract" or "uropathy" used interchangeably with "symptoms of the urinary tract" means the pathologic changes in the urinary tract. Examples of urinary tract disorders include, but are not limited to, incontinence, benign prostatic hypertrophy (BPH), prostatitis, detrusor hyperreflexia, outlet obstruction, urinary frequency, nocturia, urinary urgency, overactive bladder, pelvic hypersensitivity, urge incontinence, urethritis, prostatodynia, cystitis, idiophatic bladder hypersensitivity, and the like.

"Disease states associated with the urinary tract" or "urinary tract disease states" or "uropathy" used interchangeably with "symptoms of the urinary tract" mean the pathologic changes in the urinary tract, or dysfunction of urinary bladder smooth muscle or its innervation causing disordered urinary storage or voiding. Symptoms of the urinary tract include, but are not limited to, overactive bladder (also known as detrusor hyperactivity), outlet obstruction, outlet insufficiency, and pelvic hypersensitivity.

"Overactive bladder" or "detrusor hyperactivity" includes, but is not limited to, the changes symptomatically manifested as urgency, frequency, altered bladder capacity, incontinence, micturition threshold, unstable bladder contractions, sphincteric spasticity, detrusor hyperreflexia (neurogenic bladder), detrusor instability, and the like.

"Outlet obstruction" includes, but is not limited to, benign prostatic hypertrophy (BPH), urethral stricture disease, tumors, low flow rates, difficulty in initiating urination, urgency, suprapubic pain, and the like.

"Outlet insufficiency" includes, but is not limited to, urethral hypermobility, intrinsic sphincteric deficiency, mixed incontinence, stress incontinence, and the like.

"Pelvic Hypersensitivity" includes, but is not limited to, pelvic pain, interstitial (cell) cystitis, prostatodynia, prostatitis, vulvadynia, urethritis, orchidalgia, overactive bladder, and the like.

"Therapeutically effective amount" means an amount of a compound that, when administered to a subject for treating a disease state, is sufficient to effect such treatment for the disease state. The "therapeutically effective amount" will vary depending on the compound, disease state being treated, the severity or the disease treated, the age and relative health of the subject, the route and form of administration, the judgment of the attending medical or veterinary practitioner, and other factors.

The terms "those defined above" and "those defined herein" when referring to a variable incorporates by reference the broad definition of the variable as well as preferred, more preferred and most preferred definitions, if any.

"Treating" or "treatment" of a disease state includes:
(i) preventing the disease state, i.e. causing the clinical symptoms of the disease state not to develop in a subject that may be exposed to or predisposed to the disease state, but does not yet experience or display symptoms of the disease state.
(ii) inhibiting the disease state, i.e., arresting the development of the disease state or its clinical symptoms, or
(iii) relieving the disease state, i.e., causing temporary or permanent regression of the disease state or its clinical symptoms.

The terms "treating", "contacting" and "reacting" when referring to a chemical reaction means adding or mixing two or more reagents under appropriate conditions to produce the indicated and/or the desired product. It should be appreciated that the reaction which produces the indicated and/or the desired product may not necessarily result directly from the combination of two reagents which were initially added, i.e., there may be one or more intermediates which are produced in the mixture which ultimately leads to the formation of the indicated and/or the desired product.

Nomenclature and Structures

In general, the nomenclature used in this Application is based on AUTONOM™ v.4.0, a Beilstein Institute computerized system for the generation of IUPAC systematic nomenclature. Chemical structures shown herein were prepared using ISIS® version 2.2. Any open valency appearing on a carbon, oxygen or nitrogen atom in the structures herein indicates the presence of a hydrogen atom.

All patents and publications identified herein are incorporated herein by reference in their entirety.

COMPOUNDS OF THE INVENTION

The invention provides compounds of the formula (I):

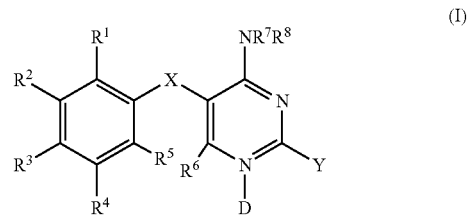

or pharmaceutically acceptable salts thereof, wherein:
X is: —$CH_2$—; —O—; —$S(O)_n$—; or —NR— wherein n is from 0 to 2 and $R^c$ is hydrogen or alkyl;
Y is: hydrogen; or —$NR^dR^e$ wherein one of $R^d$ and $R^e$ is hydrogen, and the other is: hydrogen; alkyl; cycloalkyl; cycloalkylalkyl; haloalkyl; haloalkoxy; hydroxyalkyl; alkoxyalkyl; acetyl; alkylsulfonyl; alkylsulfonylalkyl; aminocarbonyloxyalkyl; hydroxycarbonylalkyl;

hydroxyalkyloxycarbonylalkyl; aryl; aralkyl; arylsulfonyl; heteroaryl; heteroarylalkyl; heteroarylsulfonyl; heterocyclyl; or heterocyclylalkyl;

D is an optional oxygen;

$R^1$ is: alkyl; alkenyl; cycloalkyl; cycloalkenyl; halo; haloalkyl; or hydroxyalkyl;

$R^2$, $R^3$, $R^4$ and $R^5$ each independently is: hydrogen; alkyl; alkenyl; amino; halo; amido; haloalkyl; alkoxy; hydroxy; haloalkoxy; nitro; amino; hydroxyalkyl; alkoxyalkyl; hydroxyalkoxy; alkynylalkoxy; alkylsulfonyl; arylsulfonyl; cyano; aryl; heteroaryl; heterocyclyl; heterocyclylalkoxy; aryloxy; heteroaryloxy; aralkyloxy; heteroaralkyloxy; optionally substituted phenoxy; —$(CH_2)_m$-$(Z)_n$-(CO)—$R^f$ or —$(CH_2)_n$-$(Z)_n$-$SO_2$—$(NR^g)_n$—$R^f$ where m and n each independently is 0 or 1, Z is 0 or $NR^g$, $R^f$ is hydrogen, alkyl, hydroxy, alkoxy, amino, hydroxyalkyl or alkoxyalkyl, and each $R^g$ is independently hydrogen or alkyl; or $R^3$ and $R^4$ may together form an alkylene dioxy; or $R^3$ and $R^4$ together with the atoms to which they are attached may form a five or six-membered ring that optionally includes one or two heteroatoms selected from O, S and N; or $R^2$ and $R^3$ may together form an alkylene dioxy; or $R^2$ and $R^3$ together with the atoms to which they are attached may form a five or six-membered ring that optionally includes one or two heteroatoms selected from O, S and N;

$R^6$ is: hydrogen; alkyl; halo; haloalkyl; amino; or alkoxy; and one of $R^7$ and $R^8$ is hydrogen, and the other is: hydrogen; alkyl; cycloalkyl; cycloalkylalkyl; haloalkyl; haloalkoxy; hydroxyalky; alkoxyalkyl; acetyl; alkylsulfonyl; alkylsulfonylalkyl; aminocarbonyloxyalkyl; hydroxycarbonylalkyl; hydroxyalkyloxycarbonylalkyl; aryl; aralkyl; arylsulfonyl; heteroaryl; heteroarylalkyl; heteroarylsulfonyl; heterocyclyl; or heterocyclylalkyl;

provided that when X is —$CH_2$—, $R^1$ is isopropyl.

In many embodiments of formula (I), Y is —$NR^dR^e$.

In certain embodiments of formula (I), $R^5$ and $R^6$ are hydrogen.

In certain embodiments of formula (I), $R^2$ is hydrogen.

In certain embodiments of formula (I), X is —$CH_2$— or —O—. Preferably X is O.

In certain embodiments of formula (I), D is absent.

In certain embodiments of formula (I), $R^1$ is alkyl, alkenyl or cycloalkyl.

Preferably, $R^1$ is ethyl, cyclopropyl, isopropenyl or isopropyl. More preferably $R^1$ is isopropyl.

In certain embodiments formula (I), one of $R^7$ and $R^8$ is hydrogen, and the other is: alkyl, cycloalkyl; cycloalkylalkyl; haloalkyl; hydroxyalky; alkoxyalkyl; alkylsulfonylalkyl; acetyl; alkylsulfonyl; aryl; aralkyl; arylsulfonyl; heteroaryl; heteroarylalkyl; heteroarylsulfonyl; heterocyclyl; or heterocyclylalkyl.

In certain embodiments of formula (I), one of $R^7$ and $R^8$ is hydrogen and the other is alkyl, hydroxyalkyl or haloalkyl.

In certain embodiments formula (I), one of $R^7$ and $R^8$ is hydrogen, and the other is: alkyl, cycloalkyl; cycloalkylalkyl; haloalkyl; hydroxyalky; alkoxyalkyl; alkylsulfonylalkyl; acetyl; alkylsulfonyl; aryl; aralkyl; arylsulfonyl; heteroaryl; heteroarylalkyl; heteroarylsulfonyl; heterocyclyl; or heterocyclylalkyl.

In certain embodiments of formula (I), one of $R^d$ and $R^e$ is hydrogen and the other is alkyl, hydroxyalkyl or haloalkyl.

In certain embodiments of formula (I), $R^3$ and $R^4$ each independently is halo, alkoxy, haloalkoxy or alkylsulfonyl.

In certain embodiments of formula (I), $R^3$ is halo, alkoxy, haloalkoxy or hydroxy. Preferably $R^3$ is methoxy, fluoro, or chloro. More preferably $R^3$ is methoxy. In certain embodiments $R^3$ is hydroxy.

In certain embodiments of formula (I), $R^4$ is halo, alkoxy, alkylsulfonyl or heteroaryl. Preferably $R^4$ is methoxy, iodo, methanesulfonyl or heteroaryl. More preferably $R^4$ is methoxy, bromo, chloro or iodo. In specific embodiments $R^4$ may be methoxy, while in other embodiments $R^4$ may be iodo.

In certain embodiments of formula (I), $R^7$, $R^8$, $R^d$ and $R^e$ are hydrogen.

In certain embodiments of formula (I), $R^4$ is heteroaryl. The heteroaryl may be, in certain embodiments, tetrazolyl, pyrazolyl, oxazolyl, imidazolyl, thiazolyl, thiophenyl, triazolyl, furanyl, isoxazolyl, oxadiazolyl, benzothiophenyl, pyridinyl, or pyrrolyl. More specifically, the heteroaryl may be tetrazol-5-yl, pyrazol-1-yl, 3-methylpyrazol-1-yl, oxazol-2-yl, oxazol-5-yl, imidazol-2-yl, thiazol-2-yl, thiazol4-yl, thiophen-3-yl, 5-chloro-thiophen-2-yl, 1-methyl-imidazol-2-yl, imidazol-1-yl, pyrazol-3-yl, 2-methyl-thiazol-4-yl, furan-2-yl, 3,5-dimethyl-pyrazol-1-yl, 4,5-dihydrooxazol-2-yl, isoxazol-5-yl, [1,2,4]-oxadiazol-3-yl, benzo[b]thiophen-3-yl, oxazol-4-yl, furan-3-yl, 4-methyl-thiophen-2-yl, thiazol-5-yl, tetrazol-1-yl, [1,2,4]triazol-1-yl, 2-methyl-thiazol-5 -yl, 1-methyl-pyrazol-4-yl, 2-thiolyl-imidazol-1-yl, pyridin-2-yl, or 2,5-dimethyl-pyrrol-1-yl).

In certain embodiments of formula (I), $R^3$ and $R^4$ together with the atoms to which they are attached may form a five or six-membered ring that optionally includes one or two heteroatoms selected from O, S and N. In many such embodiments $R^3$ and $R^4$ together with the atoms to which they are attached may form: a five membered aromatic with one nitrogen, i.e. a pyrrol ring; a five membered aromatic with two nitrogens, i.,e., a pyrazol or imidazol ring; a five membered aromatic with one nitrogen and one oxygen, i.e., an oxazole or isoxazole ring; a five membered aromatic with one nitrogen and one sulfur, i.e., a thiazole or isothiazole ring; a five membered aromatic ring with one oxygen, i.e., a furanyl ring; or a five membered aromatic with one sulfur, i.e., a thiophenyl ring.

In certain embodiments of formula (I), $R^2$ and $R^3$ together with the atoms to which they are attached may form a five or six-membered ring that optionally includes one or two heteroatoms selected from O, S and N. In many such embodiments $R^3$ and $R^4$ together with the atoms to which they are attached may form: a five membered aromatic with one nitrogen, i.e. a pyrrol ring; a five membered aromatic with two nitrogens, i.,e., a pyrazol or imidazol ring; a five membered aromatic with one nitrogen and one oxygen, i.e., an oxazole or isoxazole ring; a five membered aromatic with one nitrogen and one sulfur, i.e., a thiazole or isothiazole ring; a five membered aromatic ring with one oxygen, i.e., a furanyl ring; or a five membered aromatic with one sulfur, i.e., a thiophenyl ring.

In one preferred embodiment of formula (I), X is —O—, $R^1$ is alkyl, alkenyl, cycloalkyl, or halo, $R^2$ is hydrogen, $R^3$ is alkoxy, hydroxy or halo, $R^4$ is alkoxy, halo, alkenyl, or heteroaryl selected from tetrazolyl, pyrazolyl, oxazolyl, imidazolyl, thiazolyl, thiophenyl, triazolyl, furanyl, isoxazolyl, oxadiazolyl, benzothiophenyl, pyridinyl and pyrrolyl, and $R^5$ and $R^6$ are hydrogen.

In another preferred embodiment of formula (I), X is —O—, $R^1$ is alkyl, alkenyl, cycloalkyl, or halo, $R^2$ is hydrogen, $R^3$ is alkoxy, hydroxy or halo, $R^4$ is alkoxy, halo, or alkenyl, and $R^5$ and $R^6$ are hydrogen.

In another preferred embodiment of formula (I), X is —O—, $R^1$ is alkyl, alkenyl, cycloalkyl, or halo, $R^2$ is hydrogen, $R^3$ is alkoxy, hydroxy or halo, $R^4$ is heteroaryl selected from tetrazolyl, pyrazolyl, oxazolyl, imidazolyl, thiazolyl, thiophenyl, triazolyl, furanyl, isoxazolyl, oxadiazolyl, benzothiophenyl, pyridinyl and pyrrolyl, and $R^5$ and $R^6$ are hydrogen.

In another preferred embodiment of formula (I), X is —O—, $R^1$ is alkyl, alkenyl, cycloalkyl, or halo, $R^2$ is hydrogen, $R^3$ is alkoxy, hydroxy or halo, $R^4$ is alkoxy, halo, or alkenyl, $R^5$ and $R^6$ are hydrogen, $R^7$ and $R^8$ are hydrogen, and one of $R^a$ and $R^b$ is hydrogen and the other is hydrogen, alkyl, hydroxyalkyl or haloalkyl.

In another preferred embodiment of formula (I), X is —O—, $R^1$ is alkyl, alkenyl, cycloalkyl, or halo, $R^2$ is hydrogen, $R^3$ is alkoxy, hydroxy or halo, $R^4$ is heteroaryl selected from tetrazolyl, pyrazolyl, oxazolyl, imidazolyl, thiazolyl, thiophenyl, triazolyl, furanyl, isoxazolyl, oxadiazolyl, benzothiophenyl, pyridinyl and pyrrolyl, $R^5$ and $R^6$ are hydrogen, $R^7$ and $R^8$ are hydrogen, and one of $R^a$ and $R^b$ is hydrogen and the other is hydrogen, alkyl, acetyl, hydroxyalkyl or haloalkyl.

In another preferred embodiment of formula (I), X is —O— or —CH$_2$—, $R^1$ is isopropyl, isopropenyl, cyclopropyl or iodo, $R^2$ is hydrogen, $R^3$ is alkoxy, hydroxy or halo, $R^4$ is alkoxy or halo, and $R^5$ and $R^6$ are hydrogen.

In another preferred embodiment of formula (I), X is —O— or —CH$_2$—, $R^1$ is isopropyl, isopropenyl, cyclopropyl or iodo, $R^2$ is hydrogen, $R^3$ is alkoxy, hydroxy or halo, $R^4$ is alkoxy or halo, $R^5$ and $R^6$ are hydrogen, $R^7$ and $R^8$ are hydrogen, and one of $R^a$ and $R^b$ is hydrogen and the other is hydrogen, alkyl, hydroxyalkyl or haloalkyl.

In another preferred embodiment of formula (I), X is —O— or —CH$_2$—, $R^1$ is isopropyl or iodo, $R^2$ is hydrogen, $R^3$ is methoxy, hydroxy, chloro, bromo or iodo, $R^4$ is methoxy, chloro, bromo or iodo, and $R^5$ and $R^6$ are hydrogen.

In another preferred embodiment of formula (I), X is —O— or —CH$_2$—, $R^1$ is isopropyl or iodo, $R^2$ is hydrogen, $R^3$ is methoxy, hydroxy, chloro, bromo or iodo, $R^4$ methoxy, chloro, bromo or iodo, $R^5$ and $R^6$ are hydrogen, $R^7$ and $R^8$ are hydrogen, and one of $R^a$ and $R^b$ is hydrogen and the other is hydrogen, alkyl, hydroxyalkyl or haloalkyl.

In another preferred embodiment of formula (I), X is —O— or —CH$_2$—, $R^1$ is isopropyl, $R^2$ is hydrogen, $R^3$ is methoxy, hydroxy, chloro, bromo or iodo, $R^4$ is methoxy, chloro, bromo or iodo, and $R^5$ and $R^6$ are hydrogen.

In another preferred embodiment of formula (I), X is —O— or —CH$_2$—, $R^1$ is isopropyl, $R^2$ is hydrogen, $R^3$ is methoxy, hydroxy, chloro, bromo or iodo, $R^4$ methoxy, chloro, bromo or iodo, $R^5$ and $R^6$ are hydrogen, $R^7$ and $R^8$ are hydrogen, and one of $R^a$ and $R^b$ is hydrogen and the other is hydrogen, alkyl, hydroxyalkyl or haloalkyl.

The compounds of the invention in many embodiments may be of the formula (II):

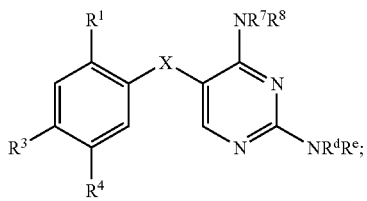

(II)

wherein:
X is: —CH$_2$—; or —O—;
$R^1$ is: alkyl; alkenyl; cycloalkyl; cycloalkenyl; or halo;

$R^3$ and $R^4$ each independently is: alkyl; alkenyl; amino; halo; amido; haloalkyl; alkoxy; hydroxy; haloalkoxy; nitro; hydroxyalkyl; alkoxyakyl; hydroxyalkoxy; alkynylalkoxy; alkylsulfonyl; arylsulfonyl; cyano; aryl; heteroaryl; heterocyclyl; heterocyclylalkoxy; aryloxy; heteroaryloxy; aralkyloxy; heteroaralkyloxy; optionally substituted phenoxy; —(CH$_2$)$_m$-(Z)$_n$-(CO)—R$^f$ or —(CH$_2$)$_m$-(Z)$_n$-SO$_2$—(NR$^g$)$_n$—R$^f$ where m and n each independently is 0 or 1, Z is O or NR$^g$, R$^f$ is hydrogen, alkyl, hydroxy, alkoxy, amino, hydroxyalkyl or alkoxyalkyl, and each R$^g$ is independently hydrogen or alkyl; or $R^3$ and $R^4$ may together form an alkylene dioxy; or $R^3$ and $R^4$ together with the atoms to which they are attached may form a five or six-membered ring that optionally includes one or two heteroatoms selected from O, S and N;

one of $R^7$ and $R^8$ is hydrogen, and the other is: hydrogen; alkyl; cycloalkyl; cycloalkylalkyl; haloalkyl; haloalkoxy; hydroxyalkyl; alkoxyalkyl; acetyl; alkylsulfonyl; alkylsulfonylalkyl; aminocarbonyloxyalkyl; hydroxycarbonylalkyl; hydroxyalkyloxycarbonylalkyl; aryl; aralkyl; arylsulfonyl; heteroaryl; heteroarylalkyl; heteroarylsulfonyl; heterocyclyl; or heterocyclylalkyl; and one of $R^d$ and $R^e$ is hydrogen, and the other is: hydrogen; alkyl; cycloalkyl; cycloalkylalkyl; haloalkyl; haloalkoxy; hydroxyalkyl; alkoxyalkyl; acetyl; alkylsulfonyl; alkylsulfonylalkyl; aminocarbonyloxyalkyl; hydroxycarbonylalkyl; hydroxyalkyloxycarbonylalkyl; aryl; aralkyl; arylsulfonyl; heteroaryl; heteroarylalkyl; heteroarylsulfonyl; heterocyclyl; or heterocyclylalkyl.

In certain embodiments of formula (II), $R^1$ is alkyl, alkenyl or cycloalkyl. Preferably, $R^1$ is ethyl, cyclopropyl, isopropenyl or isopropyl. More preferably $R^1$ is isopropyl.

In certain embodiments formula (II), one of $R^7$ and $R^8$ is hydrogen, and the other is: alkyl, cycloalkyl; cycloalkylalkyl; haloalkyl; hydroxyalky; alkoxyalkyl; alkylsulfonylalkyl; acetyl; alkylsulfonyl; aryl; aralkyl; arylsulfonyl; heteroaryl; heteroarylalkyl; heteroarylsulfonyl; heterocyclyl; or heterocyclylalkyl.

In certain embodiments of formula (II), one of $R^7$ and $R^8$ is hydrogen and the other is alkyl, hydroxyalkyl or haloalkyl.

In certain embodiments formula (II), one of $R^d$ and $R^e$ is hydrogen, and the other is: alkyl, cycloalkyl; cycloalkylalkyl; haloalkyl; hydroxyalky; alkoxyalkyl; alkylsulfonylalkyl; acetyl; alkylsulfonyl; aryl; aralkyl; arylsulfonyl; heteroaryl; heteroarylalkyl; heteroarylsulfonyl; heterocyclyl; or heterocyclylalkyl.

In certain embodiments of formula (II), one of $R^d$ and $R^e$ is hydrogen and the other is alkyl, hydroxyalkyl or haloalkyl.

In certain embodiments of formula (II), $R^3$ and $R^4$ each independently is halo, alkoxy, haloalkoxy or alkylsulfonyl.

In certain embodiments of formula (II), $R^3$ is halo, alkoxy, haloalkoxy or hydroxy. Preferably $R^3$ is methoxy, fluoro, or chloro. More preferably $R^3$ is methoxy. In certain embodiments $R^3$ is hydroxy.

In certain embodiments of formula (II), $R^4$ is halo, alkoxy, alkylsulfonyl or heteroaryl. Preferably $R^4$ is methoxy, iodo, methanesulfonyl or heteroaryl. More preferably $R^4$ is methoxy, bromo, chloro or iodo. In specific embodiments $R^4$ may be methoxy, while in other embodiments $R^4$ may be iodo.

In certain embodiments of formula (II), $R^7$, $R^8$, $R^d$ and $R^e$ are hydrogen.

In certain embodiments of formula (II), $R^4$ is heteroaryl. The heteroaryl may be, in certain embodiments, tetrazolyl, pyrazolyl, oxazolyl, imidazolyl, thiazolyl, thiophenyl, triazolyl, furanyl, isoxazolyl, oxadiazolyl, benzothiophenyl, pyridinyl, or pyrrolyl. More specifically, the heteroaryl may be tetrazol-5-yl, pyrazol-1-yl, 3-methylpyrazol-1-yl, oxazol-2-yl, oxazol-5-yl, imidazol-2-yl, thiazol-2-yl, thiazol-4-yl, thiophen-3-yl, 5-chloro-thiophen-2-yl, 1-methyl-imidazol-2-yl, imidazol-1-yl, pyrazol-3-yl, 2-methyl-thiazol-4-yl, furan-2-yl, 3,5-dimethyl-pyrazol-1-yl, 4,5-dihydrooxazol-2-yl, isoxazol-5-yl, [1,2,4]-oxadiazol-3-yl, benzo[b]thiophen-3-yl, oxazol-4-yl, furan-3-yl, 4-methyl-thiophen-2-yl, thiazol-5-yl, tetrazol-1-yl, [1,2,4]triazol-1-yl, 2-methyl-thiazol-5-yl, 1-methyl-pyrazol-4-yl, 2-thiolyl-imidazol-1-yl, pyridin-2-yl, or 2,5-dimethyl-pyrrol-1-yl).

In certain embodiments of formula (II), $R^3$ and $R^4$ together with the atoms to which they are attached may form a five or six-membered ring that optionally includes one or two heteroatoms selected from O, S and N. In many such embodiments $R^3$ and $R^4$ together with the atoms to which they are attached may form: a five membered aromatic with one nitrogen, i.e. a pyrrol ring; a five membered aromatic with two nitrogens, i.,e., a pyrazol or imidazol ring; a five membered aromatic with one nitrogen and one oxygen, i.e., an oxazole or isoxazole ring; a five membered aromatic with one nitrogen and one sulfur, i.e., a thiazole or isothiazole ring; a five membered aromatic with one oxygen, i.e., a furanyl ring; or a five membered aromatic with one sulfur, i.e., a thiophenyl ring.

In one preferred embodiment of formula (II), X is —O—, $R^1$ is alkyl, alkenyl, cycloalkyl, or halo, $R^3$ is alkoxy, hydroxy or halo, and $R^4$ is alkoxy, halo, alkenyl, or heteroaryl selected from tetrazolyl, pyrazolyl, oxazolyl, imidazolyl, thiazolyl, thiophenyl, triazolyl, furanyl, isoxazolyl, oxadiazolyl, benzothiophenyl, pyridinyl and pyrrolyl.

In another preferred embodiment of formula (II), X is —O—, $R^1$ is alkyl, alkenyl, cycloalkyl, or halo, $R^3$ is alkoxy, hydroxy or halo, and $R^4$ is alkoxy, halo, or alkenyl.

In another preferred embodiment of formula (II), X is —O—, $R^1$ is alkyl, alkenyl, cycloalkyl, or halo, $R^3$ is alkoxy, hydroxy or halo, and $R^4$ is heteroaryl selected from tetrazolyl, pyrazolyl, oxazolyl, imidazolyl, thiazolyl, thiophenyl, triazolyl, furanyl, isoxazolyl, oxadiazolyl, benzothiophenyl, pyridinyl and pyrrolyl.

In another preferred embodiment of formula (II), X is —O—, $R^1$ is alkyl, alkenyl, cycloalkyl, or halo, $R^3$ is alkoxy, hydroxy or halo, $R^4$ is alkoxy, halo, or alkenyl, $R^7$ and $R^8$ are hydrogen, and one of $R^a$ and $R^b$ is hydrogen and the other is hydrogen, alkyl, hydroxyalkyl or haloalkyl.

In another preferred embodiment of formula (II), X is —O—, $R^1$ is alkyl, alkenyl, cycloalkyl, or halo, $R^3$ is alkoxy, hydroxy or halo, $R^4$ is heteroaryl selected from tetrazolyl, pyrazolyl, oxazolyl, imidazolyl, thiazolyl, thiophenyl, triazolyl, furanyl, isoxazolyl, oxadiazolyl, benzothiophenyl, pyridinyl and pyrrolyl, $R^7$ and $R^8$ are hydrogen, and one of $R^a$ and $R^b$ is hydrogen and the other is hydrogen, alkyl, acetyl, hydroxyalkyl or haloalkyl.

In another preferred embodiment of formula (II), X is —O— or —CH$_2$—, $R^1$ is isopropyl, isopropenyl, cyclopropyl or iodo, $R^3$ is alkoxy, hydroxy or halo, and $R^4$ is alkoxy or halo.

In another preferred embodiment of formula (II), X is —O— or —CH$_2$—, $R^1$ is isopropyl, isopropenyl, cyclopropyl or iodo, $R^3$ is alkoxy, hydroxy or halo, $R^4$ is alkoxy or halo, $R^7$ and $R^8$ are hydrogen, and one of $R^a$ and $R^b$ is hydrogen and the other is hydrogen, alkyl, hydroxyalkyl or haloalkyl.

In another preferred embodiment of formula (II), X is —O— or —CH$_2$—, $R^1$ is isopropyl or iodo, $R^3$ is methoxy, hydroxy, chloro, bromo or iodo, and $R^4$ is methoxy, chloro, bromo or iodo.

In another preferred embodiment of formula (II), X is —O— or —CH$_2$—, $R^1$ is isopropyl or iodo, $R^3$ is methoxy, hydroxy, chloro, bromo or iodo, $R^4$ methoxy, chloro, bromo or iodo, $R^7$ and $R^8$ are hydrogen, and one of $R^a$ and $R^b$ is hydrogen and the other is hydrogen, alkyl, hydroxyalkyl or haloalkyl.

In another preferred embodiment of formula (II), X is —O— or —CH$_2$—, $R^1$ is isopropyl, $R^3$ is methoxy, hydroxy, chloro, bromo or iodo, and $R^4$ is methoxy, chloro, bromo or iodo.

In another preferred embodiment of formula (II), X is —O— or —CH$_2$—, $R^1$ is isopropyl, $R^3$ is methoxy, hydroxy, chloro, bromo or iodo, $R^4$ methoxy, chloro, bromo or iodo, $R^7$ and $R^8$ are hydrogen, and one of $R^a$ and $R^b$ is hydrogen and the other is hydrogen, alkyl, hydroxyalkyl or haloalkyl.

The compounds of the invention in certain embodiments may be of the formula (III):

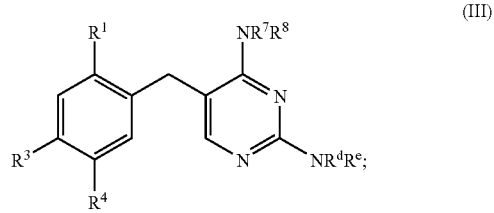

wherein:

$R^1$ is: isopropyl; isopropenyl; cyclopropyl; or iodo;

$R^3$ and $R^4$ each independently is: alkyl; alkenyl; amino; halo; amido; haloalkyl; alkoxy; hydroxy; haloalkoxy; nitro; hydroxyalkyl; alkoxyalkyl; hydroxyalkoxy; alkynylalkoxy; alkylsulfonyl; arylsulfonyl; cyano; aryl; heteroaryl; heterocyclyl; heterocyclylalkoxy; aryloxy; heteroaryloxy; aralkyloxy; heteroaralkyloxy; optionally substituted phenoxy; —(CH$_2$)$_m$-(Z)$_n$-(CO)—R$^f$ or —(CH$_2$)$_n$-(Z)$_n$-SO$_2$—(NR$^g$)$_n$—R$^f$ where m and n each independently is 0 or 1, Z is O or NR$^g$, R$^f$ is hydrogen, alkyl, hydroxy, alkoxy, amino, hydroxyalkyl or alkoxyalkyl, and each R$^g$ is independently hydrogen or alkyl; or $R^3$ and $R^4$ may together form an alkylene dioxy; or $R^3$ and $R^4$ together with the atoms to which they are attached may form a five or six-membered ring that optionally includes one or two heteroatoms selected from O, S and N;

one of $R^7$ and $R^8$ is hydrogen, and the other is: hydrogen; alkyl; cycloalkyl; cycloalkylalkyl; haloalkyl; haloalkoxy; hydroxyalkyl; alkoxyalkyl; acetyl; alkylsulfonyl; alkylsulfonylalkyl; aminocarbonyloxyalkyl; hydroxycarbonylalkyl; hydroxyalkyloxycarbonylalkyl; aryl; aralkyl; arylsulfonyl; heteroaryl; heteroarylalkyl; heteroarylsulfonyl; heterocyclyl; or heterocyclylalkyl; and one of $R^d$ and $R^e$ is hydrogen, and the other is: hydrogen; alkyl; cycloalkyl; cycloalkylalkyl; haloalkyl; haloalkoxy; hydroxyalkyl; alkoxyalkyl; acetyl; alkylsulfonyl; alkylsulfonylalkyl; aminocarbonyloxyalkyl; hydroxycarbonylalkyl; hydroxyalkyloxycarbonylalkyl; aryl; aralkyl; arylsulfonyl; heteroaryl; heteroarylalkyl; heteroarylsulfonyl; heterocyclyl; or heterocyclylalkyl.

In other embodiments the subject compounds may be of the formula (IV):

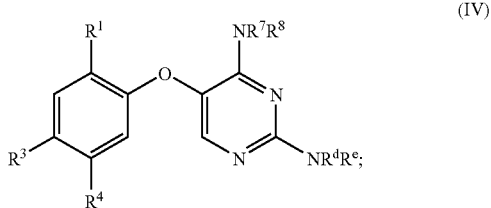

(IV)

wherein:
R¹ is: alkyl; alkenyl; cycloalkyl; cycloalkenyl or halo;
R³ and R⁴ each independently is: alkyl; alkenyl; amino; halo; amido; haloalkyl; alkoxy; hydroxy; haloalkoxy; nitro; hydroxyalkyl; alkoxyalkyl; hydroxyalkoxy; alkynylalkoxy; alkylsulfonyl; arylsulfonyl; cyano; aryl; heteroaryl; heterocyclyl; heterocyclylalkoxy; aryloxy; heteroaryloxy; aralkyloxy; heteroaralkyloxy; optionally substituted phenoxy; —(CH₂)$_n$-(Z)$_n$-(CO)—R$^f$ or —(CH₂)$_n$-(Z)$_n$-SO₂—(NR$^g$)$_n$—R$^f$ where m and n each independently is 0 or 1, Z is O or NR$^g$, R$^f$ is hydrogen, alkyl, hydroxy, alkoxy, amino, hydroxyalkyl or alkoxyalkyl, and each R$^g$ is independently hydrogen or alkyl; or R³ and R⁴ may together form an alkylene dioxy; or R³ and R⁴ together with the atoms to which they are attached may form a five or six-membered ring that optionally includes one or two heteroatoms selected from O, S and N;
one of R⁷ and R⁸ is hydrogen, and the other is: hydrogen; alkyl; cycloalkyl; cycloalkylalkyl; haloalkyl; haloalkoxy; hydroxyalkyl; alkoxyalkyl; acetyl; alkylsulfonyl; alkylsulfonylalkyl; aminocarbonyloxyalkyl; hydroxycarbonylalkyl; hydroxyalkyloxycarbonylalkyl; aryl; aralkyl; arylsulfonyl; heteroaryl; heteroarylalkyl; heteroarylsulfonyl; heterocyclyl; or heterocyclylalkyl; and
one of R$^d$ and R$^e$ is hydrogen, and the other is: hydrogen; alkyl; cycloalkyl; cycloalkylalkyl; haloalkyl; haloalkoxy; hydroxyalkyl; alkoxyalkyl; acetyl; alkylsulfonyl; alkylsulfonylalkyl; aminocarbonyloxyalkyl; hydroxycarbonylalkyl; hydroxyalkyloxycarbonylalkyl; aryl; aralkyl; arylsulfonyl; heteroaryl; heteroarylalkyl; heteroarylsulfonyl; heterocyclyl; or heterocyclylalkyl.

In certain embodiments of formula (IV), R¹ is alkyl, alkenyl, cycloalkyl or halo. Preferably, R¹ is ethyl, cyclopropyl, isopropenyl, isopropyl or iodo. More preferably R¹ is isopropyl or iodo.

In certain embodiments formula (III) or formula (IV), one of R⁷ and R⁸ is hydrogen, and the other is: alkyl, cycloalkyl; cycloalkylalkyl; haloalkyl; hydroxyalky; alkoxyalkyl; alkylsulfonylalkyl; acetyl; alkylsulfonyl; aryl; aralkyl; arylsulfonyl; heteroaryl; heteroarylalkyl; heteroarylsulfonyl; heterocyclyl; or heterocyclylalkyl.

In certain embodiments of formula (III) or formula (IV), one of R⁷ and R⁸ is hydrogen and the other is alkyl, hydroxyalkyl or haloalkyl.

In certain embodiments formula (III) or formula (IV), one of R$^d$ and R$^e$ is hydrogen, and the other is: alkyl, cycloalkyl; cycloalkylalkyl; haloalkyl; hydroxyalky; alkoxyalkyl; alkylsulfonylalkyl; acetyl; alkylsulfonyl; aryl; aralkyl; arylsulfonyl; heteroaryl; heteroarylalkyl; heteroarylsulfonyl; heterocyclyl; or heterocyclylalkyl.

In certain embodiments of formula (III) or formula (IV), one of R$^d$ and R$^e$ is hydrogen and the other is alkyl, hydroxyalkyl or haloalkyl.

In certain embodiments of formula (III) or formula (IV), R³ and R⁴ each independently is halo, alkoxy, haloalkoxy or alkylsulfonyl.

In certain embodiments of formula (III) or formula (IV), R³ is halo, alkoxy, haloalkoxy or hydroxy. Preferably R³ is methoxy, fluoro, or chloro. More preferably R³ is methoxy. In certain embodiments R³ is hydroxy.

In certain embodiments of formula (III) or formula (IV), R⁴ is halo, alkoxy, alkylsulfonyl or heteroaryl. Preferably R⁴ is methoxy, iodo, methanesulfonyl or heteroaryl. More preferably R⁴ is methoxy, bromo, chloro or iodo. In specific embodiments R⁴ may be methoxy, while in other embodiments R⁴ may be iodo.

In certain embodiments of formula (III) or formula (IV), R⁷, R⁸, R$^d$ and R$^e$ are hydrogen.

In certain embodiments of formula (III) or formula (IV), R⁴ is heteroaryl. The heteroaryl may be, in certain embodiments, tetrazolyl, pyrazolyl, oxazolyl, imidazolyl, thiazolyl, thiophenyl, triazolyl, furanyl, isoxazolyl, oxadiazolyl, benzothiophenyl, pyridinyl, or pyrrolyl. More specifically, the heteroaryl may be tetrazol-5-yl, pyrazol-1-yl, 3-methylpyrazol-1-yl, oxazol-2-yl, oxazol-5-yl, imidazol-2-yl, thiazol-2-yl, thiazol4-yl, thiophen-3-yl, 5-chloro-thiophen-2-yl, 1-methyl-imidazol-2-yl, imidazol-1-yl, pyrazol-3-yl, 2-methyl-thiazol4-yl, furan-2-yl, 3,5-dimethyl-pyrazol-1-yl, 4,5-dihydrooxazol-2-yl, isoxazol-5-yl, [1,2,4]-oxadiazol-3-yl, benzo[b]thiophen-3-yl, oxazol-4-yl, furan-3-yl, 4-methyl-thiophen-2-yl, thiazol-5-yl, tetrazol-1-yl, [1,2,4]triazol-1-yl, 2-methyl-thiazol-5-yl, 1-methyl-pyrazol4-yl, 2-thiolyl-imidazol-1-yl, pyridin-2-yl, or 2,5-dimethyl-pyrrol-1-yl).

In certain embodiments of formula (III) or formula (IV), R³ and R⁴ together with the atoms to which they are attached may form a five or six-membered ring that optionally includes one or two heteroatoms selected from O, S and N. In many such embodiments R³ and R⁴ together with the atoms to which they are attached may form: a five membered aromatic with one nitrogen, i.e. a pyrrol ring; a five membered aromatic with two nitrogens, i.,e., a pyrazol or imidazol ring; a five membered aromatic with one nitrogen and one oxygen, i.e., an oxazole or isoxazole ring; a five membered aromatic with one nitrogen and one sulfur, i.e., a thiazole or isothiazole ring; a five membered aromatic with one oxygen, i.e., a furanyl ring; or a five membered aromatic with one sulfur, i.e., a thiophenyl ring.

The compounds of the invention in certain embodiments may be of the formula (V):

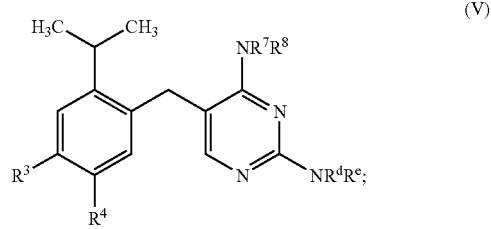

(V)

wherein:
R³ and R⁴ each independently is: alkyl; alkenyl; amino; halo; amido; haloalkyl; alkoxy; hydroxy; haloalkoxy; nitro; hydroxyalkyl; alkoxyalkyl; hydroxyalkoxy; alkynylalkoxy; alkylsulfonyl; arylsulfonyl; cyano; aryl; heteroaryl; heterocyclyl; heterocyclylalkoxy; aryloxy; heteroaryloxy; aralkyloxy; heteroaralkyloxy; optionally substituted phenoxy; —(CH₂)$_m$-(Z)$_n$-(CO)—R$^f$ or —(CH₂)$_m$-(Z)$_n$-SO₂—(NR$^g$)$_n$—R$^f$ where m and n each independently is 0 or 1, Z is O or $NR^g$, $R^f$ is hydrogen, alkyl, hydroxy, alkoxy, amino, hydroxyalkyl or alkoxyalkyl, and each $R^g$ is independently hydrogen or alkyl; or $R^3$ and $R^4$ may together form an alkylene dioxy; or $R^3$ and $R^4$ together with the atoms to which they are attached may form a five or six-membered ring that optionally includes one or two heteroatoms selected from O, S and N;

one of $R^7$ and $R^8$ is hydrogen, and the other is: hydrogen; alkyl; cycloalkyl; cycloalkylalkyl; haloalkyl; haloalkoxy; hydroxyalkyl; alkoxyalkyl; acetyl; alkylsulfonyl; alkylsulfonylalkyl; aminocarbonyloxyalkyl; hydroxycarbonylalkyl; hydroxyalkyloxycarbonylalkyl; aryl; aralkyl; arylsulfonyl; heteroaryl; heteroarylalkyl; heteroarylsulfonyl; heterocyclyl; or heterocyclylalkyl; and one of $R^d$ and $R^e$ is hydrogen, and the other is: hydrogen; alkyl; cycloalkyl; cycloalkylalkyl; haloalkyl; haloalkoxy; hydroxyalkyl; alkoxyalkyl; acetyl; alkylsulfonyl; alkylsulfonylalkyl; aminocarbonyloxyalkyl; hydroxycarbonylalkyl; hydroxyalkyloxycarbonylalkyl; aryl; aralkyl; arylsulfonyl; heteroaryl; heteroarylalkyl; heteroarylsulfonyl; heterocyclyl; or heterocyclylalkyl.

In other embodiments the subject compounds may be of the formula (VI):

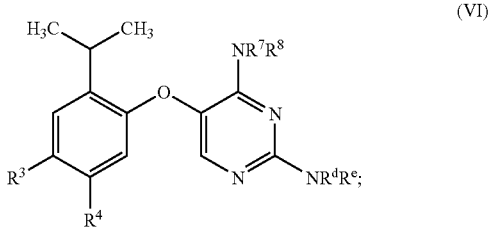

(VI)

wherein:

$R^3$ and $R^4$ each independently is: alkyl; alkenyl; amino; halo; amido; haloalkyl; alkoxy; hydroxy; haloalkoxy; nitro; hydroxyalkyl; alkoxyalkyl; hydroxyalkoxy; alkynylalkoxy; alkylsulfonyl; arylsulfonyl; cyano; aryl; heteroaryl; heterocyclyl; heterocyclylalkoxy; aryloxy; heteroaryloxy; aralkyloxy; heteroaralkyloxy; optionally substituted phenoxy; $-(CH_2)_m-(Z)_n-(CO)-R^f$ or $-(CH_2)_m-(Z)_n-SO_2-(NR^g)_n-R^f$ where m and n each independently is 0 or 1, Z is O or $NR^g$, $R^f$ is hydrogen, alkyl, hydroxy, alkoxy, amino, hydroxyalkyl or alkoxyalkyl, and each $R^g$ is independently hydrogen or alkyl; or $R^3$ and $R^4$ may together form an alkylene dioxy; or $R^3$ and $R^4$ together with the atoms to which they are attached may form a five or six-membered ring that optionally includes one or two heteroatoms selected from O, S and N;

one of $R^7$ and $R^8$ is hydrogen, and the other is: hydrogen; alkyl; cycloalkyl; cycloalkylalkyl; haloalkyl; haloalkoxy; hydroxyalkyl; alkoxyalkyl; acetyl; alkylsulfonyl; alkylsulfonylalkyl; aminocarbonyloxyalkyl; hydroxycarbonylalkyl; hydroxyalkyloxycarbonylalkyl; aryl; aralkyl; arylsulfonyl; heteroaryl; heteroarylalkyl; heteroarylsulfonyl; heterocyclyl; or heterocyclylalkyl; and one of $R^d$ and $R^e$ is hydrogen, and the other is: hydrogen; alkyl; cycloalkyl; cycloalkylalkyl; haloalkyl; haloalkoxy; hydroxyalkyl; alkoxyalkyl; acetyl; alkylsulfonyl; alkylsulfonylalkyl; aminocarbonyloxyalkyl; hydroxycarbonylalkyl; hydroxyalkyloxycarbonylalkyl; aryl; aralkyl; arylsulfonyl; heteroaryl; heteroarylalkyl; heteroarylsulfonyl; heterocyclyl; or heterocyclylalkyl.

In certain embodiments formula (V) or formula (V), one of $R^7$ and $R^8$ is hydrogen, and the other is: alkyl, cycloalkyl; cycloalkylalkyl; haloalkyl; hydroxyalky; alkoxyalkyl; alkylsulfonylalkyl; acetyl; alkylsulfonyl; aryl; aralkyl; arylsulfonyl; heteroaryl; heteroarylalkyl; heteroarylsulfonyl; heterocyclyl; or heterocyclylalkyl.

In certain embodiments of formula (V) or formula (V), one of $R^7$ and $R^8$ is hydrogen and the other is alkyl, hydroxyalkyl or haloalkyl.

In certain embodiments formula (V) or formula (V), one of $R^d$ and $R^e$ is hydrogen, and the other is: alkyl, cycloalkyl; cycloalkylalkyl; haloalkyl; hydroxyalky; alkoxyalkyl; alkylsulfonylalkyl; acetyl; alkylsulfonyl; aryl; aralkyl; arylsulfonyl; heteroaryl; heteroarylalkyl; heteroarylsulfonyl; heterocyclyl; or heterocyclylalkyl.

In certain embodiments of formula (V) or formula (V), one of $R^d$ and $R^e$ is hydrogen and the other is alkyl, hydroxyalkyl or haloalkyl.

In certain embodiments of formula (V) or formula (V), $R^3$ and $R^4$ each independently is halo, alkoxy, haloalkoxy or alkylsulfonyl.

In certain embodiments of formula (V) or formula (V), $R^3$ is halo, alkoxy, haloalkoxy or hydroxy. Preferably $R^3$ is methoxy, fluoro, or chloro. More preferably $R^3$ is methoxy. In certain embodiments $R^3$ is hydroxy.

In certain embodiments of formula (V) or formula (V), $R^4$ is halo, alkoxy, alkylsulfonyl or heteroaryl. Preferably $R^4$ is methoxy, iodo, methanesulfonyl or heteroaryl. More preferably $R^4$ is methoxy, bromo, chloro or iodo. In specific embodiments $R^4$ may be methoxy, while in other embodiments $R^4$ may be iodo.

In certain embodiments of formula (V) or formula (V), $R^7$, $R^8$, $R^d$ and $R^e$ are hydrogen.

In certain embodiments of formula (V) or formula (V), $R^4$ is heteroaryl. The heteroaryl may be, in certain embodiments, tetrazolyl, pyrazolyl, oxazolyl, imidazolyl, thiazolyl, thiophenyl, triazolyl, furanyl, isoxazolyl, oxadiazolyl, benzothiophenyl, pyridinyl, or pyrrolyl. More specifically, the heteroaryl may be tetrazol-5-yl, pyrazol-1-yl, 3-methylpyrazol-1-yl, oxazol-2-yl, oxazol-5-yl, imidazol-2-yl, thiazol-2-yl, thiazol-4-yl, thiophen-3-yl, 5-chloro-thiophen-2-yl, 1-methyl-imidazol-2-yl, imidazol-1-yl, pyrazol-3-yl, 2-methyl-thiazol-4-yl, furan-2-yl, 3,5-dimethyl-pyrazol-1-yl, 4,5-dihydrooxazol-2-yl, isoxazol-5-yl, [1,2,4]-oxadiazol-3-yl, benzo[b]thiophen-3-yl, oxazol-4-yl, furan-3-yl, 4-methylthiophen-2-yl, thiazol-5-yl, tetrazol-1-yl, [1,2,4]triazol-1-yl, 2-methyl-thiazol-5-yl, 1-methyl-pyrazol-4-yl, 2-thiolyl-imidazol-1-yl, pyridin-2-yl, or 2,5-dimethyl-pyrrol-1-yl).

In certain embodiments of formula (V) or formula (V), $R^3$ and $R^4$ together with the atoms to which they are attached may form a five or six-membered ring that optionally includes one or two heteroatoms selected from O, S and N. In many such embodiments $R^3$ and $R^4$ together with the atoms to which they are attached may form: a five membered aromatic with one nitrogen, i.e. a pyrrol ring; a five membered aromatic with two nitrogens, i.,e., a pyrazol or imidazol ring; a five membered aromatic with one nitrogen and one oxygen, i.e., an oxazole or isoxazole ring; a five membered aromatic with one nitrogen and one sulfur, i.e., a thiazole or isothiazole ring; a five membered aromatic with one oxygen, i.e., a furanyl ring; or a five membered aromatic with one sulfur, i.e., a thiophenyl ring.

In certain embodiments, the compounds of the invention may be of the formula (VII):

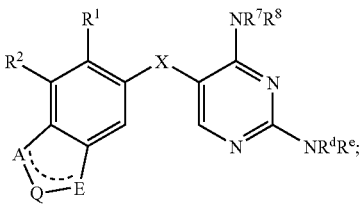

(VII)

wherein:
X is: —CH$_2$—; or —O—;
R$^1$ is: alkyl; alkenyl; cycloalkyl; cycloalkenyl; or halo;
R$^2$ is: hydrogen; alkyl; alkenyl; amino; halo; amido; haloalkyl; alkoxy; hydroxy; haloalkoxy; nitro; hydroxyalkyl; alkoxyalkyl; hydroxyalkoxy; alkynylalkoxy; alkylsulfonyl; arylsulfonyl; cyano; aryl; heteroaryl; heterocyclyl; heterocyclylalkoxy; aryloxy; heteroaryloxy; aralkyloxy; heteroaralkyloxy; optionally substituted phenoxy; or —(CH$_2$)$_m$-(Z)$_n$-(CO)—R$_f$ or —(CH$_2$)$_m$-(Z)$_n$-SO$_2$—(NR$^g$)$_n$—R$^f$ where m and n each independently is 0 or 1, Z is O or NR$^g$, R$^f$ is hydrogen, alkyl, hydroxy, alkoxy, amino, hydroxyalkyl or alkoxyalkyl, and each R$^g$ is independently hydrogen or alkyl;
one of R$^7$ and R$^8$ is hydrogen, and the other is: hydrogen; alkyl; cycloalkyl; cycloalkylalkyl; haloalkyl; haloalkoxy; hydroxyalkyl; alkoxyalkyl; acetyl; alkylsulfonyl; alkylsulfonylalkyl; aminocarbonyloxyalkyl; hydroxycarbonylalkyl; hydroxyalkyloxycarbonylalkyl; aryl; aralkyl; arylsulfonyl; heteroaryl; heteroarylalkyl; heteroarylsulfonyl; heterocyclyl; or heterocyclylalkyl;
one of R$^d$ and R$^e$ is hydrogen, and the other is: hydrogen; alkyl; cycloalkyl; cycloalkylalkyl; haloalkyl; haloalkoxy; hydroxyalkyl; alkoxyalkyl; acetyl; alkylsulfonyl; alkylsulfonylalkyl; aminocarbonyloxyalkyl; hydroxycarbonylalkyl; hydroxyalkyloxycarbonylalkyl; aryl; aralkyl; arylsulfonyl; heteroaryl; heteroarylalkyl; heteroarylsulfonyl; heterocyclyl; or heterocyclylalkyl;
Q is CR$^9$, one of A and E is O, S or NR$^{10}$ and the other is CR$^9$ or N; or
Q is N, one of A and E is NR$^{10}$ and the other is CR$^9$;
each R$^9$ is independently hydrogen, alkyl, halo or alkoxy; and
R$^{10}$ is hydrogen, alkyl, hydroxyalkyl, alkoxyalkyl, —(CH$_2$)$_m$-(Z)$_n$-(CO)—R$^f$, or —(CH$_2$)$_m$-(Z)$_n$-SO$_2$—(NR$^g$)$_n$—R$^f$.

In certain embodiments of formula (VII), A is NR$^{10}$, and Q and E are CR$^9$.
In certain embodiments of formula (VII) E is NR$^{10}$, and A and Q are CR$^9$.
In certain embodiments of formula (VII), Q is NR$^{10}$, B A and E are CR$^9$.
In certain embodiments of formula (VII), A is O, E is N, and Q is CR$^9$.
In certain embodiments of formula (VII), A is N, E is O, and Q is CR$^9$.
In certain embodiments of formula (VII), A is S, E is N, and Q is CR$^9$.
In certain embodiments of formula (VII), A is N, E is S, and Q is CR$^9$.
In certain embodiments of formula (VII), E is S, and A and Q are CR$^9$.
In certain embodiments of formula (VII), E is O, and A and Q are CR$^9$.

In certain embodiments of formula (VII), A is S, and E and Q are CR$^9$.
In certain embodiments of formula (VII), A is O, a i and Q are CR$^9$.
In certain embodiments of formula (VII), A is NR$^{10}$, Q is N, and E is CR$^9$.
In certain embodiments of formula (VII), E is NR$^{10}$, Q is N, and A is CR$^9$.
In certain embodiments of formula (VII), R$^2$ is hydrogen.
In certain embodiments of formula (VII), X is —CH$_2$— or —O—. Preferably X is O.
In certain embodiments of formula (VII), R$^1$ is alkyl, alkenyl or cycloalkyl. Preferably, R$^1$ is ethyl, cyclopropyl, isopropenyl or isopropyl. More preferably R$^1$ is isopropyl.
In certain embodiments formula (VII), one of R$^7$ and R$^8$ is hydrogen, and the other is: alkyl, cycloalkyl; cycloalkylalkyl; haloalkyl; hydroxyalky; alkoxyalkyl; alkylsulfonylalkyl; acetyl; alkylsulfonyl; aryl; aralkyl; arylsulfonyl; heteroaryl; heteroarylalkyl; heteroarylsulfonyl; heterocyclyl; or heterocyclylalkyl.
In certain embodiments of formula (VII), one of R$^7$ and R$^8$ is hydrogen and the other is alkyl, hydroxyalkyl or haloalkyl.
In certain embodiments formula (VII), one of R$^d$ and R$^e$ is hydrogen, and the other is: alkyl; cycloalkyl; cycloalkylalkyl; haloalkyl; hydroxyalky; alkoxyalkyl; alkylsulfonylalkyl; acetyl; alkylsulfonyl; aryl; aralkyl; arylsulfonyl; heteroaryl; heteroarylalkyl; heteroarylsulfonyl; heterocyclyl; or heterocyclylalkyl.
In certain embodiments of formula (VII), one of R$^d$ and R$^e$ is hydrogen and the other is alkyl, hydroxyalkyl or haloalkyl.
In certain embodiments of formula (VII), R$^7$, R$^8$, R$^d$ and R$^e$ are hydrogen.
In other embodiments of the invention, the compounds may be of the formula (VIII):

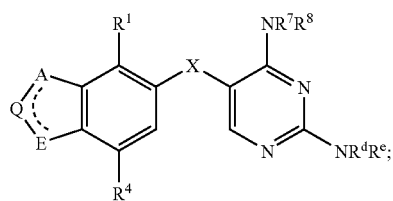

(VIII)

wherein:
X is: —CH$_2$—; or —O—;
R$^1$ is: alkyl; alkenyl; cycloalkyl; cycloalkenyl; or halo;
R$^4$ is: hydrogen; alkyl; alkenyl; amino; halo; amido; haloalkyl; alkoxy; hydroxy; haloalkoxy; nitro; hydroxyalkyl; alkoxyalkyl; hydroxyalkoxy; alkynylalkoxy; alkylsulfonyl; arylsulfonyl; cyano; aryl; heteroaryl; heterocyclyl; heterocyclylalkoxy; aryloxy; heteroaryloxy; aralkyloxy; heteroaralkyloxy; optionally substituted phenoxy; or —(CH$_2$)$_m$-(Z)$_n$-(CO)—R$^f$ or —(CH$_2$)$_m$-(Z)$_n$-SO$_2$—(NR$^g$)$_n$—R$^f$ where m and n each independently is 0 or 1, Z is O or NR$^g$, R$^f$ is hydrogen, alkyl, hydroxy, alkoxy, amino, hydroxyalkyl or alkoxyalkyl, and each R$^g$ is independently hydrogen or alkyl;
one of R$^7$ and R$^8$ is hydrogen, and the other is: hydrogen; alkyl; cycloalkyl; cycloalkylalkyl; haloalkyl; haloalkoxy; hydroxyalkyl; alkoxyalkyl; acetyl; alkylsulfonyl; alkylsulfonylalkyl; aminocarbonyloxyalkyl;

hydroxycarbonylalkyl; hydroxyalkyloxycarbonylalkyl; aryl; aralkyl; arylsulfonyl; heteroaryl; heteroarylalkyl; heteroarylsulfonyl; heterocyclyl; or heterocyclylalkyl;

one of $R^d$ and $R^e$ is hydrogen, and the other is: hydrogen; alkyl; cycloalkyl; cycloalkylalkyl; haloalkyl; haloalkoxy; hydroxyalkyl; alkoxyalkyl; acetyl; alkylsulfonyl; alkylsulfonylalkyl; aminocarbonyloxyalkyl; hydroxycarbonylalkyl; hydroxyalkyloxycarbonylalkyl; aryl; aralkyl; arylsulfonyl; heteroaryl; heteroarylalkyl; heteroarylsulfonyl; heterocyclyl; or heterocyclylalkyl;

Q is $CR^9$, one of A and E is O, S or $NR^{10}$ and the other is $CR^9$ or N; or Q is N, one of A and E is $NR^{10}$ and the other is $CR^9$;

each $R^9$ is independently hydrogen, alkyl, halo or alkoxy; and $R^{10}$ is hydrogen, alkyl, hydroxyalkyl, alkoxyalkyl, —$(CH_2)_m$-$(Z)_n$-(CO)—$R^f$, or —$(CH_2)_m$-$(Z)_n$$SO_2$—$(NR^g)_n$—$R^f$.

In certain embodiments of formula (VIII), A is $NR^{10}$, and Q and E are $CR^9$.

In certain embodiments of formula (VIII) E is $NR^{10}$, and A and Q are $CR^9$.

In certain embodiments of formula (VIII), Q is $NR^{10}$, and A and E are $CR^9$.

In certain embodiments of formula (VIII), A is O, E is N, and Q is $CR^9$.

In certain embodiments of formula (VIII), A is N, E is O, and Q is $CR^9$.

In certain embodiments of formula (VIII), A is S, E is N, and Q is $CR^9$.

In certain embodiments of formula (VIII), A is N, E is S, and Q is $CR^9$.

In certain embodiments of formula (VIII), E is S, and A and Q are $CR^9$.

In certain embodiments of formula (VIII), E is O, and A and Q are $CR^9$.

In certain embodiments of formula (VIII), A is S, and E and Q are $CR^9$.

In certain embodiments of formula (VIII), A is O, and E and Q are $CR^9$.

In certain embodiments of formula (VIII), A is $NR^{10}$, Q is N, and E is $CR^9$.

In certain embodiments of formula (VIII), E is $NR^{10}$, Q is N, and A is $CR^9$.

In certain embodiments of formula (VIII), X is —$CH_2$— or —O—. Preferably X is O.

In certain embodiments of formula (VIII), $R^1$ is alkyl, alkenyl or cycloalkyl. Preferably, $R^1$ is ethyl, cyclopropyl, isopropenyl or isopropyl. More preferably $R^1$ is isopropyl.

In certain embodiments formula (VIII), one of $R^7$ and $R^8$ is hydrogen, and the other is: alkyl, cycloalkyl; cycloalkylalkyl; haloalkyl; hydroxyalky; alkoxyalkyl; alkylsulfonylalkyl; acetyl; alkylsulfonyl; aryl; aralkyl; arylsulfonyl; heteroaryl; heteroarylalkyl; heteroarylsulfonyl; heterocyclyl; or heterocyclylalkyl.

In certain embodiments of formula (VIII), one of $R^7$ and $R^8$ is hydrogen and the other is alkyl, hydroxyalkyl or haloalkyl.

In certain embodiments formula (VIII), one of $R^d$ and $R^e$ is hydrogen, and the other is: alkyl; cycloalkyl; cycloalkylalkyl; haloalkyl; hydroxyalky; alkoxyalkyl; alkylsulfonylalkyl; acetyl; alkylsulfonyl; aryl; aralkyl; arylsulfonyl; heteroaryl; heteroarylalkyl; heteroarylsulfonyl; heterocyclyl; or heterocyclylalkyl.

In certain embodiments of formula (VIII), one of $R^d$ and $R^e$ is hydrogen and the other is alkyl, hydroxyalkyl or haloalkyl.

In certain embodiments of formula (VIII), $R^7$, $R^8$, $R^d$ and $R^e$ are hydrogen.

In certain embodiments of formula (VIII), $R^4$ is halo, alkoxy, haloalkoxy or alkylsulfonyl.

In certain embodiments of formula (VIII), $R^4$ is halo, alkoxy, alkylsulfonyl or heteroaryl. Preferably $R^4$ is methoxy, iodo, methanesulfonyl or heteroaryl. More preferably $R^4$ is methoxy, bromo, chloro or iodo. In specific embodiments $R^4$ may be methoxy, while in other embodiments $R^4$ may be iodo.

In certain embodiments of formula (VIII), $R^4$ is heteroaryl. The heteroaryl may be, in certain embodiments, tetrazolyl, pyrazolyl, oxazolyl, imidazolyl, thiazolyl, thiophenyl, triazolyl, furanyl, isoxazolyl, oxadiazolyl, benzothiophenyl, pyridinyl, or pyrrolyl. More specifically, the heteroaryl may be tetrazol-5-yl, pyrazol-1-yl, 3-methylpyrazol-1-yl, oxazol-2-yl, oxazol-5-yl, imidazol-2-yl, thiazol-2-yl, thiazol4-yl, thiophen-3-yl, 5-chloro-thiophen-2-yl, 1-methyl-imidazol-2-yl, imidazol-1-yl, pyrazol-3-yl, 2-methyl-thiazol-4-yl, furan-2-yl, 3,5-dimethyl-pyrazol-1-yl, 4,5-dihydrooxazol-2-yl, isoxazol-5-yl, [1,2,4]-oxadiazol-3-yl, benzo[b]thiophen-3-yl, oxazol4-yl, furan-3-yl, 4-methyl-thiophen-2-yl, thiazol-5-yl, tetrazol-1-yl, [1,2,4]triazol-1-yl, 2-methyl-thiazol-5-yl, 1-methyl-pyrazol4-yl, 2-thiolyl-imidazol-1-yl, pyridin-2-yl, or 2,5-dimethyl-pyrrol-1-yl).

In embodiments of the invention where any of $R^7$, $R^8$, $R^d$ or $R^e$ are heterocyclyl or a group that includes a heterocyclyl moiety, such heterocyclyl or heterocyclyl moiety may be piperidinyl, piperazinyl, tetrahydrofuranyl, tetrahydrothiopyranyl, or 1,1-dioxotetrahydrothiopyranyl. More preferably, such heterocyclyl or heterocyclyl moiety may be piperidin4-yl, 1-methyl-piperidine4-yl, 1-methanesulfonyl-piperidin4-yl, tetrahydropyran4-yl, tetrahydrothiopyran4-yl, or 1,1-dioxotrahydrothiopyran4-yl.

Where any of $R^1$, $R^2$, $R^3$, $R^4$, $R^5$, $R^6$, $R^7$, $R^8$, $R^9$, $R^{10}$, $R^c$, $R^d$, $R^e$, $R^f$, $R^g$, or $R^h$ is alkyl or contains an alkyl moiety, such alkyl is preferably lower alkyl, i.e. $C_1$-$C_6$alkyl, and more preferably $C_1$-$C_4$alkyl.

The invention also provides methods for treating a disease mediated by a $P2X_3$ receptor antagonist, a $P2X_{2/3}$ receptor antagonist, or both, the method comprising administering to a subject in need thereof an effective amount of a compound of any of formulas (I) through (VIII). The disease may be genitorurinary disease or urinary tract disease. In other instances the disease may be a disease is associated with pain. The urinary tract disease may be: reduced bladder capacity; frequenct micturition; urge incontinence; stress incontinence; bladder hyperreactivity; benign prostatic hypertrophy; prostatitis; detrusor hyperreflexia; urinary frequency; nocturia; urinary urgency; overactive bladder; pelvic hypersensitivity; urethritis; prostatitits,; pelvic pain syndrome; prostatodynia; cystitis; or idiophatic bladder hypersensitivity. The disease associated with pain may be: inflammatory pain; surgical pain; visceral pain; dental pain; premenstrual pain; central pain; pain due to burns; migraine or cluster headaches; nerve injury; neuritis; neuralgias; poisoning; ischemic injury; interstitial cystitis; cancer pain; viral, parasitic or bacterial infection; post-traumatic injury; or pain associated with irritable bowel syndrome.

Representative compounds in accordance with the methods of the invention are shown in Table 1.

TABLE 1

| # | Structure | Name |
|---|-----------|------|
| 1 | 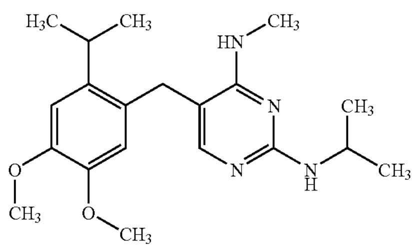 | N*2*-Isopropyl-5-(2-isopropyl-4,5-dimethoxy-benzyl)-N*4*-methyl-pyrimidine-2,4-diamine |
| 2 | 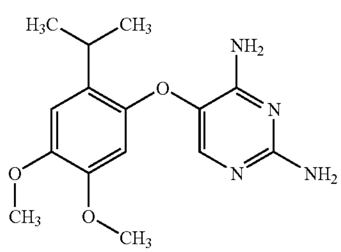 | 5-(2-Isopropyl-4,5-dimethoxy-phenoxy)-pyrimidine-2,4-diamine |
| 3 | 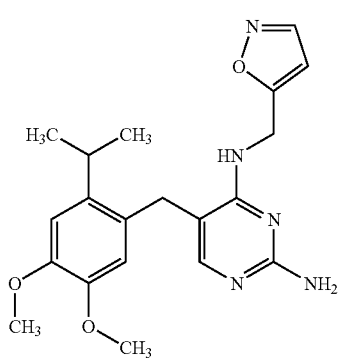 | 5-(2-Isopropyl-4,5-dimethoxy-benzyl)-N*4*-isoxazol-5-ylmethyl-pyrimidine-2,4-diamine |
| 4 | 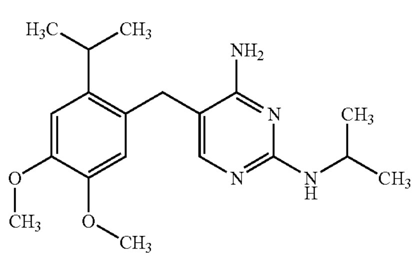 | N*2*-Isopropyl-5-(2-isopropyl-4,5-dimethoxy-benzyl)-pyrimidine-2,4-diamine |
| 5 | 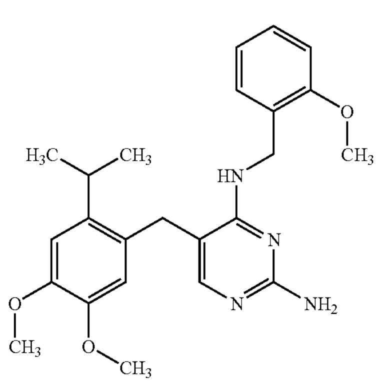 | 5-(2-Isopropyl-4,5-dimethoxy-benzyl)-N*4*-(2-methoxy-benzyl)-pyrimidine-2,4-diamine |

TABLE 1-continued

| # | Structure | Name |
|---|---|---|
| 6 | 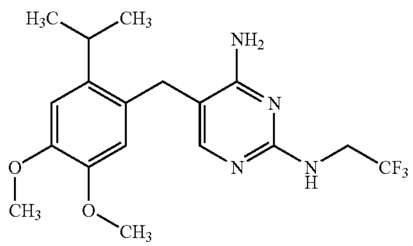 | 5-(2-Isopropyl-4,5-dimethoxy-benzyl)-N*2*-(2,2,2-trifluoro-ethyl)-pyrimidine-2,4-diamine |
| 7 | 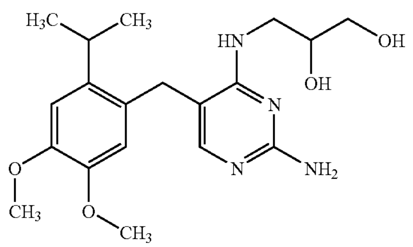 | 3-[2-Amino-5-(2-isopropyl-4,5-dimethoxy-benzyl)-pyrimidin-4-ylamino]-propane-1,2-diol |
| 8 | 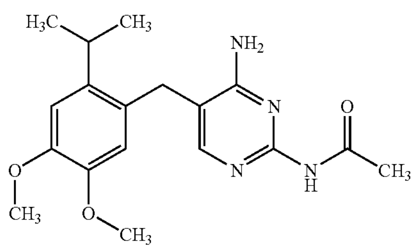 | N-[4-Amino-5-(2-isopropyl-4,5-dimethoxy-benzyl)-pyrimidin-2-yl]-acetamide |
| 9 | 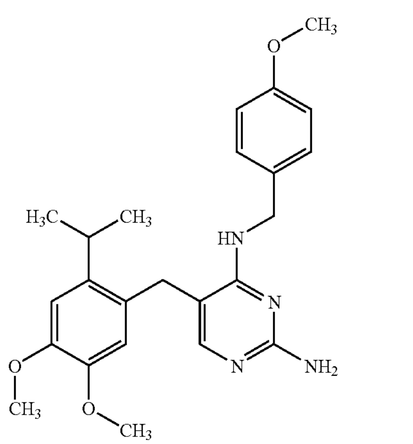 | 5-(2-Isopropyl-4,5-dimethoxy-benzyl)-N*4*-(4-methoxy-benzyl)-pyrimidine-2,4-diamine |
| 10 | 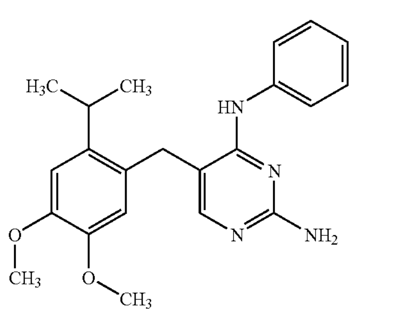 | 5-(2-Isopropyl-4,5-dimethoxy-benzyl)-N*4*-phenyl-pyrimidine-2,4-diamine |

TABLE 1-continued

| # | Structure | Name |
|---|-----------|------|
| 11 | 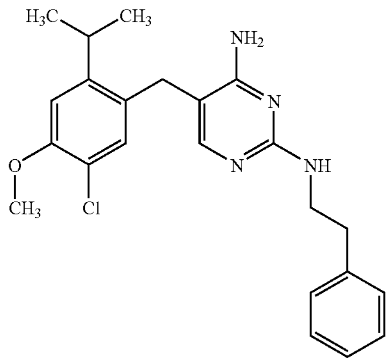 | 5-(5-Chloro-2-isopropyl-4-methoxy-benzyl)-N*2*-phenethyl-pyrimidine-2,4-diamine |
| 12 | 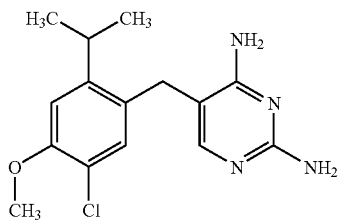 | 5-(5-Chloro-2-isopropyl-4-methoxy-benzyl)-pyrimidine-2,4-diamine |
| 13 | 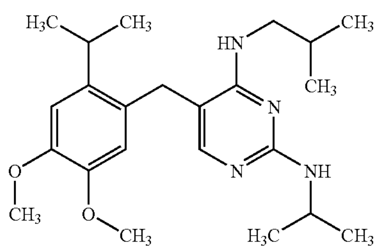 | N*4*-Isobutyl-N*2*-isopropyl-5-(2-isopropyl-4,5-dimethoxy-benzyl)-pyrimidine-2,4-diamine |
| 14 | 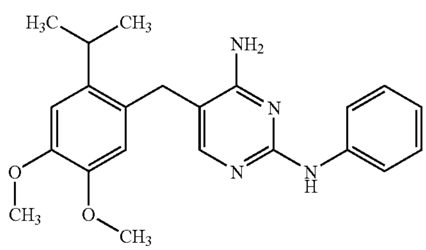 | 5-(2-Isopropyl-4,5-dimethoxy-benzyl)-N*2*-phenyl-pyrimidine-2,4-diamine |
| 15 | 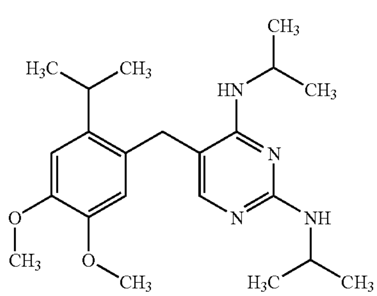 | N*2*,N*4*-Diisopropyl-5-(2-isopropyl-4,5-dimethoxy-benzyl)-pyrimidine-2,4-diamine |

TABLE 1-continued

| # | Structure | Name |
|---|---|---|
| 16 | 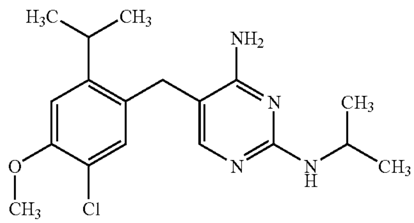 | 5-(5-Chloro-2-isopropyl-4-methoxy-benzyl)-N*2*-isopropyl-pyrimidine-2,4-diamine |
| 17 | 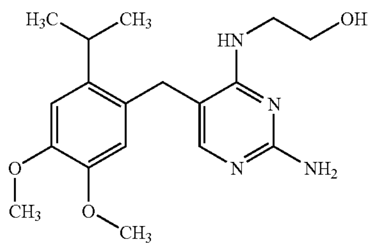 | 2-[2-Amino-5-(2-isopropyl-4,5-dimethoxy-benzyl)-pyrimidin-4-ylamino]-ethanol |
| 18 | 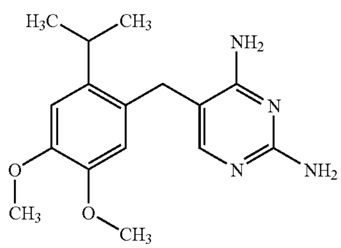 | 5-(2-Isopropyl-4,5-dimethoxy-benzyl)-pyrimidine-2,4-diamine |
| 19 | 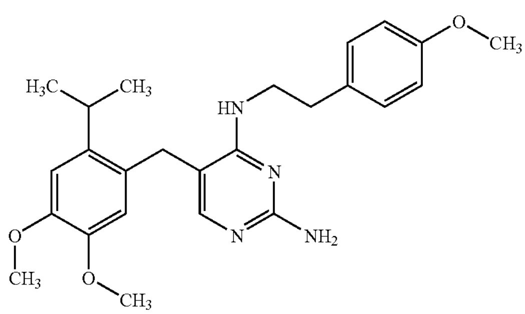 | 5-(2-Isopropyl-4,5-dimethoxy-benzyl)-N*4*-[2-(4-methoxy-phenyl)-ethyl]-pyrimidine-2,4-diamine |
| 20 | 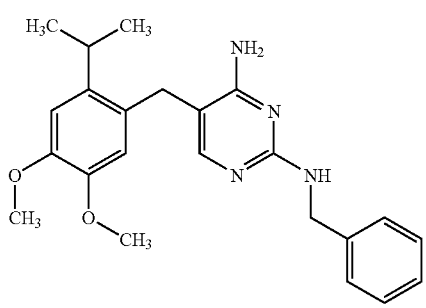 | N*2*-Benzyl-5-(2-isopropyl-4,5-dimethoxy-benzyl)-pyrimidine-2,4-diamine |

TABLE 1-continued

| # | Structure | Name |
|---|---|---|
| 21 | 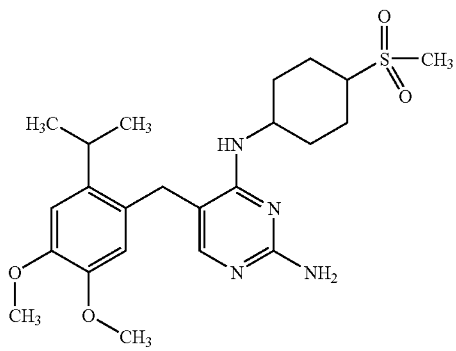 | 5-(2-Isopropyl-4,5-dimethoxy-benzyl)-N*4*-(4-methanesulfonyl-cyclohexyl)-pyrimidine-2,4-diamine |
| 22 | 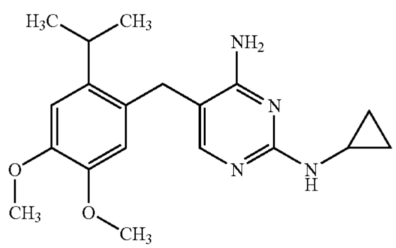 | N*2*-Cyclopropyl-5-(2-isopropyl-4,5-dimethoxy-benzyl)-pyrimidine-2,4-diamine |
| 23 | 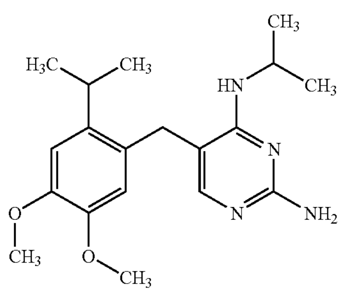 | N*4*-Isopropyl-5-(2-isopropyl-4,5-dimethoxy-benzyl)-pyrimidine-2,4-diamine |
| 24 | 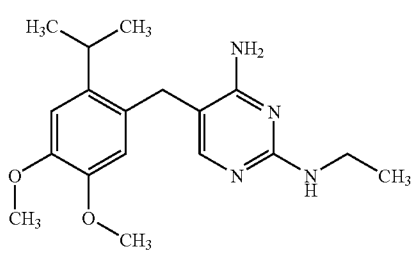 | N*2*-Ethy[5-(2-isopropyl-4,5-dimethoxy-benzyl)-pyrimidine-2,4-diamine |
| 25 | 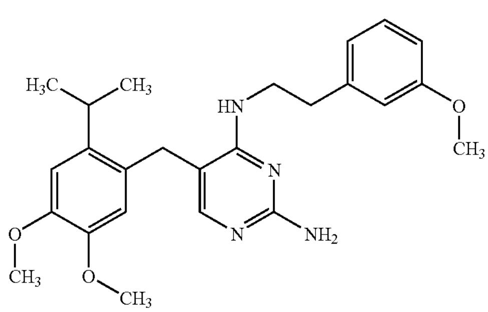 | 5-(2-Isopropyl-4,5-dimethoxy-benzyl)-N*4*-[2-(3-methoxy-phenyl)-ethyl]-pyrimidine-2,4-diamine |

TABLE 1-continued

| # | Structure | Name |
|---|---|---|
| 26 | 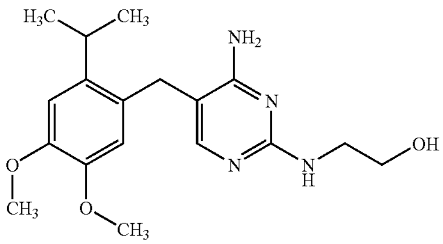 | 2-[4-Amino-5-(2-isopropyl-4,5-dimethoxy-benzyl)-pyrimidin-2-ylamino]-ethanol |
| 27 | 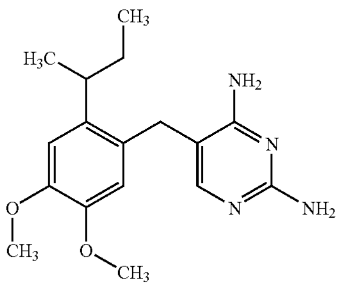 | 5-(2-sec-Butyl-4,5-dimethoxy-benzyl)-pyrimidine-2,4-diamine |
| 28 | 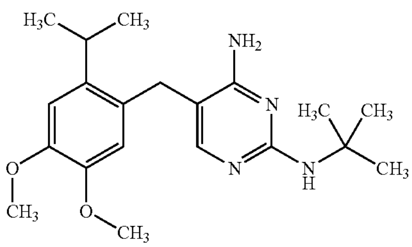 | N*2*-tert-Butyl-5-(2-isopropyl-4,5-dimethoxy-benzyl)-pyrimidine-2,4-diamine |
| 29 | 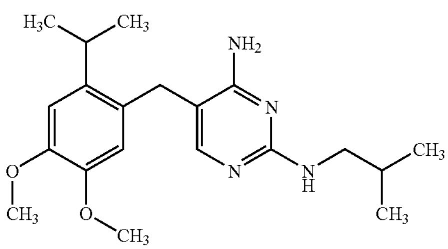 | N*2*-Isobutyl-5-(2-isopropyl-4,5-dimethoxy-benzyl)-pyrimidine-2,4-diamine |
| 30 | 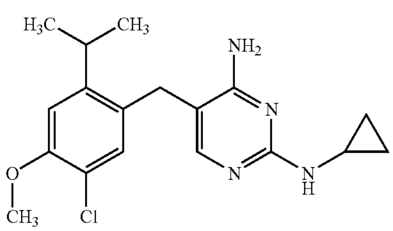 | 5-(5-Chloro-2-isopropyl-4-methoxy-benzyl)-N*2*-cyclopropyl-pyrimidine-2,4-diamine |
| 31 | 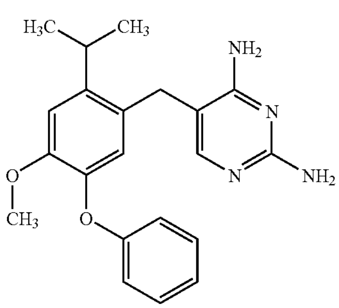 | 5-(2-Isopropyl-4-methoxy-5-phenoxy-benzyl)-pyrimidine-2,4-diamine |

TABLE 1-continued

| # | Structure | Name |
|---|---|---|
| 32 | 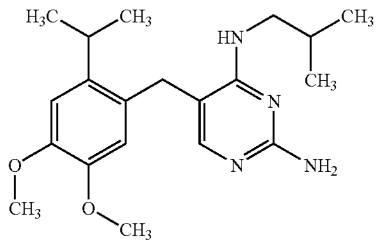 | N*4*-Isobutyl-5-(2-isopropyl-4,5-dimethoxy-benzyl)-pyrimidine-2,4-diamine |
| 33 | 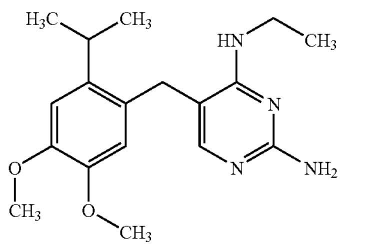 | N*4*-Ethyl-5-(2-isopropyl-4,5-dimethoxy-benzyl)-pyrimidine-2,4-diamine |
| 34 | 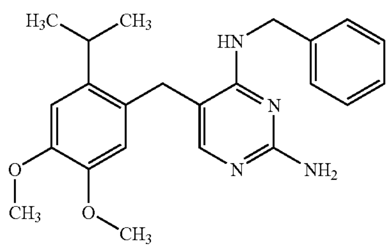 | N*4*-Benzyl-5-(2-isopropyl-4,5-dimethoxy-benzyl)-pyrimidine-2,4-diamine |
| 35 | 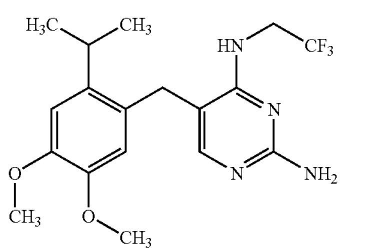 | 5-(2-Isopropyl-4,5-dimethoxy-benzyl)-N*4*-(2,2,2-trifluoro-ethyl)-pyrimidine-2,4-diamine |
| 36 | 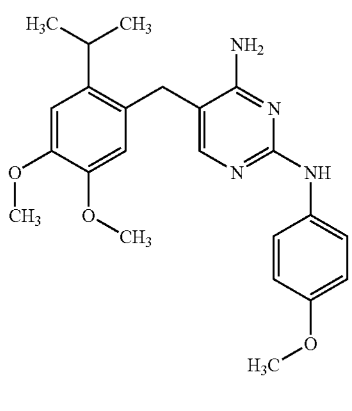 | 5-(2-Isopropyl-4,5-dimethoxy-benzyl)-N*2*-(4-methoxy-phenyl)-pyrimidine-2,4-diamine |

TABLE 1-continued

| # | Structure | Name |
|---|---|---|
| 37 | 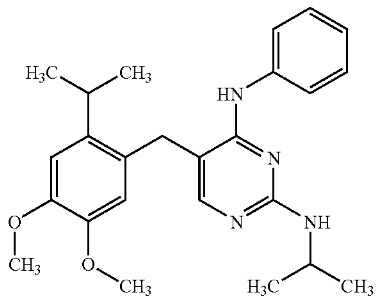 | N*2*-Isopropyl-5-(2-isopropyl-4,5-dimethoxy-benzyl)-N*4*-phenyl-pyrimidine-2,4-diamine |
| 38 | 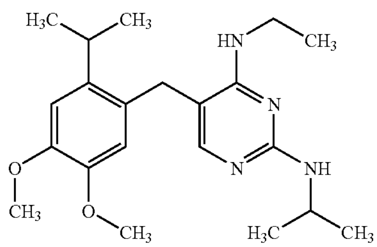 | N*4*-Ethyl-N*2*-isopropyl-5-(2-isopropyl-4,5-dimethoxy-benzyl)-pyrimidine-2,4-diamine |
| 39 | 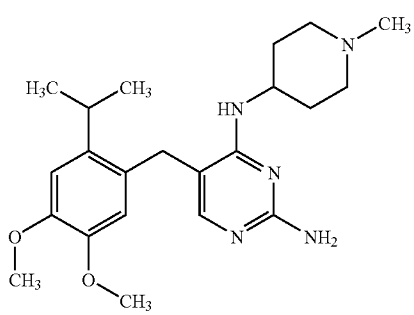 | 5-(2-Isopropyl-4,5-dimethoxy-benzyl)-N*4*-(1-methyl-piperidin-4-yl)-pyrimidine-2,4-diamine |
| 40 | 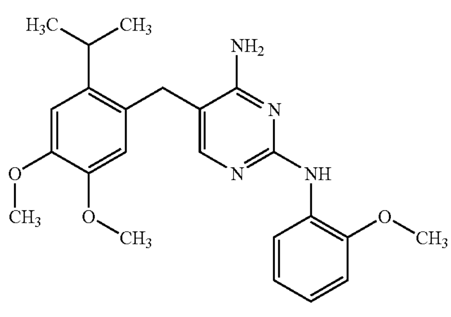 | 5-(2-Isopropyl-4,5-dimethoxy-benzyl)-N*2*-(2-methoxy-phenyl)-pyrimidine-2,4-diamine |
| 41 | 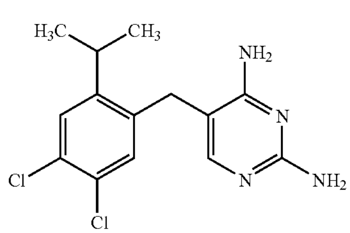 | 5-(4,5-Dichloro-2-isopropyl-benzyl)-pyrimidine-2,4-diamine |

TABLE 1-continued

| # | Structure | Name |
|---|---|---|
| 42 | 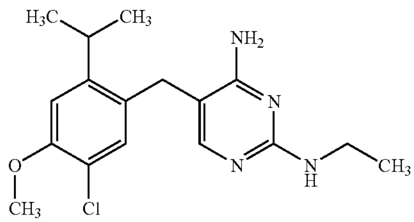 | 5-(5-Chloro-2-isopropyl-4-methoxy-benzyl)-N*2*-ethyl-pyrimidine-2,4-diamine |
| 43 | 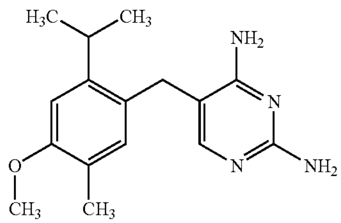 | 5-(2-Isopropyl-4-methoxy-5-methyl-benzyl)-pyrimidine-2,4-diamine |
| 44 | 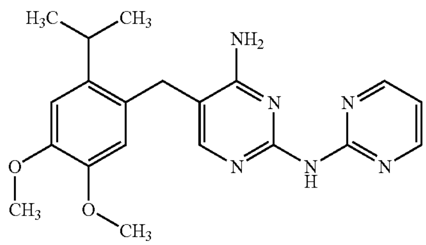 | 5-(2-Isopropyl-4,5-dimethoxy-benzyl)-N*2*-pyrimidine-2-yl-pyrimidine-2,4-diamine |
| 45 | 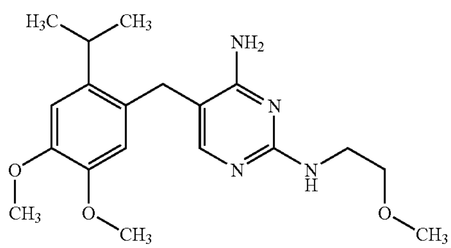 | 5-(2-Isopropyl-4,5-dimethoxy-benzyl)-N*2*-(2-methoxy-ethyl)-pyrimidine-2,4-diamine |
| 46 | 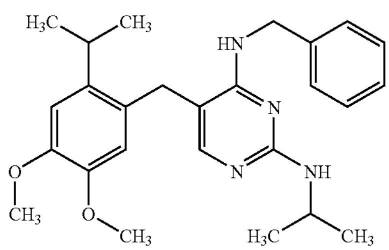 | N*4*-Benzyl-N*2*-isopropyl-5-(2-isopropyl-4,5-dimethoxy-benzyl)-pyrimidine-2,4-diamine |
| 47 | 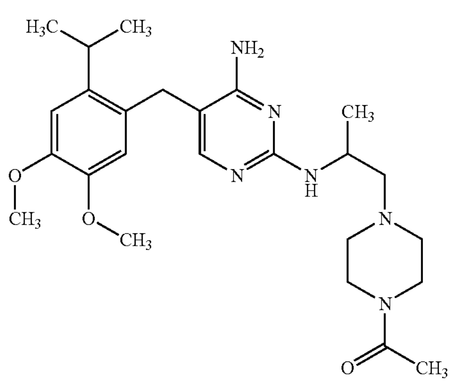 | 1-(4-{2-[4-Amino-5-(2-isopropyl-4,5-dimethoxy-benzyl)-pyrimidin-2-ylamino]-propyl}-piperazin-1-yl)-ethanone |

TABLE 1-continued

| # | Structure | Name |
|---|---|---|
| 48 | 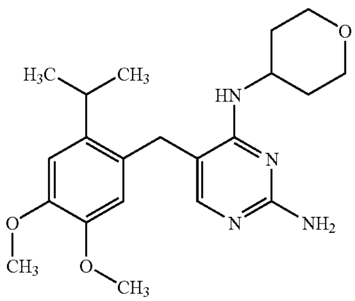 | 5-(2-Isopropyl-4,5-dimethoxy-benzyl)-N*4*-(tetrahydro-pyran-4-yl)-pyrimidine-2,4-diamine |
| 49 | 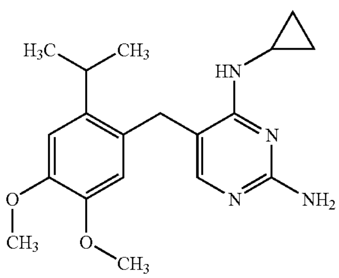 | N*4*-Cyclopropyl-5-(2-isopropyl-4,5-dimethoxy-benzyl)-pyrimidine-2,4-diamine |
| 50 | 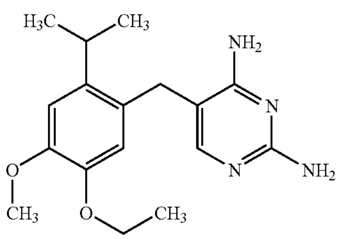 | 5-(5-Ethoxy-2-isopropyl-4-methoxy-benzyl)-pyrimidine-2,4-diamine |
| 51 | 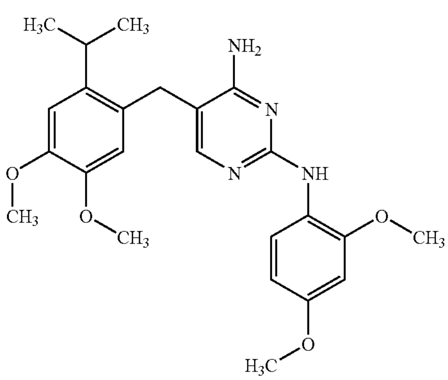 | N*2*-(2,4-Dimethoxy-phenyl)-5-(2-isopropyl-4,5-dimethoxy-benzyl)-pyrimidine-2,4-diamine |
| 52 | 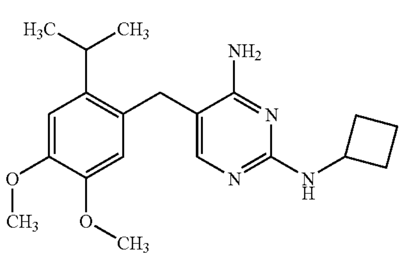 | N*2*-Cyclobutyl-5-(2-isopropyl-4,5-dimethoxy-benzyl)-pyrimidine-2,4-diamine |

TABLE 1-continued

| # | Structure | Name |
|---|---|---|
| 53 | 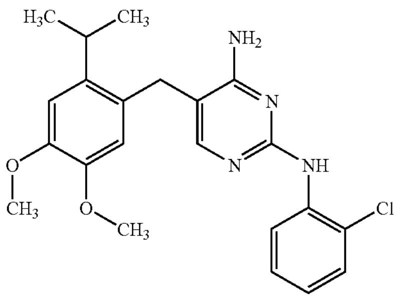 | N*2*-(2-Chloro-phenyl)-5-(2-isopropyl-4,5-dimethoxy-benzyl)-pyrimidine-2,4-diamine |
| 54 | 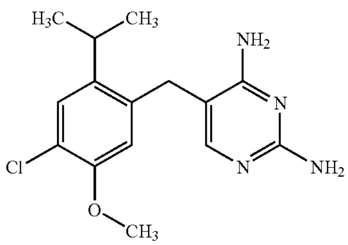 | 5-(4-Chloro-2-isopropyl-5-methoxy-benzyl)-pyrimidine-2,4-diamine |
| 55 | 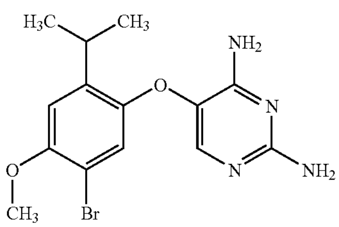 | 5-(5-Bromo-2-isopropyl-4-methoxy-phenoxy)-pyrimidine-2,4-diamine |
| 56 | 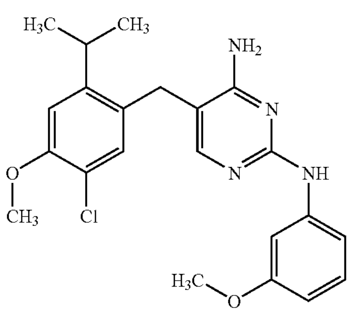 | 5-(5-Chloro-2-isopropyl-4-methoxy-benzyl)-N*2*-(3-methoxy-phenyl)-pyrimidine-2,4-diamine |
| 57 | 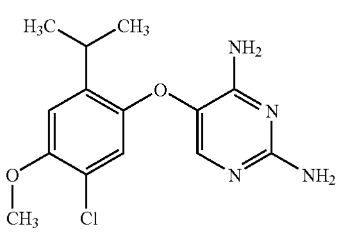 | 5-(5-Chloro-2-isopropyl-4-methoxy-phenoxy)-pyrimidine-2,4-diamine |

TABLE 1-continued
| # | Structure | Name |
|---|---|---|
| 58 | 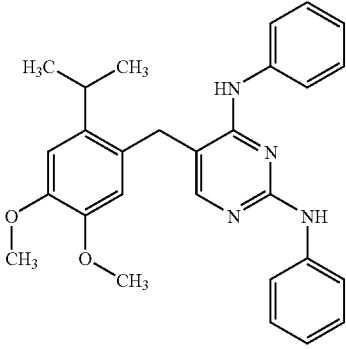 | 5-(2-Isopropyl-4,5-dimethoxy-benzyl)-N*2*,N*4*-diphenyl-pyrimidine-2,4-diamine |
| 59 | 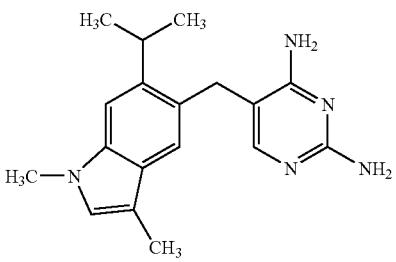 | 5-(6-Isopropyl-1,3-dimethyl-1H-indol-5-yloxy)-pyrimidine-2,4-diamine |
| 60 | 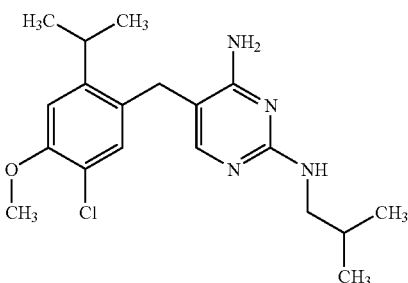 | 5-(5-Chloro-2-isopropyl-4-methoxy-benzyl)-N*2*-isobutyl-pyrimidine-2,4-diamine |
| 61 | 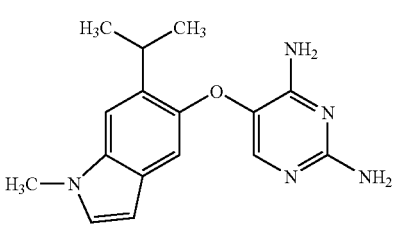 | 5-(6-Isopropyl-1-methyl-1H-indol-5-yloxy)-pyrimidine-2,4-diamine |
| 62 | 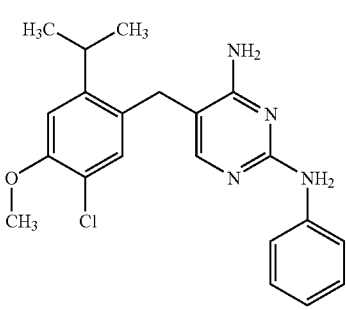 | 5-(5-Chloro-2-isopropyl-4-methoxy-benzyl)-N*2*-phenyl-pyrimidine-2,4-diamine |

TABLE 1-continued

| # | Structure | Name |
|---|---|---|
| 63 | 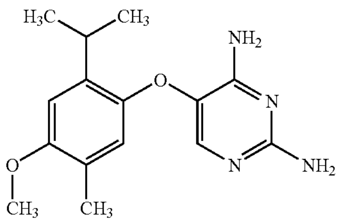 | 5-(2-Isopropyl-4-methoxy-5-methyl-phenoxy)-pyrimidine-2,4-diamine |
| 64 | 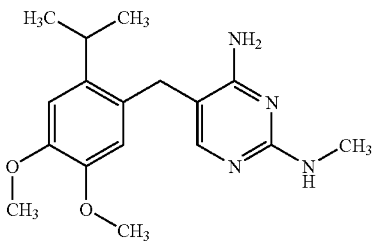 | 5-(2-Isopropyl-4,5-dimethoxy-benzyl)-N*2*-methyl-pyrimidine-2,4-diamine |
| 65 | 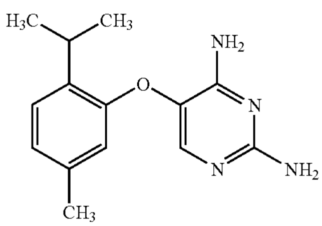 | 5-(2-Isopropyl-5-methyl-phenoxy)-pyrimidine-2,4-diamine |
| 66 | 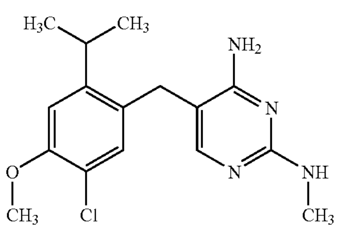 | 5-(5-Chloro-2-isopropyl-4-methoxy-benzyl)-N*2*-methyl-pyrimidine-2,4-diamine |
| 67 | 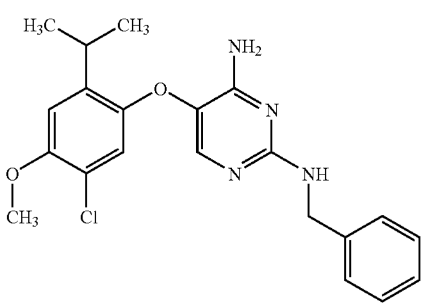 | N*2*-Benzyl-5-(5-chloro-2-isopropyl-4-methoxy-phenoxy)-pyrimidine-2,4-diamine |
| 68 | 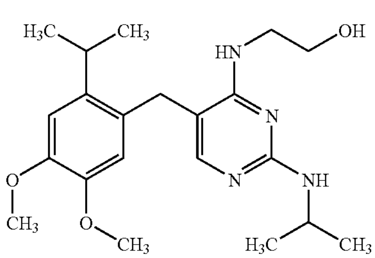 | 2-[2-Isopropylamino-5-(2-isopropyl-4,5-dimethoxy-benzyl)-pyrimidin-4-ylamino]-ethanol |

TABLE 1-continued

| # | Structure | Name |
|---|---|---|
| 69 | 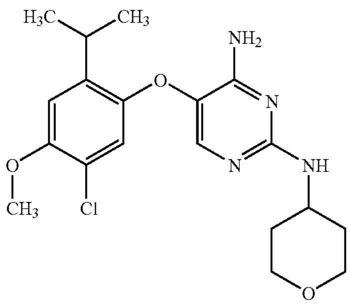 | 5-(5-Chloro-2-isopropyl-4-methoxy-phenoxy)-N*2*-(tetrahydro-pyran-4-yl)-pyrimidine-2,4-diamine |
| 70 | 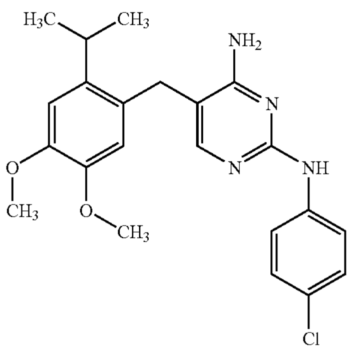 | N*2*-(4-Chloro-phenyl)-5-(2-isopropyl-4,5-dimethoxy-benzyl)-pyrimidine-2,4-diamine |
| 71 | 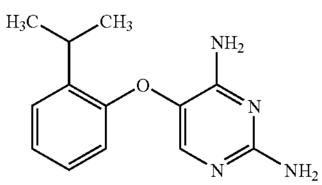 | 5-(2-Isopropyl-phenoxy)-pyrimidine-2,4-diamine |
| 72 | 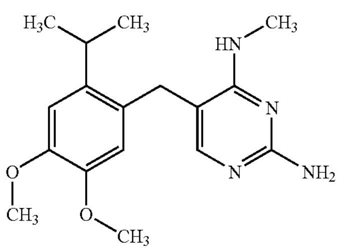 | 5-(2-Isopropyl-4,5-dimethoxy-benzyl)-N*4*-methyl-pyrimidine-2,4-diamine |
| 73 | 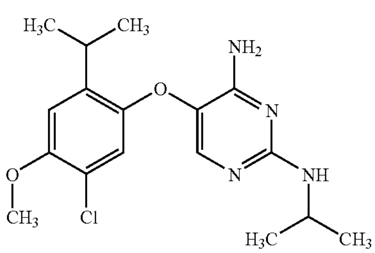 | 5-(5-Chloro-2-isopropyl-4-methoxy-phenoxy)-N*2*-isopropyl-pyrimidine-2,4-diamine |
| 74 | 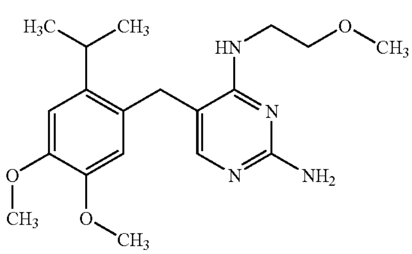 | 5-(2-Isopropyl-4,5-dimethoxy-benzyl)-N*4*-(2-methoxy-ethyl)-pyrimidine-2,4-diamine |

TABLE 1-continued

| # | Structure | Name |
|---|---|---|
| 75 | 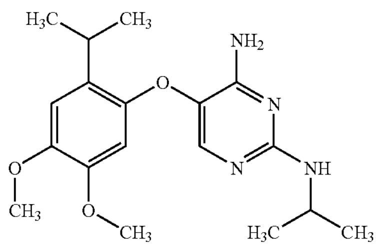 | N*2*-Isopropyl-5-(2-isopropyl-4,5-dimethoxy-phenoxy)-pyrimidine-2,4-diamine |
| 76 | 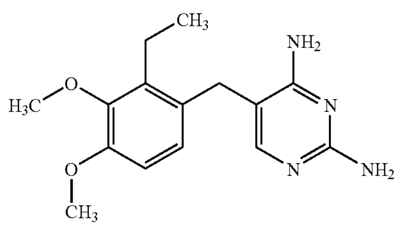 | 5-(2-Ethyl-4,5-dimethoxy-benzyl)-pyrimidine-2,4-diamine |
| 77 | 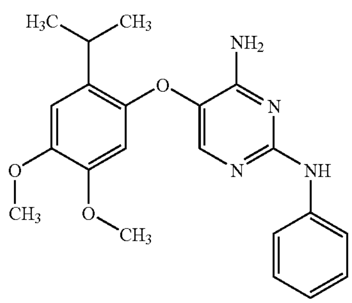 | 5-(2-Isopropyl-4,5-dimethoxy-phenoxy)-N*2*-phenyl-pyrimidine-2,4-diamine |
| 78 | 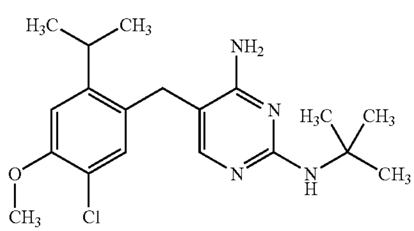 | N*2*-tert-Butyl-5-(5-chloro-2-isopropyl-4-methoxy-benzyl)-primidine-2,4-diamine |
| 79 | 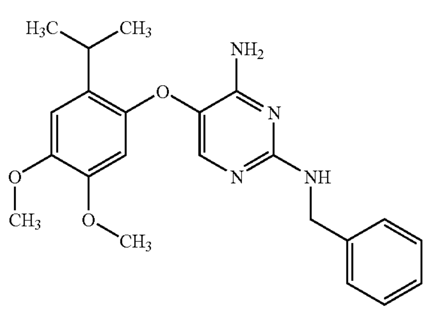 | N*2*-Benzyl-5-(2-isopropyl-4,5-dimethoxy-phenoxy)-pyrimidine-2,4-diamine |

TABLE 1-continued

| # | Structure | Name |
|---|---|---|
| 80 | 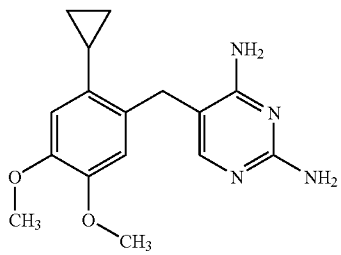 | 5-(2-Cyclopropyl-4,5-dimethoxy-benzyl)-pyrimidine-2,4-diamine |
| 81 | 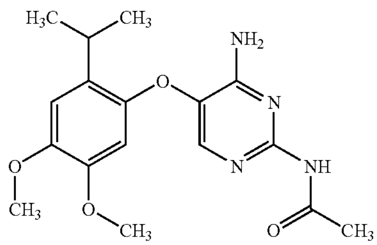 | N-[4-Amino-5-(2-isopropyl-4,5-dimethoxy-phenoxy)-pyrimidin-2-yl]-acetamide |
| 82 | 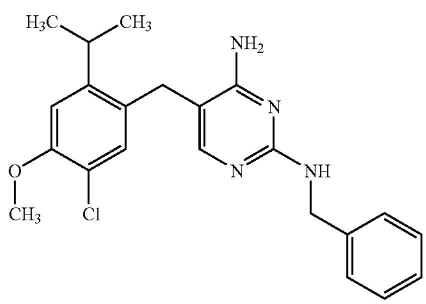 | N*2*-Benzyl-5-(5-chloro-2-isopropyl-4-methoxy-benzyl)-pyrimidine-2,4-diamine |
| 83 | 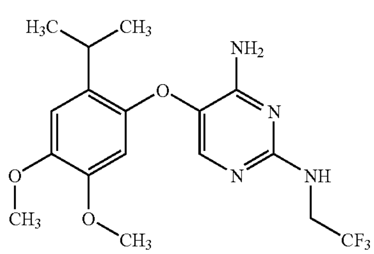 | 5-(2-Isopropyl-4,5-dimethoxy-phenoxy)-N*2*-(2,2,2-trifluoro-ethyl)-pyrimidine-2,4-diamine |
| 84 | 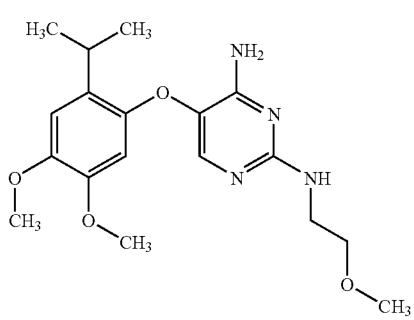 | 5-(2-Isopropyl-4,5-dimethoxy-phenoxy)-N*2*-(2-methoxy-ethyl)-pyrimidine-2,4-diamine |

TABLE 1-continued

| # | Structure | Name |
|---|---|---|
| 85 | 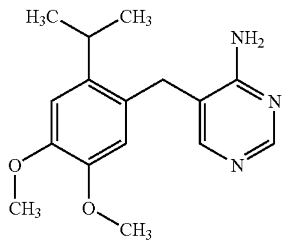 | 5-(2-Isopropyl-4,5-dimethoxy-benzyl)-pyrimidin-4-ylamine |
| 86 | 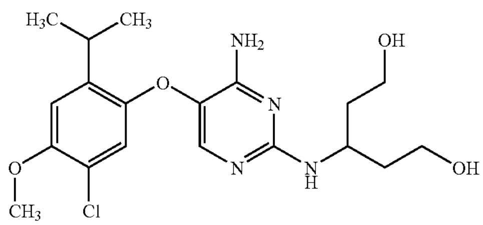 | 3-[4-Amino-5-(5-chloro-2-isopropyl-4-methoxy-phenoxy)-pyrimidin-2-ylamino]-pentane-1,5-diol |
| 87 | 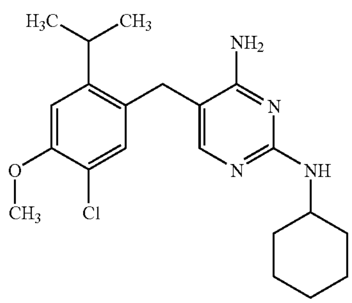 | 5-(5-Chloro-2-isopropyl-4-methoxy-benzyl)-N*2*-cyclohexyl-pyrimidine-2,4-diamine |
| 88 | 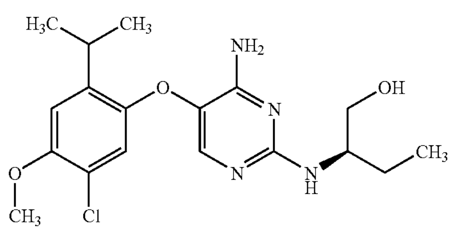 | 2-[4-Amino-5-(5-chloro-2-isopropyl-4-methoxy-phenoxy)-pyrimidin-2-ylamino]-butan-1-ol |
| 89 | 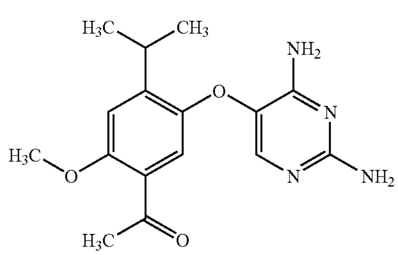 | 1-[5-(2,4-Diamino-pyrimidin-5-yloxy)-4-isopropyl-2-methoxy-phenyl]-ethanone |
| 90 | 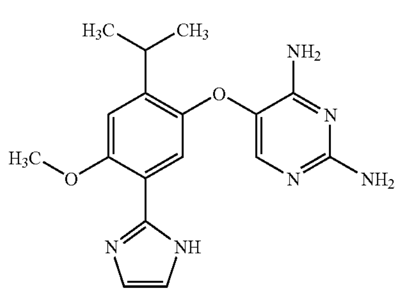 | 5-[5-(1H-Imidazol-2-yl)-2-isopropyl-4-methoxy-phenoxy]-pyrimidine-2,4-diamine |

TABLE 1-continued

| # | Structure | Name |
|---|---|---|
| 91 | 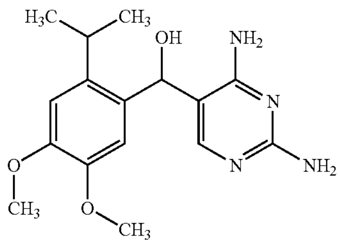 | (2,4-Diamino-pyrimidin-5-yl)-(2-isopropyl-4,5-dimethoxy-phenyl)-methanol |
| 92 | 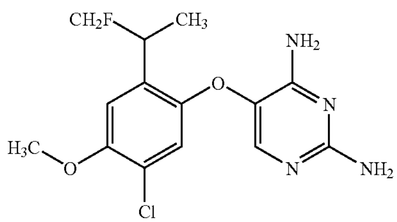 | 5-[5-Chloro-2-(2-fluoro-1-methyl-ethyl)-4-methoxy-phenoxy]-pyrimidine-2,4-diamine |
| 93 | 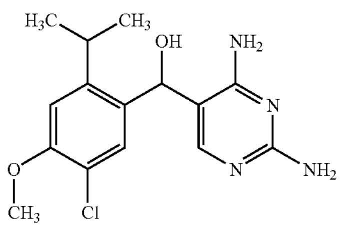 | (5-Chloro-2-isopropyl-4-methoxy-phenyl)-(2,4-diamino-pyrimidin-5-yl)-methanol |
| 94 | | 2-[4-Amino-5-(5-chloro-2-ethyl-4-methoxy-phenoxy)-pyrimidin-2-ylamino]-butan-1-ol |
| 94 | | 5-(5-Chloro-2-isopropyl-4-methoxy-phenoxy)-N*2*-*3-ethanesulfonyl-1-methyl-propyl)-pyrimidine-2,4-diamine |
| 95 | 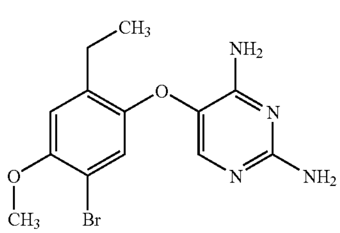 | 5-(5-Bromo-2-ethyl-4-methoxy-phenoxy)-pyrimidine-2,4-diamine |

TABLE 1-continued

| # | Structure | Name |
|---|---|---|
| 96 | 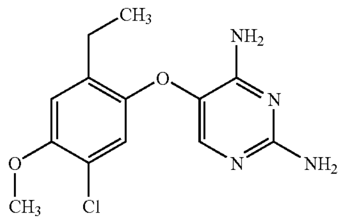 | 5-(5-Chloro-2-ethyl-4-methoxy-phenoxy)-pyrimidrne-2,4-diamine |
| 97 | 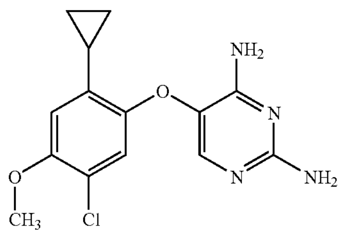 | 5-(5-Chloro-2-cyclopropyl-4-methoxy-phenoxy)-pyrimidine-2,4-diamine |
| 98 | 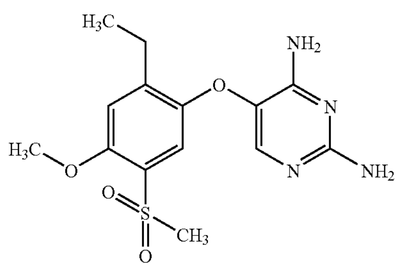 | 5-(2-Ethyl-5-methanesulfonyl-4-methoxy-phenoxy)-pyrimidine-2,4-diamine |
| 99 | 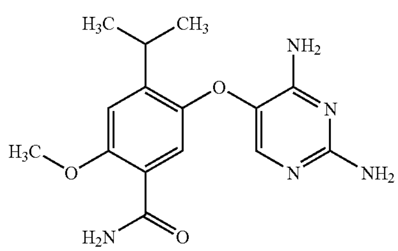 | 5-(2,4-Diamino-pyrimidin-5-yloxy)-4-isopropyl-2-methoxy-benzamide |
| 100 | 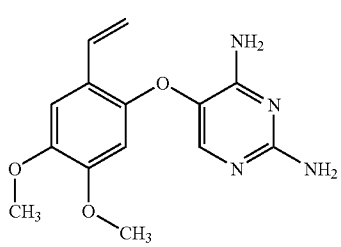 | 5-(4,5-Dimethoxy-2-vinyl-phenoxy)-pyrimidine-2,4-diamine |
| 101 | 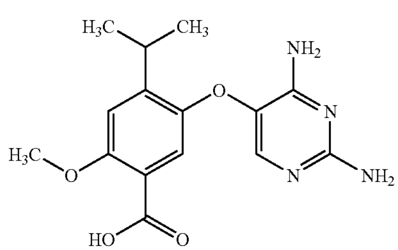 | 5-(2,4-Diamino-pyrimidin-5-yloxy)-4-isopropyl-2-methoxy-benzoic acid |

TABLE 1-continued

| # | Structure | Name |
|---|---|---|
| 102 | 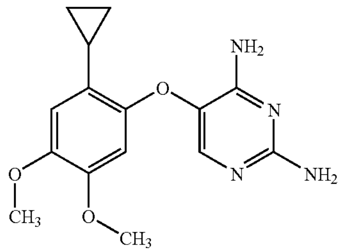 | 5-(2-Cyclopropyl-4,5-dimethoxy-phenoxy)-pyrimidine-2,4-diamine |
| 103 | 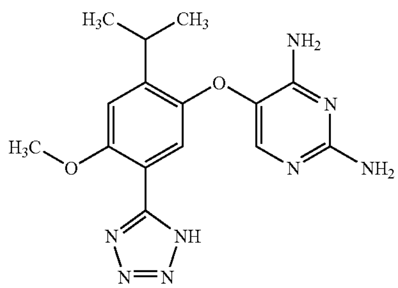 | 5-[2-Isopropyl-4-methoxy-5-(1H-tetrazol-5-yl)-phenoxy]-pyrimidine-2,4-diamine |
| 104 | 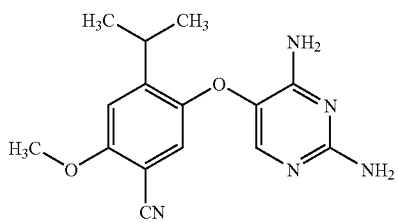 | 5-(2,4-Diamino-pyrimidin-5-yloxy)-4-isopropyl-2-methoxy-benzonitrile |
| 105 | 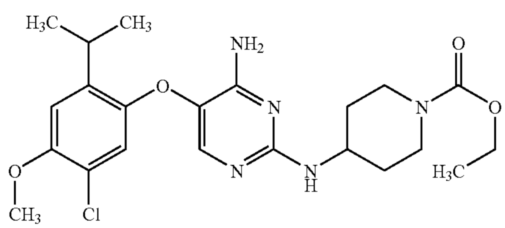 | 4-[4-Amino-5-(5-chloro-2-isopropyl-4-methoxy-phenoxy)-pyrimidin-2-ylamino]-piperidine-1-carboxylic acid ethyl ester |
| 106 | 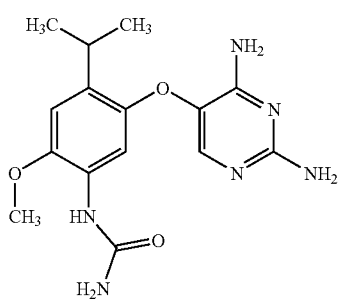 | [5-(2,4-Diamino-pyrimidin-5-yloxy)-4-isopropyl-2-methoxy-phenyl]-urea |
| 107 | 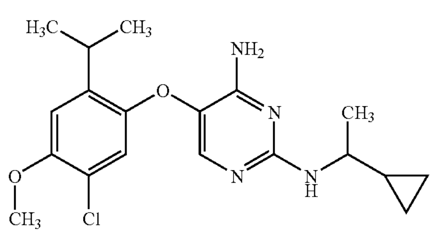 | 5-(5-Chloro-2-isopropyl-4-methoxy-phenoxy)-N*2*-(1-cyclopropyl-ethyl)-pyrimidine-2,4-diamine |

TABLE 1-continued

| # | Structure | Name |
|---|---|---|
| 108 | 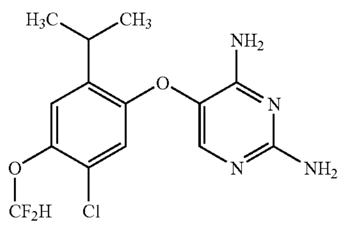 | 5-(5-Chloro-4-difluoromethoxy-2-isopropyl-phenoxy)-pyrimidine-2,4-diamine |
| 109 | 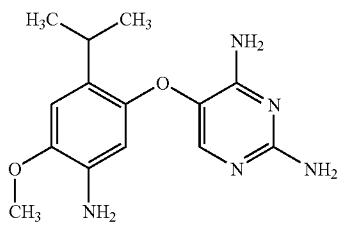 | 5-(5-Amino-2-isopropyl-4-methoxy-phenoxy)-pyrimidine-2,4-diamine |
| 110 | 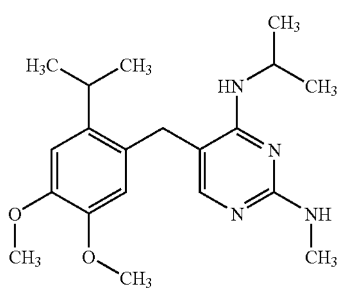 | N*4*-Isopropyl-5-(2-isopropyl-4,5-dimethoxy-benzyl)-N*2*-methyl-pyrimidine-2,4-diamine |
| 111 | 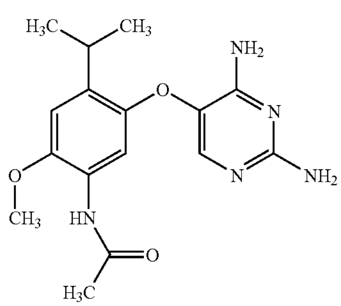 | N-[5-(2,4-Diamino-pyrimidin-5-yloxy)-4-isopropyl-2-methoxy-phenyl]-acetamide |
| 112 | 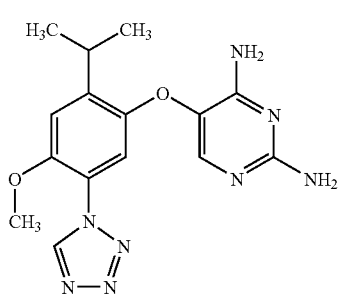 | 5-(2-Isopropyl-4-methoxy-5-tetrazol-1-yl-phenoxy)-pyrimidine-2,4-diamine |
| 113 | 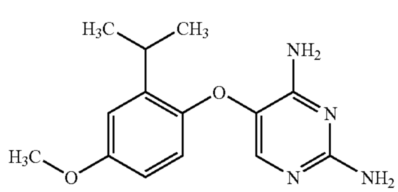 | 5-(2-Isopropyl-4-methoxy-phenoxy)-pyrimidine-2,4-diamine |

TABLE 1-continued

| # | Structure | Name |
|---|---|---|
| 114 | 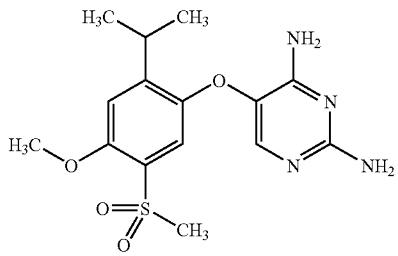 | 5-(2-Isopropyl-5-methanesulfonyl-4-methoxy-phenoxy)-pyrimidine-2,4-diamine |
|  | | 5-(2-Isopropyl-4-methoxy-5-methyl-phenoxy)-N*4*-phenyl-pyrimidine-2,4-diamine |
| 115 | 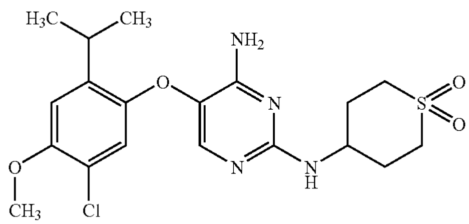 | 5-(5-Chloro-2-isopropyl-4-methoxy-phenoxy)-N*2*-(1,1-dioxo-hexahydro-1lambda*6*-thiopyran-4-yl)-pyrimidine-2,4-diamine |
| 116 | 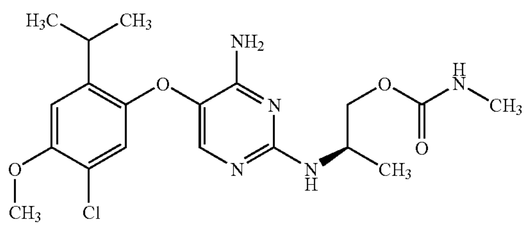 | Methyl-carbamic acid 2-[4-amino-5-(5-chloro-2-isopropyl-4-methoxy-phenoxy)-pyrimidin-2-ylamino]-propyl ester |
| 117 | 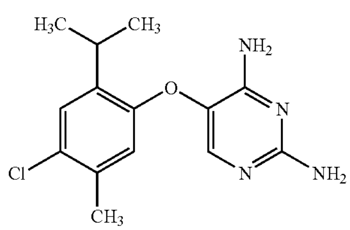 | 5-(4-Chloro-2-isopropyl-5-methyl-phenoxy)-pyrimidine-2,4-diamine |
| 118 | 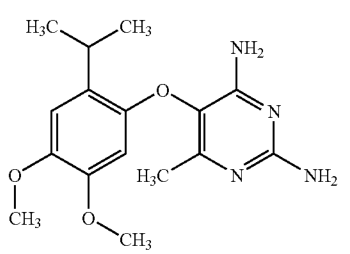 | 5-(2-Isopropyl-4,5-dimethoxy-phenoxy)-6-methyl-pyrimidine-2,4-diamine |

TABLE 1-continued

| # | Structure | Name |
|---|-----------|------|
| | | 1-(4-{2-[4-Amino-5-(5-chloro-2-isopropyl-4-methoxy-phenoxy)-pyrimidin-2-ylamino]-propyl}-piperazin-1-yl)-ethanone |
| 119 | 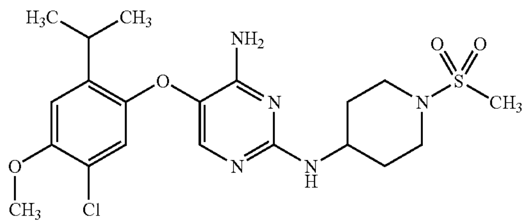 | 5-(5-Chloro-2-isopropyl-4-methoxy-phenoxy)-N*2*-(1-methanesulfonyl-piperidin-4-yl)-pyrimidine-2,4-diamine |
| 120 | 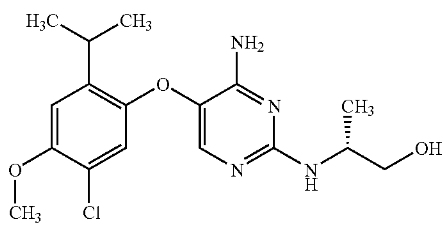 | 2-[4-Amino-5-(5-chloro-2-isopropyl-4-methoxy-phenoxy)-pyrimidin-2-ylamino]-(R)-propan-1-ol |
| 121 | 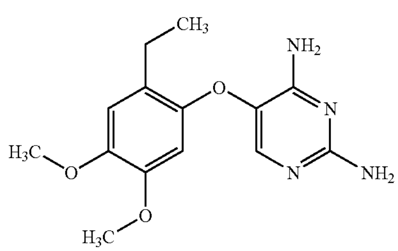 | 5-(2-Ethyl-4,5-dimethoxy-phenoxy)-pyrimidine-2,4-diamin |
| 122 | 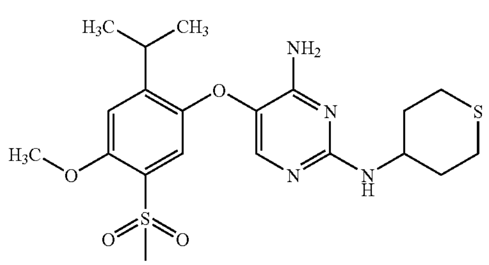 | 5-(2-Isopropyl-5-methanesulfonyl-4-methoxy-phenoxy)-$N^2$-(tetrahydro-thiopyran-4-yl)-pyrimidine-2,4-diamine |
| 123 | 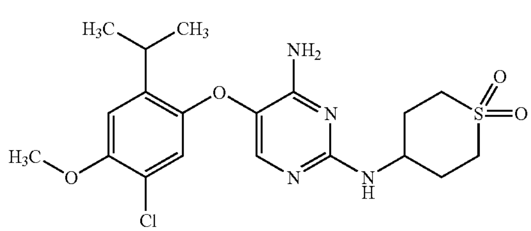 | 5-(5-Chloro-2-isopropyl-4-methoxy-phenoxy)-$N^2$-(1,1-dioxo-hexahydro-1$\lambda^6$-thiopyran-4-yl)-pyrimidine-2,4-diamine |

TABLE 1-continued
| # | Structure | Name |
|---|---|---|
| | 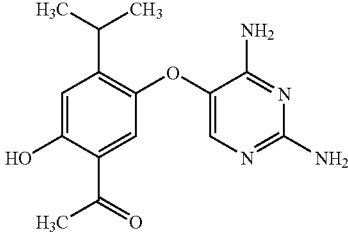 | 1-[5-(2,4-Diamino-pyrimidin-5-yloxy)-2-hydroxy-4-isopropyl-phenyl]-ethanone |
| 124 | 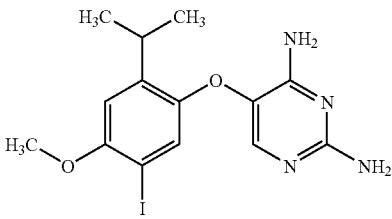 | 5-(5-Iodo-2-isopropyl-4-methoxy-phenoxy)-pyrimidine-2,4-diamine |
| 125 | 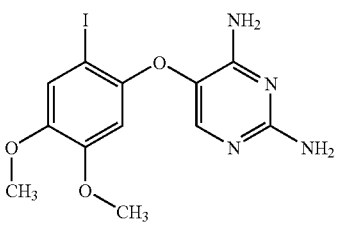 | 5-(2-Iodo-4,5-dimethoxy-phenoxy)-pyrimidine-2,4-diamine |
| 126 | 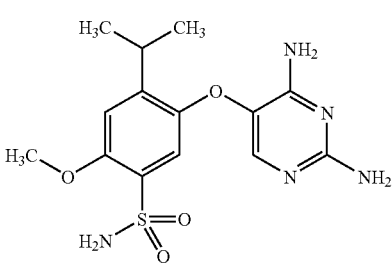 | 5-(2,4-Diamino-pyrimidin-5-yloxy)-4-isopropyl-2-methoxy-benzenesulfonamide |
| 127 | 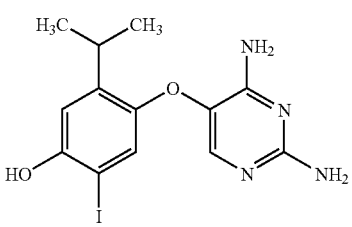 | 4-(2,4-Diamino-pyrimidin-5-yloxy)-2-iodo-5-isopropyl-phenol |
| 128 | 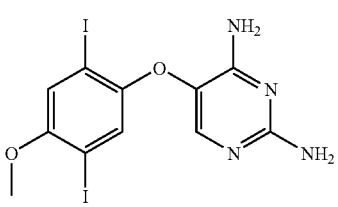 | 5-(2,5-Diiodo-4-methoxy-phenoxy)-pyrimidine-2,4-diamine |

TABLE 1-continued

| # | Structure | Name |
|---|---|---|
| 129 | 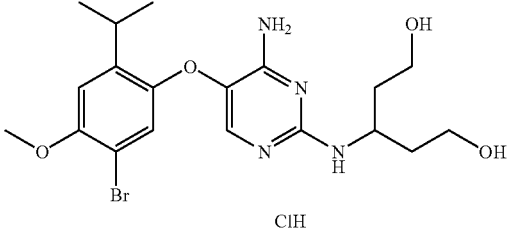 | 3-[4-Amino-5-(5-bromo-2-isopropyl-4-methoxy-phenoxy)-pyrimidm-2-ylamino]-pentane-1,5-diol |
| 130 | 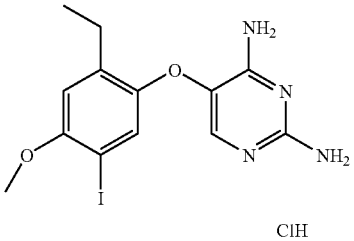 | 5-(2-Ethyl-5-iodo-4-methoxy-phenoxy)-pyrimidine-2,4-diamine |
| 131 | 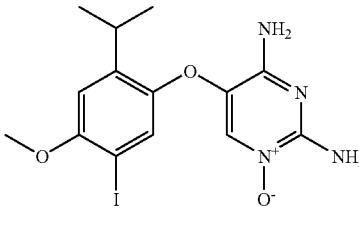 | 5-(5-Iodo-2-isopropyl-4-methoxy-phenoxy)-1-oxy-pyrimidine-2,4-diamine |
| 132 | 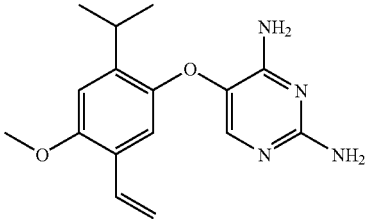 | 5-(2-Isopropyl-4methoxy-5-vinyl-phenoxy)-pyrimidine-2,4-diamine |
| 133 | 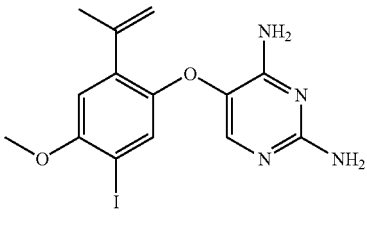 | 5-(5-Iodo-2-isopropenyl-4-methoxy-phenoxy)-pyrimidine-2,4-diamine |
| 134 | 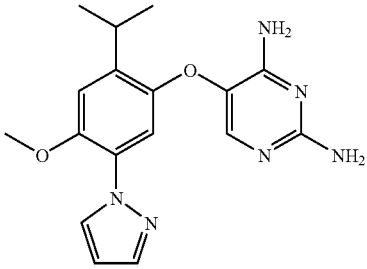 | 5-(2-Isopropyl-4-methoxy-5-pyrazol-1-yl-phenoxy)-pyrimidine-2,4-diamine |

TABLE 1-continued

| # | Structure | Name |
|---|---|---|
| 135 | 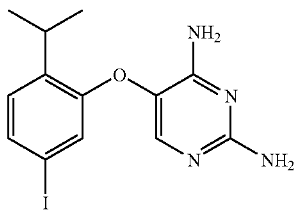 | 5-(5-Iodo-2-isopropyl-phenoxy)-pyrimidine-2,4-diamine |
| 136 | 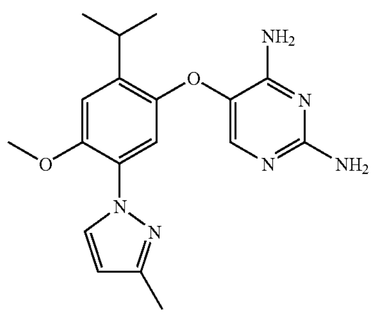 | 5-[2-Isopropyl-4-methoxy-5-(3-methyl-pyrazol-1-yl)-phenoxy]-pyrimidine-2,4-diamine |
| 137 | 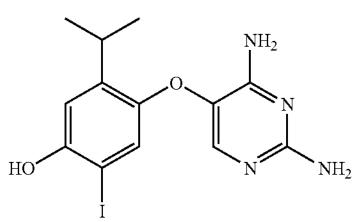 | 4-(2,4-Diamino-pyrimidin-5-ylmethyl)-2-iodo-5-isopropyl-phenol |
| 138 | 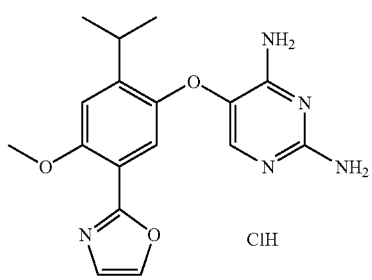 | 5-(2-Isopropyl-4-methoxy-5-oxazol-2-yl-phenoxy)-pyrimidine-2,4-diamine |
| 139 | 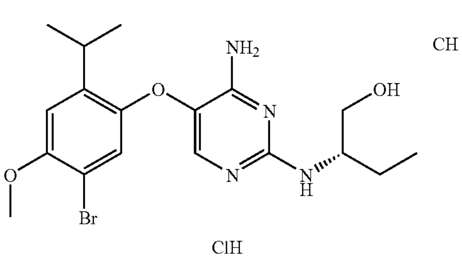 | (S)-2-[4-Amino-5-(5-bromo-2-isopropyl-4-methoxy-phenoxy)-pyrimidin-2-ylamino]-butan-1-ol |
| 140 | 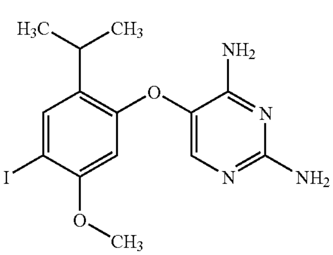 | 5-(4-Iodo-2-isopropyl-5-methoxy-phenoxy)-pyrimidine-2,4-diamine |

TABLE 1-continued

| # | Structure | Name |
|---|---|---|
| 141 | 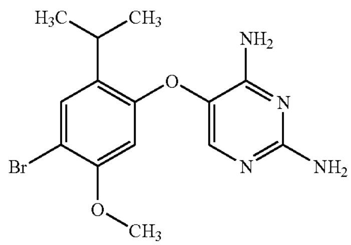 | 5-(4-Bromo-2-isopropyl-5-methoxy-phenoxy)-pyrimidine-2,4-diamine |
| 142 | 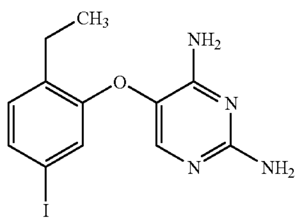 | 5-(2-Ethyl-5-iodo-phenoxy)-pyrimidine-2,4-diamine |
| 143 | 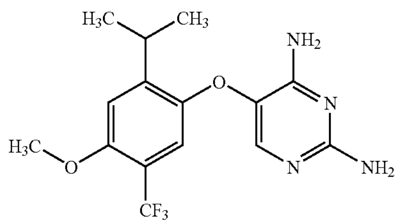 | 5-(2-Isopropyl-4-methoxy-5-trifluoromethyl-phenoxy)-pyrimidine-2,4-diamine |
| 144 | 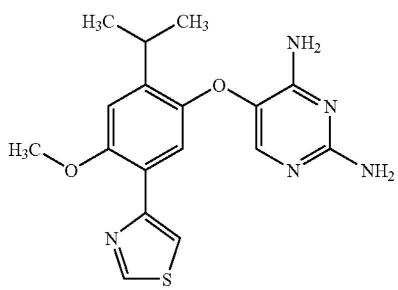 | 5-(2-Isopropyl-4-methoxy-5-thiazol-4-yl-phenoxy)-pyrimidine-2,4-diamine |
| 145 | 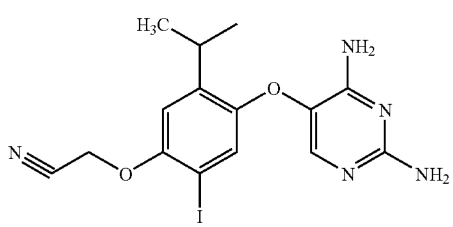 | [4-(2,4-Diamino-pyrimidin-5-yloxy)-2-iodo-5-isopropyl-phenoxy]-acetonitrile |
| 146 | 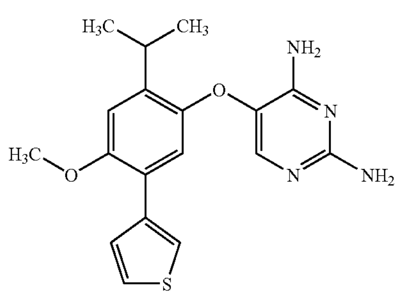 | 5-(2-Isopropyl-4-methoxy-5-thiophen-3-yl-phenoxy)-pyrimidine-2,4-diamine |

TABLE 1-continued

| # | Structure | Name |
|---|---|---|
| 147 | 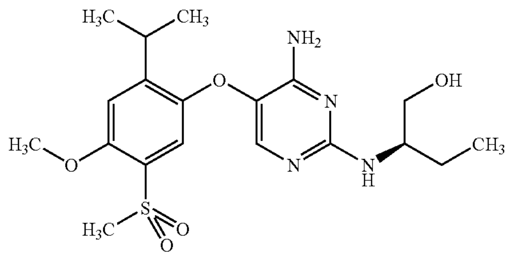 | (R)-2-[4-Amino-5-(2-isopropyl-5-methanesulfonyl-4-methoxy-phenoxy)-pyrimidin-2-ylamino]-butan-1-ol |
| 148 | 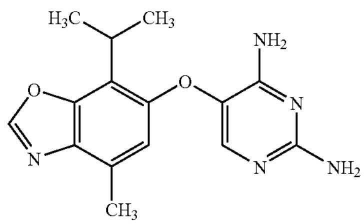 | 5-(7-Isopropyl-4-methyl-benzooxazol-6-yloxy)-pyrimidine-2,4-diamine |
| 149 | 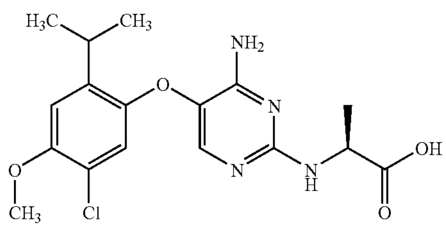 | (S)-2-[4-Amino-5-(5-chloro-2-isopropyl-4-methoxy-phenoxy)-pyrimidin-2-ylamino]-propionic acid |
| 150 | 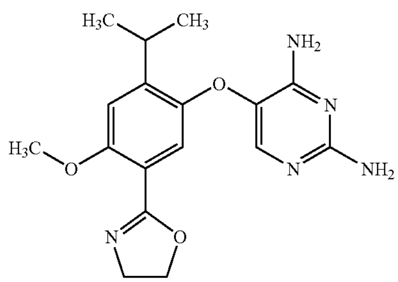 | 5-[5-(4,5-Dihydro-oxazol-2-yl)-2-isopropyl-4-methoxy-phenoxy]-pyrimidine-2,4-diamine |
| 151 | 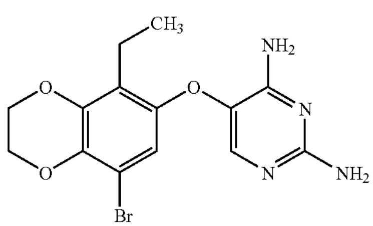 | 5-(8-Bromo-5-ethyl-2,3-dihydro-benzo[1,4]dioxin-6-yloxy)-pyrimidine-2,4-diamine |
| 152 | 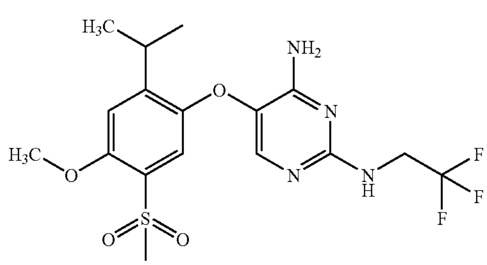 | 5-(2-Isopropyl-5-methanesulfonyl-4-methoxy-phenoxy)-N2-(2,2,2-trifluoro-ethyl)-pyrimidine-2,4-diamine |

TABLE 1-continued

| # | Structure | Name |
|---|---|---|
| 153 | 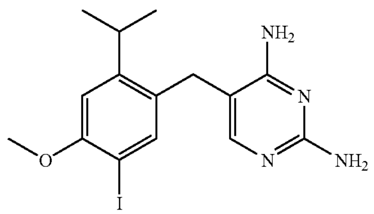 | 5-(5-Iodo-2-isopropyl-4-methoxy-benzyl)-pyrimidine-2,4-diamine |
| 154 | 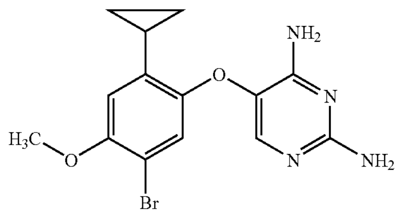 | 5-(5-Bromo-2-cyclopropyl-4-methoxy-phenoxy)-pyrimidine-2,4-diamine |
| 155 | 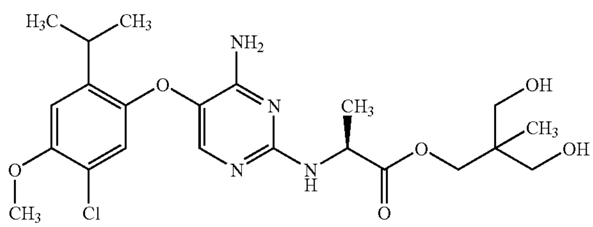 | (S)-2-[4-Amino-5-(5-chloro-2-isopropyl-4-methoxy-phenoxy)-pyrimidin-2-ylamino]-propionic acid 3-hydroxy-2-hydroxymethyl-2-methyl-propyl ester |
| 156 | 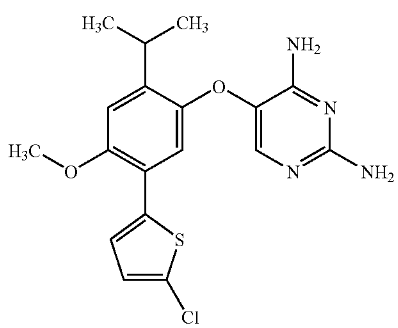 | 5-[5-(5-Chloro-thiophen-2-yl)-2-isopropyl-4-methoxy-phenoxy]-pyrimidine-2,4-diamine |
| 157 | 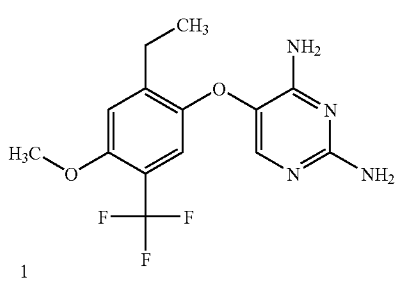 | 5-(2-Ethyl-4-methoxy-5-trifluoromethyl-phenoxy)-pyrimidine-2,4-diamine |
| 158 | 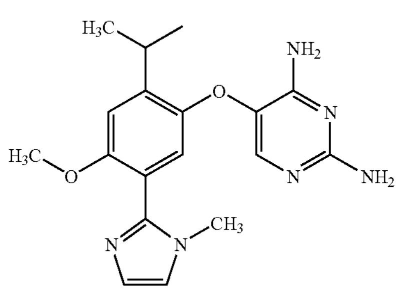 | 5-[2-Isopropyl-4-methoxy-5-(1-methyl-1H-imidazol-2-yl)-phenoxy]-pyrimidine-2,4-diamine |

TABLE 1-continued

| # | Structure | Name |
|---|---|---|
| 159 | 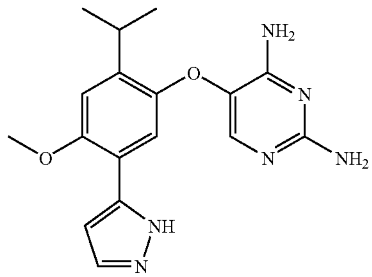 | 5-[2-Isopropyl-4-methoxy-5-(2H-pyrazol-3-yl)-phenoxy]-pyrimidine-2,4-diamine |
| 160 | 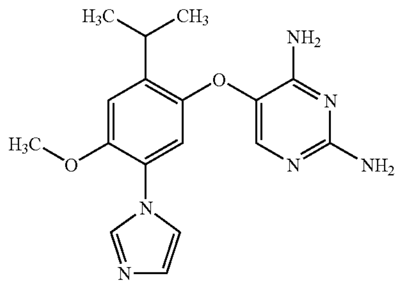 | 5-(5-Imidazol-1-yl-2-isopropyl-4-methoxy-phenoxy)-pyrimidine-2,4-diamine |
| 161 | 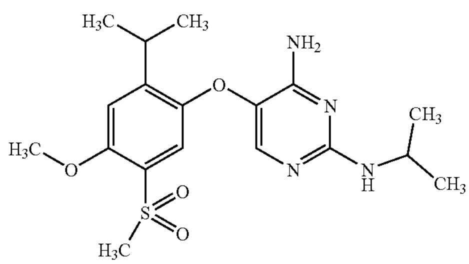 | N2-Isopropyl-5-(2-isopropyl-5-methanesulfonyl-4-methoxy-phenoxy)-pyrimidine-2,4-diamine |
| 162 | 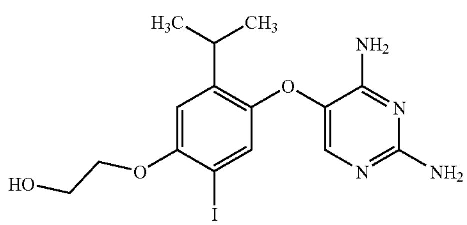 | 2-[4-(2,4-Diamino-pyrimidin-5-yloxy)-2-iodo-5-isopropyl-phenoxy]-ethanol |
| 163 | 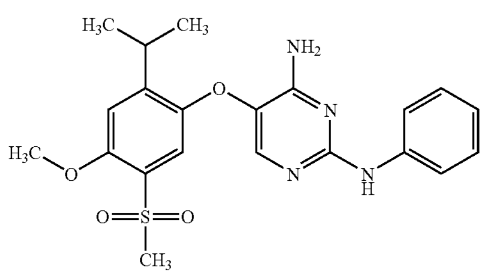 | 5-(2-Isopropyl-5-methanesulfonyl-4-methoxy-phenoxy)-N2-phenyl-pyrimidine-2,4-diamine |
| 164 | 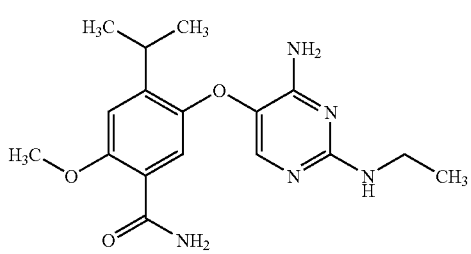 | 5-(4-Amino-2-ethyl amino-pyrimidin-5-yloxy)-4-isopropyl-2-methoxy-benzamide |

TABLE 1-continued

| # | Structure | Name |
|---|---|---|
| 165 | 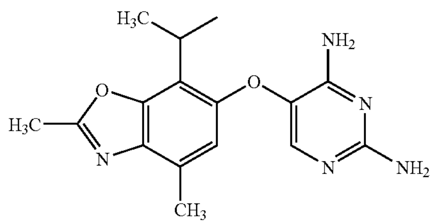 | 5-(7-Isopropyl-2,4-dimethyl-benzooxazol-6-yloxy)-pyrimidine-2,4-diamine |
| 166 | 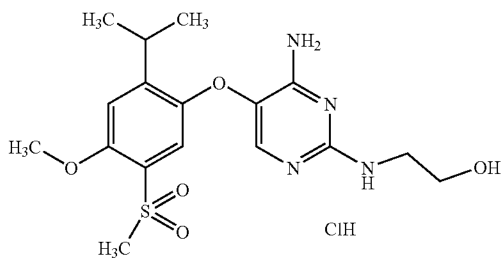 | 2-[4-Amino-5-(2-isopropyl-5-methanesulfonyl-4-methoxy-phenoxy)-pyrimidin-2-ylamino]-ethanol |
| 167 | 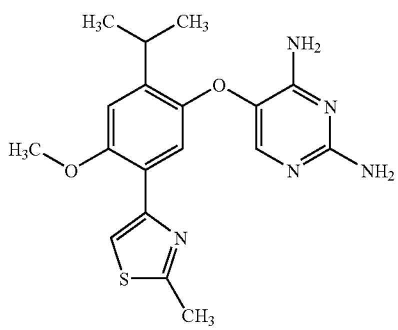 | 5-[2-Isopropyl-4-methoxy-5-(2-methyl-thiazol-4-yl)-phenoxy]-pyrimidine-2,4-diamine |
| 168 | 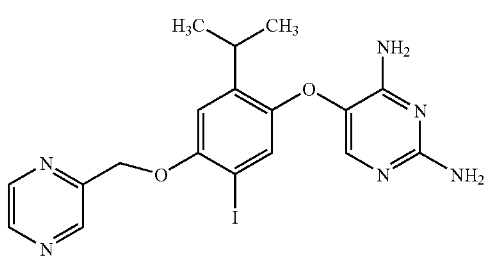 | 5-[5-Iodo-2-isopropyl-4-(pyrazin-2-ylmethoxy)-phenoxy]-pyrimidine-2,4-diamine |
| 169 | 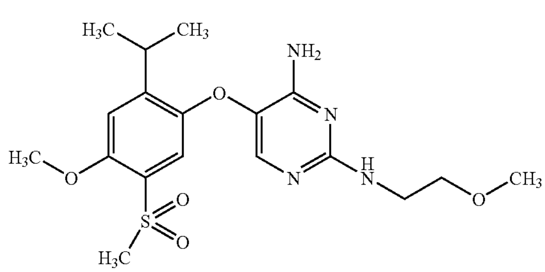 | 5-(2-Isopropyl-5-methanesulfonyl-4-methoxy-phenoxy)-N2-(2-methoxy-ethyl)-pyrimidine-2,4-diamine |

TABLE 1-continued

| # | Structure | Name |
|---|---|---|
| 170 | 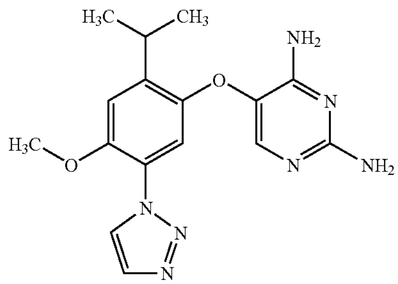 | 5-(2-Isopropyl-4-methoxy-5-[1,2,3]triazol-1-yl-phenoxy)-pyrimidine-2,4-diamine |
| 171 | 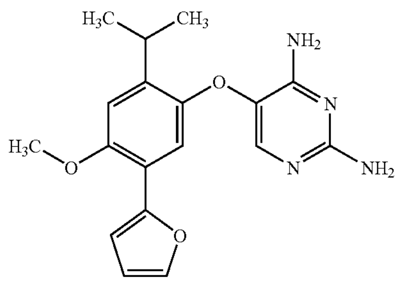 | 5-(5-Furan-2-yl-2-isopropyl-4-methoxy-phenoxy)-pyrimidine-2,4-diamine |
| 172 | 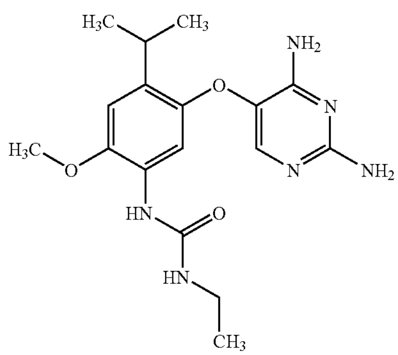 | 1-[5-(2,4-Diamino-pyrimidin-5-yloxy)-4-isopropyl-2-methoxy-phenyl]-3-ethyl-urea |
| 173 | 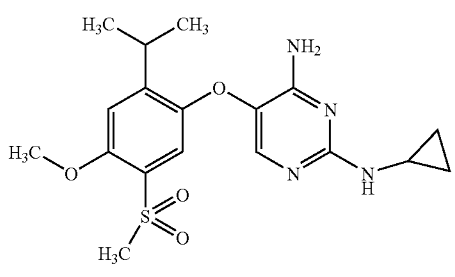 | N2-Cyclopropyl-5-(2-isopropyl-5-methanesulfonyl-4-methoxy-phenoxy)-pyrimidine-2,4-diamine |
| 174 | 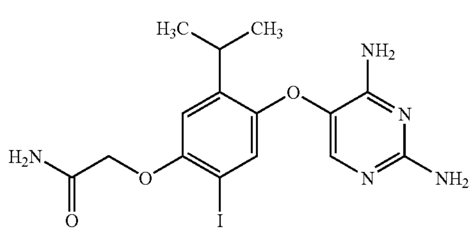 | 2-[4-(2,4-Diamino-pyrimidin-5-yloxy)-2-iodo-5-isopropyl-phenoxy]-acetamide |

TABLE 1-continued

| # | Structure | Name |
|---|---|---|
| 175 | 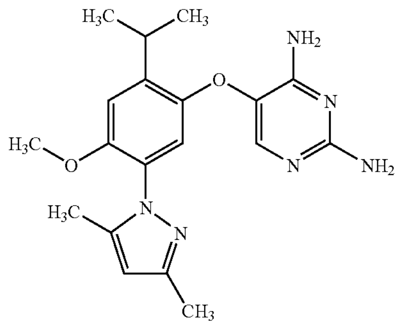 | 5-[5-(3,5-Dimethyl-pyrazol-1-yl)-2-isopropyl-4-methoxy-phenoxy]-pyrimidine-2,4-diamine |
| 176 | 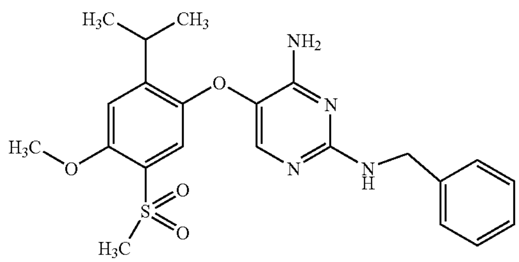 | N2-Benzyl-5-(2-isopropyl-5-methanesulfonyl-4-methoxy-phenoxy)-pyrimidine-2,4-diamine |
| 177 | 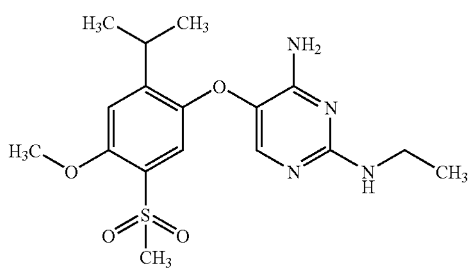 | N2-Ethyl-5-(2-isopropyl-5-methanesulfonyl-4-methoxy-phenoxy)-pyrimidine-2,4-diamine |
| 178 | 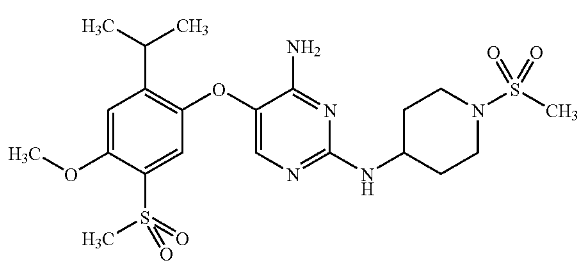 | 5-(2-Isopropyl-5-methanesulfonyl-4-methoxy-phenoxy)-N2-(1-methanesulfonyl-piperidin-4-yl)-pyrimidine-2,4-diamine |
| 179 | 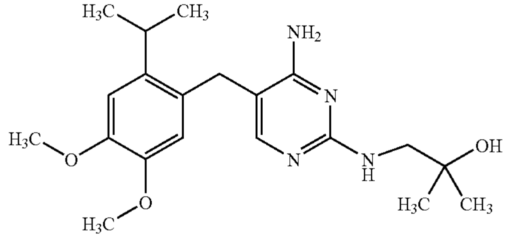 | 1-[4-Amino-5-(2-isopropyl-4,5-dimethoxy-benzyl)-pyrimidin-2-ylamino]-2-methyl-propan-2-ol |

TABLE 1-continued

| # | Structure | Name |
|---|---|---|
| 180 | 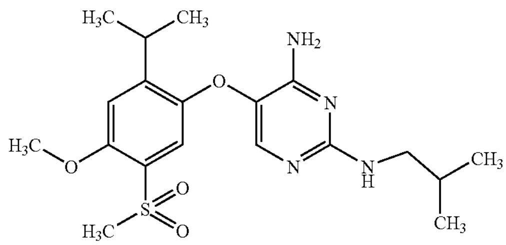 | N2-Isobutyl-5-(2-isopropyl-5-methanesulfonyl-4-methoxy-phenoxy)-pyrimidine-2,4-diamine |
| 181 | 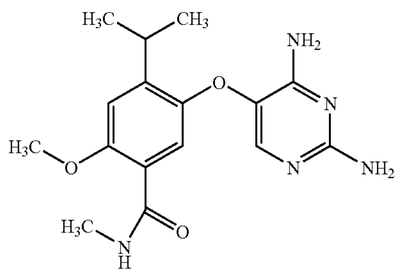 | 5-(2,4-Diamino-pyrimidin-5-yloxy)-4-isopropyl-2-methoxy-N-methyl-benzamide |
| 182 | 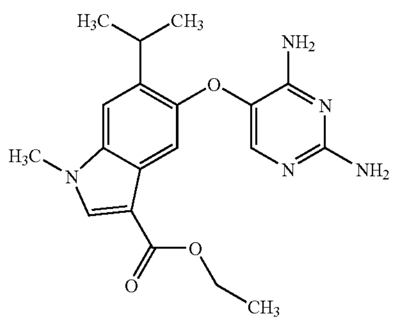 | 5-(2,4-Diamino-pyrimidin-5-yloxy)-6-isopropyl-1-methyl-1H-indole-3-carboxylic acid ethyl ester |
| 183 | 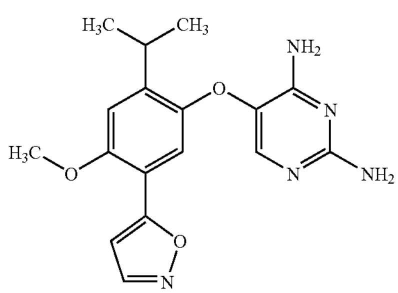 | 5-(2-Isopropyl-5-isoxazol-5-yl-4-methoxy-phenoxy)-pyrimidine-2,4-diamine |
| 184 | 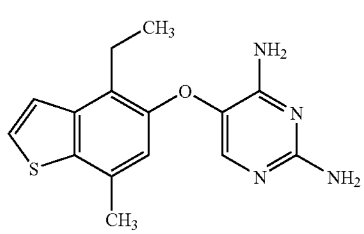 | 5-(4-Ethyl-7-methyl-benzo[b]thiophen-5-yloxy)-pyrimidine-2,4-diamine |

TABLE 1-continued

| # | Structure | Name |
|---|---|---|
| 185 | 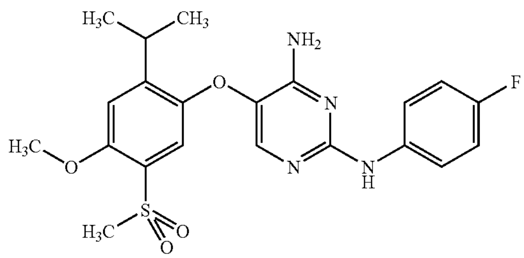 | N2-(4-Fluoro-phenyl)-5-(2-isopropyl-5-methanesulfonyl-4-methoxy-phenoxy)-pyrimidine-2,4-diamine |
| 186 | 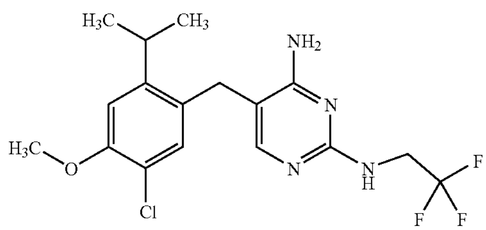 | 5-(5-Chloro-2-isopropyl-4-methoxy-benzyl)-N2-(2,2,2-trifluoro-ethyl)-pyrimidine-2,4-diamine |
| 187 | 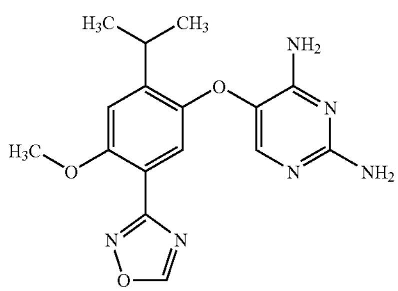 | 5-(2-Isopropyl-4-methoxy-5-[1,2,4]oxadiazol-3-yl-phenoxy)-pyrimidine-2,4-diamine |
| 188 | 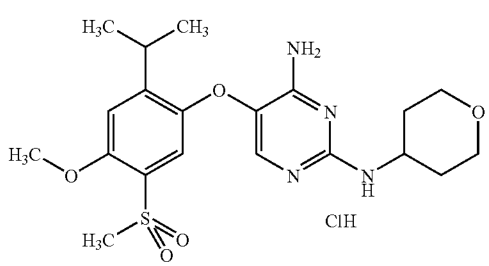 | 5-(2-Isopropyl-5-methanesulfonyl-4-methoxy-phenoxy)-N2-(tetrahydro-pyran-4-yl)-pyrimidine-2,4-diamine |
| 189 | 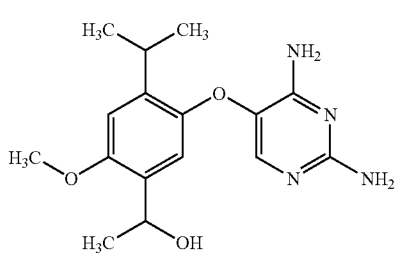 | 1-[5-(2,4-Diamino-pyrimidin-5-yloxy)-4-isopropyl-2-methoxy-phenyl]-ethanol |
| 190 | 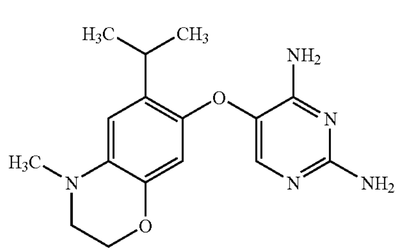 | 5-(6-Isopropyl-4-methyl-3,4-dihydro-2H-benzo[1,4]oxazin-7-yloxy)-pyrimidine-2,4-diamine |

TABLE 1-continued

| # | Structure | Name |
|---|---|---|
| 191 | 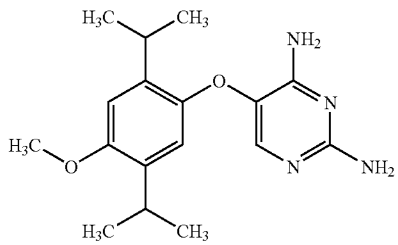 | 5-(2,5-Diisopropyl-4-methoxy-phenoxy)-pyrimidine-2,4-diamine |
| 192 | 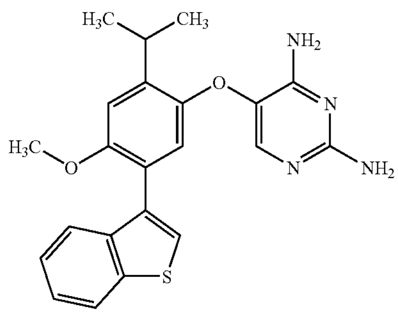 | 5-(5-Benzo[b]thiophen-3-yl-2-isopropyl-4-methoxy-phenoxy)-pyrimidine-2,4-diamine |
| 193 | 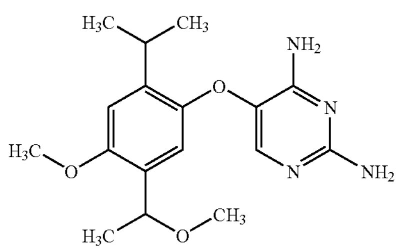 | 5-[2-Isopropyl-4-methoxy-5-(1-methoxy-ethyl)-phenoxy]-pyrimidine-2,4-diamine |
| 194 | 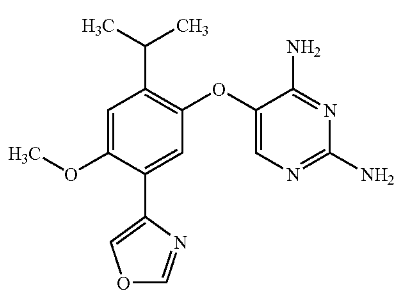 | 5-(2-Isopropyl-4-methoxy-5-oxazol-4-yl-phenoxy)-pyrimidine-2,4-diamine |
| 195 | 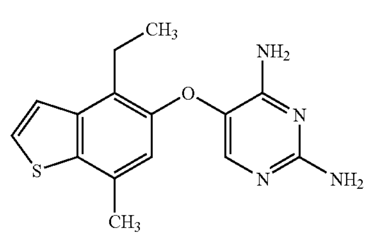 | 5-(4-Ethyl-7-methyl-benzo[b]thiophen-5-yloxy)-pyrimidine-2,4-diamine |

TABLE 1-continued

| # | Structure | Name |
|---|---|---|
| 196 | 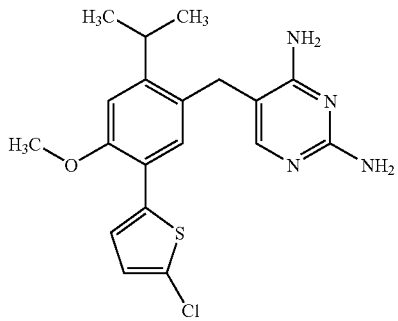 | 5-[5-(5-Chloro-thiophen-2-yl)-2-isopropyl-4-methoxy-benzyl]-pyrimidine-2,4-diamine |
| 197 | 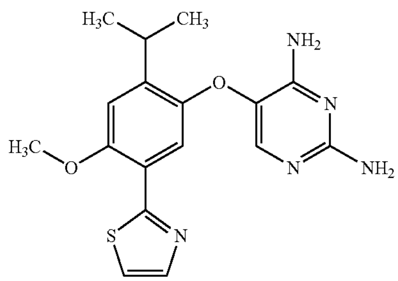 | 5-(2-Isopropyl-4-methoxy-5-thiazol-2-yl-phenoxy)-pyrimidine-2,4-diamine |
| 198 | 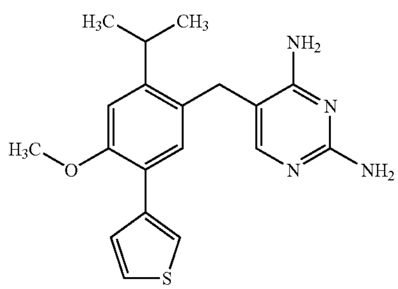 | 5-(2-Isopropyl-4-methoxy-5-thiophen-3-yl-benzyl)-pyrimidine-2,4-diamine |
| 199 | 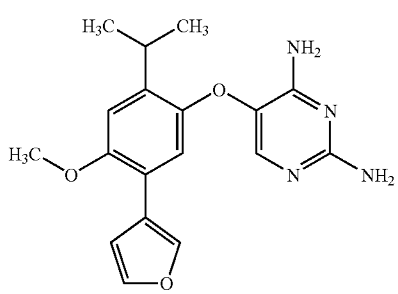 | 5-(5-Furan-3-yl-2-isopropyl-4-methoxy-phenoxy)-pyrimidine-2,4-diamine |
| 200 | 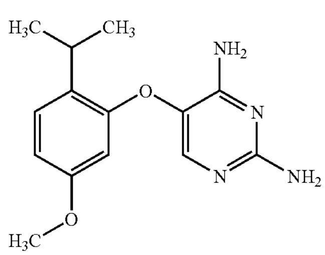 | 5-(2-Isopropyl-5-methoxy-phenoxy)-pyrimidine-2,4-diamine |

| # | Structure | Name |
|---|---|---|
| 201 | 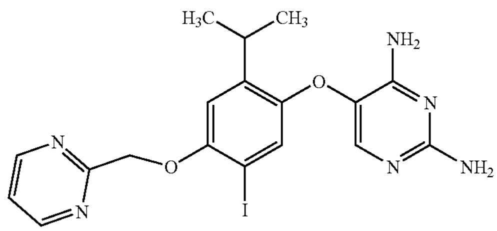 | 5-[5-Iodo-2-isopropyl-4-(pyrimidin-2-ylmethoxy)-phenoxy]-pyrimidine-2,4-diamine |
| 202 | 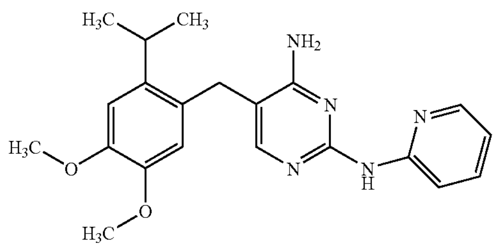 | 5-(2-Isopropyl-4,5-dimethoxy-benzyl)-N2-pyridin-2-yl-pyrimidine-2,4-diamine |
| 203 | 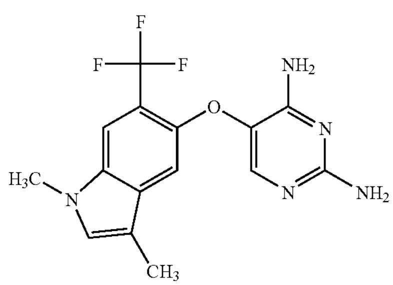 | 5-(1,3-Dimethyl-6-trifluoromethyl-1H-indol-5-yloxy)-pyrimidine-2,4-diamine |
| 204 | 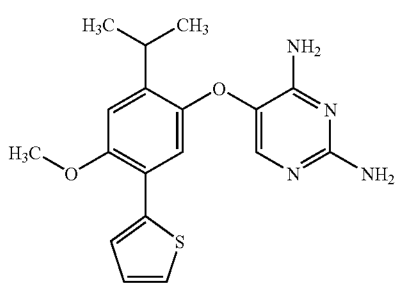 | 5-(2-Isopropyl-4-methoxy-5-thiophen-2-yl-phenoxy)-pyrimidine-2,4-diamine |
| 205 | 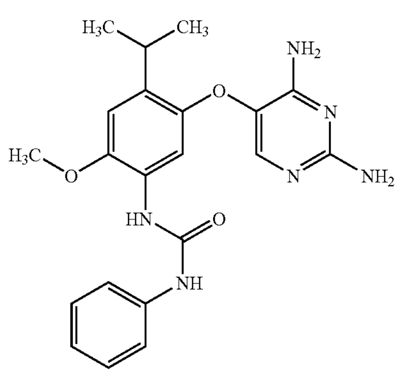 | 1-[5-(2,4-Diamino-pyrimidin-5-yloxy)-4-isopropyl-2-methoxy-phenyl]-3-phenyl-urea |

TABLE 1-continued

| # | Structure | Name |
|---|---|---|
| 206 | 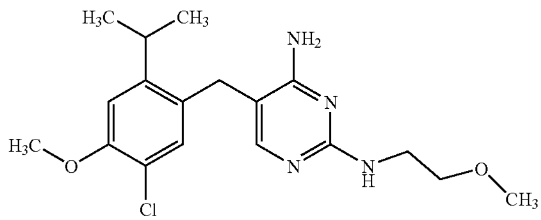 | 5-(5-Chloro-2-isopropyl-4-methoxy-benzyl)-N²-(2-methoxy-ethyl)-pyrimidine-2,4-diamine |
| 207 | 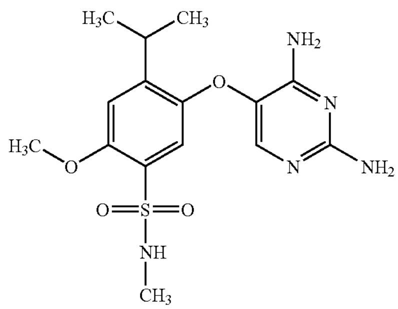 | 5-(2,4-Diamino-pyrimidin-5-yloxy)-4-isopropyl-2-methoxy-N-methyl-benzenesulfonamide |
| 208 | 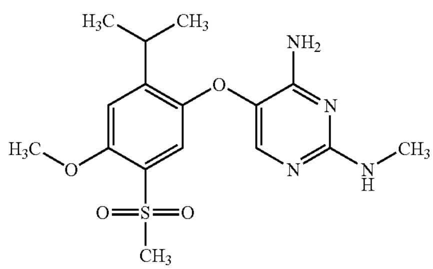 | 5-(2-Isopropyl-5-methanesulfonyl-4-methoxy-phenoxy)-N2-methyl-pyrimidine-2,4-diamine |
| 209 | 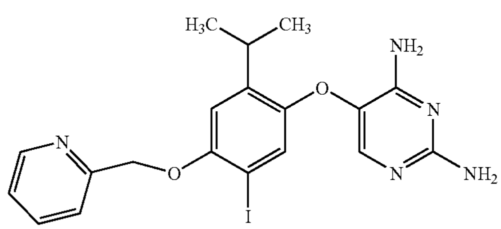 | 5-[5-Iodo-2-isopropyl-4-(pyridin-2-ylmethoxy)-phenoxy]-pyrimidine-2,4-diamine |
| 210 | 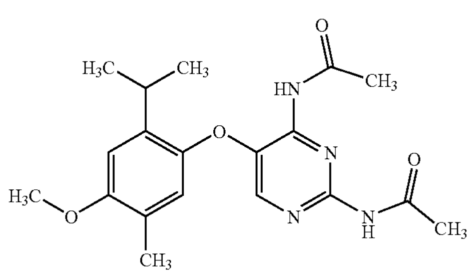 | N-[2-Acetylamino-5-(2-isopropyl-4-methoxy-5-methyl-benzyl)-pyrimidin-4-yl]-acetamide |
| 211 | 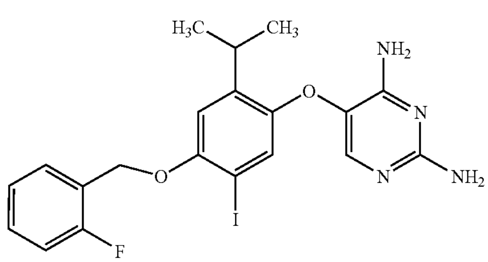 | 5-[4-(2-Fluoro-benzyloxy)-5-iodo-2-isopropyl-phenoxy]-pyrimidine-2,4-diamine |

TABLE 1-continued

| # | Structure | Name |
|---|---|---|
| 212 | 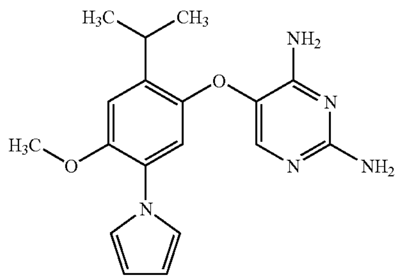 | 5-(2-Isopropyl-4-methoxy-5-pyrrol-1-yl-phenoxy)-pyrimidine-2,4-diamine |
| 213 | 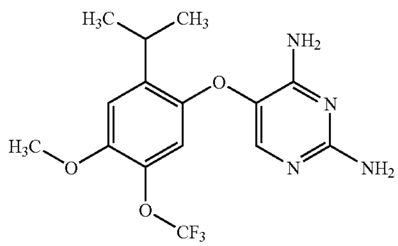 | 5-(2-Isopropyl-4-methoxy-5-trifluoromethoxy-phenoxy)-pyrimidine-2,4-diamine |
| 214 | 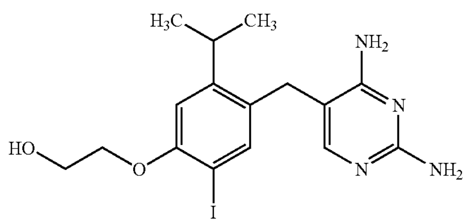 | 2-[4-(2,4-Diamino-pyrimidin-5-ylmethyl)-2-iodo-5-isopropyl-phenoxy]-ethanol |
| 215 | 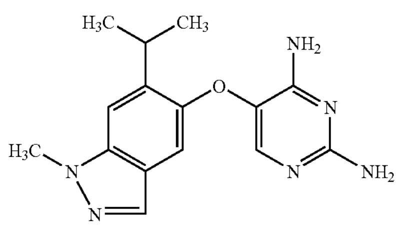 | 5-(6-Isopropyl-1-methyl-1H-indazol-5-yloxy)-pyrimidine-2,4-diamine |
| 216 | 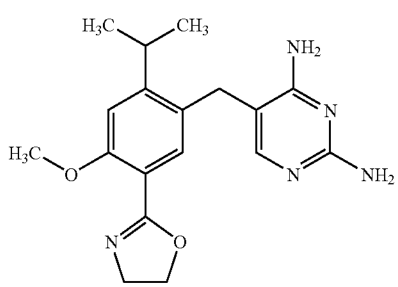 | 5-[5-(4,5-Dihydro-oxazol-2-yl)-2-isopropyl-4-methoxy-benzyl]-pyrimidine-2,4-diamine |
| 217 | 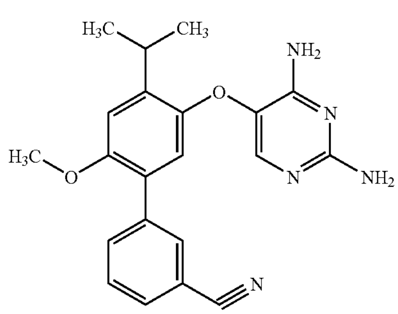 | 5'-(2,4-Diamino-pyrimidin-5-yloxy)-4'-isopropyl-2'-methoxy-biphenyl-3-carbonitrile |

TABLE 1-continued

| # | Structure | Name |
|---|---|---|
| 218 | 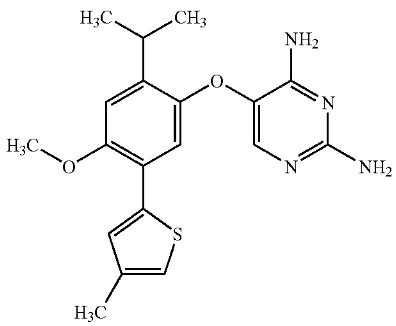 | 5-[2-Isopropyl-4-methoxy-5-(4-methyl-thiophen-2-yl)-phenoxy]-pyrimidine-2,4-diamine |
| 219 | 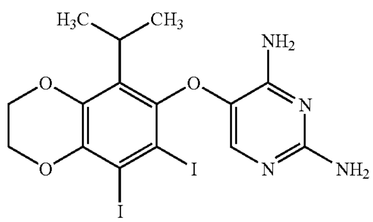 | 5-(7,8-Diiodo-5-isopropyl-2,3-dihydro-benzo[1,4]dioxin-6-yloxy)-pyrimidine-2,4-diamine |
| 220 | 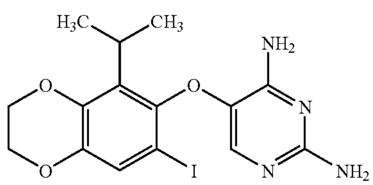 | 5-(7-Iodo-5-isopropyl-2,3-dihydro-benzo[1,4]dioxin-6-yloxy)-pyrimidine-2,4-diamine |
| 221 | 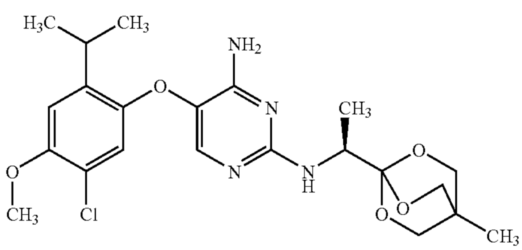 | 5-(5-Chloro-2-isopropyl-4-methoxy-phenoxy)-$N^2$-[(S)-1-(4-methyl-2,6,7-trioxa-bicyclo[2.2.2]oct-1-yl)-ethyl]-pyrimidine-2,4-diamine |
| 222 | 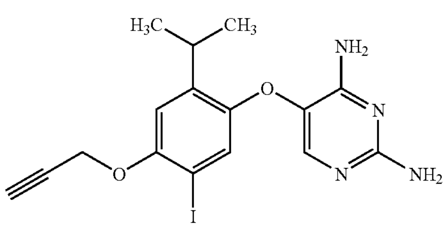 | 5-(5-Iodo-2-isopropyl-4-prop-2-ynyloxy-phenoxy)-pyrimidine-2,4-diamine |
| 223 | 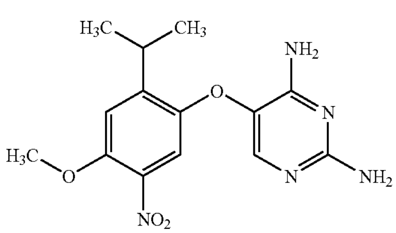 | 5-(2-Isopropyl-4-methoxy-5-nitro-phenoxy)-pyrimidine-2,4-diamine |

TABLE 1-continued

| # | Structure | Name |
|---|---|---|
| 224 | 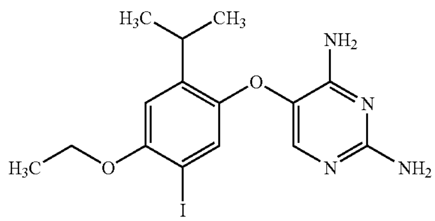 | 5-(4-Ethoxy-5-iodo-2-isopropyl-phenoxy)-pyrimidine-2,4-diamine |
| 225 | 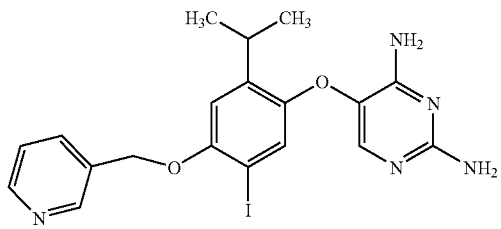 | 5-[5-Iodo-2-isopropyl-4-(pyridin-3-ylmethoxy)-phenoxy]-pyrimidine-2,4-diamine |
| 226 | 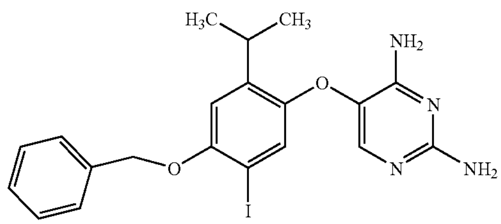 | 5-(4-Benzyloxy-5-iodo-2-isopropyl-phenoxy)-pyrimidine-2,4-diamine |
| 227 | 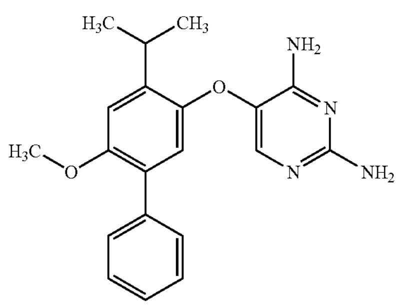 | 5-(4-Isopropyl-6-methoxy-biphenyl-3-yloxy)-pyrimidine-2,4-diamine |
| 228 | 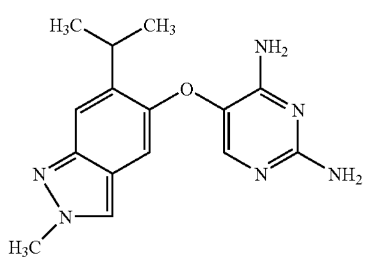 | 5-(6-Isopropyl-2-methyl-2H-indazol-5-yloxy)-pyrimidine-2,4-diamine |
| 229 | 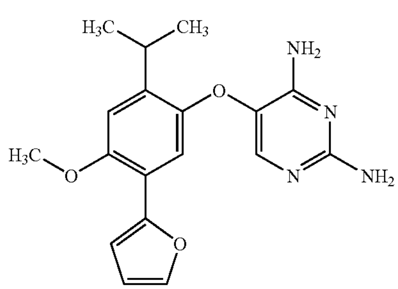 | 5-(5-Furan-2-yl-2-isopropyl-4-methoxy-benzyl)-pyrimidine-2,4-diamine |

TABLE 1-continued

| # | Structure | Name |
|---|---|---|
| 230 | 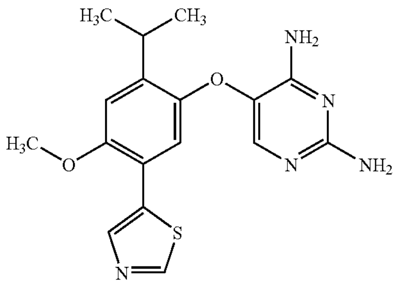 | 5-(2-Isopropyl-4-methoxy-5-thiazol-5-yl-phenoxy)-pyrimidine-2,4-diamine |
| 231 | 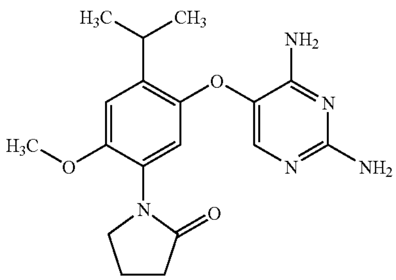 | 1-[5-(2,4-Diamino-pyrimidin-5-yloxy)-4-isopropyl-2-methoxy-phenyl]-pyrrolidin-2-one |
| 232 | 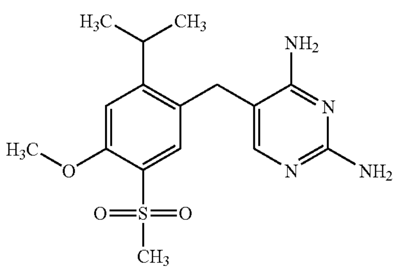 | 5-(2-Isopropyl-5-methanesulfonyl-4-methoxy-benzyl)-pyrimidine-2,4-diamine |
| 233 | 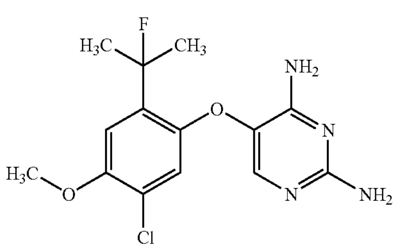 | 5-[5-Chloro-2-(1-fluoro-1-methyl-ethyl)-4-methoxy-phenoxy]-pyrimidine-2,4-diamine |
| 234 | 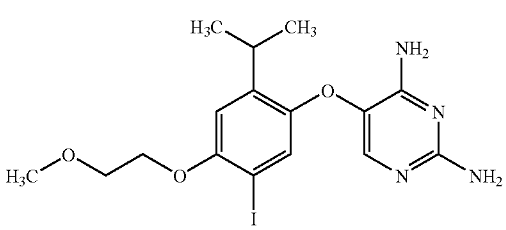 | 5-[5-Iodo-2-isopropyl-4-(2-methoxy-ethoxy)-phenoxy]-pyrimidine-2,4-diamine |

TABLE 1-continued

| # | Structure | Name |
|---|-----------|------|
| 235 | 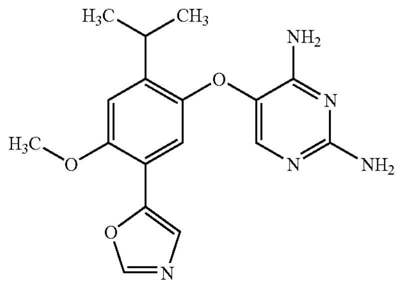 | 5-(2-Isopropyl-4-methoxy-5-oxazol-5-yl-phenoxy)-pyrimidine-2,4-diamine |
| 236 | 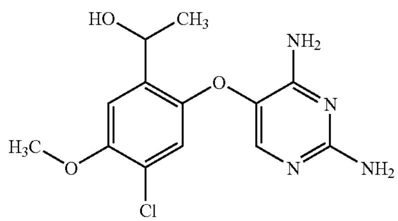 | 1-[4-Chloro-2-(2,4-diamino-pyrimidin-5-yloxy)-5-methoxy-phenyl]-ethanol |
| 237 | 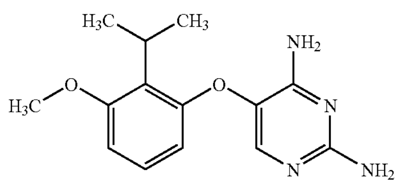 | 1-[4-Chloro-2-(2,4-diamino-pyrimidin-5-yloxy)-5-methoxy-phenyl]-ethanol |
| 238 | 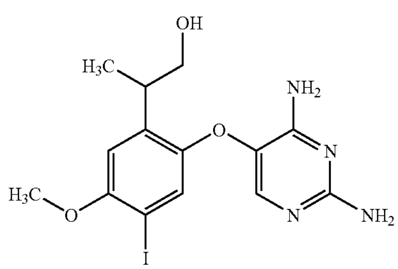 | 2-[2-(2,4-Diamino-pyrimidin-5-yloxy)-4-iodo-5-methoxy-phenyl]-propan-1-ol |
| 239 | 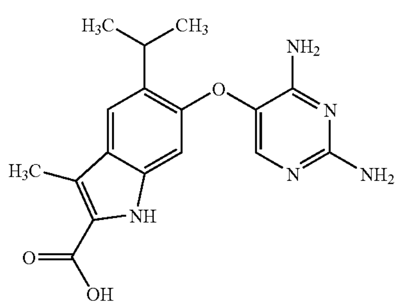 | 6-(2,4-Diamino-pyrimidin-5-yloxy)-5-isopropyl-3-methyl-1H-indole-2-carboxylic acid |
| 240 | 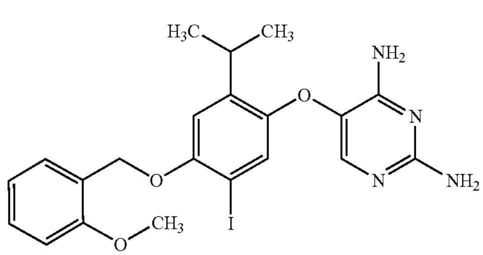 | 5-[5-Iodo-2-isopropyl-4-(2-methoxy-benzyloxy)-phenoxy]-pyrimidine-2,4-diamine |

TABLE 1-continued

| # | Structure | Name |
|---|---|---|
| 241 | 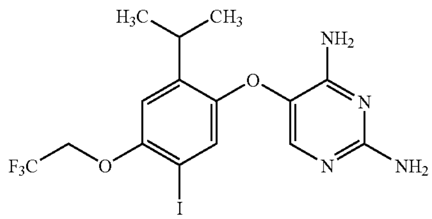 | 5-[5-Iodo-2-isopropyl-4-(2,2,2-trifluoro-ethoxy)-phenoxy]-pyrimidine-2,4-diamine |
| 242 | 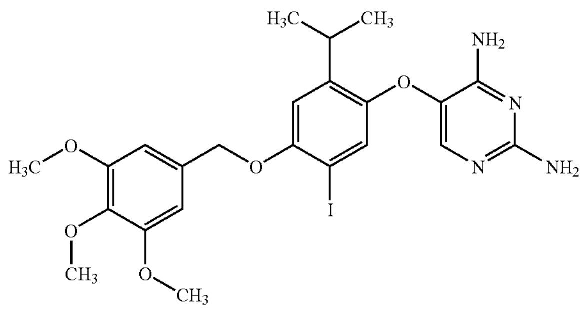 | 5-[5-Iodo-2-isopropyl-4-(3,4,5-trimethoxy-benzyloxy)-phenoxy]-pyrimidine-2,4-diamine |
| 243 | 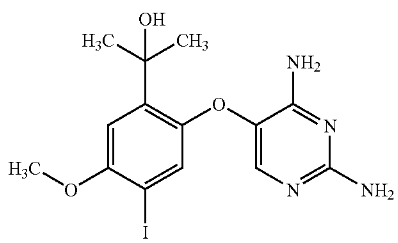 | 2-[2-(2,4-Diamino-pyrimidin-5-yloxy)-4-iodo-5-methoxy-phenyl]-propan-2-ol |
| 244 | 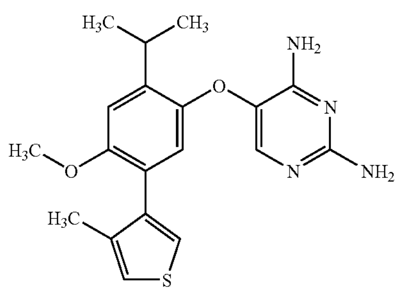 | 5-[2-Isopropyl-4-methoxy-5-(4-methyl-thiophen-3-yl)-phenoxy]-pyrimidine-2,4-diamine |
| 245 | 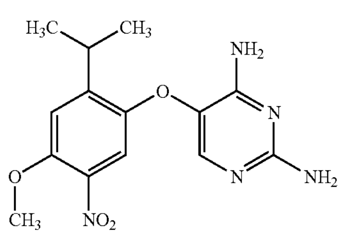 | 5-(2-Isopropyl-4-methoxy-5-nitro-phenoxy)-pyrimidine-2,4-diamine |
| 246 | 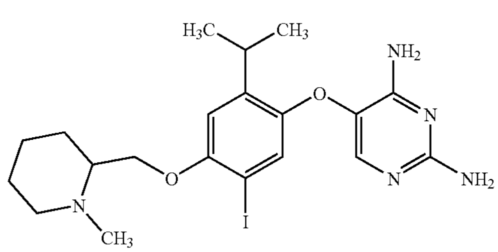 | 5-[5-Iodo-2-isopropyl-4-(1-methyl-piperidin-2-ylmethoxy)-phenoxy]-pyrimidine-2,4-diamine |

TABLE 1-continued

| # | Structure | Name |
|---|---|---|
| 247 | 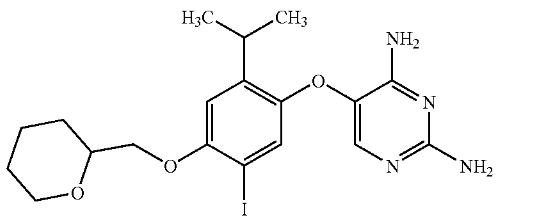 | 5-[5-Iodo-2-isopropyl-4-(tetrahydro-pyran-2-ylmethoxy)-phenoxy]-pyrimidine-2,4-diamine |
| 248 | 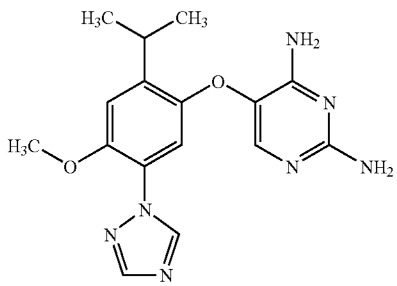 | 5-(2-Isopropyl-4-methoxy-5-[1,2,4]triazol-1-yl-phenoxy)-pyrimidine-2,4-diamine |
| 249 | 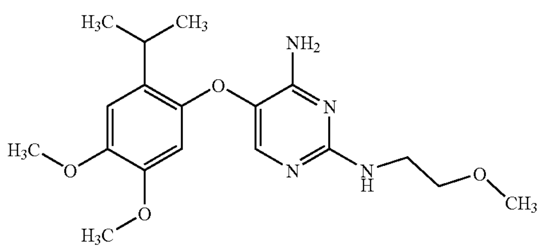 | 5-(2-Isopropyl-4,5-dimethoxy-phenoxy)-$N^2$-(2-methoxy-ethyl)-pyrimidine-2,4-diamine |
| 250 | 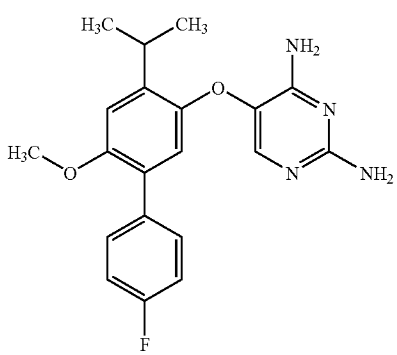 | 5-(4'-Fluoro-4-isopropyl-6-methoxy-biphenyl-3-yloxy)-pyrimidine-2,4-diamine |
| 251 | 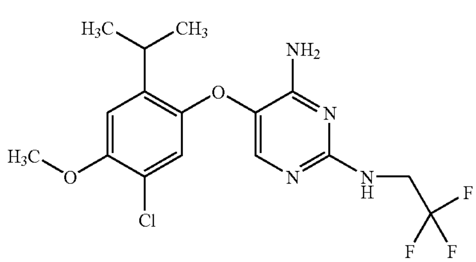 | 5-(5-Chloro-2-isopropyl-4-methoxy-phenoxy)-$N^2$-(2,2,2-trifluoro-ethyl)-pyrimidine-2,4-diamine |

TABLE 1-continued

| # | Structure | Name |
|---|---|---|
| 252 | 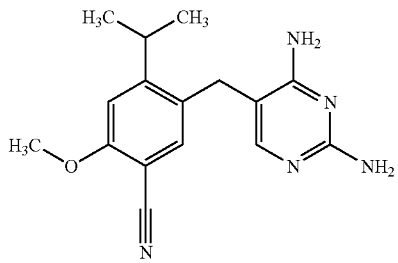 | 5-(2,4-Diamino-pyrimidin-5-ylmethyl)-4-isopropyl-2-methoxy-benzonitrile |
| 253 | 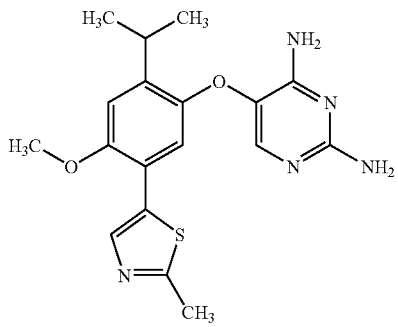 | 5-[2-Isopropyl-4-methoxy-5-(2-methyl-thiazol-5-yl)-phenoxy]-pyrimidine-2,4-diamine |
| 254 | 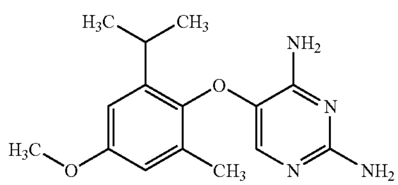 | 5-(2-Isopropyl-4-methoxy-6-methyl-phenoxy)-pyrimidine-2,4-diamine |
| 255 | 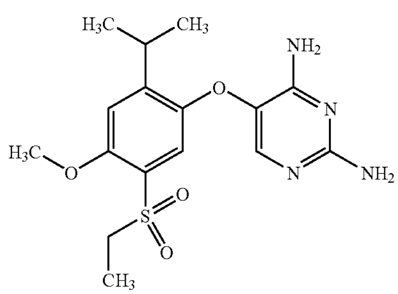 | 5-(5-Ethanesulfonyl-2-isopropyl-4-methoxy-phenoxy)-pyrimidine-2,4-diamine |
| 256 | 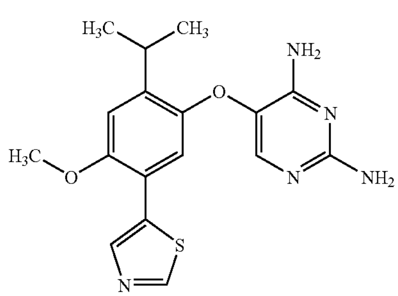 | 5-(2-Isopropyl-4-methoxy-5-thiazol-5-yl-benzyl)-pyrimidine-2,4-diamine |

TABLE 1-continued

| # | Structure | Name |
|---|---|---|
| 257 | 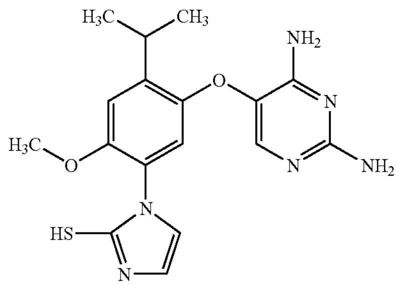 | 1-[5-(2,4-Diamino-pyrimidin-5-yloxy)-4-isopropyl-2-methoxy-phenyl]-1H-imidazole-2-thiol |
| 258 | 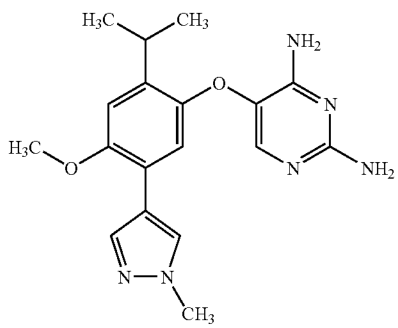 | 5-[2-Isopropyl-4-methoxy-5-(1-methyl-1H-pyrazol-4-yl)-phenoxy]-pyrimidine-2,4-diamine |
| 259 | 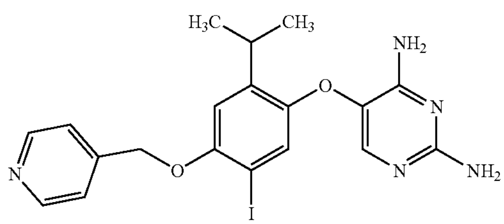 | 5-[5-Iodo-2-isopropyl-4-(pyridin-4-ylmethoxy)-phenoxy]-pyrimidine-2,4-diamine |
| 269 | 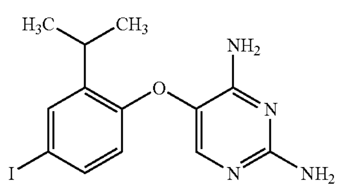 | 5-(4-Iodo-2-isopropyl-phenoxy)-pyrimidine-2,4-diamine |
| 261 | 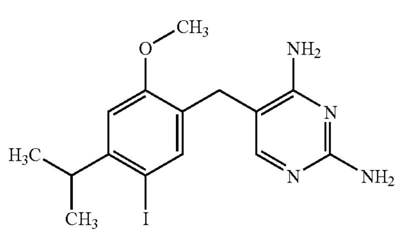 | 5-(5-Iodo-4-isopropyl-2-methoxy-benzyl)-pyrimidine-2,4-diamine |
| 262 | 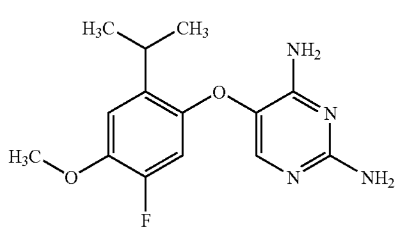 | 5-(5-Fluoro-2-isopropyl-4-methoxy-phenoxy)-pyrimidine-2,4-diamine |

TABLE 1-continued

| # | Structure | Name |
|---|---|---|
| 26 | 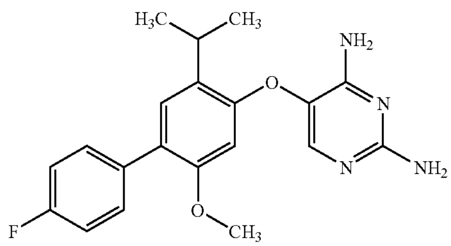 | 5-(4'-Fluoro-5-isopropyl-2-methoxy-biphenyl-4-yloxy)-pyrimidine-2,4-diamine |
| 264 | 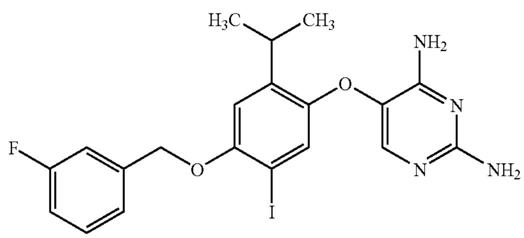 | 5-[4-(3-Fluoro-benzyloxy)-5-iodo-2-isopropyl-phenoxy]-pyrimidine-2,4-diamine |
| 265 | 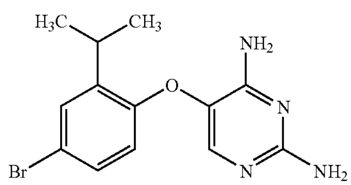 | 5-(4-Bromo-2-isopropyl-phenoxy)-pyrimidine-2,4-diamine |
| 266 | 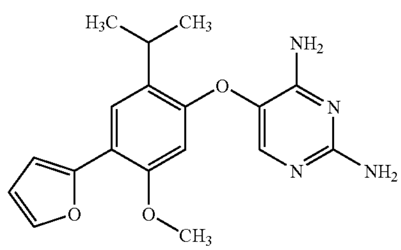 | 5-(4-Furan-2-yl-2-isopropyl-5-methoxy-phenoxy)-pyrimidine-2,4-diamine |
| 267 | 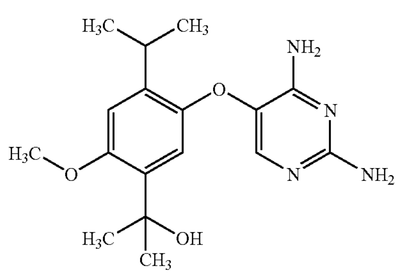 | 2-[5-(2,4-Diamino-pyrimidin-5-yloxy)-4-isopropyl-2-methoxy-phenyl]-propan-2-ol |
| 268 | 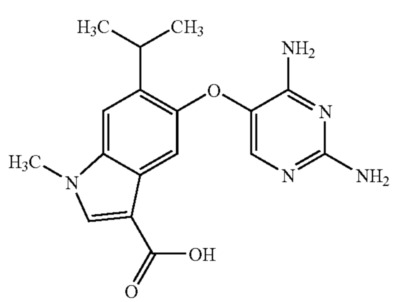 | 5-(2,4-Diamino-pyrimidin-5-yloxy)-6-isopropyl-1-methyl-1H-indole-3-carboxylic acid |

TABLE 1-continued

| # | Structure | Name |
|---|---|---|
| 269 | 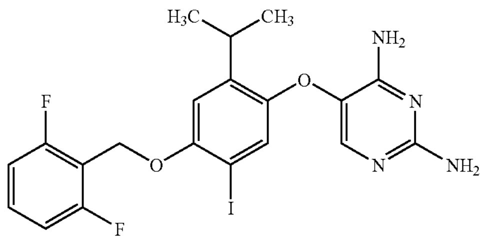 | 5-[4-(2,6-Difluoro-benzyloxy)-5-iodo-2-isopropyl-phenoxy]-pyrimidine-2,4-diamine |
| 270 | 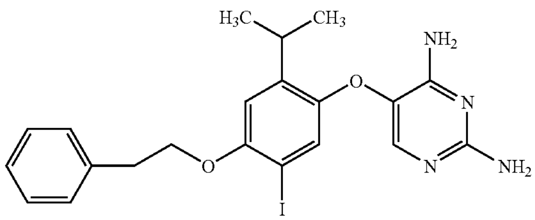 | 5-(5-Iodo-2-isopropyl-4-phenethyloxy-phenoxy)-pyrimidine-2,4-diamine |
| 271 | 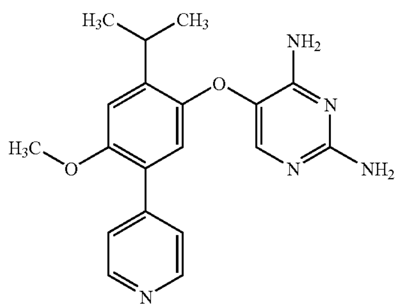 | 5-(2-Isopropyl-4-methoxy-5-pyridin-4-yl-phenoxy)-pyrimidine-2,4-diamine |
| 272 | 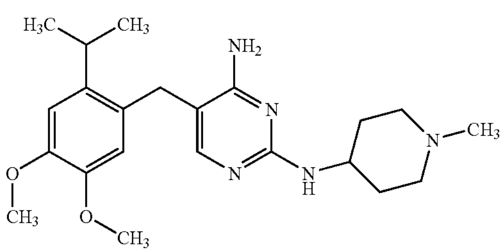 | 5-(2-Isopropyl-4,5-dimethoxy-benzyl)-$N^2$-(1-methyl-piperidin-4-yl)-pyrimidine-2,4-diamine |
| 273 | 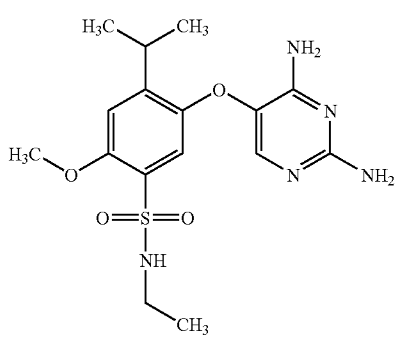 | 5-(2,4-Diamino-pyrimidin-5-yloxy)-N-ethyl-4-isopropyl-2-methoxy-benzenesulfonamide |

TABLE 1-continued

| # | Structure | Name |
|---|---|---|
| 274 | 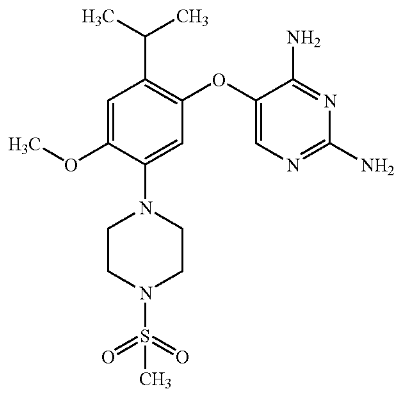 | 5-[2-Isopropyl-5-(4-methanesulfonyl-piperazin-1-yl)-4-methoxy-phenoxy]-pyrimidine-2,4-diamine |
| 275 | 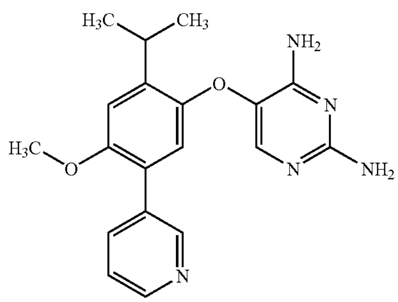 | 5-(2-Isopropyl-4-methoxy-5-pyridin-3-yl-phenoxy)-pyrimidine-2,4-diamine |
| 276 | 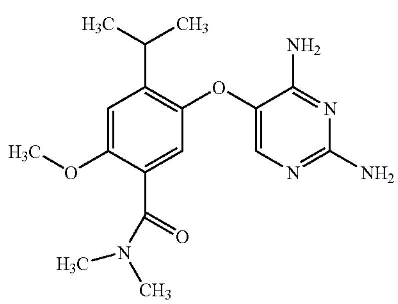 | 5-(2,4-Diamino-pyrimidin-5-yloxy)-4-isopropyl-2-methoxy-N,N-dimethyl-benzamide |
| 277 | 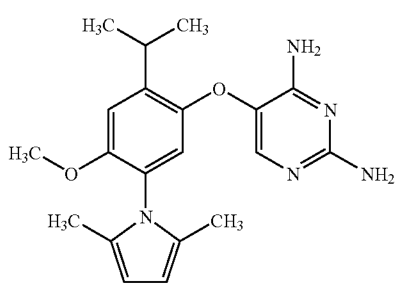 | 5-[5-(2,5-Dimethyl-pyrrol-1-yl)-2-isopropyl-4-methoxy-phenoxy]-pyrimidine-2,4-diamine |
| 278 | 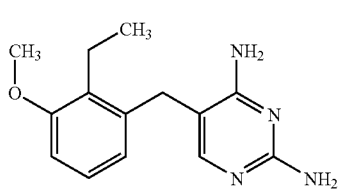 | 5-(2-Ethyl-3-methoxy-benzyl)-pyrimidine-2,4-diamine |

TABLE 1-continued

| # | Structure | Name |
|---|---|---|
| 279 | 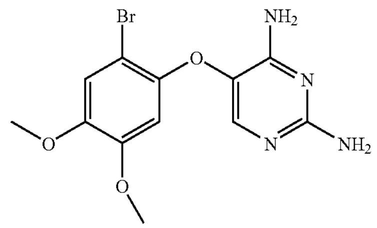 | 5-(2-Bromo-4,5-dimethoxy-phenoxy)-pyrimidine-2,4-diamine |
| 280 | 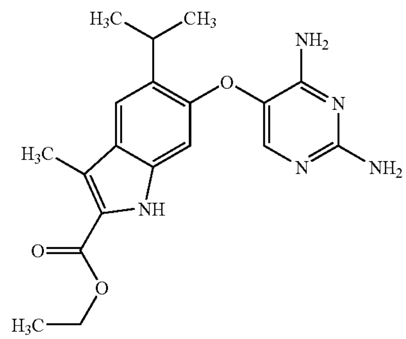 | 6-(2,4-Diamino-pyrimidin-5-yloxy)-5-isopropyl-3-methyl-1H-indole-2-carboxylic acid ethyl ester |

Synthesis

Compounds of the present invention can be made by a variety of methods depicted in the illustrative synthetic reaction schemes shown and described below.

The starting materials and reagents used in preparing these compounds generally are either available from commercial suppliers, such as Aldrich Chemical Co., or are prepared by methods known to those skilled in the art following procedures set forth in references such as *Fieser and Fieser's Reagents for Organic Synthesis;* Wiley & Sons: New York, 1991, Volumes 1-15; *Rodd's Chemistry of Carbon Compounds*, Elsevier Science Publishers, 1989, Volumes 1-5 and Supplementals; and *Organic Reactions*, Wiley & Sons: New York, 1991, Volumes 1-40. The following synthetic reaction schemes are merely illustrative of some methods by which the compounds of the present invention can be synthesized, and various modifications to these synthetic reaction schemes can be made and will be suggested to one skilled in the art having referred to the disclosure contained in this Application.

The starting materials and the intermediates of the synthetic reaction schemes can be isolated and purified if desired using conventional techniques, including but not limited to, filtration, distillation, crystallization, chromatography, and the like. Such materials can be characterized using conventional means, including physical constants and spectral data.

Unless specified to the contrary, the reactions described herein preferably are conducted under an inert atmosphere at atmospheric pressure at a reaction temperature range of from about −78° C. to about 150° C., more preferably from about 0° C. to about 125° C., and most preferably and conveniently at about room (or ambient) temperature, e.g., about 20° C.

Scheme A below illustrates one synthetic procedure usable to prepare specific compounds of formula (I) wherein X is methylene, Y is —NR$^d$R$^e$, and R$^1$, R$^2$, R$^3$, R$^4$, R$^5$, R$^6$, R$^7$, R$^8$, R$^d$, and R$^e$ are as defined herein.

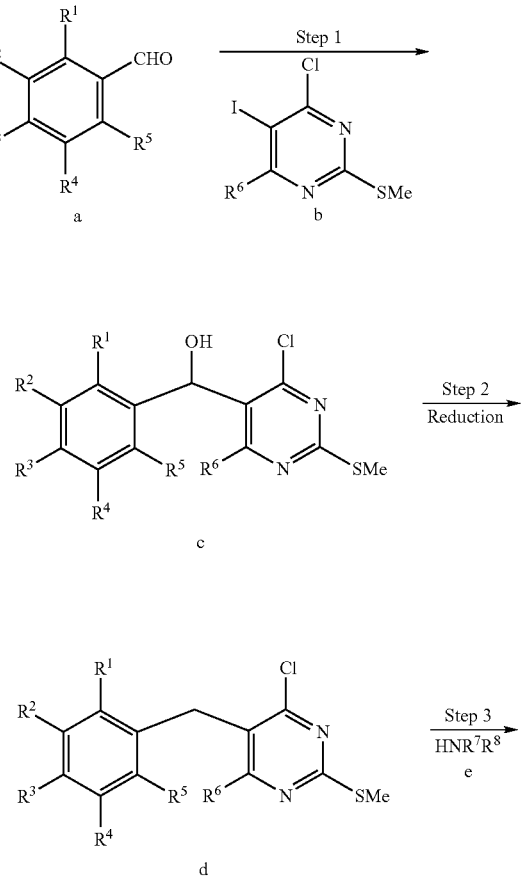

SCHEME A

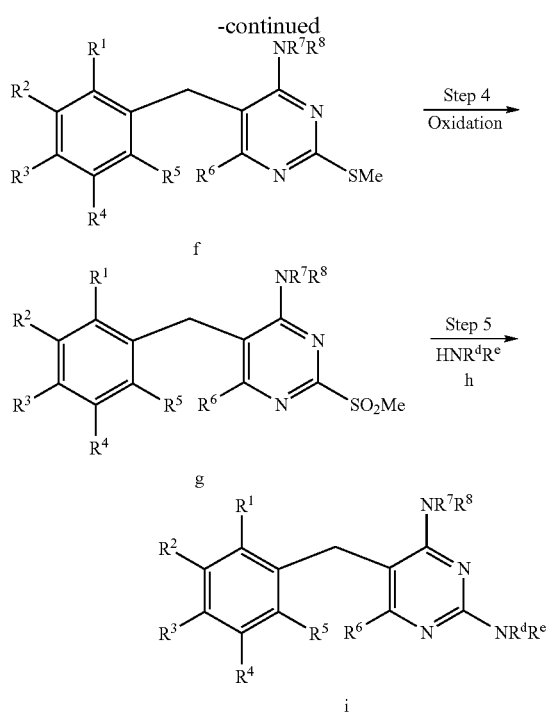

In Step 1 of Scheme A, benzaldehyde a is alkylated with the Grignard reagent derived from 4-chloro-5-iodo-2-methylsulfanyl-pyrimidine b or like iodopyrimidine to provide an alpha-hydroxy benzyl pyrimidine c. The iodopyrimidine used in this step may be prepared according to the procedure described by T. Sakamoto, et al., Chem. Pharm. Bull., 34 1986, p. 2719. Numerous substituted benzaldehydes a are commercially available or are readily prepared by techniques well known to those skilled in the art. In many instances, a "masked aldehyde", such as an imine or oxazoline, may be used used to allow introduction of desired functionalities to benzaldehyde a, after which the masked aldehyde is deprotected to provide the free aldehyde group. Aldehyde protection schemes of this sort are shown in the experimental examples below.

The reaction of step 1 may be carried out in the presence of an alkyl magnesium bromide under dry polar aprotic solvent conditions.

In step 2, alpha-hydroxy benzyl pyrimidine c is reduced to provide benzyl pyrimidine d. The reduction of step 2 may be achieved using triethylsilane and trifluoroacetic acid under polar solvent conditions.

In step 3, a first amination by reaction of amine e with benzyl pyrimidine d yields benzyl aminopyrimidine f. Amine e may comprise any suitable primary or secondary amine having functionalities $R^7$ or $R^8$ in accordance with the invention. Amine e may comprise, for example, ammonia, methylamine, ethylamine, isopropylamine, aniline, benzylamine, phenylethylamine, cyclopropylamine, dimethylamine, aziridine, pyrrolidine, piperidine, or the like. The amination of step 3 may be carried out by heating benzyl pyrimidine d in the presence of excess amine e under sealed conditions.

In step 4, an oxidation of the methylsulfanyl group of benzyl aminopyrimidine f is carried out to afford amino methanesulfonyl benzylpyrimidine g. The oxidation of step 4 may be carried out using metachloroperbenzoic acid (mCPBA), OXONE®, or like oxidizing agent under mild, polar solvent conditions.

A second amination occurs in step 6 in which amino methanesulfonyl benzylpyrimidine g is treated with amine h to displace the methanesulfonyl group and provide diamino benzylpyrimidine i. The diamino benzylpyrimidine i is a compound of formula (I) and is usable in the methods of the invention. The amination of step 6 may be achieved by heating amino methanesulfonyl benzylpyrimidine g in the presence of excess amine h under mild pressure and polar solvent conditions.

Numerous variations on the above procedure are possible and will suggest themselves to those skilled in the art upon review of this disclosure. For example, various pyrimidine reagents may be used in place of iodopyrimidine b in step 1. In such variation, described in the experimental examples below, benzaldehyde a may be treated with 5-lithio-2,6-dimethoxypyrimidine (Mathson, R. J. et al., JOC 55(10) 1990 3410-12) to form a dimethoxy benzyl pyrimidine alchohol which is subsequently oxidized with $MnO_2$. The resultant ketone can then be aminated to displace the methoxy groups to yield a diamino benzylpyrimidine in accordance with the invention.

Scheme B below illustrates another synthetic procedure usable to prepare specific compounds of formula (I) above, wherein X is O, Y is —$NR^dR^e$, $R^7$ and $R^8$ are hydrogen, and $R^1$, $R^2$, $R^3$, $R^4$, $R^5$, $R^d$, and $R^e$ are as defined herein.

SCHEME B

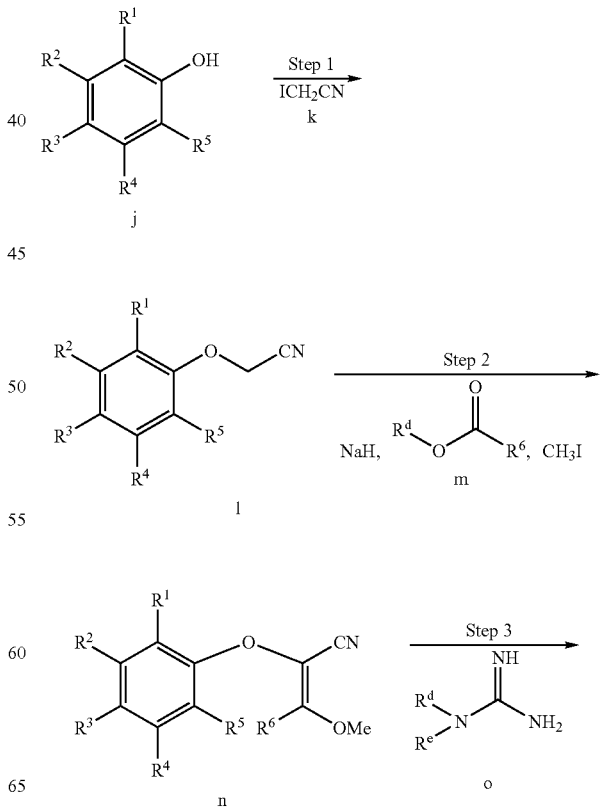

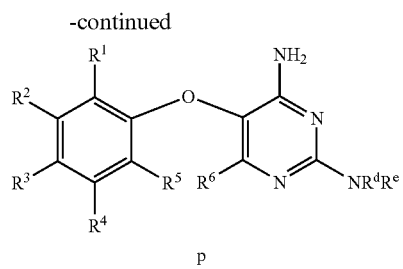

p

In step 1 of Scheme B, an O-alkylation is carried out by reaction of phenol i with a haloacetonitrile such as iodoacetonitrile k, to afford cyano ether l. Numerous substituted phenols i are either commercially available or may be prepared by techniques well known in the art for use in step 1. For example, the substituted benzaldehydes a of Scheme A above may be converted to the corresponding phenols i via Baeyer-Villiger oxidation using peracid such as mCPBA, as illustrated in the experimental examples below. The alkylation of step 1 may be effected in the presence of mild base under polar aprotic solvent conditions.

In step 2, a cyano enol ether compound n is formed by treatment of cyano ether l with a strong base such as sodium hydride, followed by introduction of ester m to form an enolate (not shown), that in turn is alkylated by addition of iodomethane or other alkyl halide. This step may be carried out under polar aprotic solvent conditions.

In step 3 cyano enol ether n is reacted with guanidine compound o in the presence of base, under polar aprotic conditions, to yield diaminopyrimidine (VI). The diaminopyrimidine (VI) is a compound of formula (I) usable in the methods of the invention.

As in the case of Scheme A discussed above, numerous variations on the procedure of Scheme B are possible and will be readily apparent to those skilled in the art. For example, selective amination of the —$NH_2$ group of diamino pyrimidine, using reductive amination or like technique, may be used to introduce $R^7$ and $R^8$ functionalities in accordance with formula (I).

Yet another procedure usable for preparation of the subject compounds is shown in Scheme C, wherein $R^1$, $R^2$, $R^3$, $R^4$ and $R^5$ are as defined herein. Scheme C represents the well-known synthesis of "ormetoprim" and "trimethoprim" antibacterials. This synthetic procedure is reported by Manchand et al., Journal of Organic Chemistry 1992, 57, 3531-3535.

SCHEME C

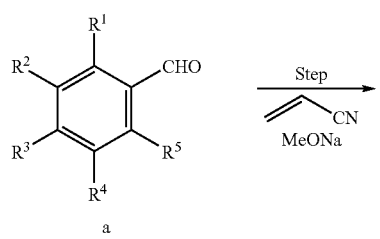

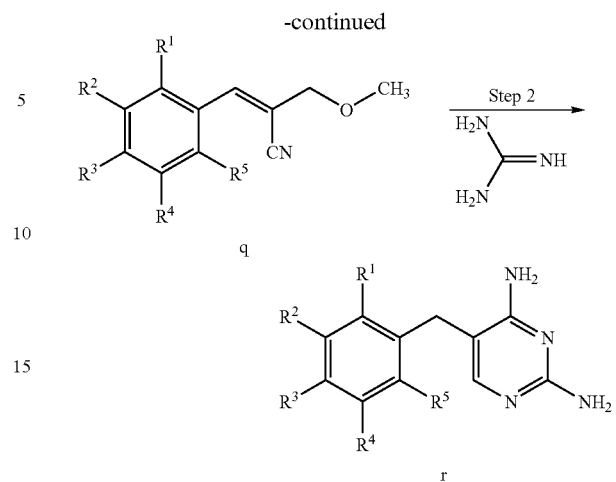

q r

In the procedure of Scheme C, benzaldehyde a is treated with acrylonitrile in the presence of sodium methoxide in step 1 to afford a phenyl methoxymethyl cinnamonitrile compound g, which in turn is reacted with guanidine in step 2 to yield the diaminopyrimidine r. Diamino pyrimidine r is a compound of formula (I) in which X is —$CH_2$—, Y is —$NH_2$ and $R^6$, $R^7$ and $R^8$ are hydrogen.

The procedure of Scheme C is effective for use with benzaldehydes a in which groups $R^1$ and $R^5$ are small such that the aldehyde functionality in step 1, and methoxymethyl cinnamonitrile functionality in step 2, are relatively unhindered. However, the introduction, for example, of $R^1$ as an isopropyl or larger alkyl group, reduces the yield of step 1 nominally to zero. Table 2 below summarizes the relative yields provided by Scheme C for various benzaldehyde starting materials.

TABLE 2

| | $R^1$ | $R^2$ | $R^3$ | $R^4$ | $R^5$ | Yield % |
|---|---|---|---|---|---|---|
| 1 | H | —H | —OMe | —OMe | —H | 67% |
| 2 | —OMe | —H | —OMe | —OMe | —H | 37% |
| 3 | —$CH_3$ | —H | —OMe | —OMe | —H | 34% |
| 4 | —Et | —H | —OMe | —OMe | —H | 18% |
| 5 | -Isopropyl | —H | —OMe | —OMe | —H | <1% |

The commercially available benzaldehydes represented by compounds 1-3 of Table 2 all result in effective synthesis of diaminopyrimidines. Introduction of an ethyl group as $R^1$ significantly reduced yield of Scheme C, and introduction of an isopropyl are larger group as $R^1$ resulted in essentially no product from the reaction of Scheme C.

Specific details for producing compounds of the invention are described in the Examples section below.

Utility

The compounds of the invention are usable for the treatment of a wide range of genitorurinary diseases, conditions and disorders, including urinary tract disease states associated with bladder outlet obstruction and urinary incontinence conditions such as reduced bladder capacity, frequency of micturition, urge incontinence, stress incontinence, bladder hyperreactivity, benign prostatic hypertrophy (BPH), prostatitis, detrusor hyperreflexia, urinary frequency, nocturia, urinary urgency, overactive bladder, pelvic hypersensitivity, urethritis, prostatititis, pelvic pain syndrome, prostatodynia, cystitis, and idiophatic bladder hypersensitivity, and other symptoms related to overactive bladder.

The compounds of the invention are expected to find utility as analgesics in the treatment of diseases and conditions associated with pain from a wide variety of causes, including, but not limited to, inflammatory pain, surgical pain, visceral pain, dental pain, premenstrual pain, central pain, pain due to burns, migraine or cluster headaches, nerve injury, neuritis, neuralgias, poisoning, ischemic injury, interstitial cystitis, cancer pain, viral, parasitic or bacterial infection, post-traumatic injuries (including fractures and sports injuries), and pain associated with functional bowel disorders such as irritable bowel syndrome.

Administration and Pharmaceutical Composition

The invention includes pharmaceutical compositions comprising at least one compound of the present invention, or an individual isomer, racemic or non-racemic mixture of isomers or a pharmaceutically acceptable salt or solvate thereof, together with at least one pharmaceutically acceptable carrier, and optionally other therapeutic and/or prophylactic ingredients.

In general, the compounds of the invention will be administered in a therapeutically effective amount by any of the accepted modes of administration for agents that serve similar utilities. Suitable dosage ranges are typically 1-500 mg daily, preferably 1-100 mg daily, and most preferably 1-30 mg daily, depending upon numerous factors such as the severity of the disease to be treated, the age and relative health of the subject, the potency of the compound used, the route and form of administration, the indication towards which the administration is directed, and the preferences and experience of the medical practitioner involved. One of ordinary skill in the art of treating such diseases will be able, without undue experimentation and in reliance upon personal knowledge and the disclosure of this Application, to ascertain a therapeutically effective amount of the compounds of the present invention for a given disease.

Compounds of the invention may be administered as pharmaceutical formulations including those suitable for oral (including buccal and sub-lingual), rectal, nasal, topical, pulmonary, vaginal, or parenteral (including intramuscular, intraarterial, intrathecal, subcutaneous and intravenous) administration or in a form suitable for administration by inhalation or insufflation. The preferred manner of administration is generally oral using a convenient daily dosage regimen which can be adjusted according to the degree of affliction.

A compound or compounds of the invention, together with one or more conventional adjuvants, carriers, or diluents, may be placed into the form of pharmaceutical compositions and unit dosages. The pharmaceutical compositions and unit dosage forms may be comprised of conventional ingredients in conventional proportions, with or without additional active compounds or principles, and the unit dosage forms may contain any suitable effective amount of the active ingredient commensurate with the intended daily dosage range to be employed. The pharmaceutical compositions may be employed as solids, such as tablets or filled capsules, semisolids, powders, sustained release formulations, or liquids such as solutions, suspensions, emulsions, elixirs, or filled capsules for oral use; or in the form of suppositories for rectal or vaginal administration; or in the form of sterile injectable solutions for parenteral use. Formulations containing about one (1) milligram of active ingredient or, more broadly, about 0.01 to about one hundred (100) milligrams, per tablet, are accordingly suitable representative unit dosage forms.

The compounds of the invention may be formulated in a wide variety of oral administration dosage forms. The pharmaceutical compositions and dosage forms may comprise a compound or compounds of the present invention or pharmaceutically acceptable salts thereof as the active component. The pharmaceutically acceptable carriers may be either solid or liquid. Solid form preparations include powders, tablets, pills, capsules, cachets, suppositories, and dispersible granules. A solid carrier may be one or more substances which may also act as diluents, flavouring agents, solubilizers, lubricants, suspending agents, binders, preservatives, tablet disintegrating agents, or an encapsulating material. In powders, the carrier generally is a finely divided solid which is a mixture with the finely divided active component. In tablets, the active component generally is mixed with the carrier having the necessary binding capacity in suitable proportions and compacted in the shape and size desired. The powders and tablets preferably contain from about one (1) to about seventy (70) percent of the active compound. Suitable carriers include but are not limited to magnesium carbonate, magnesium stearate, talc, sugar, lactose, pectin, dextrin, starch, gelatine, tragacanth, methylcellulose, sodium carboxymethylcellulose, a low melting wax, cocoa butter, and the like. The term "preparation" is intended to include the formulation of the active compound with encapsulating material as carrier, providing a capsule in which the active component, with or without carriers, is surrounded by a carrier, which is in association with it. Similarly, cachets and lozenges are included. Tablets, powders, capsules, pills, cachets, and lozenges may be as solid forms suitable for oral administration.

Other forms suitable for oral administration include liquid form preparations including emulsions, syrups, elixirs, aqueous solutions, aqueous suspensions, or solid form preparations which are intended to be converted shortly before use to liquid form preparations. Emulsions may be prepared in solutions, for example, in aqueous propylene glycol solutions or may contain emulsifying agents, for example, such as lecithin, sorbitan monooleate, or acacia. Aqueous solutions can be prepared by dissolving the active component in water and adding suitable colorants, flavors, stabilizers, and thickening agents. Aqueous suspensions can be prepared by dispersing the finely divided active component in water with viscous material, such as natural or synthetic gums, resins, methylcellulose, sodium carboxymethylcellulose, and other well known suspending agents. Solid form preparations include solutions, suspensions, and emulsions, and may contain, in addition to the active component, colorants, flavors, stabilizers, buffers, artificial and natural sweeteners, dispersants, thickeners, solubilizing agents, and the like.

The compounds of the invention may be formulated for parenteral administration (e.g., by injection, for example bolus injection or continuous infusion) and may be presented in unit dose form in ampoules, pre-filled syringes, small volume infusion or in multi-dose containers with an added preservative. The compositions may take such forms as suspensions, solutions, or emulsions in oily or aqueous vehicles, for example solutions in aqueous polyethylene glycol. Examples of oily or nonaqueous carriers, diluents, solvents or vehicles include propylene glycol, polyethylene glycol, vegetable oils (e.g., olive oil), and injectable organic esters (e.g., ethyl oleate), and may contain formulatory agents such as preserving, wetting, emulsifying or suspending, stabilizing and/or dispersing agents. Alternatively, the active ingredient may be in powder form, obtained by aseptic isolation of sterile solid or by lyophilization from solution for constitution before use with a suitable vehicle, e.g., sterile, pyrogen-free water.

The compounds of the invention may be formulated for topical administration to the epidermis as ointments, creams or lotions, or as a transdermal patch. Ointments and creams may, for example, be formulated with an aqueous or oily base with the addition of suitable thickening and/or gelling agents. Lotions may be formulated with an aqueous or oily base and will in general also containing one or more emulsifying agents, stabilizing agents, dispersing agents, suspending agents, thickening agents, or coloring agents. Formulations suitable for topical administration in the mouth include lozenges comprising active agents in a flavored base, usually sucrose and acacia or tragacanth; pastilles comprising the active ingredient in an inert base such as gelatine and glycerine or sucrose and acacia; and mouthwashes comprising the active ingredient in a suitable liquid carrier.

The compounds of the invention may be formulated for administration as suppositories. A low melting wax, such as a mixture of fatty acid glycerides or cocoa butter is first melted and the active component is dispersed homogeneously, for example, by stirring. The molten homogeneous mixture is then poured into convenient sized molds, allowed to cool, and to solidify.

The compounds of the invention may be formulated for vaginal administration. Pessaries, tampons, creams, gels, pastes, foams or sprays containing in addition to the active ingredient such carriers as are known in the art to be appropriate.

The subject compounds may be formulated for nasal administration. The solutions or suspensions are applied directly to the nasal cavity by conventional means, for example, with a dropper, pipette or spray. The formulations may be provided in a single or multidose form. In the latter case of a dropper or pipette, this may be achieved by the patient administering an appropriate, predetermined volume of the solution or suspension. In the case of a spray, this may be achieved for example by means of a metering atomizing spray pump.

The compounds of the invention may be formulated for aerosol administration, particularly to the respiratory tract and including intranasal administration. The compound will generally have a small particle size for example of the order of five (5) microns or less. Such a particle size may be obtained by means known in the art, for example by micronization. The active ingredient is provided in a pressurized pack with a suitable propellant such as a chlorofluorocarbon (CFC), for example, dichlorodifluoromethane, trichlorofluoromethane, or dichlorotetrafluoroethane, or carbon dioxide or other suitable gas. The aerosol may conveniently also contain a surfactant such as lecithin. The dose of drug may be controlled by a metered valve. Alternatively the active ingredients may be provided in a form of a dry powder, for example a powder mix of the compound in a suitable powder base such as lactose, starch, starch derivatives such as hydroxypropylmethyl cellulose and polyvinylpyrrolidine (PVP). The powder carrier will form a gel in the nasal cavity. The powder composition may be presented in unit dose form for example in capsules or cartridges of e.g., gelatine or blister packs from which the powder may be administered by means of an inhaler.

When desired, formulations can be prepared with enteric coatings adapted for sustained or controlled release administration of the active ingredient. For example, the compounds of the present invention can be formulated in transdermal or subcutaneous drug delivery devices. These delivery systems are advantageous when sustained release of the compound is necessary and when patient compliance with a treatment regimen is crucial. Compounds in transdermal delivery systems are frequently attached to an skin-adhesive solid support. The compound of interest can also be combined with a penetration enhancer, e.g., Azone (1-dodecylazacycloheptan-2-one). Sustained release delivery systems are inserted subcutaneously into the subdermal layer by surgery or injection. The subdermal implants encapsulate the compound in a lipid soluble membrane, e.g., silicone rubber, or a biodegradable polymer, e.g., polylactic acid.

The pharmaceutical preparations are preferably in unit dosage forms. In such form, the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

Other suitable pharmaceutical carriers and their formulations are described in *Remington: The Science and Practice of Pharmacy* 1995, edited by E. W. Martin, Mack Publishing Company, 19th edition, Easton, Pa. Representative pharmaceutical formulations containing a compound of the present invention are described below.

EXAMPLES

The following preparations and examples are given to enable those skilled in the art to more clearly understand and to practice the present invention. They should not be considered as limiting the scope of the invention, but merely as being illustrative and representative thereof.

Preparation 1

N-(2-(R)-Hydroxy-1-methyl-ethyl)-guanidine

Step 1

Bis-benzyloxycarbonyl-N-(2-(R)-Hydroxy-1-methyl-ethyl)-guanidine

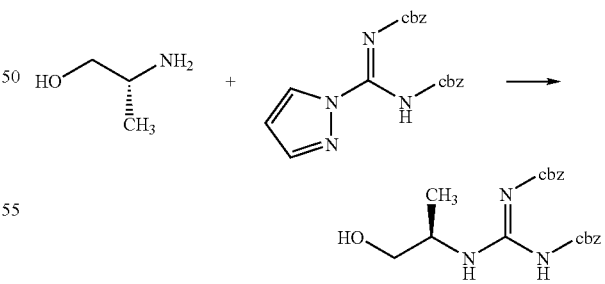

To a solution of R-(−)-2-amino-1-propanol (0.59 g, 8.0 mmol) in 50 mL THF was added pyrrazole carboxamidine (3.0 g, 8.0 mmol, prepared as described by M. S. Berbatowicz et al., *Tetrahedron,* 34 1993 p.3389). After 16 hours the mixture was concentrated in vacuo. Purification via flash chromatography (93:7 ethyl acetate/$CH_2Cl_2$) afforded bis-benzyloxycarbonyl-N-(2-(R)-hydroxy-1-methyl-ethyl)-guanidine (3.0 g, 97%) as a white solid.

Step 2

N-(2-(R)-Hydroxy-1-methyl-ethyl)-guanidine

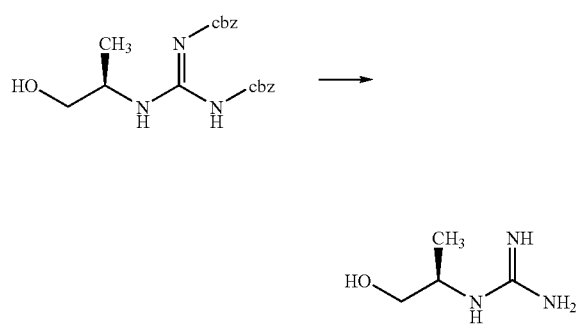

To a solution of bis-benzyloxycarbonyl-N-(2-(R)-hydroxy-1-methyl-ethyl)-guanidine in 75 mL EtOH was added 10% Pd/C (0.10 g). The mixture was stirred under 1 Atmosphere of $H_2$. After 16 hours the mixture was filtered through a pad of celite and concentrated in vacuo to give N-(2-(R)-hydroxy-1-methyl-ethyl)-guanidine (0.44 g, 69%).

Using the appropriate amines with the above procedure, the following guainidine compounds were also prepared:

N-(3-Ethanesulfonyl-1-methyl-propyl)-guanidine;
4-Guanidino-piperidine-1-carboxylic acid ethyl ester;
N-(1-Cyclopropyl-ethyl)-guanidine;
N-(Tetrahydro-thiopyran-4-yl)-guanidine;
N-[2-(4-Acetyl-piperazin-1-yl)-1-methyl-ethyl]-guanidine;
N-(1-Hydroxymethyl-propyl)-guanidine
N-(1-Methanesulfonyl-piperidin-4-yl)-guanidine; and
N-[3-Hydroxy-1-(2-hydroxy-ethyl)-propyl]-guanidine.

Example 1

5-[4,5-Dimethoxy-2-(1-methyl-2-phenyl-ethyl)-benzyl]-pyrimidine-2,4-diamine

The synthetic procedure used in this Example is outlined in Scheme D.

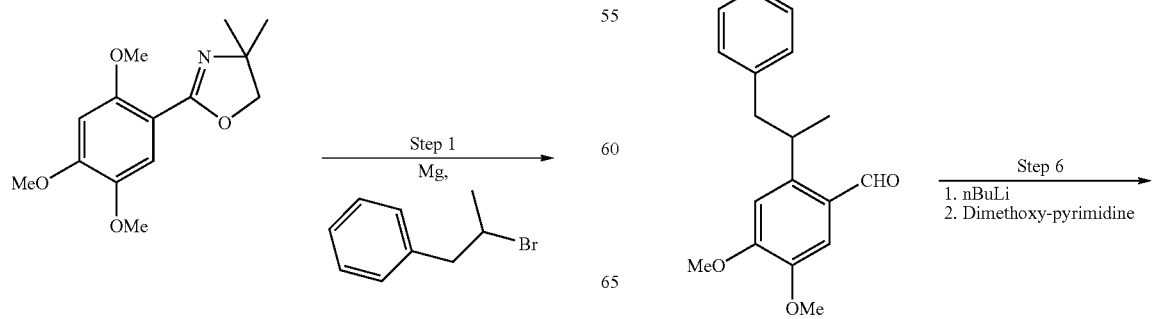

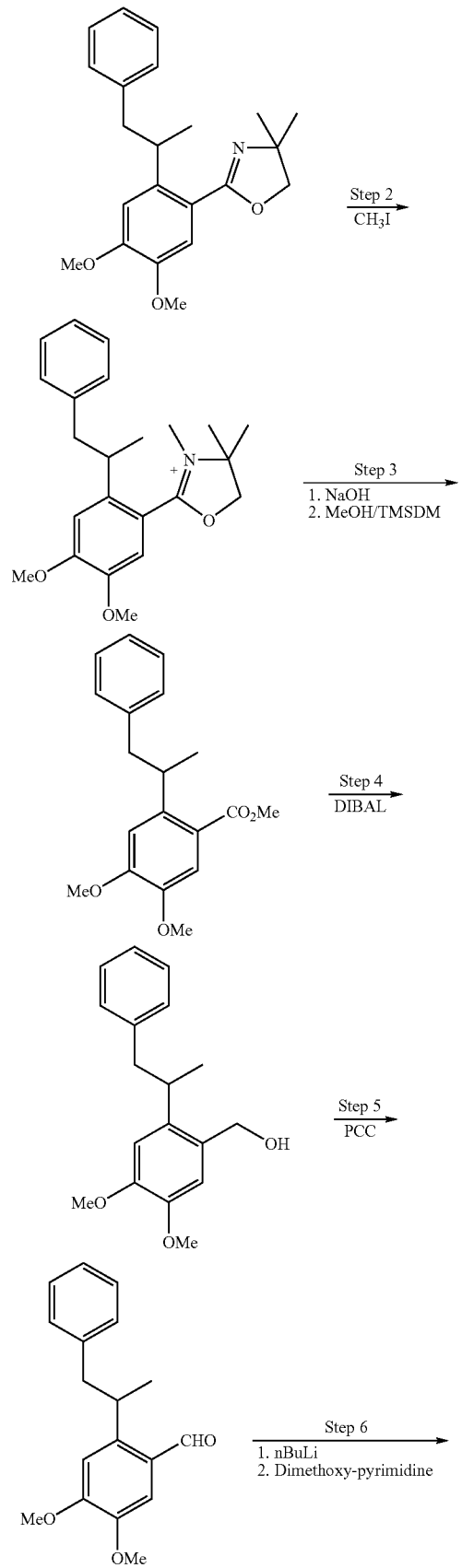

-continued

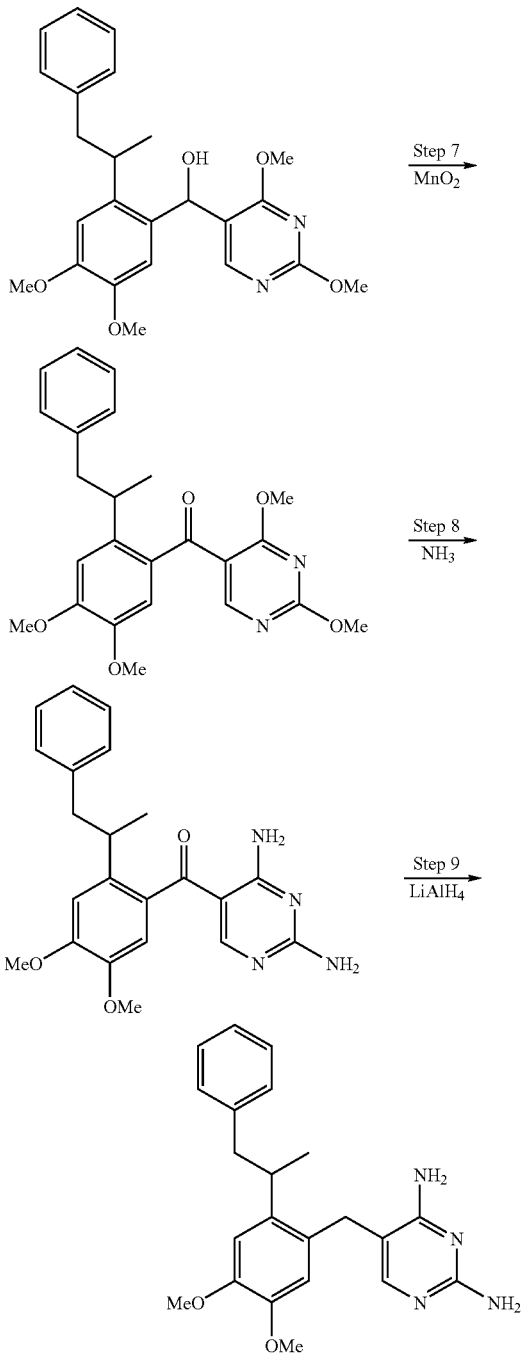

Step 1. 2-[4,5-Dimethoxy-2-(1-methyl-2-phenyl-ethyl)-phenyl]-4,4-dimethyl4,5-dihydro-oxazole

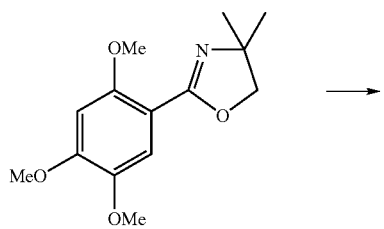

-continued

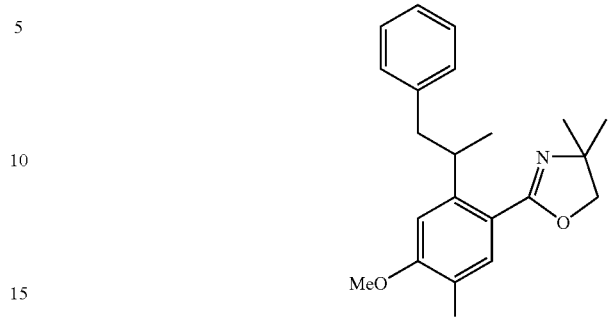

The 4,4-dimethyl-2-(2,4,5-trimethoxy-phenyl)-4,5-dihydro-oxazole oxazoline used in this step was prepared according to the procedure reported by Meyers, A. I. et al., *J Org Chem* 43 1978,pp.1372-1379.

To a rapidly stirring suspension of magnesium turnings (1.32 g, 54.5 mol) and in 35 mL tetrahydrofuran (THF) was added 1,2-dibromoethane (0.10 mL) in one portion. 2-bromo-1-phenylpropane (10.86 g, 54.5 mmol) was added at a rate that maintained the internal temperature at 40 °C. After 2.5 hours the cloudy suspension was transferred via canula to a solution of 4,4-dimethyl-2-(2,4,5-trimethoxy-phenyl)-4,5-dihydro-oxazole oxazoline (10.013 g, 36.4 mmol) in 50 mL THF. After 18 hours the solution cooled to 0° C. and quenched by the slow addition of 10% NH$_4$Cl. 500 mL H$_2$O was added and the mixture was extracted with ethyl acetate, washed with H$_2$O, and washed with brine. The combined organics were dried over Na$_2$SO$_4$, filtered and concentrated in vacuo to give a crude solid. Purifications via flash chromatography (4:1 hexane/ethyl acetate) afforded 2-[4,5-dimethoxy-2-(1-methyl-2-phenyl-ethyl)-phenyl]-4,4-dimethyl-4,5-dihydro-oxazole as a clear viscous oil (7.833 g, 41%).

Step 2. 2-[4,5-Dimethoxy-2-(1-methyl-2-phenyl-ethyl)-phenyl]-3,4,4-trimethyl-4,5-dihydro-oxazolium iodide

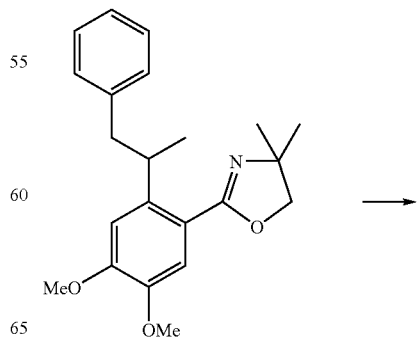

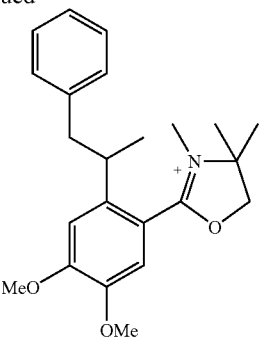

To a solution of 2-[4,5-dimethoxy-2-(1-methyl-2-phenyl-ethyl)-phenyl]-4,4-dimethyl-4,5-dihydro-oxazole (7.515 g, 21.3 mmol) in 50 mL NO₂CH₃ was added iodomethane (2.65 mL, 42.5 mmol). The solution was warmed to 110 ° C. After 3 hours the solution was cooled and concentrated in vacuo to give 2-[4,5-dimethoxy-2-(1-methyl-2-phenyl-ethyl)-phenyl]-3,4,4-trimethyl-4,5-dihydro-oxazolium iodide (10.108 g) as an orange solid.

Step 3.
4,5-Dimethoxy-2-(1-methyl-2-phenyl-ethyl)-benzoic acid methyl ester

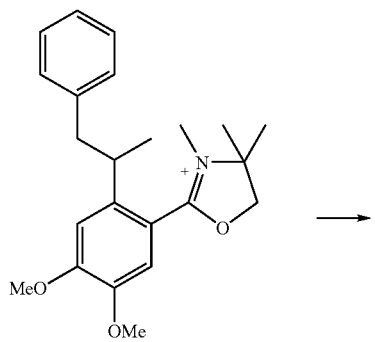

To a solution of 2-[4,5-dimethoxy-2-(1-methyl-2-phenyl-ethyl)-phenyl]-3,4,4-trimethyl-4,5-dihydro-oxazolium iodide (5.132 g, 10.4 mmol) in 52 mL methanol was added 4 M NaOH (5.2 mL, 20.7 mmol). The solution was warmed to reflux. After 16 hours the solution was cooled to 0° C. and acidified to pH=1 with concentrated HCl. The mixture was extracted with ethyl acetate, washed with H₂O and washed with brine. The combined organics were dried over Na₂SO₄, filtered and concentrated in vacuo to give a crude acid (3.228 g). A portion of this acid (2.919 g, 9.73 mmol) was dissolved in a mixture of 70 mL benzene and 20 mL MeOH. Trimethylsilyldiazomethane (6.3 mL, 2.0 M in hexanes) was added drop-wise. After 30 minutes the solution was concentrated in vacuo to give 4,5-dimethoxy-2-(1-methyl-2-phenyl-ethyl)-benzoic acid methyl ester as an oil (2.886 g).

Step 4. [4,5-Dimethoxy-2-(1-methyl-2-phenyl-ethyl)-phenyl]-methanol

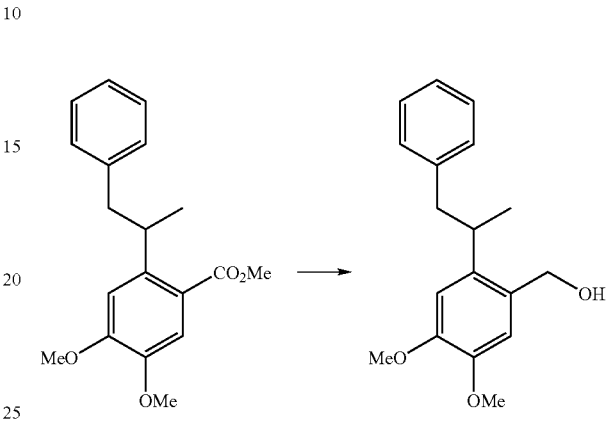

Diisobutyl aluminum hydride (22.9 mL, 1.0 M in THF) was added to a solution of 4,5-dimethoxy-2-(1-methyl-2-phenyl-ethyl)-benzoic acid methyl ester (2.886 g, 9.2 mmol) in 100 mL THF at −78° C. over 10 min. The mixture was allowed to stir for 1 h and warmed to room temperature. After 1.5 hours the mixture was quenched by the slow addition of 50 mL saturated Rochelle's salt. After rapidly stirring for 30 minutes the mixture was filtered through a pad of celite and concentrated in vacuo. H₂O was added and the slurry was extracted with ethyl acetate, washed with H₂O and washed with brine. The combined organics were dried over Na₂SO₄, filtered and concentrated in vacuo to give a crude oil. Purification via flash chromatography (3:1 hexane/ethyl acetate) afforded [4,5-dimethoxy-2-(1-methyl-2-phenyl-ethyl)-phenyl]-methanol as a clear oil (1.269 g, 48%).

Step 5. 4,5-Dimethoxy-2-(1-methyl-2-phenyl-ethyl)-benzaldehyde

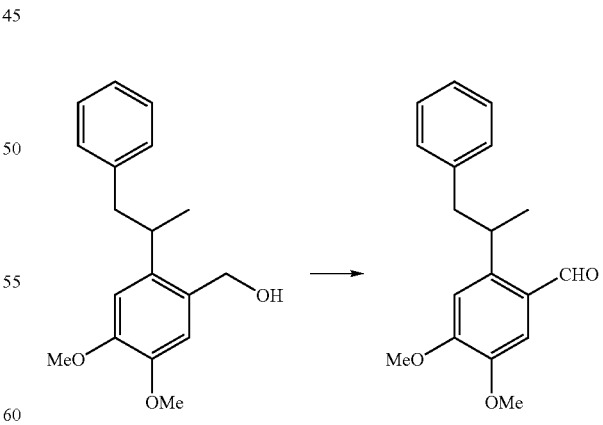

A solution of pyridinium chlorochromate (1.253 g, 5.8 mmol) in 40 mL CH₂Cl₂ was cooled to 0° C. [4,5-Dimethoxy-2-(1-methyl-2-phenyl-ethyl)-phenyl]-methanol (1.110 g, 3.88 mmol) in 5.0 mL CH₂Cl₂ was added drop-wise and allowed to stir for 45 minutes. The mixture was diluted in 200 mL Et₂O, filtered through celite and concentrated in vacuo to

143 afford a dark brown oil. Purification via flash chromatography (9:1 hexane/ethyl acetate) gave 4,5-dimethoxy-2-(1-methyl-2-phenyl-ethyl)-benzaldehyde (0.840 g, 76%) as a clear oil.

Step 6. [4,5-Dimethoxy-2-(1-methyl-2-phenyl-ethyl)-phenyl]-(2,4-dimethoxy-pyrimidin-5-yl)-methanol

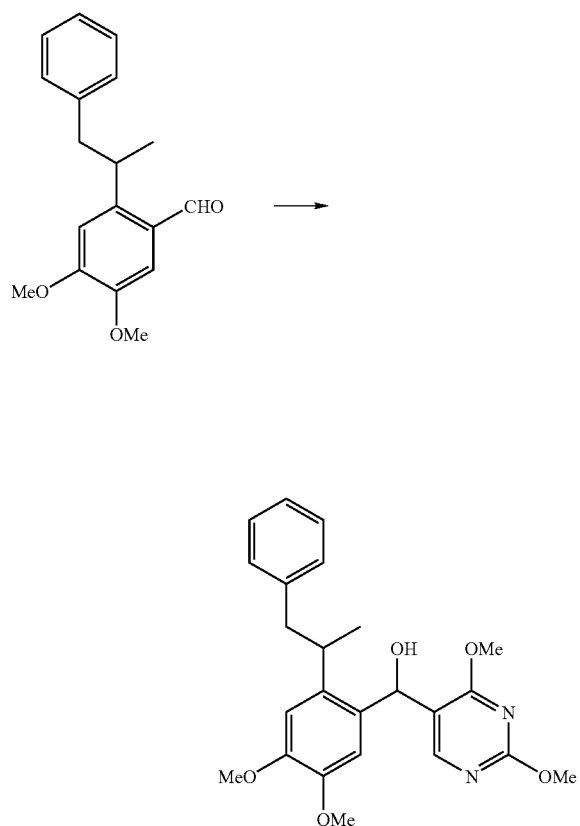

Freshly distilled 2,2,6,6-tetramethyl piperidine (0.85 mL, 5.0 mmol) was dissolved in 20 mL THF and cooled to 0° C. n-Butyllithium (2.0 mL, 2.5 M in hexanes) was added dropwise over 5 minutes and the mixture was allowed to stir for 30 minutes and then cooled to −78° C. 2,4-Dimethoxypyrimidine (0.353 g, 2.52 mmol) was added drop-wise over 5 min. After 45 min the solution was transferred via a dry ice cooled cannula to a solution of 4,5-dimethoxy-2-(1-methyl-2-phenyl-ethyl)-benzaldehyde (0.717 g, 2.52 mmol) in 20 mL THF at −78° C. After stirring for 1 hour the solution was warmed to room temperature and quenched by the slow addition of 50 mL 10% NH$_4$Cl. After 100 mL of H$_2$O was added the mixture was extracted with ethyl acetate, washed with H$_2$O and washed with brine. The combined organics were dried over Na$_2$SO$_4$, filtered and concentrated in vacuo to give an orange oil. Purification via flash chromatography (3:2 hexane/ethyl acetate) afforded [4,5-dimethoxy-2-(1-methyl-2-phenyl-ethyl)-phenyl]-(2,4-dimethoxy-pyrimidin-5-yl)-methanol (0.551 g, 52%) as a clear oil.

144

Step 7. [4,5-Dimethoxy-2-(1-methyl-2-phenyl-ethyl)-phenyl]-(2,4-dimethoxy-pyrimidin-5-yl)-methanone

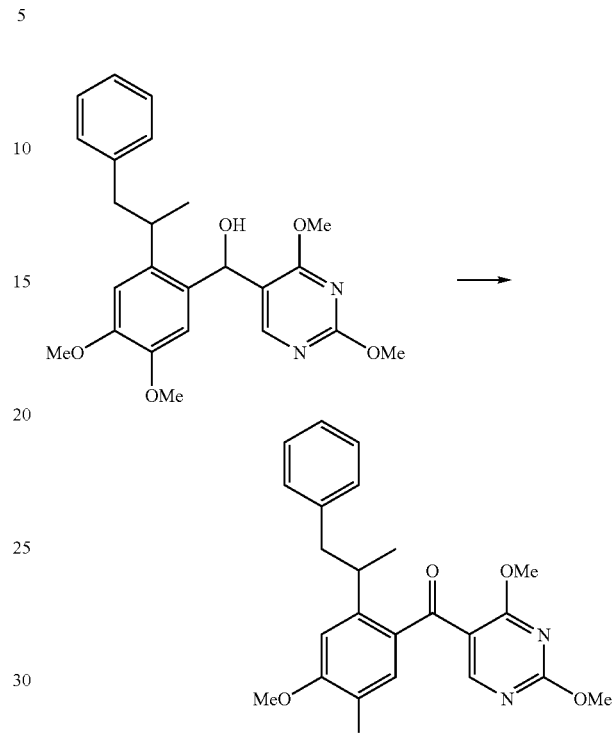

To a solution of [4,5-dimethoxy-2-(1-methyl-2-phenyl-ethyl)-phenyl]-(2,4-dimethoxy-pyrimidin-5-yl)-methanol (0.418 g, 0.9 mmol) in 20 mL toluene was added MnO$_2$ (0.335 g, 4.7 mmol). The mixture was warmed to reflux and H$_2$O was removed via a Dean-Stark trap. After 1 hour the mixture was cooled, filtered through a pad of celite and concentrated in vacuo to give a crude oil. Purification via flash chromatography (7:3 hexane/ethyl acetate) afforded [4,5-dimethoxy-2-(1-methyl-2-phenyl-ethyl)-phenyl]-(2,4-dimethoxy-pyrimidin-5-yl)-methanone (0.258 g, 62%) as a clear oil.

Step 8. (2,4-Diamino-pyrimidin-5-yl)-[4,5-dimethoxy-2-(1-methyl-2-phenyl-ethyl)-phenyl]-methanone

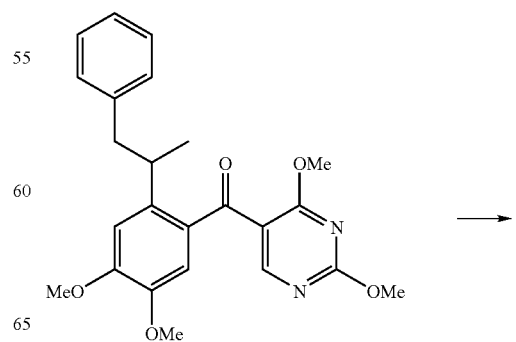

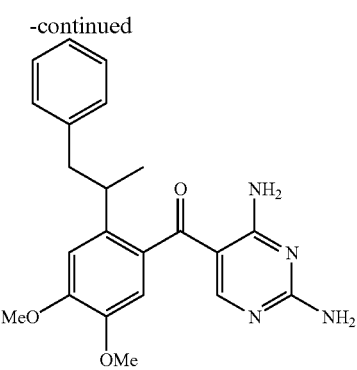

A solution of [4,5-dimethoxy-2-(1-methyl-2-phenyl-ethyl)-phenyl]-(2,4-dimethoxy-pyrimidin-5-yl)-methanone (0.212 g, 0.5 mmol) in 5.0 mL MeOH was added to ammonia (15 mL, 7.0M in MeOH) in a sealed tube. The mixture was heated to 80° C. After 16 hours the solution was cooled and concentrated in vacuo to give a dark solid. Purification via flash chromatography (95:5 CH$_2$Cl$_2$/MeOH) afforded (2,4-diamino-pyrimidin-5-yl)-[4,5-dimethoxy-2-(1-methyl-2-phenyl-ethyl)-phenyl]-methanone (0.162 g, 86%) as a white solid.

Step 9. 5-[4,5-Dimethoxy-2-(1-methyl-2-phenyl-ethyl)-benzyl]-1-pyrimidine-2,4-diamine

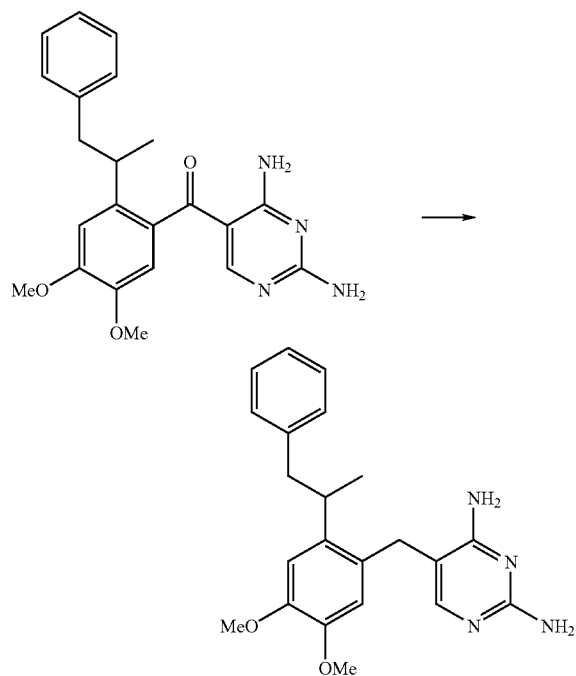

To a solution of (2,4-diamino-pyrimidin-5-yl)-[4,5-dimethoxy-2-(1-methyl-2-phenyl-ethyl)-phenyl]-methanone (0.413 g, 0.4 mmol) in 10 mL THF was added LiAlH$_4$ (0.73 mL, 1.0 M in THF) over 5 min. After gas evolution ceased the mixture was warmed to reflux. After 3 h the mixture was cooled to 0° C. and quenched by the Fieser method. After 30 min the mixture was filtered through a pad of celite and concentrated in vacuo to give a crude white solid. To a solution of this solid in 5 mL CH$_2$Cl$_2$ was added trifluoroacetic acid (1.1 mL, 14.0 mmol) followed by triethylsilane (0.4 mL, 2.8 mmol). After 30 min 50 mL 10% K$_2$CO$_3$ was as added and the mixture was extracted with ethyl acetate and washed with brine. The combined organics were dried over Na$_2$SO$_4$, filtered and concentrated in vacuo. Purification via flash chromatography (95:5 CH$_2$Cl$_2$) afforded 5-[4,5-dimethoxy-2-(1-methyl-2-phenyl-ethyl)-benzyl]-pyrimidine-2,4-diamine (0.066 g, 58%) as a white foam; melting point (HCl salt) 227.1-227-4° C.

Using the procedure of Example 1 described above, but replacing 2-bromo-1-phenyl propane in step 1 with 2-bromopropane or other alkyl bromides, and replacing ammonia in step 8 with various alkyl or benzyl amines, afforded a variety of compounds under essential the same reaction conditions. Additional compounds are prepared using the procedure outlined in Example 1 are shown in Table 1.

Example 2

5-(5-Bromo-2-isopropyl-4-methoxy-phenoxy)-pyrimidine-2,4-diamine

The synthetic procedure used in this Example is outlined in Scheme E.

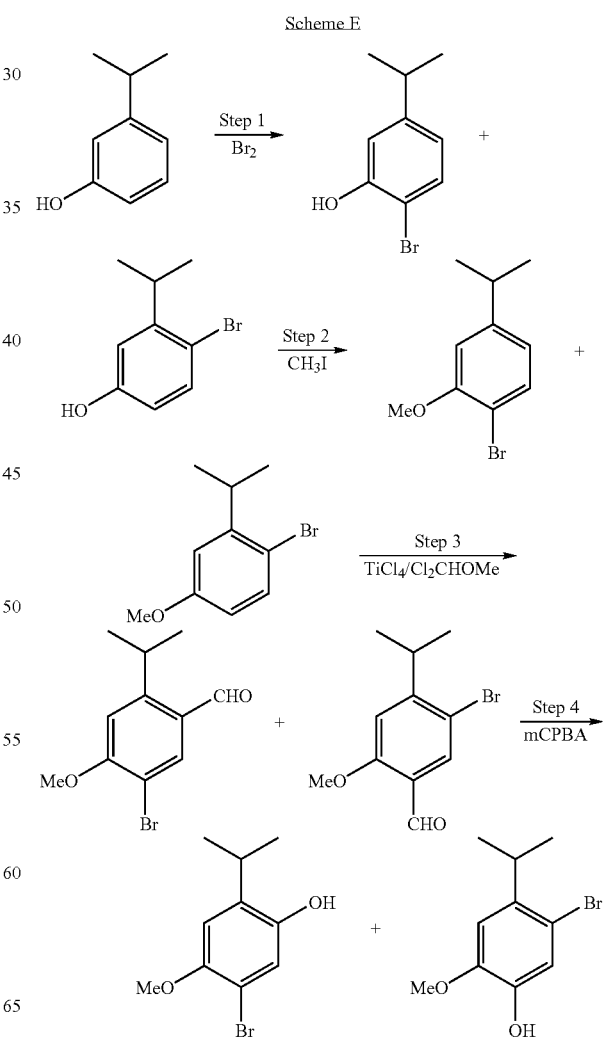

147

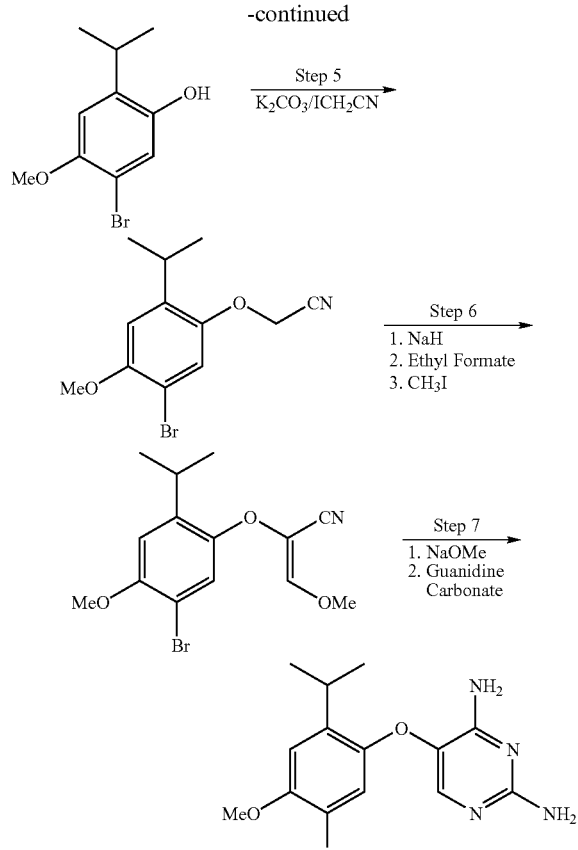

Step 1. 2-Bromo-5-isopropyl-phenol

A solution of 3-isopropyl phenol (4.975 g, 36.5 mmol) in 37 mL of CCl$_4$ was cooled to −20° C. Bromine (1.9 mL, 38.4 mmol) was dissolved in 5.0 mL CCl$_4$ and added drop-wise at such a rate that the internal temperature was maintained below −10° C. The mixture was allowed to warm to room temperature. After 12 hours the mixture was taken up in 100 mL CH$_2$Cl$_2$, washed with H$_2$O and then with brine. The combine organics were dried over Na$_2$SO$_4$, filtered and concentrated in vacuo to give 8.663 g of a 1:1 mixture of 2-bromo-5-isopropyl-phenol and 4-bromo-5-isopropyl phe-

148 nol as a dark oil). These two isomers were inseparable and were used together in step 2 below.

Step 2. 1-Bromo-4-isopropyl-2-methoxy-benzene

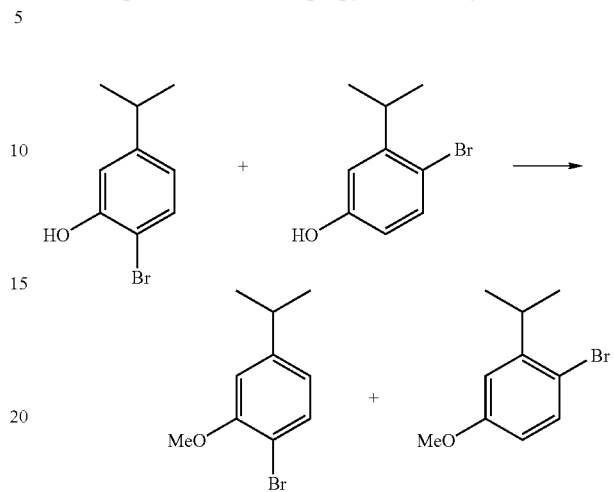

To a mixture of 2-bromo-5-isopropyl-phenol and 4-bromo-5-isopropyl phenol from step 1 (8.663 g, 40.3 mmol), K$_2$CO$_3$ (16.710 g, 120.9 mmol) in 50 mL DMF, was added iodomethane (3.0 mL, 48.3 mmol) with mechanical stirring. The mixture was warmed to 50° C. for 4 hours. After cooling to room temperature 300 mL H$_2$O was added and the solution was extracted with diethyl ether (Et$_2$O), washed with H$_2$O and washed with brine. The combined organics were dried over MgSO$_4$, filtered and concentrated in vacuo to give 1-bromo-4-isopropyl-2-methoxy-benzene and 1-bromo-2-isopropyl4-methoxy-benzene (6.621 g, 72%) as a 1:1 inseparable mixture in the form of a pale yellow oil. This mixture of regioisomers was used directly in step 3 below.

Step 3.
5-Bromo-2-isopropyl-4-methoxy-benzaldehyde

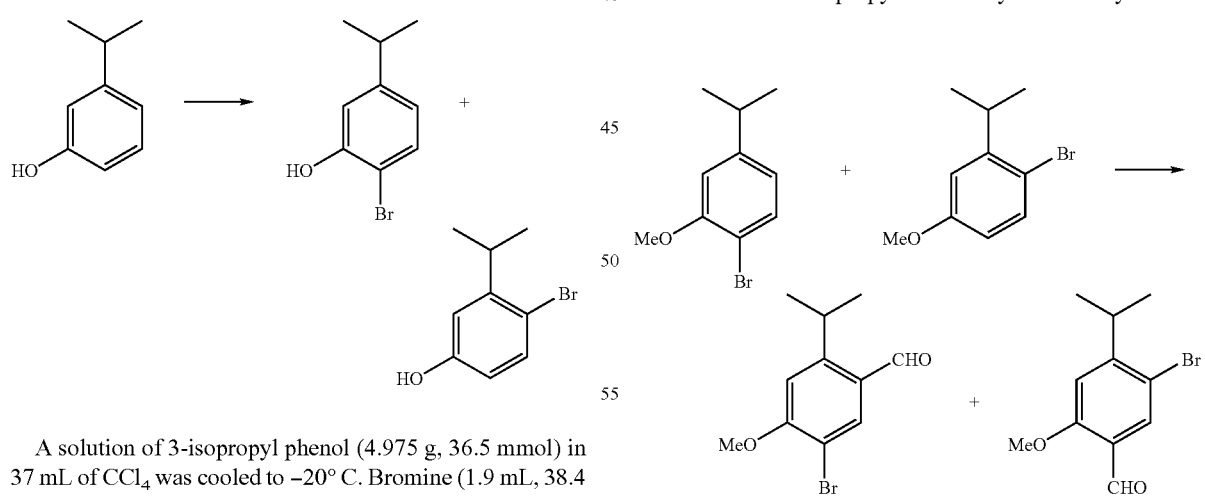

To a solution of 1-bromo-4-isopropyl-2-methoxy-benzene and 1-bromo-2-isopropyl-4-methoxy-benzene from step 2 (6.621 g, 28.9 mmol) in 100 mL 1,2 dichloroethane was added TiCl$_4$ (6.3 mL, 57.8 mmol) at 0° C. After 10 minutes, dichloromethoxymethane (Cl$_2$CHOMe) (2.6 mL, 28.9 mmol) was added and the mixture was warmed to reflux. After 3 hours the mixture was cooled poured over ice and acidified with 50 mL 2 M HCl. The resulting slurry was extracted with CH₂Cl₂, and washed with brine. The combined organics were dried over MgSO₄, filtered and concentrated in vacuo to give a dark-green oil. Purification via flash chromatography (96:4 hexane/ethyl acetate) afforded 5-bromo-2-isopropyl-4-methoxy-benzaldehyde and 5-bromo-4-isopropyl-2-methoxy-benzaldehyde (2.876 g, 39%, 6.621 g, 72%) as a 1:1 mixture of inseparable isomers in the form of an orange oil, which was used directly in step 4.

Step 4. 5-Bromo-2-isopropyl4-methoxy-phenol

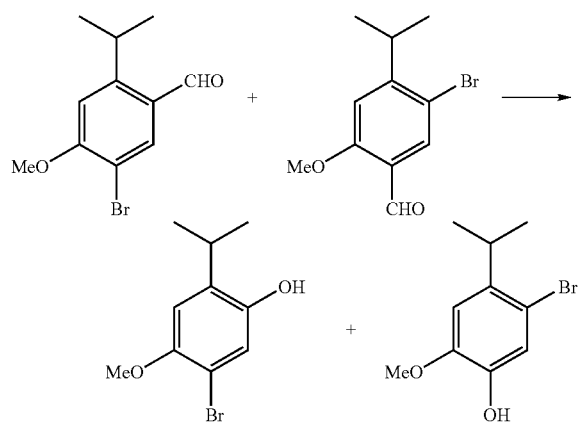

To a solution of 5-bromo-2-isopropyl4-methoxy-benzaldehyde and 5-bromo4-isopropyl-2-methoxy-benzaldehyde from step 3 (2.87 g, 11.2 mmol) in 25 mL CH₂Cl₂ was added mCPBA (2.31 g, 13.4 mmol). After 16 hours the mixture was taken up in 150 ml CH₂Cl₂ and washed with sat NaHCO₃, and then with brine. The combined organic layers were dried over Na₂SO₄, filtered and concentrated in vacuo to give an oil that was taken up in 50 mL MeOH and 30 mL 4M NaOH. After 2 hours the mixture was evaporated, diluted with water and acidified to pH=1 with concentrated HCl. The mixture was extracted with ethyl acetate (3×100 mL) and washed with 100 mL brine. The combined organics were dried over Na₂SO₄, filtered and evaporated to give a mixture of 5-bromo-2-isopropyl-4-methoxy-phenol and 2-bromo-5-isopropyl-4-methoxy-phenol as an orange residue. These regioisomers were separable by flash chromatography (gradient:hexane, 7:3, 1:1 hexane/CH₂Cl₂) to afford 5-bromo-2-isopropyl-4-methoxy-phenol (0.929, 34%) as a yellow oil which was used in the following step, and 2-bromo-5-isopropyl-4-methoxy-phenol (0.404 g, 15%) as a yellow solid.

Step 5. (5-Bromo-2-isopropyl-4-methoxy-phenoxy)-acetonitrile

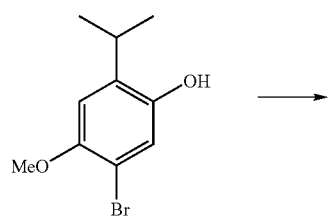

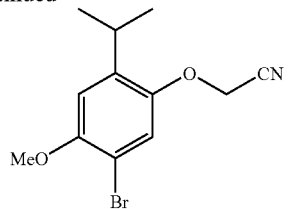

To a mixture of 5-bromo-2-isopropyl-4-methoxy-phenol from step 4 (0.831 g, 3.4 mmol) and K₂CO₃ (0.562 g, 4.1 mmol) in 17 mL dimethyl formamide (DMF) was added iodoacetonitrile (0.594 g, 3.6 mmol). The mixture was warmed to 60° C. for 30 minutes and then allowed to cool to room temperature. After cooling to room temperature the mixture was taken up in 50 mL of H₂O and extracted with 1:1 toluene/ethyl acetate, washed with H₂O and then with brine. The combined organic layers were dried over Na₂SO₄, filtered and conectrated in vacuo to give a crude solid. Purification via flash chromatography (1:1 hexane/CH₂Cl₂) afforded (5-bromo-2-isopropyl-4-methoxy-phenoxy)-acetonitrile (0.611 g, 63%) as a while solid.

Step 6. 2-(5-Bromo-2-isopropyl-4-methoxy-phenoxy)-3-methoxy-acrylonitrile

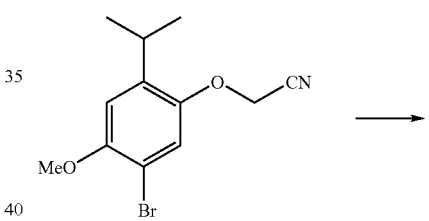

Sodium hydride (0.122 g, 5.0 mmol, 60% w/w) was washed with dry hexanes and evaporated under a stream of nitrogen. 10 mL THF was added and the mixture was cooled to 0° C. (5-Bromo-2-isopropyl-4-methoxy-phenoxy)-acetonitrile (0.577 g, 2.03 mmol) was added in portions. After 30 min ethyl formate (4.9 mL, 60.9 mmol) was added and the solution was warmed to 80° C. After 4.5 hours the mixture was cooled and 5.0 mL iodomethane was added in one portion. After 16 hours the solution was quenched with H₂O, concentrated in vacuo, extracted with ethyl acetate, washed with H₂O and then washed with brine. The combined organic layers were dried over Na₂SO₄, filtered and concentrated in vacuo. Purification via flash chromatography (9:1 hexane/ethyl acetate) afforded 2-(5-bromo-2-isopropyl-4-methoxy-phenoxy)-3-methoxy-acrylonitrile (0.319 g, 48%) as a white solid.

Step 7. 5-(5-Bromo-2-isopropyl-4-methoxy-phenoxy)-pyrimidine-2,4-diamine

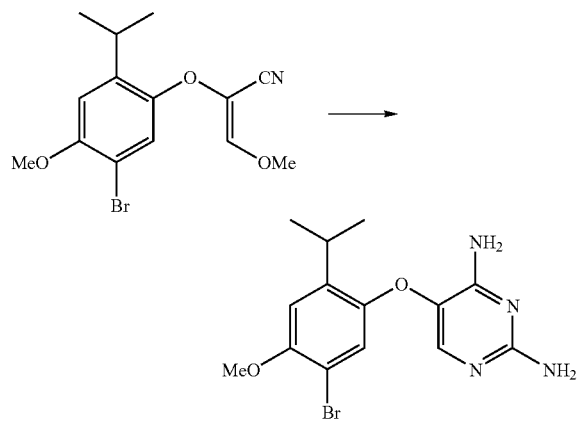

To a solution of 2-(5-bromo-2-isopropyl-4-methoxy-phenoxy)-3-methoxy-acrylonitrile (0.282 g, 0.9 mmol) and guanidine carbonate (0.078 g, 0.4 mmol) in 10.0 mL dimethyl sulfoxide (DMSO) was added sodium methoxide (1.0 mL, 1.0M in MeOH). The mixture was warmed to 120° C. The methanol was collected via a short-path condenser. After 3 h the mixture was cooled and concentrated in vacuo to give a crude oil. Purification via flash chromatography (95:5 CH$_2$Cl$_2$/MeOH) afforded 17 (0.246 g, 77%) as a pink solid; Mass Spec M+H=352. The above procedure may be used with various different phenols in step 1 and/or substituted guanidines in step 7 under essentially the same reaction conditions to produce additional compounds. Additional compounds made according to the procedure of Example 2 are shown in Table 1.

Example 3

N*4*-Ethyl-5-(2-isopropyl-4,5-dimethoxy-benzyl)-pyrimidine-2,4-diamine

The synthetic procedure used in this Example is outlined in Scheme F.

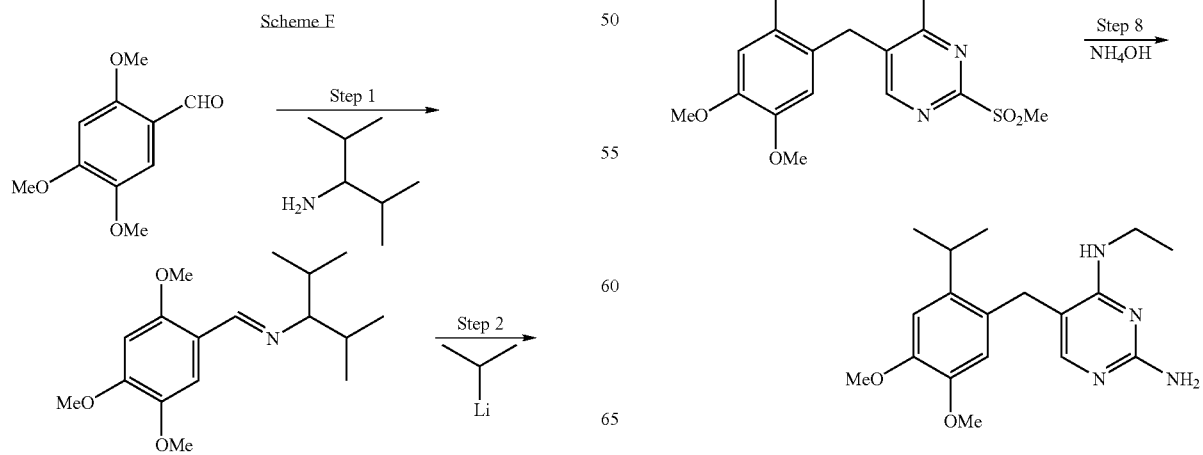

Step 1. (1-Isopropyl-2-methyl-propyl)-(2,4,5-tri-methoxy-benzylidene)-amine

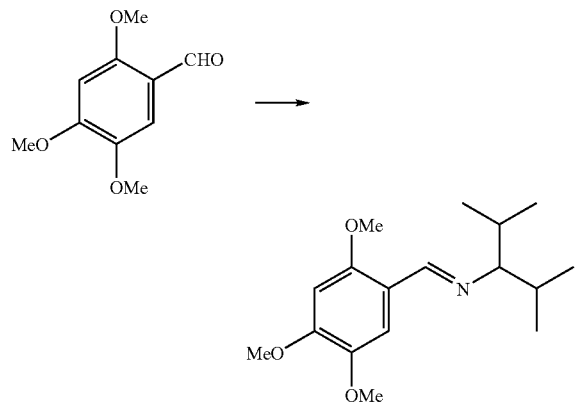

To a solution of 2,4,5-trimethoxybenzaldehyde (20.10 g, 102.4 mmol) in 200 mL of toluene was added 2,4-dimethyl-pentyl-3-amine and p-toluene sulfonic acid (0.1 g). The mixture was warmed to reflux. The generated $H^2O$ as removed with a Dean-Stark trap. After 3 h, the solution was cooled, washed with 50 mL saturated $NaHCO_3$, dried over $Na_2SO_4$ and filtered. The solution was concentrated in vacuo to give a yellow syrup. Purification via Kügel-Rhor distillation (80° C., 200 mTorr) gave (1-isopropyl-2-methyl-propyl)-(2,4,5-trimethoxy-benzylidene)-amine (28.70 g, 96% ) as a pale yellow solid.

Step 2. (2-Isopropyl-4,5-dimethoxy-benzylidene)-(1-isopropyl-2-methyl-propyl)-amine

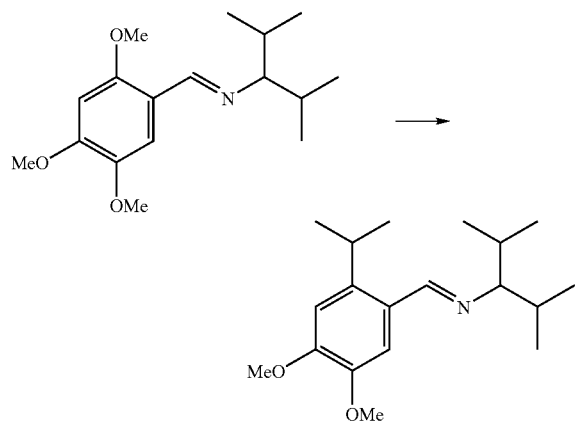

To a solution of (1-isopropyl-2-methyl-propyl)-(2,4,5-trimethoxy-benzylidene)-amine (1.024 g, 3.5 mmol) in 35 ml THF at −78° C. was added isopropyllithium (6.0 mL, 0.7 M in pentane) drop-wise over 5 minutes. The solution was allowed to stir 30 min at −78° C. After warming to room temperature over 45 minutes the mixture was quenched by the addition of 5 mL of 10% $NH_4Cl$ and concentrated in vacuo. 100 mL of $H_2O$ was added and the mixture was extracted with ethyl acetate, washed with $H_2O$ and then brine. The combined organic layers were dried over $Na_2SO_4$, filtered and concentrated in vacuo to give (2-isopropyl4,5-dimethoxy-benzylidene)-(1-isopropyl-2-methyl-propyl)-amine as a yellow oil.

Step 3. 2-Isopropyl-4,5-dimethoxy-benzaldehyde

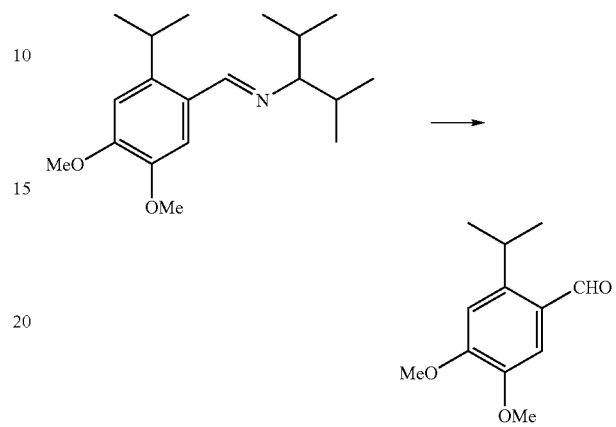

(2-Isopropyl-4,5-dimethoxy-benzylidene)-(1-isopropyl-2-methyl-propyl)-amine was dissolved in 30 ml of THF. HCl (4.1 mL, 4 M) was added and the mixture was warmed to reflux. After 3 hours the mixture was cooled concentrated in vacuo. 100 mL of $H_2O$ was added and the mixture was extracted with ethyl acetate, washed with $H_2O$ and then with brine. The combined organic layers were dried over $Na_2SO_4$, filtered and concentrated in vacuo to give an orange oil. Purification via flash chromatography (85:15 hexane/ethyl acetate) gave 2-isopropyl-4,5-dimethoxy-benzaldehyde (0.331 g, 43%) as a clear oil

Step 4. (4-Chloro-2-methylsulfanyl-pyrimidin-5-yl)-(2-isopropyl-4,5-dimethoxy-phenyl)-methanol

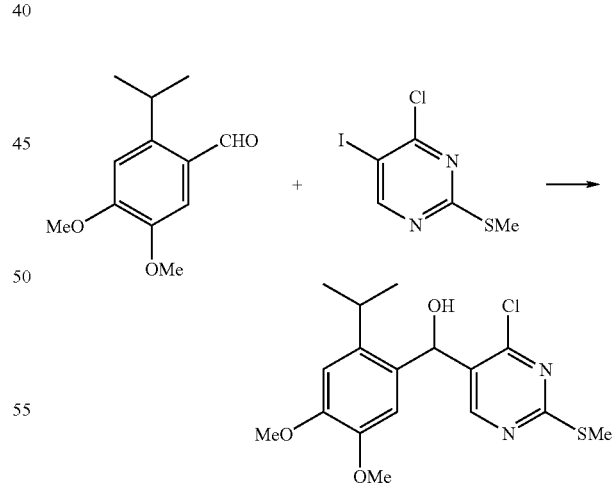

The 4-chloro-5-iodo-2-methylsulfanyl-pyrimidine used in this step was prepared according to the procedure described by T. Sakamoto, et al., Chem. Pharm. Bull., 34 1986, p. 2719.

To a solution of 4-chloro-5-iodo-2-methylsulfanyl-pyrimidine (1.10 g, 3.9 mmol) in 20 mL THF at −40° C. was added isopropyl magnesium bromide (2.3 mL, 2 M in THF) ) over 5 minutes. After 30 minutes, 2-isopropyl-4,5-dimethoxy-benzaldehyde from step 3 (1.04 g, 4.6 mmol) was added and the solution was warmed to room temperature. The mixture was quenched by the addition of brine, and extracted with CH$_2$Cl$_2$. The combined organic layers were dried over Na$_2$SO$_4$, filtered and concentrated in vacuo. Purification via flash chromatography (ethyl acetate) afforded (4-chloro-2-methylsulfanyl-pyrimidin-5-yl)-(2-isopropyl-4,5-dimethoxy-phenyl)-methanol (1.168 g, 82%) as a light yellow solid.

Step 5. 4-Chloro-5-(2-isopropyl-4,5-dimethoxy-benzyl)-2-methylsulfanyl-pyrimidine

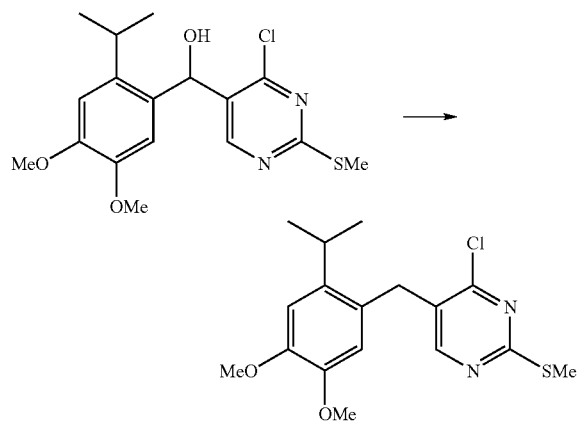

To a solution of (4-chloro-2-methylsulfanyl-pyrimidin-5-yl)-(2-isopropyl-4,5-dimethoxy-phenyl)-methanol (6.5 g, 17.6 mmol) in 200 mL CH$_2$Cl$_2$ was added triethylsilane (28.0 mL, 176 mmol) and trifluoroacetic acid (TFA) (70 mL, 881 mmol). After 2 hours the solution was concentrated in vacuo, 10% K$_2$CO$_3$ was added and extracted with CH$_2$Cl$_2$. The combined organic layers were washed with brine, dried over Na$_2$SO$_4$, filtered and concentrated in vacuo. Purification via flash chromatography (4:1 hexanes/ethyl acetate) afforded 4-chloro-5-(2-isopropyl-4,5-dimethoxy-benzyl)-2-methylsulfanyl-pyrimidine (5.60 g, 91%) as a clear oil.

Step 6. Ethyl-[5-(2-isopropyl-4,5-dimethoxy-benzyl)-2-methylsulfanyl-pyrimidin-4-yl]-amine

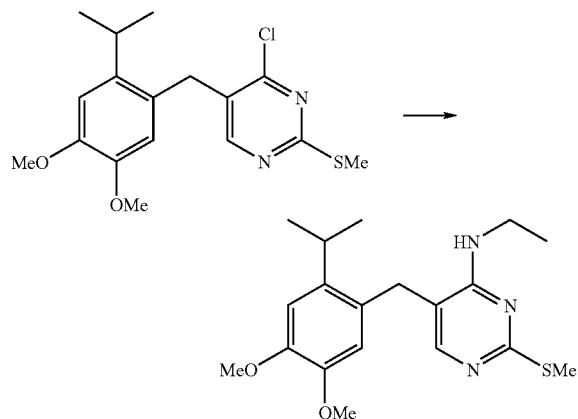

To a glass pressure vessel containing 4-chloro-5-(2-isopropyl-4,5-dimethoxy-benzyl)-2-methylsulfanyl-pyrimidine (0.212 g, 0.6 mmol) was added 5.0 mL ethyl amine via a cold finger condenser. The vessel was capped and warmed to 50° C. After 16 hours the solution was cooled to room temperature, evaporated and taken up in H$_2$O. The mixture was extracted with ethyl acetate, washed with H$_2$O and then washed with brine. The combined organic layers were dried over Na$_2$SO$_4$, filtered and evaporated in vacuo. Purification via flash chromatography (4:1 hexane/ethyl acetate) afforded ethyl-[5-(2-isopropyl-4,5-dimethoxy-benzyl)-2-methylsulfanyl-pyrimidin-4-yl]-amine (0.136 g, 63%) as a white solid.

Step 7. Ethyl-[5-(2-isopropyl-4,5-dimethoxy-benzyl)-2-methanesulfonyl-pyrimidin-4-yl]-amine

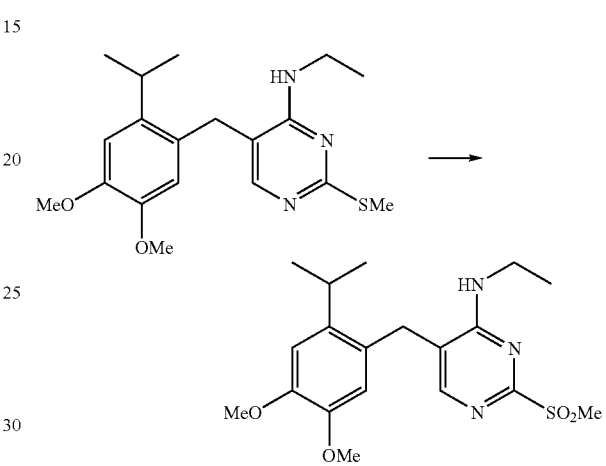

To a solution of ethyl-[5-(2-isopropyl-4,5-dimethoxy-benzyl)-2-methylsulfanyl-pyrimidin-4-yl]-amine (0.129 g, 0.4 mmol) in 20 mL 1:1 1H$_2$O/THF was added OXONE® (0.461 g, 0.8 mmol) in 4.0 mL H$_2$O. After 2 hours, 50 mL H$_2$O was added and the mixture was extracted with ethyl acetate, washed with H$_2$O and washed with brine. The combined organic layers were dried over Na$_2$SO$_4$, filtered and concentrated in vacuo to give ethyl-[5-(2-isopropyl-4,5-dimethoxy-benzyl)-2-methanesulfonyl-pyrimidin-4-yl]-amine (0.131 g, 92%) as a white foam.

Step 8. N*4*-Ethyl-5-(2-isopropyl-4,5-dimethoxy-benzyl)-pyrimidine-2,4-diamine

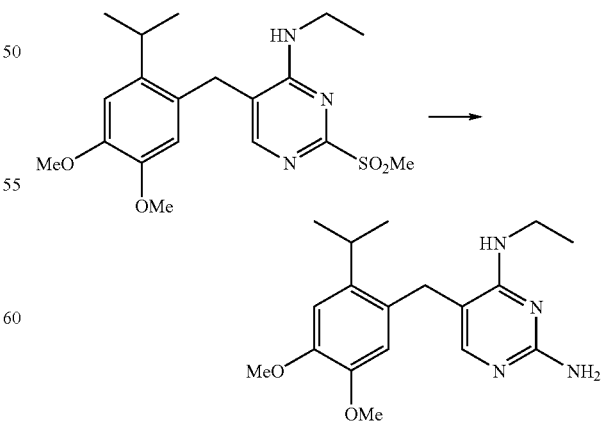

To ethyl-[5-(2-isopropyl-4,5-dimethoxy-benzyl)-2-methanesulfonyl-pyrimidin-4-yl]-amine (0.078g, 0.2 mmol) in microwave reactor vial was added 2.0 mL dimethoxy ethane and 0.5 mL concentrated NH₄OH. The vial was capped and placed in a microwave reactor. The internal temperature was warmed to 145° C. After 2 hours an additional portion of 0.4 mL concentrated NH₄OH was added and the mixture was heated an additional 2 hours. The mixture was cooled and concentrated in vacuo. Purification via flash chromatography (96:4 CH₂Cl₂/MeOH) afforded N*4*-ethyl-5-(2-isopropyl-4,5-dimethoxy-benzyl)-pyrimidine-2,4-diamine (0.031 g, 47%) as a pale yellow solid; Mass Spec M+H=329. Use of different alkyllithium reagents in step 1 and/or different substituted amines in steps 6 and 8 of the above procedure afforded additional compounds under the same or very similar reaction conditions. Additional compounds made by the procedure of Example 3 are shown in Table 1.

Example 4

2-[4-Amino-5-(5-chloro-2-isopropyl-4-methoxy-phenoxy)-pyrimidin-2-ylamino]-(R)-propan-1-ol The synthetic procedure used in this Example is outlined in Scheme G.

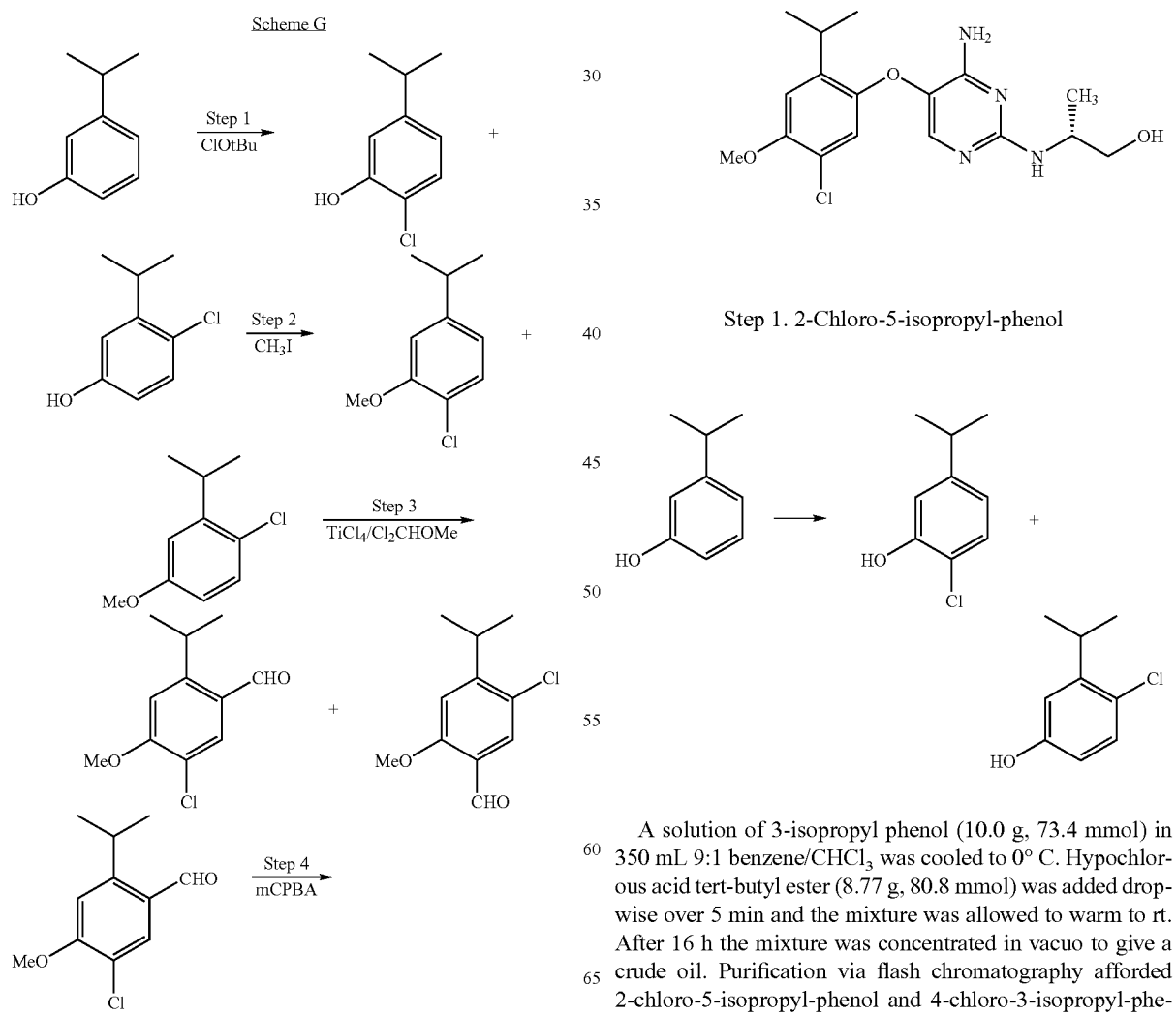

Step 1. 2-Chloro-5-isopropyl-phenol

A solution of 3-isopropyl phenol (10.0 g, 73.4 mmol) in 350 mL 9:1 benzene/CHCl₃ was cooled to 0° C. Hypochlorous acid tert-butyl ester (8.77 g, 80.8 mmol) was added dropwise over 5 min and the mixture was allowed to warm to rt. After 16 h the mixture was concentrated in vacuo to give a crude oil. Purification via flash chromatography afforded 2-chloro-5-isopropyl-phenol and 4-chloro-3-isopropyl-phenol (6.540 g, 52%) as a 7:3 inseparable mixture of isomers in the form of a pale yellow oil. The combined regioisomers were used together in the following step.

Step 2. 1-Chloro4-isopropyl-2-methoxy-benzene

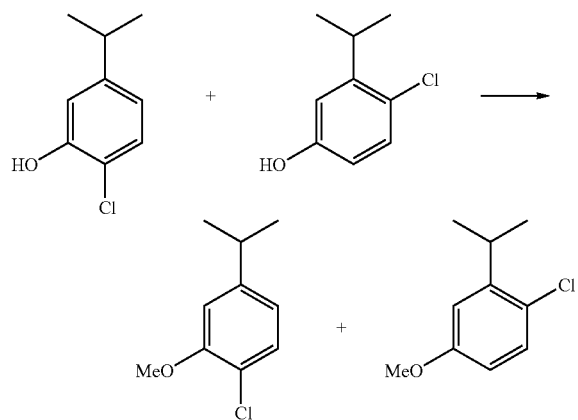

To a solution of 2-chloro-5-isopropyl-phenol and 4-chloro-3-isopropyl-phenol from step 1 (8.694 g, 47.1 mmol) in 50 mL DMF was added $K_2CO_3$. Iodomethane (3.5 mL, 56.5 mmol) was added and the mixture was warmed to 50° C. After 4 hours $H_2O$ was added. The mixture was extracted with ethyl acetate, washed with $H_2O$, washed and washed with brine. The combined organic layers were dried over $Na_2SO_4$, filtered and concentrated in vacuo to give 1-chloro-4-isopropyl-2-methoxy-benzene and 1-chloro-2-isopropyl-4-methoxy-benzene (9.289 g) as a 7:3 inseparable mixture in the form of a pale yellow oil, which was used directly in the following step.

Step 3. 5-Chloro-2-isopropyl-4-methoxy-benzaldehyde

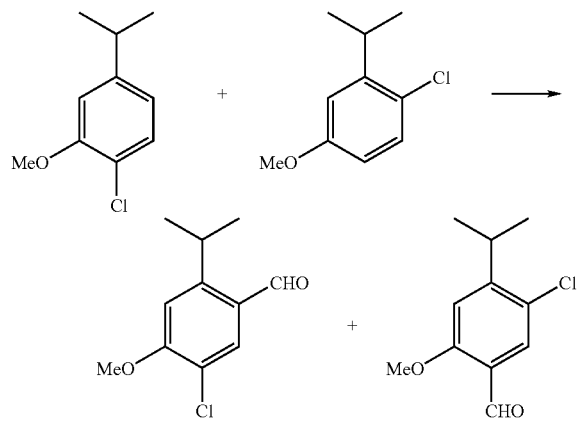

Using the procedure of step 3 of Example 2, the combined 1-chloro-4-isopropyl-2-methoxy-benzene and 1-chloro-2-isopropyl-4-methoxy-benzene (3.715 g, 20.1 mmol) were treated with $TiCl_4$ followed by $Cl_2CHOMe$ to give a mixture of 5-chloro-2-isopropyl-4-methoxy-benzaldehyde and 5-chloro-4-isopropyl-2-methoxy-benzaldehyde as a yellow oil. These regioisomers were separable by flash chromatography (gradient:hexane, 7:3, 1:1 hexane/$CH_2Cl_2$) to afford 5-chloro-2-isopropyl-4-methoxy-benzaldehyde (1.269 g, 30%) as a pale yellow solid.

Step 4. 5-Chloro-2-isopropyl-4-methoxy-phenol

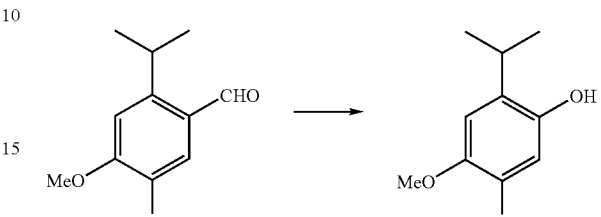

Using the procedure of step 4 from Example 2 described above, 5-chloro-2-isopropyl-4-methoxy-benzaldehyde (3.203 g, 15.1 mmol) afforded 5-chloro-2-isopropyl-4-methoxy-phenol (1.768 g, 58%) as s clear oil.

Step 5. (5-Chloro-2-isopropyl-4-methoxy-phenoxy)-acetonitrile

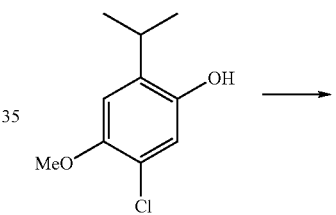

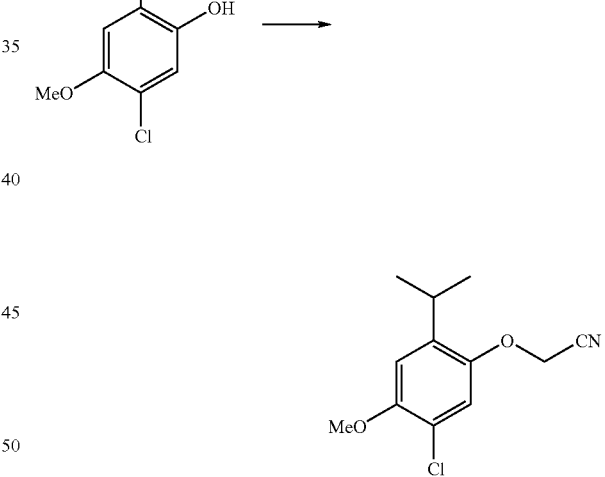

To a solution of 5-chloro-2-isopropyl-4-methoxy-phenol (10.36 g, 51.6 mmol) in 40 mL DMF was added $K_2CO_3$ (8.55 g, 62.0 mmol) and the mixture was heated to 65° C. After 15 minutes iodoacetonitrile (9.05 g, 54.2 mmol) was added and the mixture was heated to 80° C. for 1 hour. The mixture was cooled, poured into an ice/$H_2O$ mixture and extracted with 1:1 toluene/hexane. The combined organics were washed with brine, dried over $Na_2SO_4$, filtered and concentrated in vacuo. The crude product was purified by passing through a short plug of silica to afford (5-chloro-2-isopropyl-4-methoxy-phenoxy)-acetonitrile (11.97 g, 97%) as a white solid.

Step 6. 2-(5-Chloro-2-isopropyl-4-methoxy-phenoxy)-3-methoxy-acrylonitrile

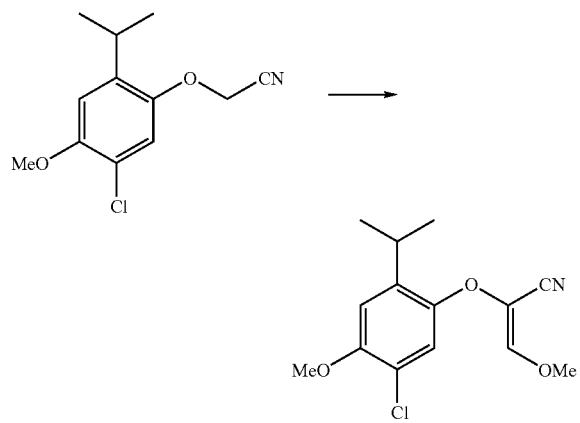

To a solution of (5-chloro-2-isopropyl-4-methoxy-phenoxy)-acetonitrile (1.44 g, 6.0 mmol) and ethyl formate (2.2 g, 29.2 mmol) in 7 mL 1,2-dimethoxy ethane at 5° C. was added 95% NaH (0.15 g, 6.0 mmol) in one portion. The mixture was warmed to room temperature. After 1 hour 95% NaH (0.15 g, 6.0 mmol) was added in one portion. After 1 hour 10 mL iodomethane was added and the mixture was allowed to stir for 16 hour. The mixture was concentrated in vacuo, 1N HCl was added and the mixture was extracted with ethyl acetate. The combined organic layers were washed with brine, dried over $Na_2SO_4$, filtered and concentrated in vacuo. Purification via flash chromatography (85:15 hexane/ethyl acetate) afforded 2-(5-chloro-2-isopropyl-4-methoxy-phenoxy)-3-methoxy-acrylonitrile (1.41 g, 84%) as a white solid.

Step 7. 2-[4-Amino-5-(5-chloro-2-isopropyl-4-methoxy-phenoxy)-pyrimidin-2-ylamino]-(R)-propan-1-ol

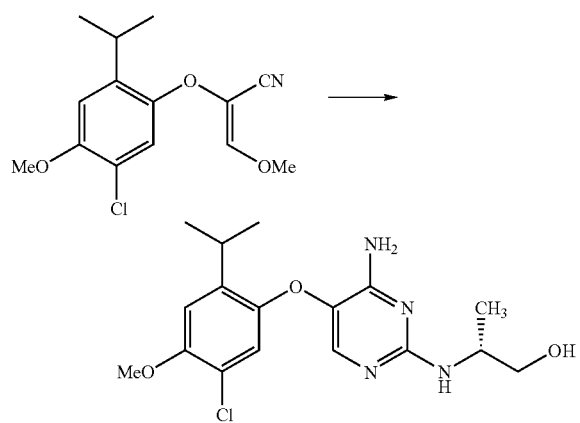

To a solution of 2-(5-chloro-2-isopropyl-4-methoxy-phenoxy)-3-methoxy-acrylonitrile (0.20 g, 0.7 mmol) in 1 mL DMSO was added N-(2-(R)-hydroxy-1-methyl-ethyl)-guanidine from Preparation 1 (0.10 g, 0.8 mmol). The solution was warmed to 120° C. After 45 minutes the solution was cooled, taken up in $H_2O$, and extracted with ethyl acetate. The combined organic layers were washed with $H_2O$, dried over $NaSO_4$, filtered and concentrated in vacuo. Purification via flash chromatography (95:5 $CH_2Cl_2$/MeOH) afforded 2-[4-Amino-5-(5-chloro-2-isopropyl-4-methoxy-phenoxy)-pyrimidin-2-ylamino]-(R)-propan-1-ol (0.128 g, 50%) as a solid; Mass Spec M+H=366.

Example 5

2-[4-Amino-5-(5-chloro-2-ethyl-4-methoxy-phenoxy)-pyrimidin-2-ylamino]-butan-1-ol

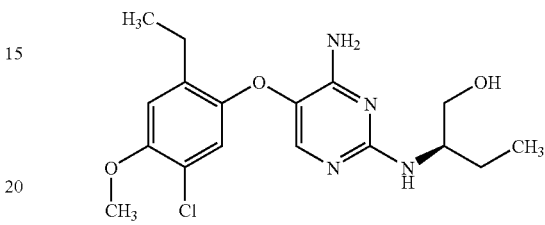

To a solution of N-(2-(R)-hydroxy-1-methyl-ethyl)-guanidine from Preparation 1 (0.15 g, 1.1 mmol) in 1 mL of dry DMSO was added 2-(5-chloro-2-isopropyl-4-methoxy-phenoxy)-3-methoxy-acrylonitrile (0.23 g, 0.9 mmol) from step 6 of Example 4. The mixture was heated at 120° C. for 3.0 hours. The reaction mixture was cooled and 20 mL of water was added and was extracted with EtOAc (2×50 mL). The combined organic solution was then washed with water (3×50 mL), then with Brine. The solution was dried over $MgSO_4$, filtered and concentrated. The compound was purified by column chromatography on Silica Gel using 2% MeOH/dichloromethane. The fractions containing the product were combined and evaporated under reduced pressure to give crude product. This product was suspended in 2 mL of ether, and 0.6 mL of 1M HCl/ether (1.5 eq.) was added. 30 minutes later, the solid was filtered and washed with ether to give 160 mg of 2-[4-Amino-5-(5-chloro-2-isopropyl-4-methoxy-phenoxy)-pyrimidin-2-ylamino]-(R)-propan-1-ol as a hydrochloride salt: Mass Spec M+H=367; MP; 111.4-116.9° C.

The above procedure was used with various different phenols and amino guanidines under essentially the same reaction conditions to produce additional compounds, which are shown in Table 1.

Example 6

N*2*-(1,1-Dioxo-hexahydro-1lambda*6*-thiopyran-4-yl-5-(2-isopropyl-4,5-dimethoxy-phenoxy)-pyrimidine-2,4-diamine

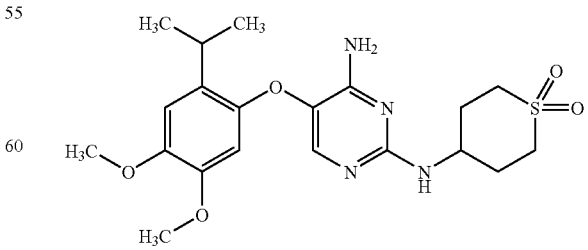

5-(2-Isopropyl-4,5-dimethoxy-phenoxy)-N*2*-(tetrahydro-thiopyran-4-yl)-pyrimidine-2,4-diamine was prepared according to the procedure of example 5, using 2-(2-isopropyl-4,5-dimethoxy-phenoxy)-3-methoxy-acrylonitrile (prepared using the procedure of Example 4) together with N-(tetrahydro-thiopyran-4-yl)-guanidine from Preparation 1.

To a mixture of 5-(2-isopropyl-4,5-dimethoxy-phenoxy)-N*2*-(tetrahydro-thiopyran-4-yl)-pyrimidine-2,4-diamine (0.19 g, 0.46 mmol) in 25 mL of methanol and 25 mL of water was added the OXONE (1.73 g, 1.4 mmol). This mixture was stirred at room temperature overnight. The reaction mixture was diluted with water (50 mL) and extracted with EtOAc (3×50 mL). The organic solution was washed with Brine, dried over MgSO$_4$. The solution was filtered and concentrated. The residue was purified on one preparative TLC plate (20×40 cm) eluting with EtOAc. Product recovered was stirred with 1.5 eq of 1M HCl/ether to afford 25 mg of N*2*-(1,1-dioxo-hexahydro-1lambda*6*-thiopyran-4-yl)-5-(2-isopropyl-4,5-dimethoxy-phenoxy)-pyrimidine-2,4-diamine HCl salt): MS (M+H); 441: MP; 255.1-257.8° C.

Example 7

Methyl-carbamic acid 2-[4-amino-5-(5-chloro-2-isopropyl-4-methoxy-phenoxy)-pyrimidin-2-ylamino]-propyl ester

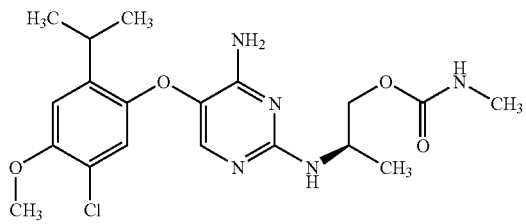

1,1-Carbonyldiimidazole (0.97 g, 6 mmol) was added to a solution of 2-[4-Amino-5-(5-chloro-2-isopropyl-4-methoxyphenoxy)-pyrimidin-2-ylamino]-(R)-propan-1-ol from Example 4 (0.22 g, 0.6 mmol) in 20 mL of THF at room temperature. The mixture was stirred for 2 hours and methylamine (3 mL, 2M/THF, 0.6 mmol) was added. The reaction mixture was stirred overnight and concentrated under reduced pressure, diluted with water (75 mL), and extracted with EtOAc (2×75 mL). The organic phase was washed with Brine and dried with MgSO$_4$. The solution was filtered and concentrated. The residue was purified on two Silica preparative TLC plates (20×40 cm) eluting with 5% MeOH/dichloromethane affording 143 mg of methyl-carbamic acid 2-[4-amino-5-(5-chloro-2-isopropyl-4-methoxy-phenoxy)-pyrimidin-2-ylamino]-propyl ester: MS (M+H); 424: MP; 63.5-69.4° C.

Example 8

5-(4,5-Dimethoxy-2-methyl-benzyl)-pyrimidine-2,4-diamine

The synthetic procedure used in this Example is outlined in Scheme H.

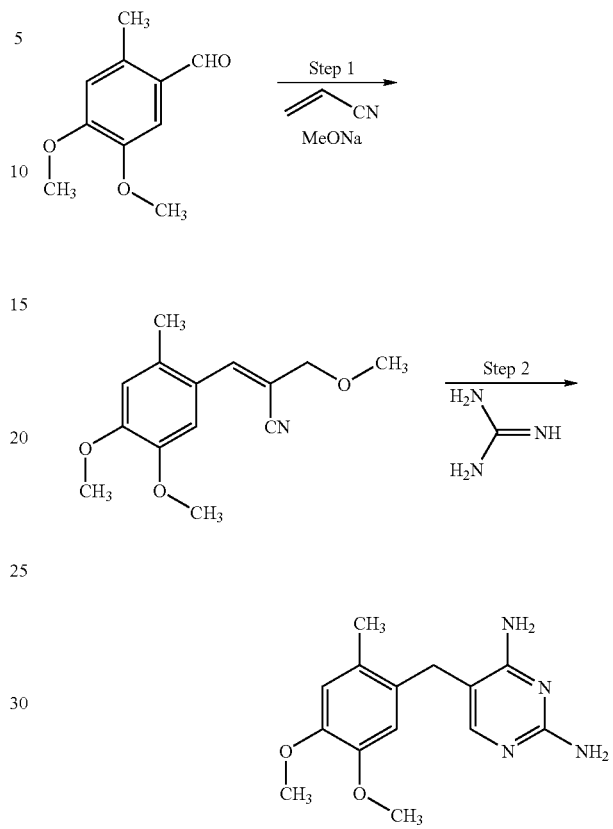

This Example follows the procedure described by Manchand et al., Journal of Organic Chemistry 1992, 57, 3531-3535. Briefly, in step 1 4,5-dimethoxy-2-methyl-benzaldehyde and sodium methoxide were dissolved in cold methanol and stirred under nitrogen at room temperature for 18 hours. The mixture was cooled to −15° C., and crude 3-(4,5-dimethoxy-2-methyl-phenyl)-2-methoxymethyl-acrylonitrile was collected as filtrate.

In step 2, 3-(4,5-dimethoxy-2-methyl-phenyl)-2-methoxymethyl-acrylonitrile and sodium methoxide were dissolved in dry DMSO and stirred for 3.5 hours at 85° C. under nitrogen. Guanidine carbonate was then added to the stirring solution, after which the temperature was raised to 125° C. for three hours, during which methanol removed via a Dean-Stark trap. The solution was cooled to room temperature, diluted with water, and the crude filtrate was recrystallized in DMF to yield 5-(4,5-dimethoxy-2-methyl-benzyl)-pyrimidine-2,4-diamine as a white solid. Mp: 232° C. Mass Spec (M+H): 275.

Additional compounds made by Example 2 are shown in Table 1.

Example 9

5-(6-Isopropyl-1,3-dimethyl-1H-indol-5-yloxy)-pyrimidine-2,4-diamine

The synthetic procedure used in this Example is outlined in Scheme I.

SCHEME I

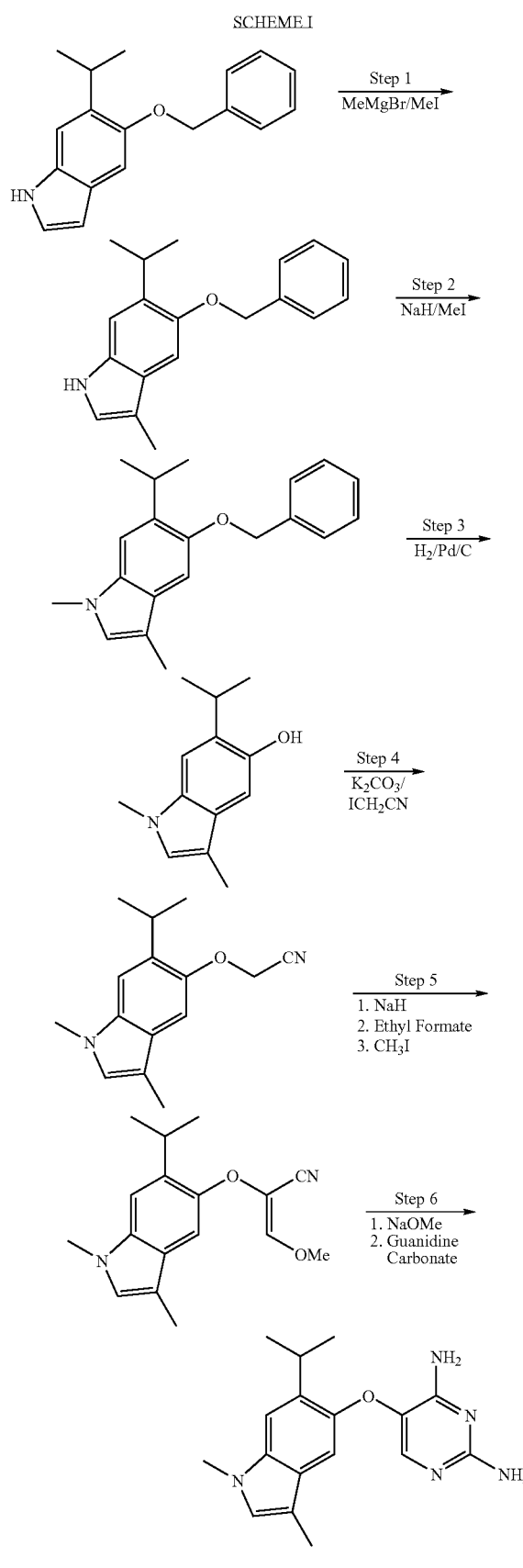

The 5-benzyloxy-6-isopropyl-1H-indole utilized in step 1 of this Example was prepared from 1-{2-[(5-benzyloxy)-4-(1-methylethyl)-2-nitrophenyl]ethenyl}-pyrrolidine according to the procedure reported by Leonardi et al., "Synthesis and Pharmacological Evaluation of New Indole Derivatives Structurally Related to Thymoxamine", *Eur. J. Med. Chem.* (1994), 29, 551-559. The methylation of step 3 below also follows the procedure described by Leonardi et al.

Step 1.
5-Benzyloxy-6-isopropyl-3-methyl-1H-indole

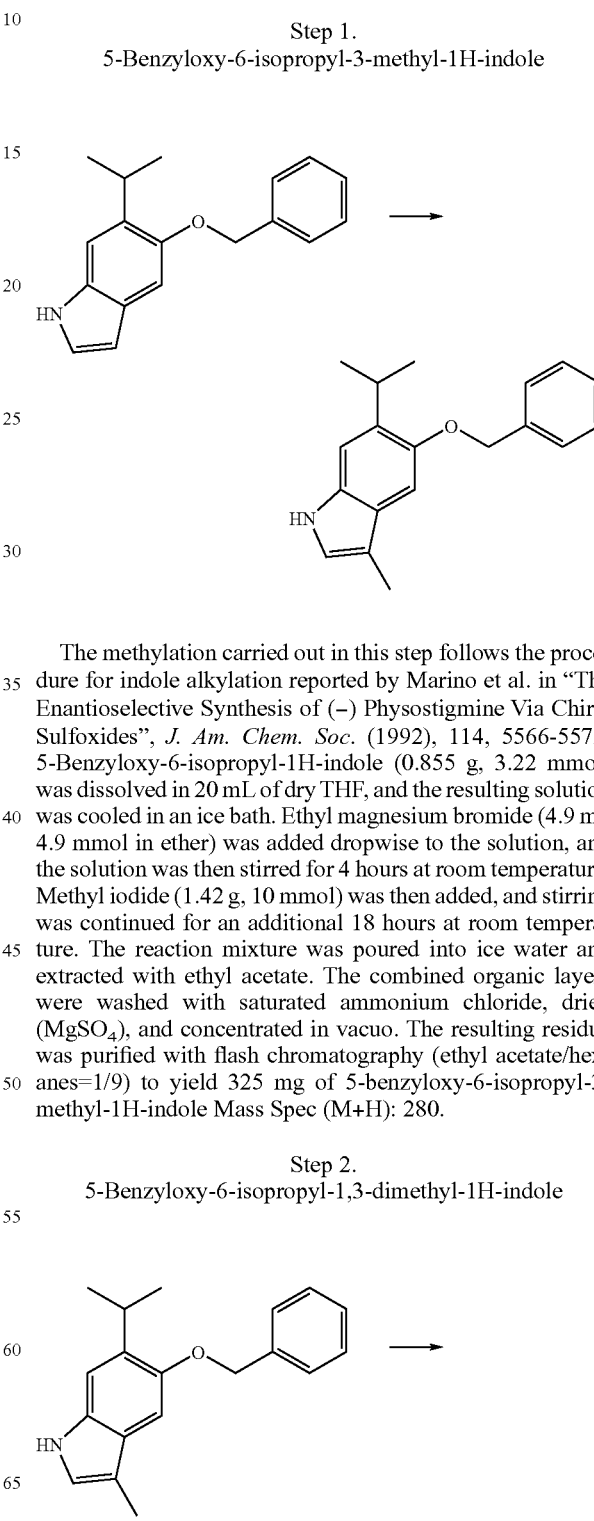

The methylation carried out in this step follows the procedure for indole alkylation reported by Marino et al. in "The Enantioselective Synthesis of (–) Physostigmine Via Chiral Sulfoxides", *J. Am. Chem. Soc.* (1992), 114, 5566-5572. 5-Benzyloxy-6-isopropyl-1H-indole (0.855 g, 3.22 mmol) was dissolved in 20 mL of dry THF, and the resulting solution was cooled in an ice bath. Ethyl magnesium bromide (4.9 ml, 4.9 mmol in ether) was added dropwise to the solution, and the solution was then stirred for 4 hours at room temperature. Methyl iodide (1.42 g, 10 mmol) was then added, and stirring was continued for an additional 18 hours at room temperature. The reaction mixture was poured into ice water and extracted with ethyl acetate. The combined organic layers were washed with saturated ammonium chloride, dried (MgSO$_4$), and concentrated in vacuo. The resulting residue was purified with flash chromatography (ethyl acetate/hexanes=1/9) to yield 325 mg of 5-benzyloxy-6-isopropyl-3-methyl-1H-indole Mass Spec (M+H): 280.

Step 2.
5-Benzyloxy-6-isopropyl-1,3-dimethyl-1H-indole

167

-continued

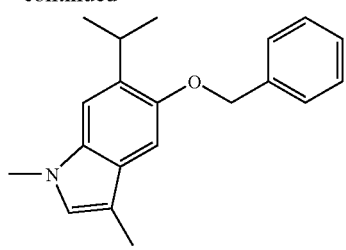

5-Benzyloxy-6-isopropyl-3-methyl-1H-indole (0.320 g, 1.15 mmol), KOH (0.264 g, 4.7 mmol), benzyl tributylammonium chloride (0.071 g, 0.230 mmol), and methyl iodide (0.107 mL, 1.72 mmol) were added to 3 mL of toluene. The resulting mixture was stirred for 4 hours at 90° C., cooled to room temperature, poured into water, and extracted with ethyl acetate 2 times. The combined organic layers were washed with water, dried (MgSO$_4$), and evaporated in vacuo to provide a crude oil that was was purified with flash chromatography (ethyl acetate/hexanes=1/9); yield 270 mg of 5-benzyloxy-6-isopropyl-1,3-dimethyl-1H-indole.

Step 3. 6-Isopropyl-1,3-dimethyl-1H-indol-5-ol

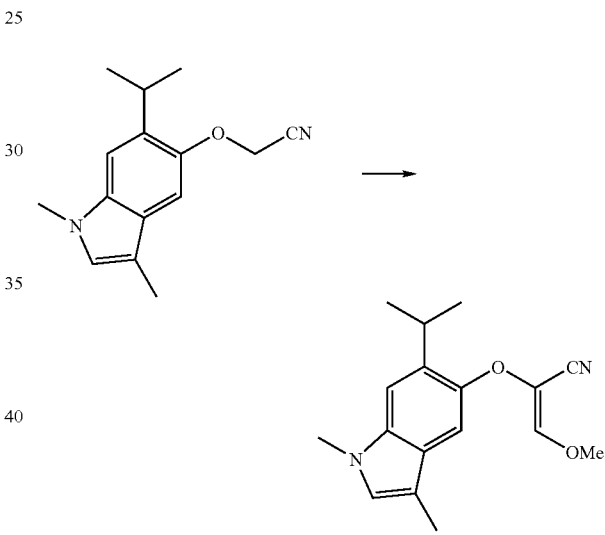

5-Benzyloxy-6-isopropyl-1,3-dimethyl-1H-indole (0.270 g, 1.30 mmol) and Pd/C 10% (0.150 g) were added to 10 mL of methanol, and the mixture was hydrogenated in a Parr apparatus for 1.5 hours at 55 psi, at room temperature. The catalyst was removed by filtration and the solvent was removed in vacuo. The residue was purified with flash chromatography (5% ethyl acetate in hexanes) to yield 210 mg of 6-isopropyl-1,3-dimethyl-1H-indol-5-ol.

168

Step 4. (6-Isopropyl-1,3-dimethyl-1H-indol-5-yloxy)-acetonitrile

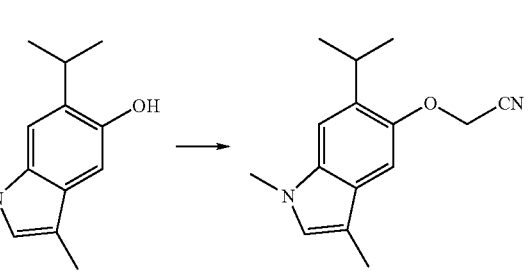

(6-Isopropyl-1,3-dimethyl-1H-indol-5-yloxy)-acetonitrile was prepared from 6-isopropyl-1,3-dimethyl-1H-indol-5-ol by treatment with iodoacetonitrile using the procedure of step 5 of Example 2 above.

Step 5. 2-(6-Isopropyl-1,3-dimethyl-1H-indol-5-yloxy)-4-methoxy-but-2-enenitrile 2-(6-Isopropyl-1,3-dimethyl-1H-indol-5-yloxy)-4-methoxy-but-2-enenitrile was prepared from (6-isopropyl-1,3-dimethyl-1H-indol-5-yloxy)-acetonitrile by treatment with sodium hydride and methyl iodide using the procedure of step 6 of Example 2 above.

Step 6. 5-(6-Isopropyl-1,3-dimethyl-1H-indol-5-yloxy)-pyrimidine-2,4-diamine

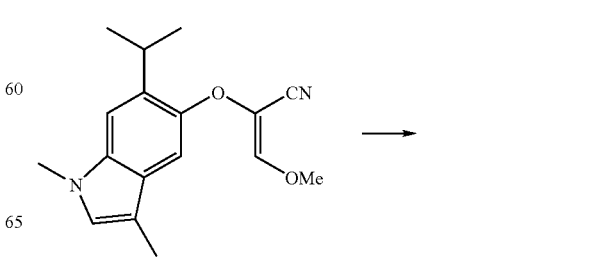

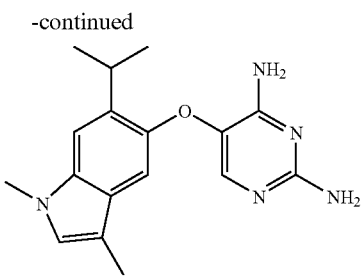

5-(6-Isopropyl-1,3-dimethyl-1H-indol-5-yloxy)-pyrimidine-2,4-diamine was prepared from 2-(6-isopropyl-1,3-dimethyl-1H-indol-5-yloxy)-4-methoxy-but-2-enenitrile by treatment with guanidine carbonate and sodium methoxide using the procedure of step 7 of Example 2 above. This material was dissolved in 2.5 ml absolute ethanol, and 820 ml of 1 N HCl in diethyl ether was added with stirring. Diethyl ether was added slowly until small crystals formed, and the solution was then placed in a −10 C freezer for 18 hours. The solid that had formed was collected by filtration, washed with diethyl ether, and dried under vacuum at 45 C to give 171 mg. of the hydrochloride salt, Mp: 185.1° C.

5-(6-Isopropyl-1-methyl-1H-indol-5-yloxy)-pyrimidine-2,4-diamine was also prepared using the above procedure, but omitting the 3-methylation of step 1. MS (M+H): 298.

Example 10

5-(2-Isopropyl-4-methoxy-5-methylphenoxy)-N*4*-phenyl-pyrimidine-2,4-diamine

The synthetic procedure used in this Example is outlined in Scheme J.

Scheme J

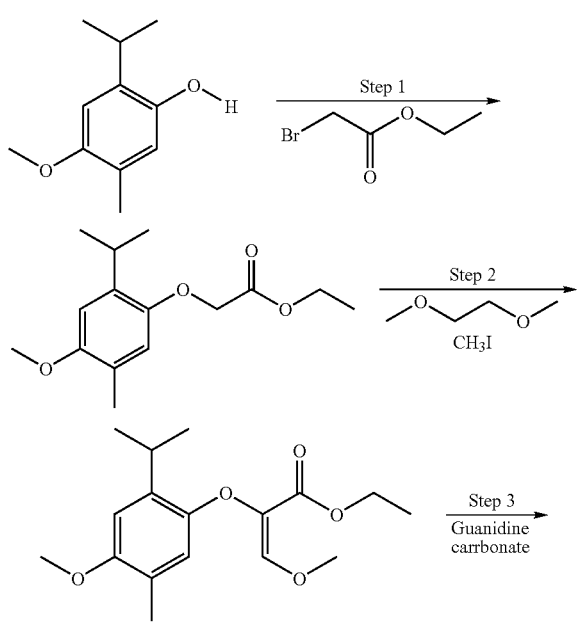

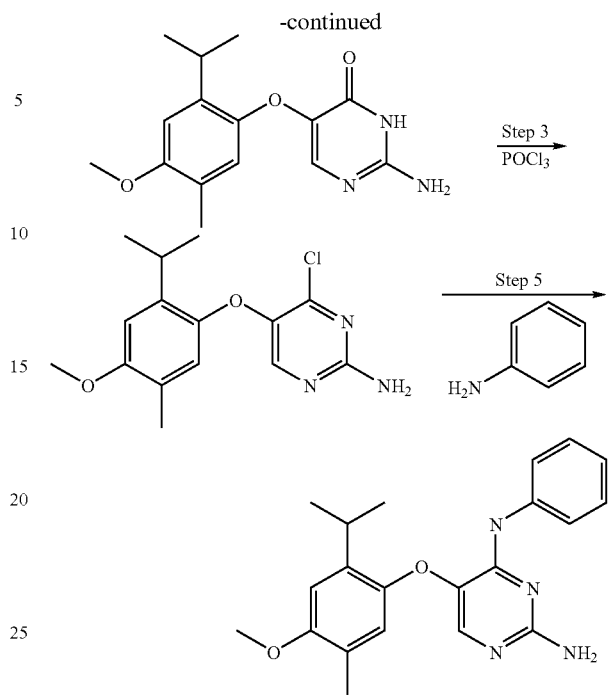

Step 1.
(2-Isopropyl-4-methoxy-5-methyl-phenoxy)-acetic acid ethyl ester

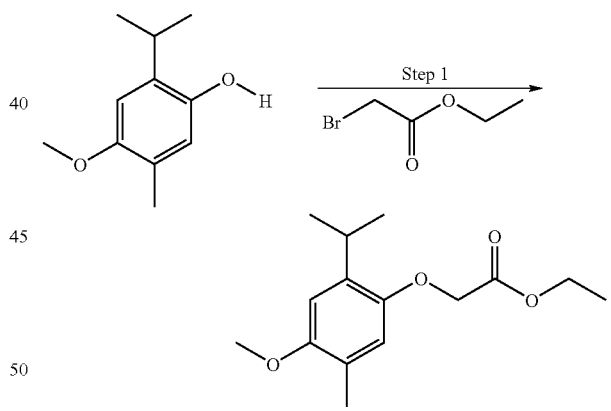

To a solution of 2-isopropyl-4-methoxy-5-methyl-phenol (3.933 g, 21.8 mmol) in acetone (100 ml) was added potassium carbonate (20 g, 145 mmol) and ethyl bromoacetate (5 ml, 45.1 mmol). The mixture refluxed over night and was filtered through celite. The filtrate was concentrated under reduced pressure and the residue was partitioned between ethyl acetate and water. The organic phase was washed with brine and dried over anhydrous sodium sulfate. After removal of drying agent, the organic solution was concentrated under reduced pressure. The residue was purified with silica gel chromatography (10% to 15% methylene chloride in hexane) to yield (2-isopropyl-4-methoxy-5-methyl-phenoxy)-acetic acid ethyl ester as white solid (4.78 g, 82%).

Step 2. 2-(2-Isopropyl-4-methoxy-5-methyl-phenoxy)-3-methoxy-acrylic acid ethyl ester

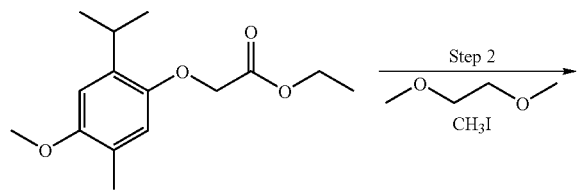

To a solution of (2-isopropyl-4-methoxy-5-methyl-phenoxy)-acetic acid ethyl ester (4.42 g, 16.6 mmol) in anhydrous 1,2-dimethoxy ethane (60 ml) was added sodium hydride (60% in mineral oil, 3.5 g, 87.5 mmol) at room temperature. After 5 minutes of stirring, ethyl formate (40 ml, 495 mmol) was added. The mixture was heated at 85° C. for 7 hours. After cooling to room temperature, iodomethane was added and stirring was continued overnight. Solvent was concentrated under reduced pressure and the residue was partitioned between ethyl acetate and water. The organic phase was washed with brine and dried over anhydrous sodium sulfate. After removal of drying agent, the organic solution was concentrated under reduced pressure. The residue was purified with silica gel chromatography (10% to 30% ethyl acetate in hexane) to yield 2-(2-isopropyl-4-methoxy-5-methyl-phenoxy)-3-methoxy-acrylic acid ethyl ester as a pale yellow oil (1.19 g, 23%).

Step 3. 2-Amino-5-(2-isopropyl-4-methoxy-5-methyl-phenoxy)-3H-pyrimidin-4-one

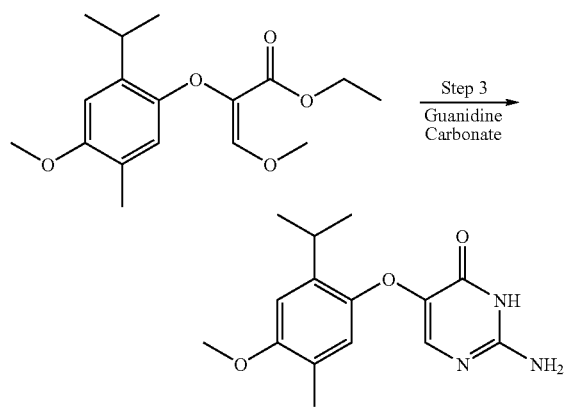

To a solution of NaOMe [prepared from sodium (0.05 g, 2.17 mmol) in anhydrous methanol (5 ml)], was added guanidine carbonate. After 5 minutes, a solution of 2-(2-isopropyl-4-methoxy-5-methyl-phenoxy)-3-methoxy-acrylic acid ethyl ester (0.22 g, 0.713 mmol) in anhydrous DMSO (10 ml) was added. The mixture was heated at 120° C. for 3 hours and was cooled and partitioned between ethyl acetate and water. The organic phase was washed with brine and dried over anhydrous sodium sulfate. After removal of drying agent, the organic solution was concentrated under reduced pressure. The residue was purified with silica gel chromatography (5% methanol in methylene chloride/0.1% concentrated NH$_4$OH) to yield 2-amino-5-(2-isopropyl-4-methoxy-5-methyl-phenoxy)-3H-pyrimidin-4-one as pale yellow solid (0.045 g, 22%). MS M+H=290.

Step 4. 4-Chloro-5-(2-isopropyl-4-methoxy-5-methyl-phenoxy)-pyrimidin-2-ylamine

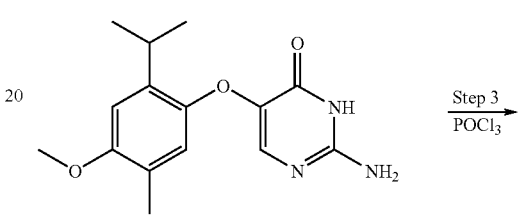

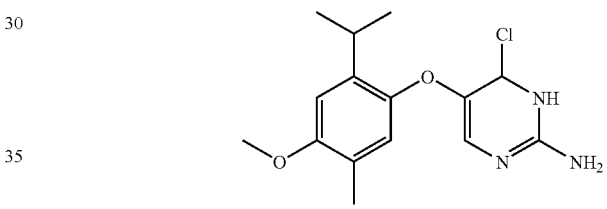

A mixture of 2-amino-5-(2-isopropyl-4-methoxy-5-methyl-phenoxy)-3H-pyrimidin-4-one in phosphorus oxychloride (5 ml) was heated at 110° C. for 40 minutes and stirred at room temperature over night. Solvent was removed under reduced pressure and ice water was added. The aqueous solution was basified with potassium carbonate to pH 9, and extracted with methylene chloride. The organic phase was washed with brine and dried over anhydrous sodium sulfate. After removal of drying agent, the organic solution was concentrated under reduced pressure to yield 4-chloro-5-(2-isopropyl-4-methoxy-5-methyl-phenoxy)-pyrimidin-2-ylamine as yellow solid (0.043 g, 88%). MS M+H=308.

Step 5. 5-(2-Isopropyl-4-methoxy-5-methylphenoxy)-N*4*-phenyl-pyrimidine-2,4-diamine

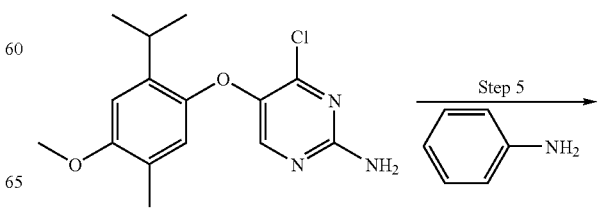

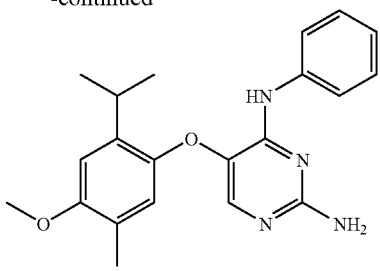

A suspension of 4-chloro-5-(2-isopropyl-4-methoxy-5-methyl-phenoxy)-pyrimidin-2-ylamine (0.043 g, 0.14 mmol) in aniline (4 ml) was placed in a sealed tube and heated at 100° C. over night. Methylene chloride was added and insoluble solid was removed by filtration through celite. The combined methylene chloride filtrate was washed with water and dried over anhydrous sodium sulfate. After removal of the drying agent, the organic phase was concentrated under reduced pressure. The residue was purified with silica gel chromatography (2% methanol in methylene chloride) to yield a yellow oily residue, which was further purified with preparative TLC and HPLC (5 to 100% acetonitrile in water with 0.1% trifluoroacetic acid to yield 5-(2-Isopropyl-4-methoxy-5-methyl-phenoxy)-N*4*-phenyl-pyrimidine-2,4-diamine, M+H: 365.

Example 11

5-(2-Cyclopropyl-4,5-dimethoxy-phenoxy)-pyrimidine-2,4-diamine

Step 1. 4-Cyclopropyl-1,2-dimethoxy-benzene

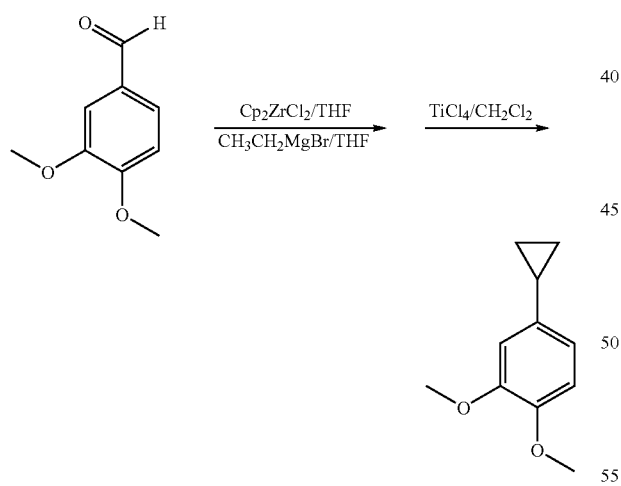

To a solution of zirconocene dichloride (1.76 g, 6.02 mmols) in dry tetrahydrofuran (25 ml), was slowly added ethylmagnesium bromide (12 ml, 1 M in tetrahydrofuran, 12 mmol) at −78° C. The green solution was stirred for 15 minutes at −78° C. and then warmed to 2° C. until the reaction color turned red (15 minutes). A solution of 3,4-dimethoxy-benzaldehyde (1.00 g, 6.02 mmol) in dry tetrahydrofuran (20 ml) was added and the reaction was allowed to warm up to room temperature over 1.5 hours. Solvent was removed under reduced pressure, and dichloromethane (20 ml) was added. The reaction mixture was cooled to 0° C. and titanium chloride (IV) (6 ml, 1M in dichloromethan, 6 mmol) was added. The reaction was allowed to warm up to room temperature over 30 minutes, and quenched with saturated ammonium chloride solution. The mixture was filtered through celite and portioned between dichloromethane and water. The combined dichloromethane was washed with saturated aqueous solution of ammonium chloride, saturated aqueous sodium bicarbonate and brine. The organic phase was dried over anhydrous sodium sulfate and concentrated under reduced pressure. The residue was purified by silica gel chromatography (gradient: 8% to 30% ethyl acetate in hexane) to yield 4-cyclopropyl-1,2-dimethoxy-benzene as yellow oily residue (0.2 g, 19%). Ref: Vincent Gandon et al. Eur. J. Org. Chem. 2000, 3713.

Step 2. 5-(2-Cyclopropyl-4,5-dimethoxy-phenoxy)-pyrimidine-2,4-diamine

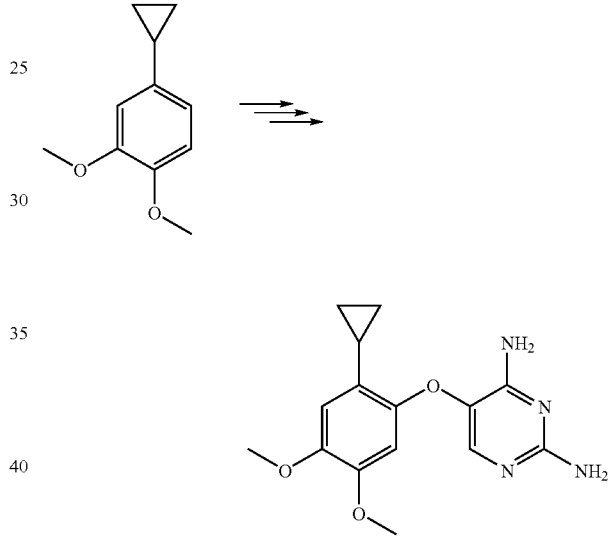

5-(2-Cyclopropyl-4,5-dimethoxy-phenoxy)-pyrimidine-2,4-diamine was prepared from 4-cyclopropyl-1,2-dimethoxy-benzene following the procedure of step 1 and steps 3-7 of Example 2 above.

Example 12

5-(5-Chloro-2-cyclopropyl-4-methoxy-phenoxy)-pyrimidine-2,4-diamine

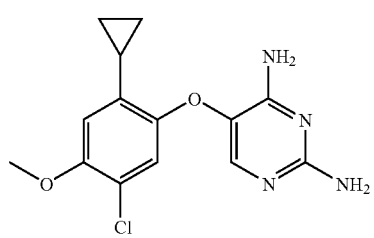

Step 1. 1-Chloro-4-cyclopropyl-2-methoxy-benzene

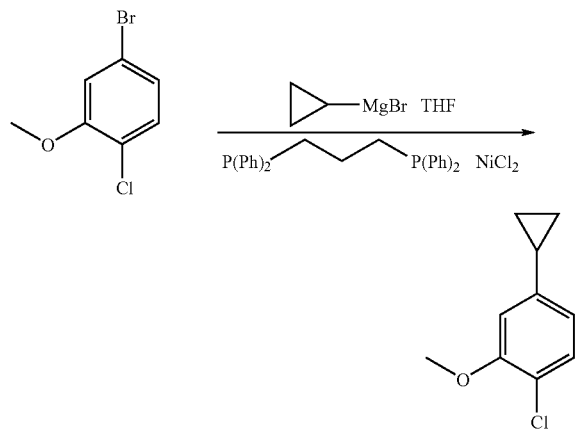

To a solution of 4-bromo-1-chloro-2-methoxy-benzene (1.45 g, 6.55 mmol) in dry tetrahydrofuran (10 ml), was added {1,3-bis (diphenylphosphino)-propane} dichloronickel (II) and cyclopropylmagnesium bromide (46 ml, 0.5 M in tetrahydrofuran, 23 mmols) at room temperature. The solution was stirred at room temperature for 2 hours, and then heated at 65° C. for 48 hours. Aqueous hydrochloric acid solution (1 N, 20 mL) was added, and the mixture was then cooled to room temperature and stirred for 30 minutes. The reaction mixture was partitioned between ethyl acetate and water. The combined organic phase was washed with brine, dried over anhydrous sodium sulfate, and concentrated under reduced pressure. The residue was purified by silica gel chromatography (2% ethyl acetate in hexane) to yield 1-chloro-4-cyclopropyl-2-methoxy-benzene as yellow oily residue (0.81 g, 67%).

Step 2. 5-(5-Chloro-2-cyclopropyl-4-methoxy-phenoxy)-pyrimidine-2,4-diamine

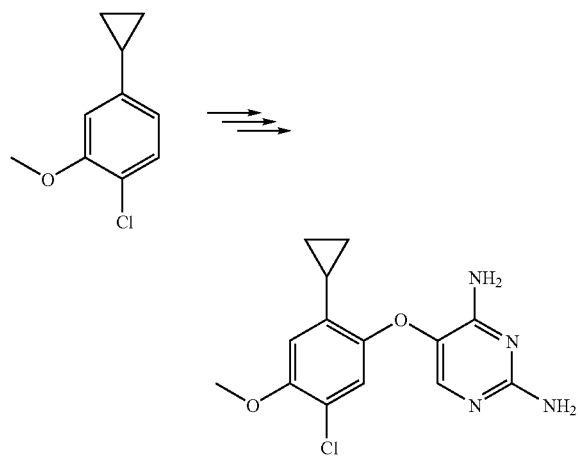

5-(5-Chloro-2-cyclopropyl-4-methoxy-phenoxy)-pyrimidine-2,4-diamine was prepared from 4-cyclopropyl-1,2-dimethoxy-benzene following the procedure of step 1 and steps 3-7 of Example 2 above.

Example 13

5-(2-Isopropyl-5-methanesulfonyl-4-methoxy-phenoxy)-pyrimidine-2,4-diamine

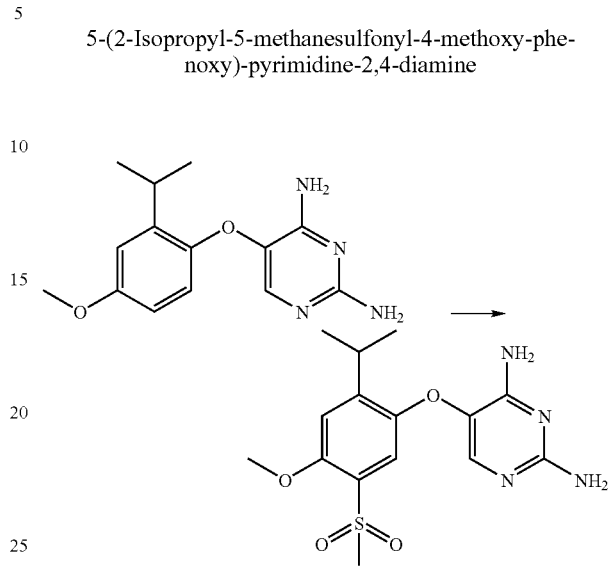

To a mixture of 5-(2-isopropyl-4-methoxy-phenoxy)-pyrimidine-2,4-diamine (0.32g, 1.17 mmol), prepared according to Example 2, and methanesulfonic anhydride (0.81 g, 4.67 mmol) was added trifluoromethanesulfonic acid (0.45 g, 3.00 mmol), and the mixture was heated at 80° C. for 16 hrs. The reaction mixture was poured into ice water, basified with saturated NaHCO₃ solution and extracted into dichloromethane, which was dried over Na₂SO₄, filtered and concentrated in vacuo. The residue was purified via flash chromatography on silica gel (3%CH₃OH in CH₂Cl₂ with 0.1%NH₄OH) gave 5-(2-isopropyl-5-methanesulfonyl-4-methoxy-phenoxy)-pyrimidine-2,4-diamine as a white solid (0.248 g, 90%; 0.107 g), MS (M+H): 353.

Example 14

5-[5-(2,3-Dihydro-1H-tetrazol-5-yl)-2-isopropyl-4-methoxy-phenoxy]-pyrimidine-2,4-diamine

Step 1 5-(5-Iodo-2-isopropyl-4-methoxy-phenoxy)-pyrimidine-2,4-diamine

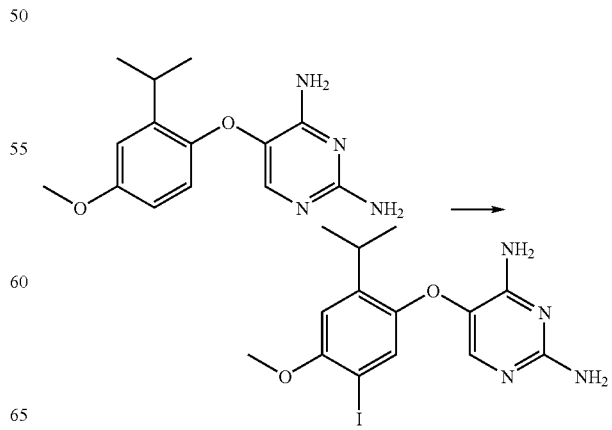

To a solution of 5-(2-isopropyl-4-methoxy-phenoxy)-pyrimidine-2,4-diamine (0.40 g, 1.44 mmol) in glacial acetic acid (4 ml) at room temperature was added a solution of iodine monochloride (0.28 g, 1.76 mmol) in glacial acetic acid (4 ml). Water (6 ml) was also added, and the reaction was stirred for 16 hours, after which another portion of iodine monochloride (0.4 g, 2.47 mmol) in glacial acetic acid (4 ml) was added. The reaction mixture was stirred for an additional hour at room temperature. The acidic mixture was basified with saturated $NaHCO_3$ solution and extracted into dichloromethane. The organic layer was dried over $Na_2SO_4$, filtered and concentrated in vacuo. The residue was purified via flash chromatography (5% $CH_3OH$ in $CH_2CL_2$ with 0.1% $NH_4OH$) to give 5-(5-iodo-2-isopropyl-4-methoxy-phenoxy)-pyrimidine-2,4-diamine as beige colored solid (0.536 g, 92%). M+H 400.

Step 2. 5-(2,4-Diamino-pyrimidin-5-yloxy)-4-isopropyl-2-methoxy-benzonitrile

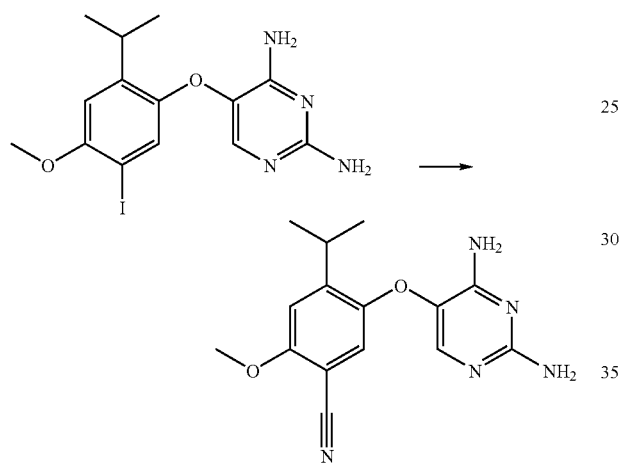

A mixture of 5-(5-iodo-2-isopropyl-4-methoxy-phenoxy)-pyrimidine-2,4-diamine (0.37 g, 0.925 mmol) and CuCN (0.12 g, 1.39 mmol) in DMF (5 ml) was heated at 120° C. for 3 hours. Water (100 ml) was added, and the precipitate was collected. The residue was triturated with methanolic dichloromethane (10% $CH_3OH$ in $CH_2Cl_2$ with 0.1% $NH_4OH$) to release the product from its copper complex and filtered. The filtrate was concentrated and purified via flash chromatography (3% $CH_3OH$ in $CH_2Cl_2$ with 0.1% $NH_4OH$) to give 5-(2,4-diamino-pyrimidin-5-yloxy)-4-isopropyl-2-methoxy-benzonitrile as white solid (0.12 g, 44%): M+H 300.

Step 3. 5-[5-(2,3-Dihydro-1H-tetrazol-5-yl)-2-isopropyl-4-methoxy-phenoxy]-pyrimidine-2,4-diamine

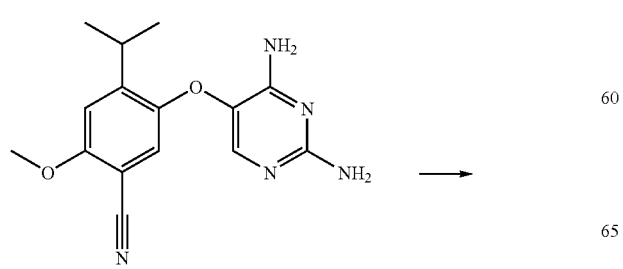

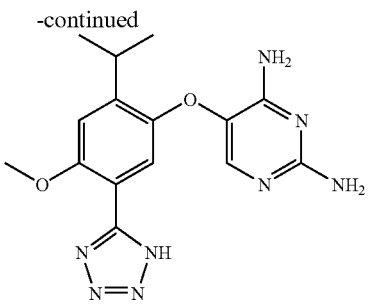

To a hot solution of 5-(2,4-diamino-pyrimidin-5-yloxy)4-isopropyl-2-methoxy-benzonitrile (0.2 g, 0.67 mmol) in xylene (15 ml) at 120° C. was added azidotributyltin (1.10 g, 0.67 mmol), and the reaction mixture was heated for two hours. Another portion of azidotributyltin (1.10 g, 3.34 mmol) was added, and the mixture was heated for another five hours. The reaction mixture was cooled to 0° C. and bubbled with HCl gas for five minutes. The solid formed was collected by filtration and washed with $CH_2Cl_2$ (3×5 ml). Purification of the solid by preparative HPLC (15-95% $CH_3CN$ in water, 10 minute gradient) gave 5-[5-(2,3-dihydro-1H-tetrazol-5-yl)-2-isopropyl-4-methoxy-phenoxy]-pyrimidine-2,4-diamine HCl salt, as white solid (62 mg, 25%). M+H 343.

Example 15

5-[5-(1H-Imidazol-2-yl)-2-isopropyl-4-methoxy-phenoxy]-pyrimidine-2,4-diamine

Step 1. 5-[5-(4,5-Dihydro-1H-imidazol-2-yl)-2-isopropyl-4-methoxy-phenoxy]-pyrimidine-2,4-diamine

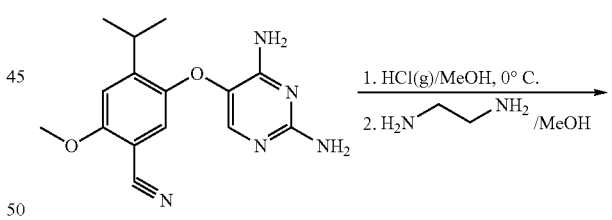

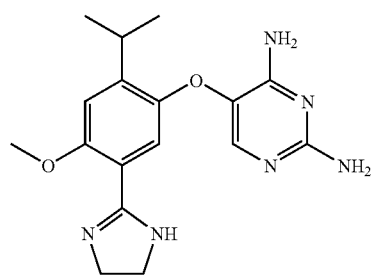

To a cooled (0° C.) suspension of 5-(2,4-diamino-pyrimidin-5-yloxy)-4-isopropyl-2-methoxy-benzonitrile (0.138 g, 0.461 mmol) in dry methanol (15 ml) was bubbled with HCl gas for 10 minutes and refrigerated overnight. Solvent was evaporated under reduced pressure to give a yellow solid which was redissolved in dry methanol (10 ml). Ethylene diamine (0.034 ml, 0.509 mmol) was added and the reaction mixture was refluxed for 20 hours and concentrated under reduced pressure. The residue was purified by silica gel chromatography (gradient: 7-50% methanol in methylene chloride/0.1% concentrated NH₄OH) to yield 5-[5-(4,5-dihydro-1H-imidazol-2-yl)-2-isopropyl-4-methoxy-phenoxy]-pyrimidine-2,4-diamine which was crystalized from methanol/ethyl acetate/ether as a white solid, (0.053 g, 33%).

Step 2. 5-[5-(1H-Imidazol-2-yl)-2-isopropyl-4-methoxy-phenoxy]-pyrimidine-2,4-diamine

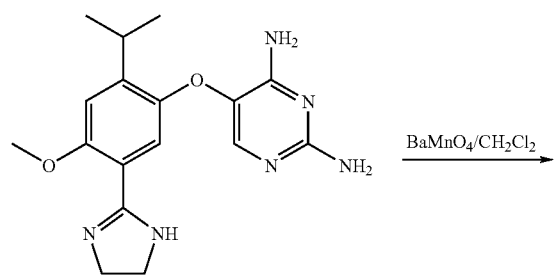

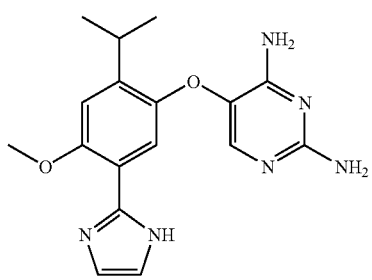

To a solution of 5-[5-(4,5-dihydro-1H-imidazol-2-yl)-2-isopropyl-4-methoxy-phenoxy]-pyrimidine-2,4-diamine (0.033 g, 0,096 mmol) in dry methylene chloride (25 ml) was added barium manganate (0.4 g, 1.56 mmol). The reaction mixture refluxed over night, after which more of barium manganate (0.1 g) was added, and the mixture was refluxed for another 6 hours. The reaction mixture was filtered through celite, and the filtrate was concentrated under reduced pressure. The residue was purified with preparative TLC (8% methanol in methylene chloride/0.1% concentrated ammonium hydroxide) to yield 5-[5-(1H-imidazol-2-yl)-2-isopropyl-4-methoxy-phenoxy]-pyrimidine-2,4-diamine as pale yellow solid (0.026 g, 41%).

Example 16

1-[5-(2,4-Diamino-pyrimidin-5-yloxy)-4-isopropyl-2-methoxy-phenyl]-ethanone and 1-[5-(2,4-Diamino-pyrimidin-5-yloxy)-2-hydroxy-4-isopropyl-phenyl]-ethanone

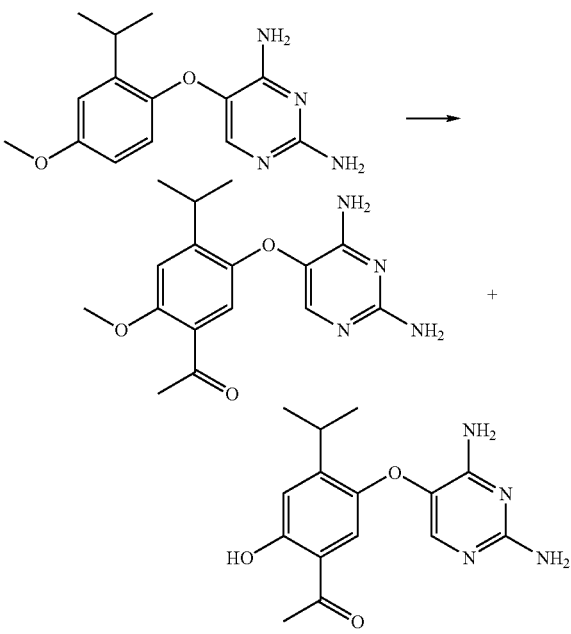

5-(2-isopropyl-4-methoxy-phenoxy)-pyrimidine-2,4-diamine in anhydrous dichloroethane (20 mL) was added to trifluoroacetic acid (0.06 mL, 0.77 mmol), acetyl chloride (0.31 mL, 4.37 mmol), and aluminum trichloride (583 mg, 4.37 mmol). After stirring for 22 hours at room temperature, water (1.2 mL) was added to the reaction at 0° C. The mixture was dried using anhydrous sodium sulfate and concentrated in vacuo. Aqueous sodium hydroxide (0.2M, 10 mL) was added to the residue and the mixture was heated at 100° C. for 1 hour. After cooling, the reaction was extracted with dichloromethane. The dichloromethane layer was dried using anhydrous magnesium sulfate, concentrated, and purified with silica gel column chromatography eluting with 96/4/0.1 dichloromethane/methanol/ammonium hydroxide to yield 1-[5-(2,4-diamino-pyrimidin-5-yloxy)-4-isopropyl-2-methoxy-phenyl]-ethanone (72 mg, 31%) as off-white solid, MS (M+H)=317. Also recovered was 1-[5-(2,4-diamino-pyrimidin-5-yloxy)-2-hydroxy-4-isopropyl-phenyl]-ethanone (43 mg, 20%) as pale yellow solid, MS (M+H)=303.

Example 17

5-(2,4-Diamino-pyrimidin-5-yloxy)-4-isopropyl-2-methoxy-benzoic acid

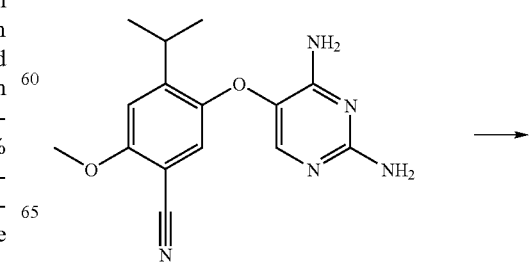

-continued

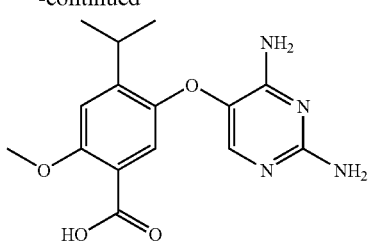

To a suspension of 5-(2,4-diamino-pyrimidin-5-yloxy)-4-isopropyl-2-methoxy-benzonitrile (50 mg, 0.17 mmol, from Example 15) in ethanol (1 mL) was added sodium hydroxide (174 mg, 4.34 mmol, dissolved in 1 mL water). After refluxing overnight, the reaction was cooled in an ice bath. Aqueous hydrochloric acid (3M) was added until the pH of the reaction was 7. The white solid precipitate was collected, washed with small amounts of water and dichloromethane, and dried to yield 5-(2,4-diamino-pyrimidin-5-yloxy)-4-isopropyl-2-methoxy-benzoic acid: (51 mg, 96%, MS (M+H)=319), which was converted to the hydrochloride salt.

Example 18

5-(2,4-Diamino-pyrimidin-5-yloxy)-4-isopropyl-2-methoxy-benzamide

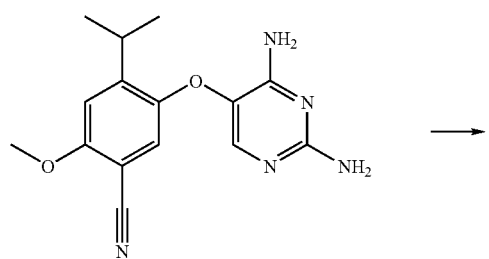

To 5-(2,4-diamino-pyrimidin-5-yloxy)-4-isopropyl-2-methoxy-benzonitrile (49 mg, 0.16 mmol, from Example 15) suspended in ethanol (1 mL) was added sodium hydroxide (64 mg, 1.60 mmol, dissolved in 1 mL water). The reaction was heated at 110° C. for 5 hours, cooled, and washed with dichloromethane (25 mL). The dichloromethane layer was concentrated and purified by preparatory TLC plates (92/8/0.5 dichloromethane/methanol/ammonium hydroxide) to yield 5-(2,4-diamino-pyrimidin-5-yloxy)-4-isopropyl-2-methoxy-benzamide as white solid (9 mg, 17%, MS (M+H)=318), which was converted to the hydrochloride salt.

Example 19

[5-(2,4-Diamino-pyrimidin-5-yloxy)-4-isopropyl-2-methoxy-phenyl]-urea

Step 1. 5-(5-Amino-2-isopropyl-4-methoxy-phenoxy)-pyrimidine-2,4-diamine

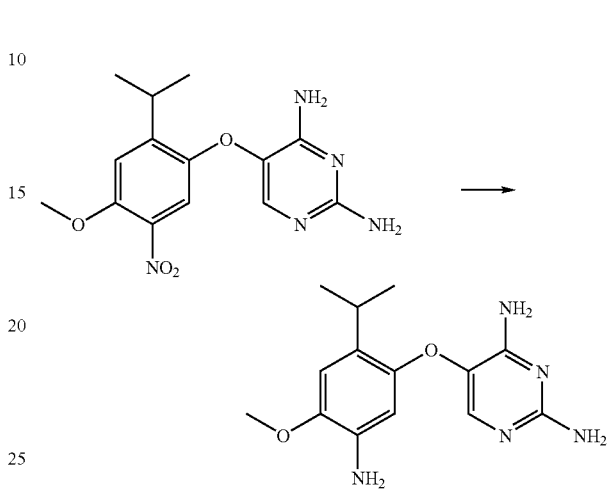

To 5-(2-isopropyl-4-methoxy-5-nitro-phenoxy)-pyrimidine-2,4-diamine (2.1 g, 6.58 mmol) suspended in ethanol (150 mL) in a Parr bomb, was added 10% palladium on charcoal (210 mg). After hydrogenation in the Parr hydrogenator overnight at 35 psi, the reaction was filtered through celite. The celite pad was washed with ethanol and ethyl acetate and the filtrate was concentrated. Purification with silica gel column chromatography (92/8/0.1 dichloromethane/methanol/ammonium hydroxide) gave 5-(5-amino-2-isopropyl-4-methoxy-phenoxy)-pyrimidine-2,4-diamine as a pale orange solid (468 mg, 25%, (M+H)$^+$=290), which was converted to the hydrochloride salt.

Step 2. [5-(2,4-Diamino-pyrimidin-5-yloxy)-4-isopropyl-2-methoxy-phenyl]-urea

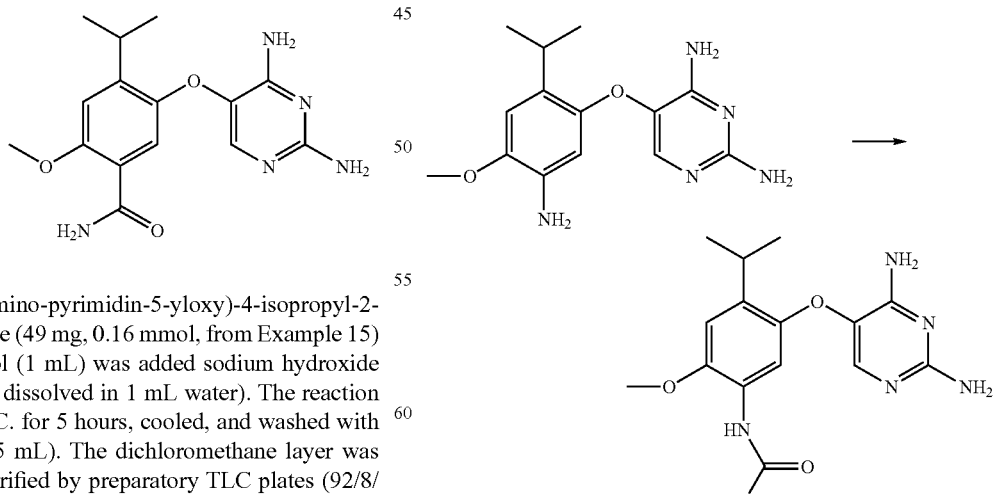

To 5-(5-amino-2-isopropyl-4-methoxy-phenoxy)-pyrimidine-2,4-diamine (314 mg, 1.09 mmol) suspended in water (3 mL) was added acetic acid (0.25 mL, 4.34 mmol). Once all solids had dissolved, sodium cyanate (71 mg, 1.09 mmol, dissolved in 1.5 mL water) was added dropwise. After 30 minutes, the reaction was concentrated and purified with silica gel column chromatography eluting with 92/8/0.1 dichloromethane/methanol/ammonium hydroxide to yield [5-(2,4-diamino-pyrimidin-5-yloxy)-4-isopropyl-2-methoxy-phenyl]-urea as an off-white solid (244 mg, 68%, M+H)$^+$= 333), which was converted to a hydrochloride salt:

Example 20

N-[5-(2,4-Diamino-pyrimidin-5-yloxy)-4-isopropyl-2-methoxyphenyl]-acetamide

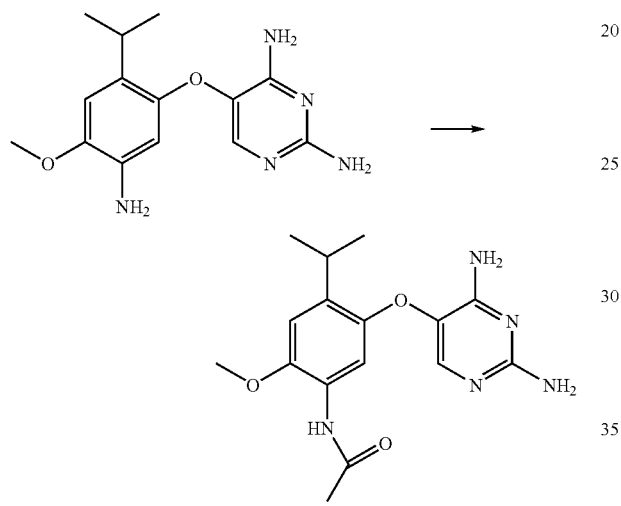

To 5-(5-amino-2-isopropyl-4-methoxy-phenoxy)-pyrimidine-2,4-diamine (100 mg, 0.35 mmol, from Example 17) dissolved in anhydrous dichloromethane (10 mL) was added anhydrous pyridine (0.03 mL, 0.38 mmol). To this reaction mixture at 0° C. was added acetyl chloride (0.03 mL, 0.38 mmol). After stirring at room temperature for 1 hour, the reaction was concentrated and purified with preparatory TLC (93/7/0.5 dichloromethane/methanol/ammonium hydroxide) to yield an off-white solid (74 mg mixture of bis- and tris-acetylated products). To this solid was added aqueous sodium hydroxide (0.2 M, 2 mL), and the mixture was refluxed for 1 hour, cooled, and washed with dichloromethane (10 mL). The dichloromethane layer was dried using anhydrous magnesium sulfate and concentrated in vacuo to yield N-[5-(2,4-diamino-pyrimidin-5-yloxy)-4-isopropyl-2-methoxy-phenyl]-acetamide as a white solid (53 mg, 46%, M+H)$^+$=332) which was converted to a hydrochloride salt:

Example 21

5-(2-Isopropyl-4-methoxy-5-nitro-phenoxy)-pyrimidine-2,4-diamine

The synthetic procedure used in this Example is outlined in Scheme K

SCHEME K

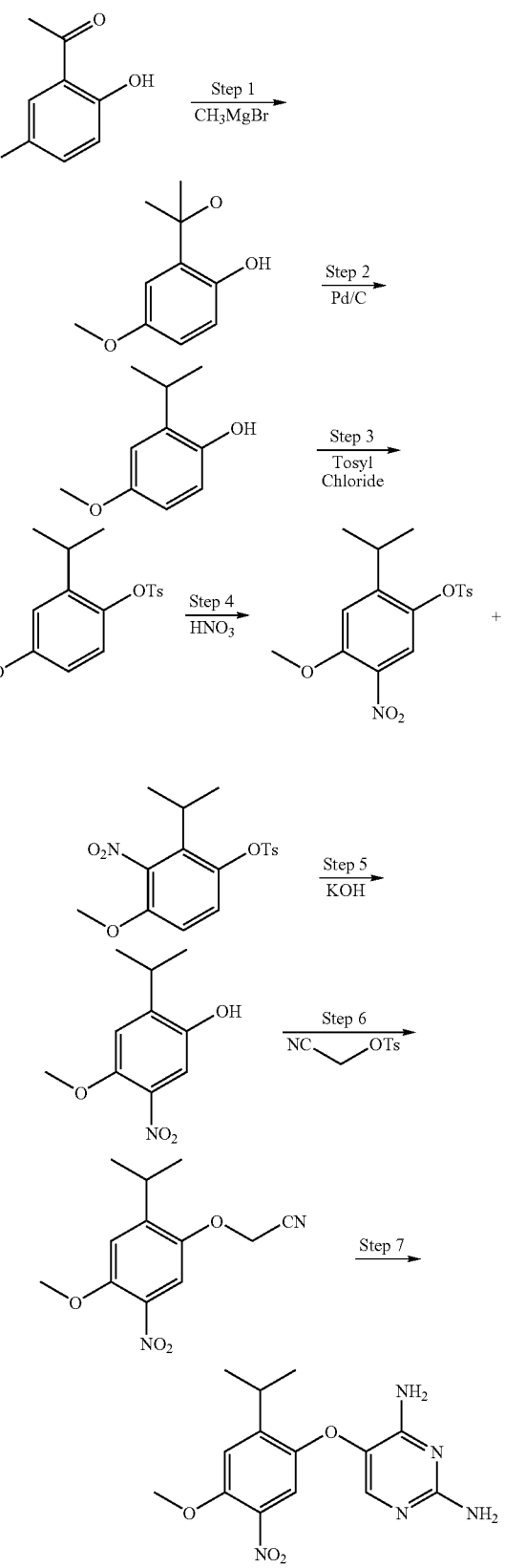

Step 1.
2-(1-Hydroxy-1-methyl-ethyl)-4-methoxy-phenol

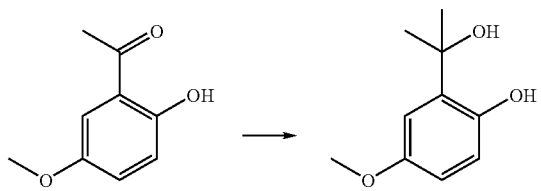

To a solution of methylmagnesium bromide (221 ml, 665 mmol) in 800 ml THF at 0° C. was added 1-(2-hydroxy-5-methoxy-phenyl)-ethanone (20.21 g, 302 mmol) in portions over 30 min. The mixture was allowed to warm to room temperature. After 16 h the mixture was quenched by the slow addition of 10% $NH_4Cl$, carefully acidified to pH=1 (slow addition) with concentrated HCl and extracted with $Et_2O$. The combined organics were washed with $H_2O$, washed with brine, died over $MgSO_4$, filtered and concentrated in vacuo to give 2-(1-hydroxy-1-methyl-ethyl)-4-methoxy-phenol (50.57 g, 100%) as a tan solid.

Step 2. 2-Isopropyl-4-methoxy-phenol

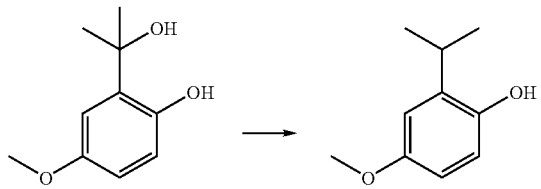

To a solution of 2-(1-hydroxy-1-methyl-ethyl)-4-methoxy-phenol (50.57 g, 278 mmol) in 550 ml AcOH was added 10% Pd/C (as a slurry in 20 ml $H_2O$). Ammonium formate (87.52 g, 1388 mmol) was added in portions. The mixture was warmed to 100° C. for 1 hour, cooled and filtered through a pad of celite. The celite pad was washed with ethyl acetate. The mother liquor was mixed with $H_2O$ and extracted with ethyl acetate. The combined organics were washed with $H_2O$, washed with brine, dried over $Na_2SO_4$, filtered and concentrated in vacuo to give 2-isopropyl-4-methoxy-phenol (44.74 g, 97%) as a pale yellow oil.

Step 3. Toluene-4-sulfonic acid 2-isopropyl-4-methoxy-phenyl ester

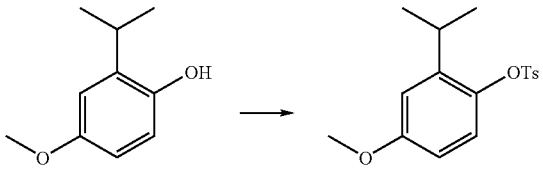

To a solution of 2-isopropyl-4-methoxy-phenol (56.91 g, 342 mmol) triethylamine (57.3.0 ml, 411 mmol) in 750 ml $CH_2Cl_2$ was cooled to 0° C. p-Toluenesulfonyl chloride (68.54 g, 360 mmol) in 250 ml $CH_2Cl_2$ was added drop-wise at a rate that maintained the internal temperature<10° C. The mixture was allowed to warm to rt. After 16 h, $H_2O$ was added and the mixture was extracted with $CH_2Cl_2$. The combined organics were washed with brine, dried with $Na_2SO_4$, filtered and concentrated in vacuo to afford a crude solid. Recrystallization from hexanes afforded toluene-4-sulfonic acid 2-isopropyl-4-methoxy-phenyl ester (81.67 g, 74%) as white needles.

Step 4. Toluene-4-sulfonic acid 2-isopropyl-4-methoxy-5-nitro-phenyl ester

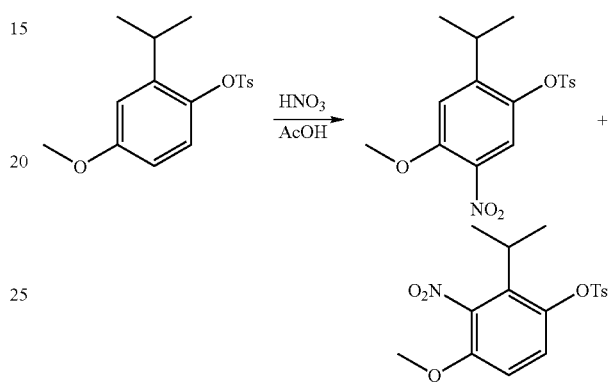

To a solution of toluene-4-sulfonic acid 2-isopropyl-4-methoxy-phenyl ester (19.00 g, 59 mmol) in 118 mL AcOH was added 236 ml fuming $HNO_3$ over 20 min. After 16 h the solution was pouring into a rapidly stirring slurry of 2 l of ice/$H_2O$. After 15 min the precipitate was filtered, washed with $H_2O$ and dried under vacuum (50° C.) to give toluene-4-sulfonic acid 2-isopropyl-4-methoxy-5-nitro-phenyl ester (21.27 g, 98%) and toluene-4-sulfonic acid 2-isopropyl-4-methoxy-3-nitro-phenyl ester and as a pale yellow solid (7:1 inseperable mixture).

Step 5. 2-Isopropyl-4-methoxy-5-nitro-phenol

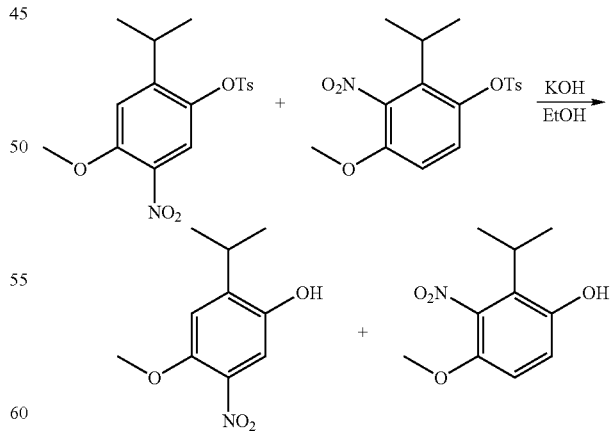

A solution of toluene-4-sulfonic acid 2-isopropyl-4-methoxy-5-nitro-phenyl ester and 2-isopropyl-4-methoxy-3-nitro-phenyl ester (21.20 g, 58 mmol ) and 175 mL 2M KOH in 350 mL EtOH was warmed to 100° C. After 45 minutes the mixture was cooled, evaporated and taken up in 1 l of water.

The solution was acidified to pH=1 with 12 M HCl and extracted with ethyl acetate. The combined organics were washed with H₂O, brine, dried over Na₂SO₄, filtered and concentrated in vacuo. The crude oil was purified via flash chromatography (gradient: 95:5 to 4:1 hexane/ethyl acetate) to afford 3-amino-2-isopropyl-5-nitro-phenol (10.03 g, 81%) as a yellow solid and 3-amino-2-isopropyl-3-nitro-phenol (1.32 g, 11%) as a yellow oil.

Step 6. (2-Isopropyl-4-methoxy-5-nitro-phenoxy)-acetonitrile

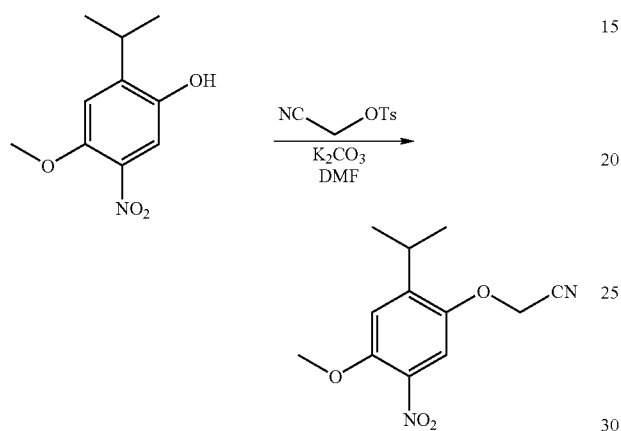

A mixture of 3-amino-2-isopropyl-5-nitrophenol (9.94 g, 47 mmol), K₂CO₃ (13.00 g, 94 mmol) and toluenenesulfonic acid cyanomethyl ester (10.93 g, 52 mmol) in 500 mL DMF was warmed to 50° C. After 16 h the mixture was cooled, poured into 500 mL H₂O and extracted with toluene/ethyl acetate (1:1). The combined organics were washed with H₂O, washed with brine, filtered and concentrated in vacuo. The crude solid was recrystallized from EtOH to afford (2-isopropyl-4-methoxy-5-nitro-phenoxy)-acetonitrile (8.95 g, 76%) as a yellow crystalline solid.

Step 7. 5-(2-Isopropyl-4-methoxy-5-nitro-phenoxy)-pyrimidine-2,4-diamine

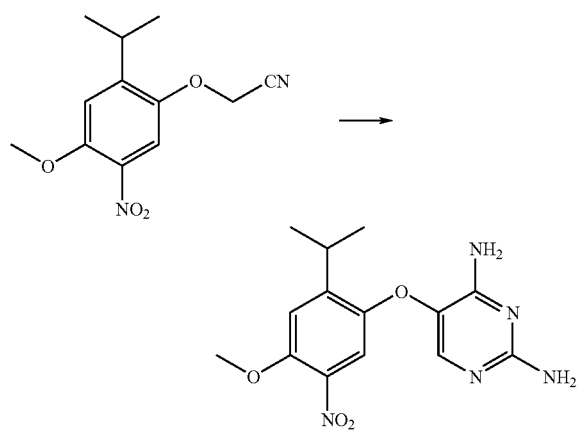

A mixture of (2-isopropyl-4-methoxy-5-nitro-phenoxy)-acetonitrile (8.785 g, 35.5 mmol) and Brederick's reagent (14.6 mL, 70.9 mmol) was warmed to 100° C. After 45 min the mixture was evaporated under reduced pressure (50° C., 50 mtorr) to give an orange solid. The solid was added to a solution of aniline hydrochloride (9.19 g, 70.9 mmol) in 150 mL of EtOH. The mixture was warmed to reflux. After 16 hr additional aniline hydrochloride (4.596 g, 35.5 mmol) was added mixture was continued at reflux for 4 h. The solution was concentrated in vacuo and poured into H₂O. The mixture was extracted with ethyl acetate, washed with H₂O, washed with brine, dried over Na₂SO₄, and concentrated in vacuo to afford a yellow-green solid. This crude product was added to a mixture of 200 mL NMP and guanidine carbonate (17.70 g, 98 mmol) and warmed to 130° C. After 5 hours the mixture was cooled then poured onto 2 l of an ice/H₂O mixture. The resulting precipitate was filtered, washed with H₂O and dried under vacuum (50° C.). The crude solid was recrystallized from EtOH to afford 5-(2-isopropyl-4-methoxy-5-nitro-phenoxy)-pyrimidine-2,4-diamine (8.14 g, 63%, 3 steps) as a yellow crystalline solid (solvated 1:1 with EtOH). (M+H)⁺= 320.

Example 22

1-[5-(2,4-Diamino-pyrimidin-5-yloxy)-4-isopropyl-2-methoxy-phenyl]-3-ethyl-urea

Step 1. 5-(5-Amino-2-Isopropyl-4-methoxy-phenoxy)-pyrimidine-2,4-diamine

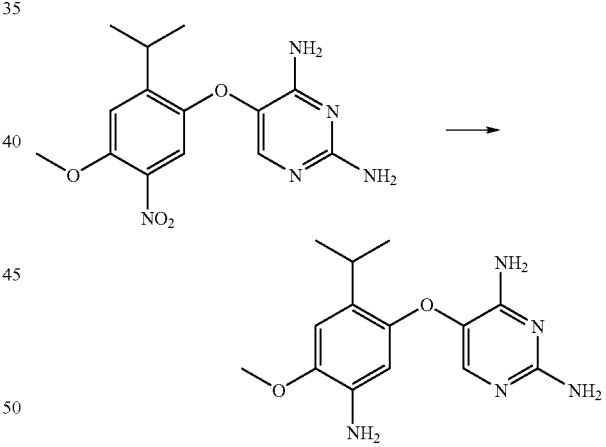

To a solution of 5-(2-isopropyl-4-methoxy-5-nitro-phenoxy)-pyrimidine-2,4-diamine (2.953 g, 9.2 mmol) in 250 mL EtOH and 25 AcOH was added 10% Pd/C. The mixture was placed under 50 psi of H₂ via a Parr hydrogenator. After 2.5 h the mixture was filtered through a pad of celite. The pad was washed with ethyl acetate and the solution was partially concentrated in vacuo. The residue was taken up in 500 mL H₂O and cooled to 0° C. The solution was adjusted to pH=12 with 50% NaOH extracted with ethyl acetate. The combined organics were washed with H₂O, washed with brine, dried over Na₂SO₄, filtered and concentrated in vacuo to afford 5-(5-amino-2-Isopropyl-4-methoxy-phenoxy)-pyrimidine-2,4-diamine (2.156 g, 82%) as a dark-orange solid.

Step 2. 1-[5-(2,4-Diamino-pyrimidin-5-yloxy)-4-isopropyl-2-methoxy-phenyl]-3-ethyl-urea

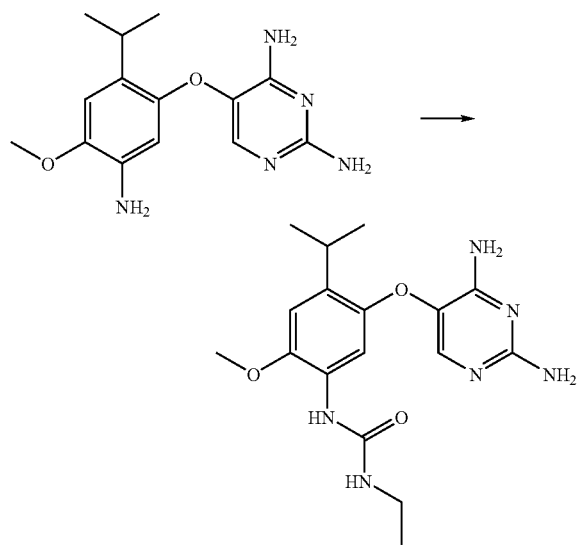

A solution of 5-(5-amino-2-Isopropyl-4-methoxy-phenoxy)-pyrimidine-2,4-diamine (0.117 g, 0.4 mmol) and ethyl isocyanate (0.034 g, 0.5 mmol) in 4 mL of toluene was heated to 100° C. in a sealed tube. After 5 h the solution was cooled and concentrated in vacuo gave a brown solid. Purification via flash chromatography (CH$_2$Cl$_2$/MeOH 97:3) afforded 1-[5-(2,4-diamino-pyrimidin-5-yloxy)-4-isopropyl-2-methoxy-phenyl]-3-ethyl-urea (0.120 g, 83%) as a white solid; (M+H)= 361.

Example 23

1-[5-(2,4-diamino-pyrimidin-5-yloxy)-4-isopropyl-2-methoxy-phenyl]-3-phenyl-urea

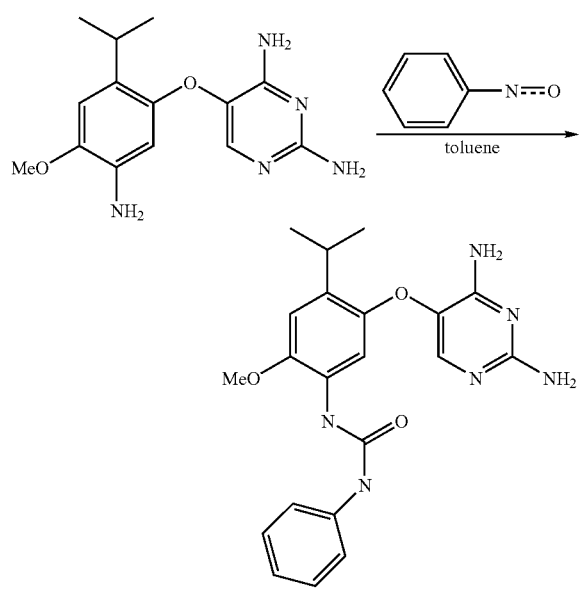

5-(5-amino-2-Isopropyl-4-methoxy-phenoxy)-pyrimidine-2,4-diamine (0.309 g, 1.1 mmol) was converted, as described in the above procedure, to 1-[5-(2,4-diamino-pyrimidin-5-yloxy)-4-isopropyl-2-methoxy-phenyl]-3-phenyl-urea (0.122 g, 28%) as white solid; [MH]$^+$=408.

Example 24

5-(2-Isopropyl-4-methoxy-5-pyrrol-1-yl-phenoxy)-pyrimidine-2,4-diamine

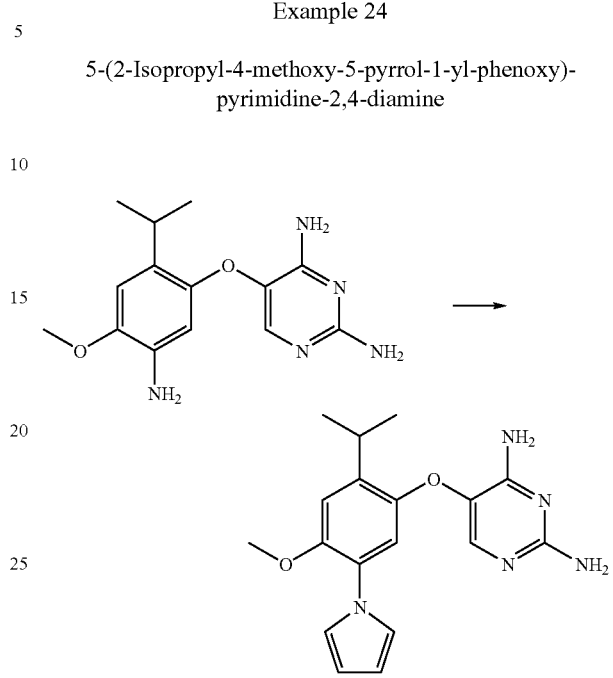

To a solution of 5-(5-amino-2-Isopropyl-4-methoxy-phenoxy)-pyrimidine-2,4-diamine (0.303 g, 1.0 mmol) in 15 mL AcOH was added 2,5-dimethoxypyran (0.152 g, 1.2 mmol). The solution was warmed to reflux. After 2 h the solution was cooled and poured over ice/H$_2$O. The solution was converted to pH=8 with 50% NaOH and extracted with ethyl acetate (3×75 mL). The combined organics were washed with H$_2$O, washed with brine, dried with Na$_2$SO$_4$, filtered and concentrated in vacuo to give a brown solid. Purification via flash chromatography (CH$_2$Cl$_2$/MeOH 97:3) afforded 5-(2-isopropyl-4-methoxy-5-pyrrol-1-yl-phenoxy)-pyrimidine-2,4-diamine (0.244 g, 72%) as a pale yellow solid. (M+H)=340.

Similarly prepared from from 5-(5-amino-2-Isopropyl-4-methoxy-phenoxy)-pyrimidine-2,4-diamine (0.313 g, 1.1 mmol) and 2,5-hexanedione (0.14 ml, 1.2 mmol) was 5-[5-(2,5-Dimethyl-pyrrol-1-yl)-2-isopropyl-4-methoxy-phenoxy]-pyrimidine-2,4-diamine, (0.259 g, 64%). (M+H)=368.

Example 25

5-(2-Isopropyl-4-methoxy-5-[1,2,3]triazol-1-yl-phenoxy)-pyrimidine-2,4-diamine

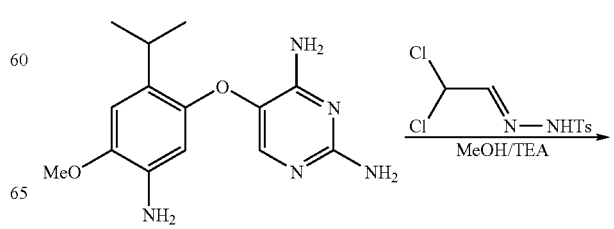

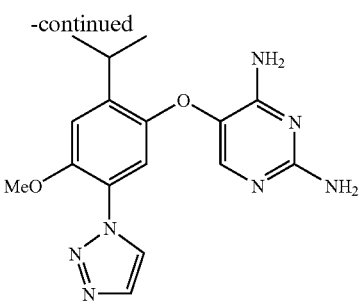

Following the procedure of Harada et al., *Heterocycles* 1998, 48, 695-702, to a solution of 5-(5-amino-2-isopropyl-4-methoxy-phenoxy)-pyrimidine-2,4-diamine (0.400 g, 1.8 mmol) in 5 ml methanol at 0° C. was added trimethylamime (0.308 g, 3.0 mmol) and hydrazine 1,1-dichloroethyl hydrazine tosylate (0.388 g, 1.4 mmol). The solution was warmed to 50° C. After 4 h the mixture was concentrated in vacuo and extracted with CH$_2$Cl$_2$. The combined organics were washed with H$_2$O, washed with brine, dried over Na$_2$SO$_4$, filtered, and concentrated in vacuo. Purification via flash chromatography (94:6 CH$_2$Cl$_2$/MeOH) afforded 5-(2-sopropyl4-methoxy-5-[1,2,3]triazol-1-yl-phenoxy)-pyrimidine-2,4-diamine (0.145 g, 31%) a white solid; [MH]$^+$=342.

Example 26

1-[5-(4-Amino-2-methyl-pyrimidin-5-yloxy)-4-isopropyl-2-methoxy-phenyl]pyrrolidin-2-one Step 1. 4-Chloro-N-[5-(2,4-diamino-pyrimidin-5-yloxy)-4-isopropyl-2-methoxy-phenyl]-butyramide

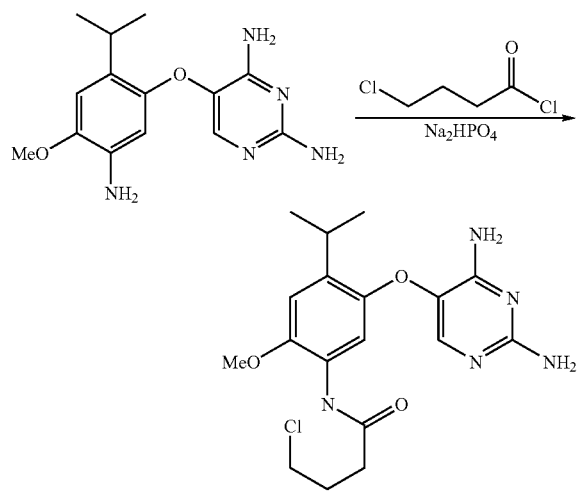

To a solution of 5-(5-amino-2-isopropyl-4-methoxy-phenoxy)-pyrimidine-2,4-diamine (0.400 g, 1.4 mmol) in 15 ml CHCl$_3$ and Na$_2$HPO$_4$ (0.392 g, 2.8 mmol) was added 4-chlorobutyryl chlorode (0.194 g, 1.4 mmol) drop-wise. After 4.5 h, H$_2$O and CH$_2$Cl$_2$ were added and the mixture was allowed to stir 15 min. The mixture was neutralized with 2N Na$_2$CO$_3$ and extracted with CH$_2$Cl$_2$. The combined organics were washed with brine, dried over Na$_2$SO$_4$, filtered and concentrated in vacuo to afford 4-chloro-N-[5-(2,4-diamino-pyrimidin-5-yloxy)-4-isopropyl-2-methoxy-phenyl]-butyramide (0.495 g, 91%) as brown foam; [MH]$^+$=394.

Step 2. 1-[5-(4-Amino-2-methyl-pyrimidin-5-yloxy)-4-isopropyl-2-methoxy-phenyl]-pyrrolidin-2-one

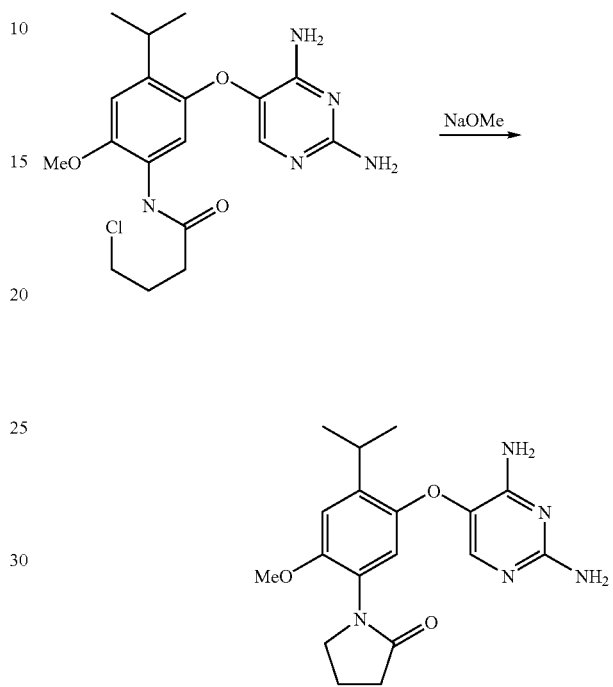

To a solution of 5 ml 1.9 M NaOMe in MeOH was added 4-Chloro-N-[5-(2,4-diamino-pyrimidin-5-yloxy)-4-isopropyl-2-methoxy-phenyl]-butyramide (0.495 g, 1.3 mmol). After 6 h the solution was concentrated in vacuo. The residue was taken up in ethyl acetate, washed with H$_2$O, washed with brine, dried over Na$_2$SO$_4$, filtered and concentrated in vacuo to give 1-[5-(4-amino-2-methyl-pyrimidin-5-yloxy)4-isopropyl-2-methoxy-phenyl]-pyrrolidin-2-one (0.230 g, 47%) as white solid; [MH]$^+$=358; mp (HCl salt)>300° C.

Example 27

1-[5-(2,4-Diamino-pyrimidin-5-yloxy)-4-isopropyl-2-methoxy-phenyl]-1H-imidazole-2-thiol Step 1. 5-(2-Isopropyl-5-isothiocyanato-4-methoxy-phenoxy)-pyrimidine-2,4-diamine

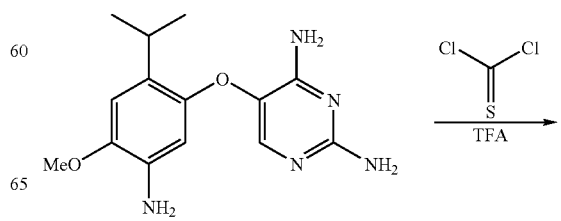

-continued

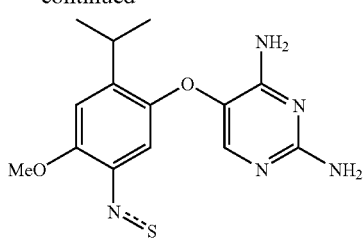

To a solution of 5-(5-amino-2-isopropyl-4-methoxy-phenoxy)-pyrimidine-2,4-diamine (0.100 g, 0.4 mmol) in 1 ml H$_2$O and TFA (0.040 g, 0.4 mmol) was added thiophosgene (0.040 g, 0.4 mmol). After 1 h the mixture was neutralized with 2M NaOH and extracted with CH$_2$Cl$_2$. The combined organics were washed with brine, dried over Na$_2$SO$_4$, filtered and concentrated in vacuo to afford 5-(2-isopropyl-5-isothiocyanato4-methoxy-phenoxy)-pyrimidine-2,4-diamine (0.042 g, 36%) as brown foam [MH]$^+$=334.

Step 2. 1-[5-(2,4-Diamino-pyrimidin-5-yloxy)-4-isopropyl-2-methoxy-phenyl]-1H-imidazole-2-thiol

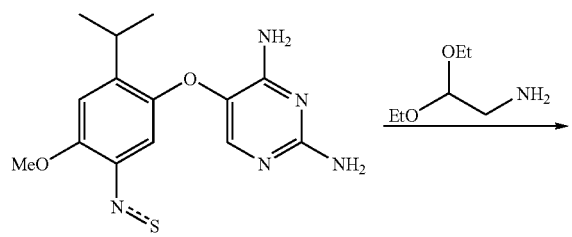

To a solution of amino acetal (0.173 g, 1.3 mmol) in 10 ml EtOH was added a solution of thio-isocyanate (0.430 g, 1.3 mmol) in 2 ml EtOH. The mixture was warmed to reflux. After 30 min the mixture was cooled, concentrated in vacuo and suspended in 1M HCl and refluxed again for another 30 min reaction was neutralized with saturated NaHCO$_3$ and extracted with CH$_2$Cl$_2$. The combined organics were washed with brine, dried over Na$_2$SO$_4$, filtered and concentrated in vacuo to afford 1-[5-(2,4-diamino-pyrimidin-5-yloxy)-4-isopropyl-2-methoxy-phenyl]-1H-imidazole-2-thiol (0.298 g, 50%) as white solid [MH]$^+$=373.

Example 28

5-(5-Imidazol-1-yl-2-isopropyl-4-methoxy-phenoxy)-pyrimidine-2,4-diamine

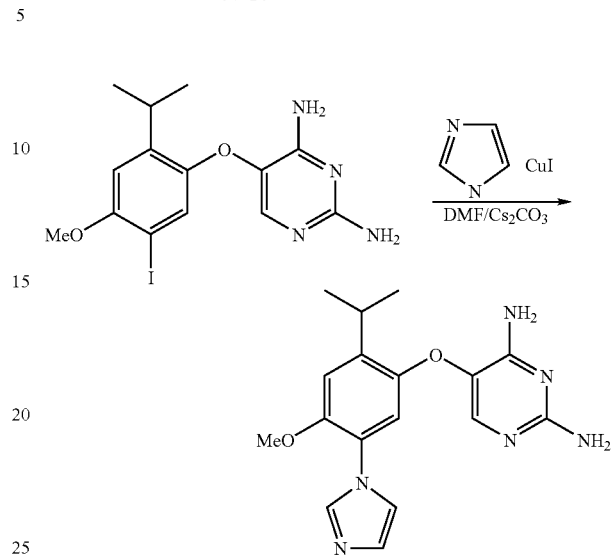

A suspension of 5-iodo-diaminopyrimidine (0.294 g, 0.74 mmol), imidazole (0.120 g, 1.8 mmol), CuI (0.070 g, 0.4 mmol), and Cs$_2$CO$_3$ (0.616 g, 1.9 mmol) in 4 ml DMF was heated to 100° C. After 72 hours the mixture was cooled, diluted with H$_2$O and extracted with ethyl acetate. The combined organics were washed with brine, dried over Na$_2$SO$_4$, filtered and concentrated in vacuo. Purification via preparative TLC (94:6 CH$_2$Cl$_2$/MeOH) afforded 5-(5-imidazol-1-yl-2-isopropyl-4-methoxy-phenoxy)-pyrimidine-2,4-diamine (0.020 g, 8%) as a white solid; [MH]$^+$=341.

Example 29

2-[5-(2,4-Diaminopyrimidin-5-yloxy)-4-isopropyl-2-methoxy-phenyl]-propan-2-ol

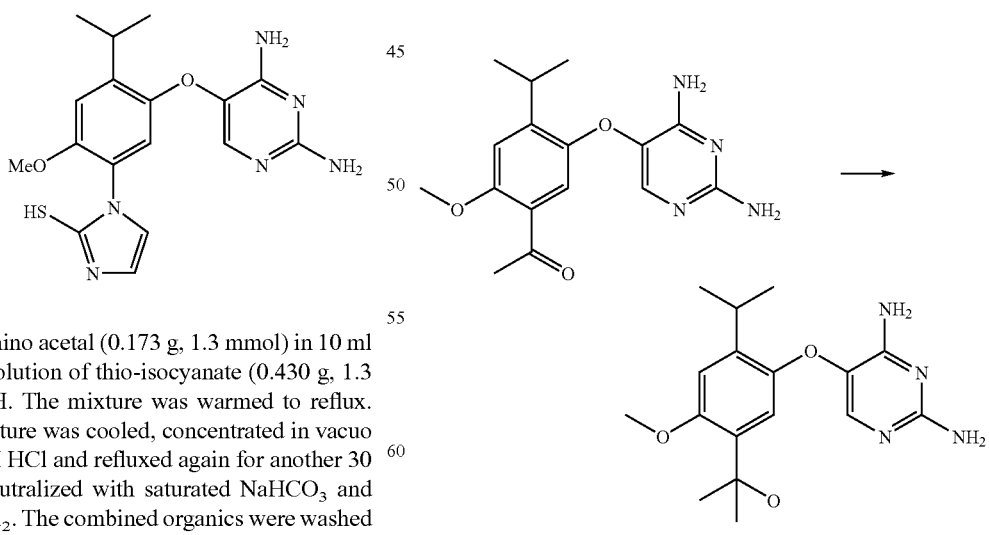

To a solution of methylmagnesium bromide (83.4 mmol, 27.8 ml, 3.0 M in Et$_2$O) in 83 mL THF at 0° C. was added 1-[5-(2,4-diamino-pyrimidin-5-yloxy)-4-isopropyl-2-methoxy-phenyl]-ethanone (2.523 g, 8.3 mmol, from Example 16) in portions. After 16 h the mixture was cooled to 0° C. and was quenched by the addition 10% NH₄Cl. H₂O was added and the mixture was extracted with ethyl acetate. The combined organics were washed with H₂O, washed with brine, dried over NaHCO₃, filtered and concentrated in vacuo. The crude solid was taken up in 31 ml DMF. K₂CO₃ (0.65 g, 4.7 mmol) and iodomethane (0.098 ml, 1.6 mmol) were added and the mixture was warmed to 50° C. Additional portions of iodomethane (0.019 mL, 0.6 mmol) was added at 1, 2 and 3 hr. After 16 h the mixture was cooled and 10% NH₄Cl and extracted with ethyl acetate. The combined organics were washed with H₂O, washed with brine, dried with Na₂SO₄, filtered and concentrated in vacuo to give 2-[5-(2,4-diaminopyrimidin-5-yloxy)-4-isopropyl-2-methoxy-phenyl]-propan-2-ol (0.711 g, yiled) as a white solid. [MH]⁺=333.

Example 30

5-(2,5-Diiosopropyl-methoxy-phenoxy)-pyrimidine-2,4-diamine

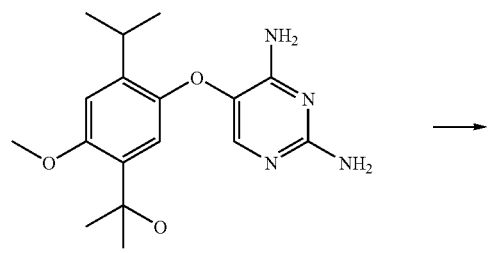

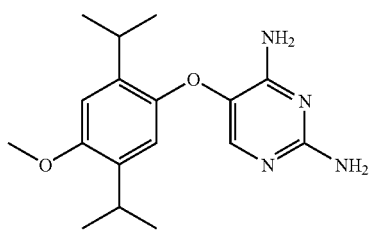

To a solution of 2-[5-(2,4-diaminopyrimidin-5-yloxy)-4-isopropyl-2-methoxy-phenyl]-propan-2-ol: (0.350 g, 1.1 mmol) in 10 ml CH₂Cl₂ was added trifluoroacetic acid (4.0 ml, 52.6 mmol) and triethylsilane (1.7 ml, 10.5 mmol). After 30 min saturated NaHCO₃ was added an the mixture was extracted with ethyl acetate. The combined organics were washed with brine, dried over Na₂SO₄, filtered and concentrated in vacuo to give a crude oil. Purification via flash chromatography (96:4 CH₂Cl₂/MeOH) gave 5-(2,5-diiosopropyl-methoxy-phenoxy)-pyrimidine-2,4-diamine (0.225 g, 68%) as a white solid. [MH]⁺=317.

Example 31

1-[5-(2,4-Diamino-pyrimidine-5-yloxy)-4-isopropyl-2-methoxy-phenyl]-ethanol

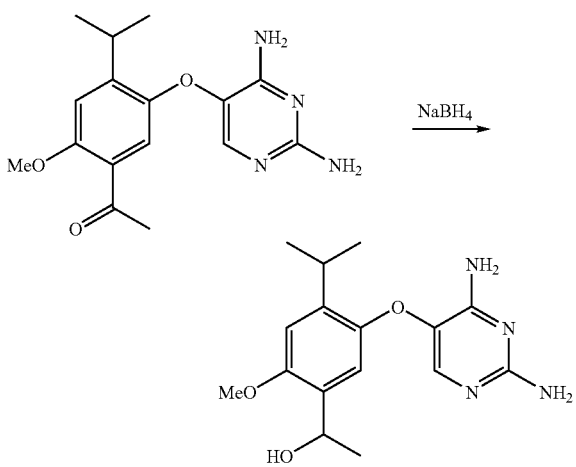

To a solution of 1-[5-(2,4-diamino-pyrimidin-5-yloxy)-4-isopropyl-2-methoxy-phenyl]-ethanone (2.500 g, 8.3 mmol) in 100 ml MeOH was slowly added NaBH₄ (1.566 g, 41.4 mmol) at 0° C. The solution was allowed to warm to rt. After 20 h, the saturated NH₄Cl was added, the mixture was concentrated in vacuo and extracted with ethyl acetate. The combined organics were washed with brine, dried over Na₂SO₄, filtered and concentrated in vacuo. Purification via silica gel column chromatography (9:1 CH₂Cl₂/MeOH) afforded to 1-[5-(2,4-diamino-pyrimidine-5-yloxy)-4-isopropyl-2-methoxy-phenyl]-ethanol (1.613 g, 60%) as white foam; [MH]⁺=301.

Example 32

5-(2-Isopropyl-4-methoxy-5-vinyl-phenoxy)-pyrimidine-2,4-diamine and 5-[2-Isopropyl-4-methoxy-5-(1-methoxy-ethyl)-phenoxy]-pyrimidine-2,4-diamine

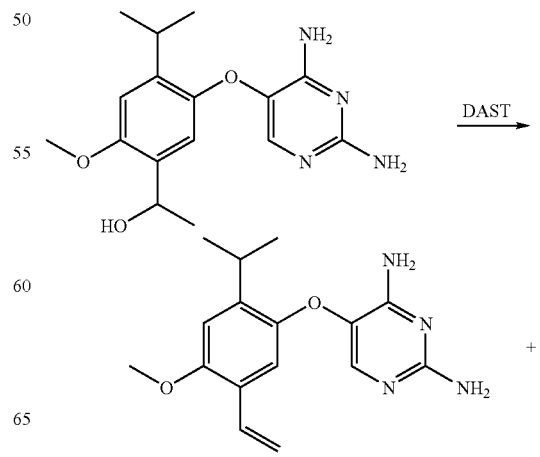

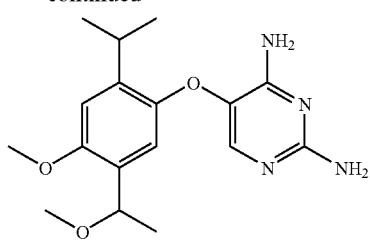

To a solution of 1-[5-(2,4-Diamino-pyrimidin-5-yloxy)4-isopropyl-2-methoxy-phenyl]-ethanol (1.613 g, 5.3 mmol) in 30 ml CH$_2$Cl$_2$ at −78° C. was added DAST (0.935 g, 5.8 mmol). After stirring 1.5 h, saturated NaHCO$_3$ was added and the mixture was extracted by CH$_2$Cl$_2$. The combined organics were washed with brine and dried Na$_2$SO$_4$, filtered and concentrated in vacuo. Purification via silica gel chromatography (95:5 CH$_2$Cl$_2$/MeOH) gave 5-(2-Isopropyl-4-methoxy-5-vinyl-phenoxy)-pyrimidine-2,4-diamine (0.044 g, 3%) as a foam ([MH]$^+$=301) and 5-[2-Isopropyl-4-methoxy-5-(1-methoxy-ethyl)-phenoxy]-pyrimidine-2,4-diamine(0.075 g, 4%) as foam. [MH]$^+$=303.

Example 33

The synthetic procedure used in this Example is outlined in Scheme M.

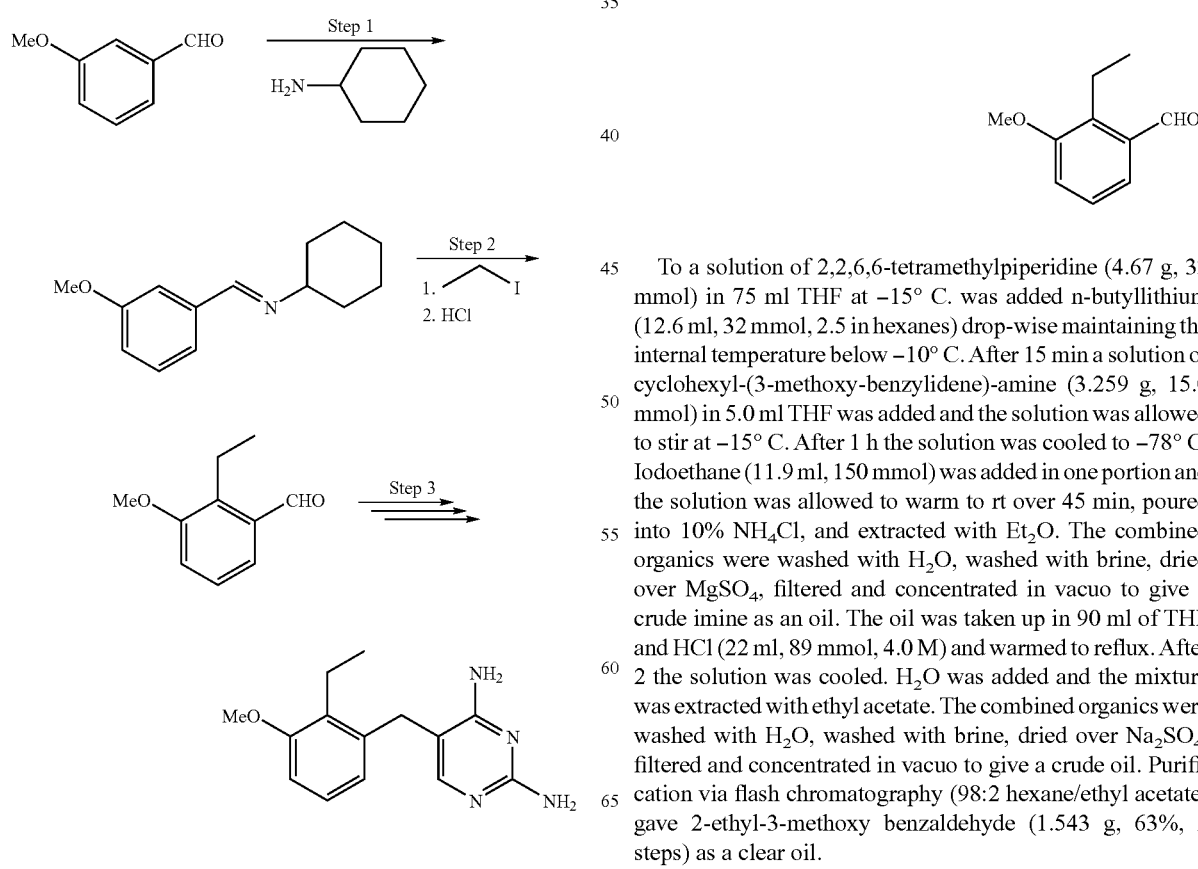

Step 1. Cyclohexyl-(3-methoxy-benzylidene)-amine

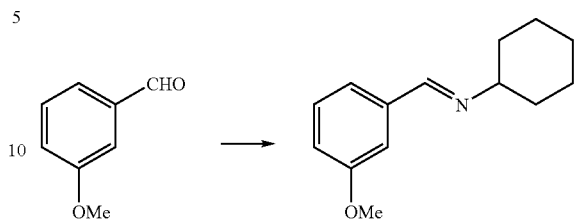

3-Methoxy benzaldehyde (10.105 g, 74.2 mmol) was converted, as described in step 1 of Example 3, to Cyclohexyl-(3-methoxy-benzylidene)-amine (15.08 g, 94%) as a clear oil.

Step 2. 2-Ethyl-3-methoxy benzaldehyde

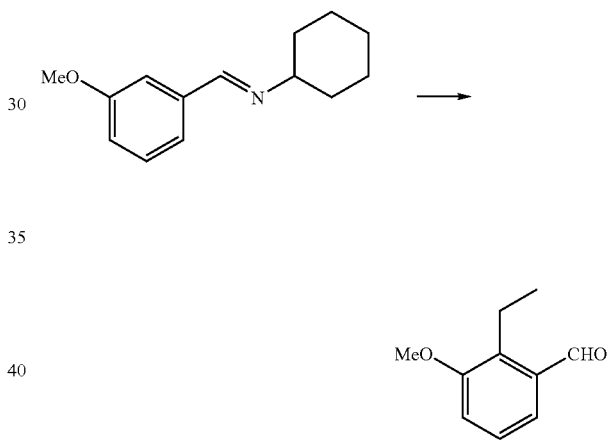

To a solution of 2,2,6,6-tetramethylpiperidine (4.67 g, 33 mmol) in 75 ml THF at −15° C. was added n-butyllithium (12.6 ml, 32 mmol, 2.5 in hexanes) drop-wise maintaining the internal temperature below −10° C. After 15 min a solution of cyclohexyl-(3-methoxy-benzylidene)-amine (3.259 g, 15.0 mmol) in 5.0 ml THF was added and the solution was allowed to stir at −15° C. After 1 h the solution was cooled to −78° C. Iodoethane (11.9 ml, 150 mmol) was added in one portion and the solution was allowed to warm to rt over 45 min, poured into 10% NH$_4$Cl, and extracted with Et$_2$O. The combined organics were washed with H$_2$O, washed with brine, dried over MgSO$_4$, filtered and concentrated in vacuo to give a crude imine as an oil. The oil was taken up in 90 ml of THF and HCl (22 ml, 89 mmol, 4.0 M) and warmed to reflux. After 2 the solution was cooled. H$_2$O was added and the mixture was extracted with ethyl acetate. The combined organics were washed with H$_2$O, washed with brine, dried over Na$_2$SO$_4$, filtered and concentrated in vacuo to give a crude oil. Purification via flash chromatography (98:2 hexane/ethyl acetate) gave 2-ethyl-3-methoxy benzaldehyde (1.543 g, 63%, 2 steps) as a clear oil.

Step 3. 5-(2-Ethyl-3-methoxy-benzyl)-pyrimidine-2,4-diamine

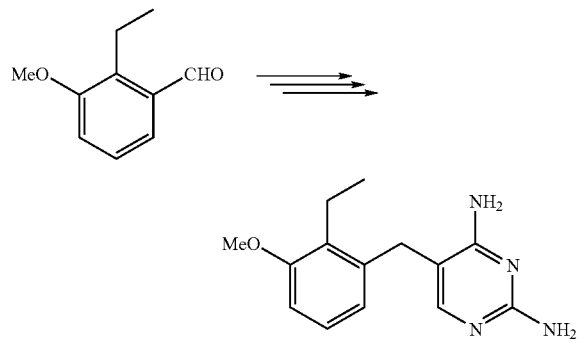

Following the procedure of steps 4-8 of Example 3, 2-ethyl-3-methoxy benzaldehyde (1.025 g, 6.24 mmol) afforded 5-(2-Ethyl-3-methoxy-benzyl)-pyrimidine-2,4-diamine (0.154 g, 10%, 2 steps) as a pale yellow solid. [MH$^+$]=259.

Example 34

5-(5-Chloro-2-isopropyl-4-methoxy-benzyl)-N$^2$-(2,2,2-trifloro-ethyl)pyrimidine-2,4-diamine The synthetic procedure used in this Example is outlined in Scheme M.

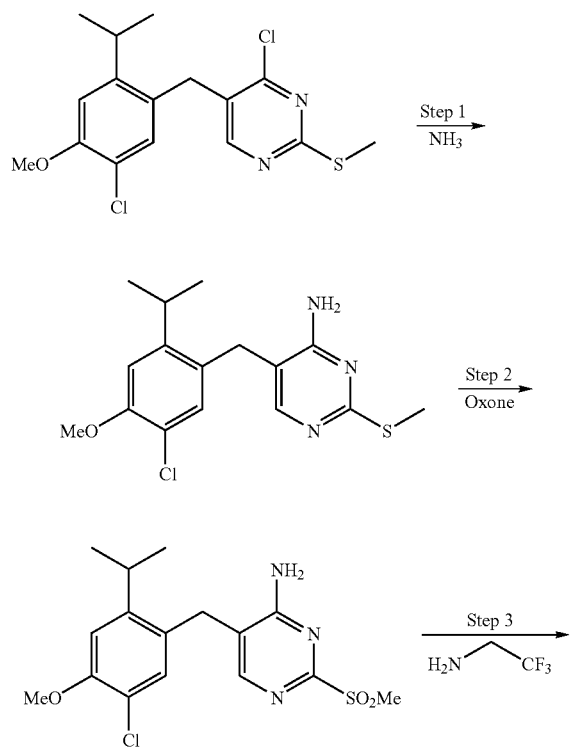

Step 1. 5-(5-Chloro-2-isopropyl-4-methoxy-benzyl)-2-methylsulfanyl-pyrimidin-4-ylamine

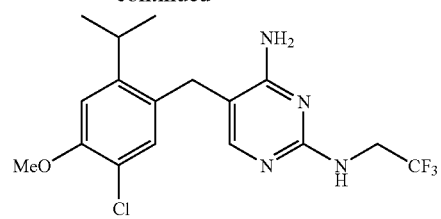

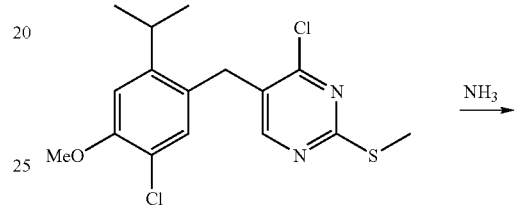

To 25 ml of saturated NH$_3$ in EtOH was added 4-Chloro-5-(5-chloro-2-isopropyl-4-methoxy-benzyl)-2-methylsulfanyl-pyrimidine (0.580 g, 1.6 mmol). The solution was warmed to 85° C. in a sealed reaction vessel. After 3 days the solution was cooled, concentrated in vacuo and suspended in CH$_2$Cl$_2$. The precipitate was filtered and the mother liquor was concentrated in vacuo. Purification via flash chromatography (7:3 hexane/ethyl acetate) afforded 5-(5-chloro-2-isopropyl-4-methoxy-benzyl)-2-methylsulfanyl-pyrimidin-4-ylamine (0.504 g, 92%) as a white solid.

Step 2. 5-(5-Chloro-2-isopropyl-4-methoxy-benzyl)-2-methylsulfonyl-pyrimidine-4-ylamine

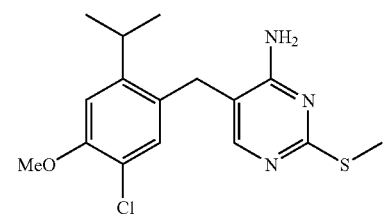

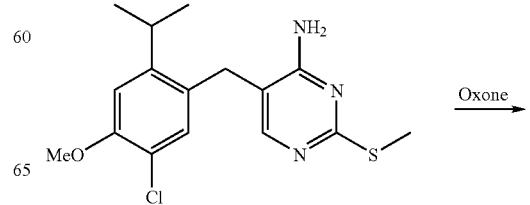

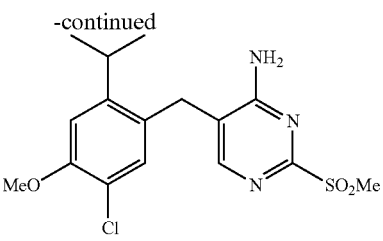

To a solution of 4-chloro-5-(5-chloro-2-isopropyl-4-methoxy-benzyl)-2-methylsulfanyl-pyrimidine (0.320 g, 0.9 mmol) in 15 ml THF and 15 ml H$_2$O was added Oxone (1.227 g, 2 mmol) in portions. After 16 h the solution was concentrated in vacuo and extracted with ethyl acetate. The combined organics were washed with brine, dried over Na$_2$SO$_4$, filtered, and concentrated in vacuo. Purification via flash chromatography afforded 5-(5-chloro-2-isopropyl-4-methoxy-benzyl)-2-methylsulfonyl-pyrimidine4-ylamine (0.333, 96%) as a white solid.

Step 3. 5-(5-Chloro-2-isopropyl-4-methoxy-benzyl)-N -(2,2,2-trifloro-ethyl)-pyrimidine-2,4-diamine

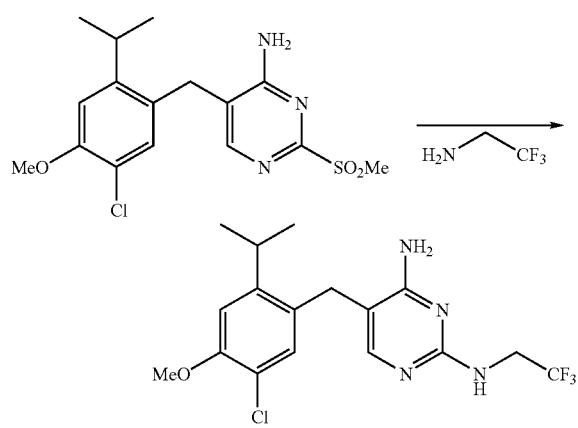

To a solution of 5-(5-chloro-2-isopropyl-4-methoxy-benzyl)-2-methylsulfonyl-pyrimidine-4-ylamine (0.050 g, 0.1 mmol) in 3 ml DME was added 0.5 ml 2,2,2-trifluoro-ethyl amine. The mixture was heated in the microwave (130° C., 10 barr). After 22 h the mixture was concentrated in vacuo. Purification via reverse phase preparative HPLC afforded the TFA salt of 5-(5-chloro-2-isopropyl-4-methoxy-benzyl)-N$^2$-(2,2,2-trifloro-ethyl)-pyrimidine-2,4-diamine (0.010 g, 19%) as a white solid); [MH]$^+$=389.

Similarly prepared from 5-(5-Chloro-2-isopropyl-4-methoxy-benzyl)-2-methylsulfonyl-pyrimidine-4-ylamine (0.100 g, 0.3 mmol) but using 2-methoxyethylamine was 5-(5-Chloro-2-isopropyl-4-methoxy-benzyl)-N$^2$-(2-methoxy-ethyl)-pyrimidine-2,4-diamine (0.068 g, 63%) as a white solid; [MH]$^+$=365.

Example 35

5-[5-Chloro-2-(1-fluoro-1-methyl-ethyl)-4-methoxy-phenoxy]-pyrimidine-2,4-diamine The synthetic procedure used in this Example is outlined in Scheme N.

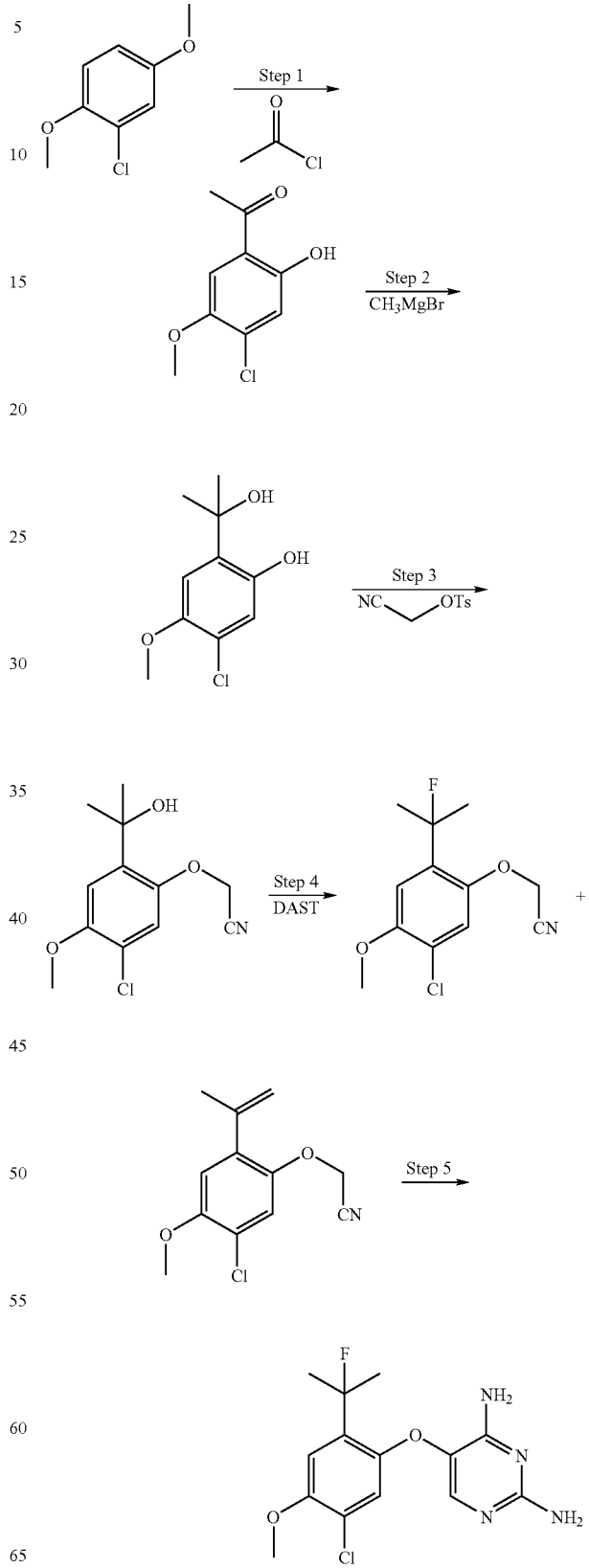

Step 1.
1-(4-Chloro-2-hydroxy-5-methoxy-phenyl)-ethanone

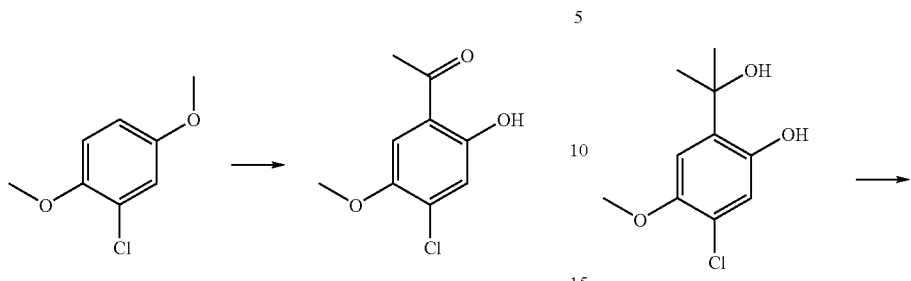

To a mixture of AlCl$_3$ (8.89 g, 59 mmol) in CH$_2$Cl$_2$ at −10° C. was added acetyl chloride (4.1 ml, 58 mmol) drop-wise while maintaining the internal temperature below 0° C. After 20 min 2-Chloro-1,4-dimethoxybenzene (10.0 g, 8.3 mmol) was dissolved in 8 ml CH$_2$Cl$_2$ and added to the above solution drop-wise while maintaining the internal temperature below 0° C. After 20 min the mixture was warmed to room temperature for 1 hour then warmed to reflux. After 21 h the solution was cooled, poured over a mixture of ice and concentrated HCl and extracted with dichloromethane. The combined organics were concentrated in vacuo and recrytsallized from H$_2$O/EtOH to afford 1-(4-chloro-2-hydroxy-5-methoxy-phenyl)-ethanone (8.78 g, 85%) as a solid.

Step 2. 5-Chloro-2-(1-hydroxy-1-methyl-ethyl)-4-methoxy-phenol

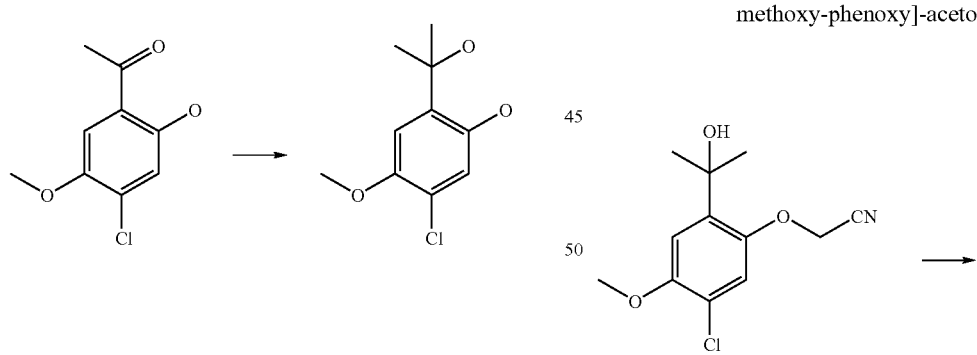

To a solution of 1-(4-chloro-2-hydroxy-5-methoxy-phenyl)-ethanone (9.80 g, 49 mmol) in 90 mL THF at 0° C. was added methyl magnesium bromide (37 mL, 112 mmol, 3.0 M in Et$_2$O. After 2 h the reaction was quenched by the addition of 10% NH$_4$Cl. The mixture was adjusted to pH=1 with 2M HCl and extracted with ethyl acetate. The combined organics were washed with H$_2$O, washed with brine, dried with MgSO$_4$, filtered and concentrated in vacuo to give a crude solid. Purification via flash chromatography afforded alcohol 5-chloro-2-(1-hydroxy-1-methyl-ethyl)-4-methoxy-phenol (11.85 g, more than 100%) as a yellow solid.

Step 3. [5-Chloro-2-(1-hydroxy-1-methyl-ethyl)-4-methoxy-phenoxy]-pyrimidine-2,4-diamine

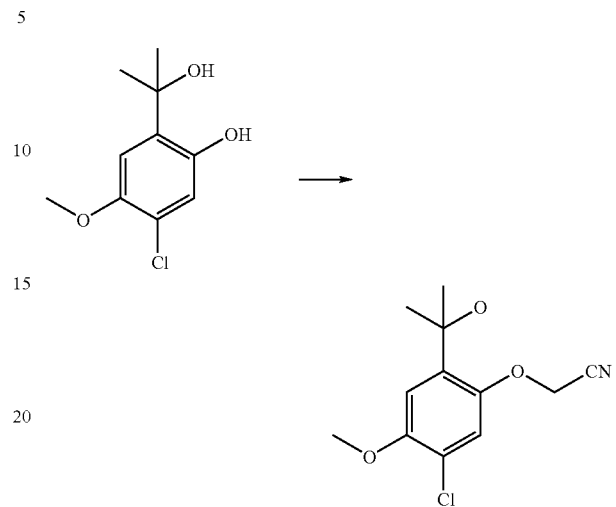

To a mixture of 5-chloro-2-(1-hydroxy-1-methyl-ethyl)4-methoxy-phenol (2.00 g, 9 mmol) and K$_2$CO$_3$ (2.55 g, 19 mmol) in 50 mL DMF was added toluenesulfonyl cyano ethyl ester (2.34 g, 11 mmol). The mixture was allowed to stir at room temperature. After 16 h the mixture was poured into 200 ml water and extracted with ethyl acetate. The combined organics were washed with water, washed with brine, dried over Na$_2$SO$_4$, filtered and concentrated in vacuo to give a crude solid. Purification via flash chromatography (7:3 hexane/ethyl acetate) to afford [5-chloro-2-(1-hydroxy-1-methyl-ethyl)-4-methoxy-phenoxy]-pyrimidine-2,4-diamine (1.62 g, 69%) as a white solid.

Step 4. 5-[5-Chloro-2-(1-fluoro-1-methyl-ethyl)-methoxy-phenoxy]-acetonitrile

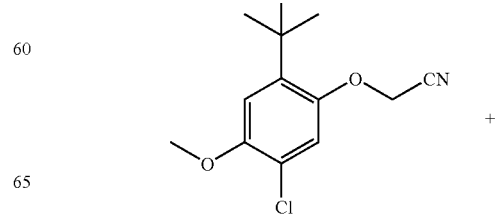

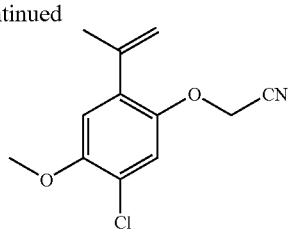

To a solution of [5-chloro-2-(1-hydroxy-1-methyl-ethyl)-4-methoxy-phenoxy]-pyrimidine-2,4-diamine (1.432 g, 5.6 mmol) in 50 ml CH$_2$Cl$_2$ at −78° C. was added DAST (0.77 ml, 5.9 mmol) drop-wise. After 1.5 the solution was warmed to rt and quenched by the addition of saturated NaHCO$_3$ solution and extracted with CH$_2$Cl$_2$. The combined organics were washed with brine, dried over Na$_2$SO$_4$, filtered and concentrated in vacuo to give an inseparable mixture (9:1) of 5-[5-chloro-2-(1-fluoro-1-methyl-ethyl)-methoxy-phenoxy]-acetonitrile (1.543 g) and (5-Chloro-2-isopropenyl-4-methoxyphenoxy)-acetonitrile as a pale brown oil.

Step 5. 5-[5-Chloro-2-(1-fluoro-1-methyl-ethyl)-methoxy-phenoxy]-pyrimidine-2,4-diamine

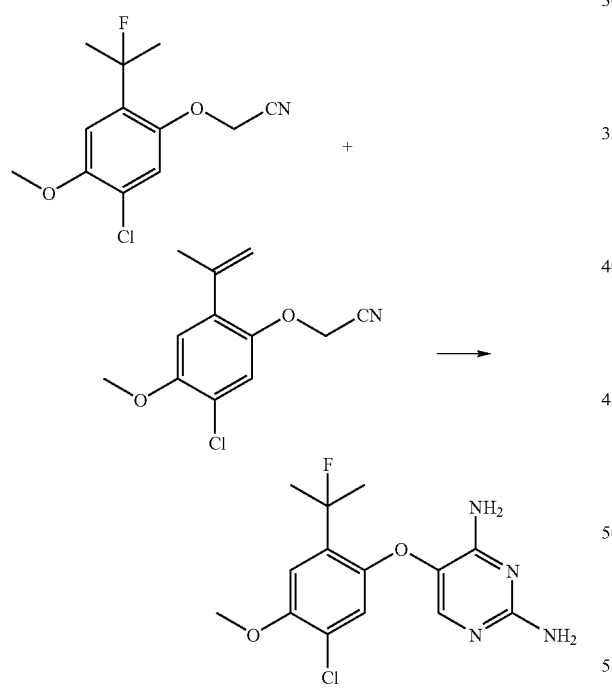

[5-Chloro-2-(1-fluoro-1-methyl-ethyl)-methoxy-phenoxy]-acetonitrile (1.447 g, 4.2 mmol) was converted, as describe in steps 6 and 7 of Example 2, to 5-[5-chloro-2-(1-fluoro-1-methyl-ethyl)-methoxy-phenoxy]-pyrimidine-2,4-diamine (0.263 g, 10% for three steps) as a yellow solid; mp=220.1-220.6° C. (HCl salt); [MH]$^+$=328.

Similarly prepared, but starting with 3-fluoro-1,4-dimethoxybenzene, and using hydrogenation with Pd/C in step 4 instead of DAST, was 5-(5-Fluoro-2-isopropyl-4-methoxy-phenoxy)-pyrimidine-2,4-diamine (0.778 g, 42%); mp (HCl salt)=239-241° C.; [MH]$^+$=293.

Example 36

5-(8-Bromo-5-ethyl-2,3-dihydro-benzo[1,4]dioxin-6-yloxy)-pyrimidine-2,4-diamine

The synthetic procedure used in this Example is outlined in Scheme O.

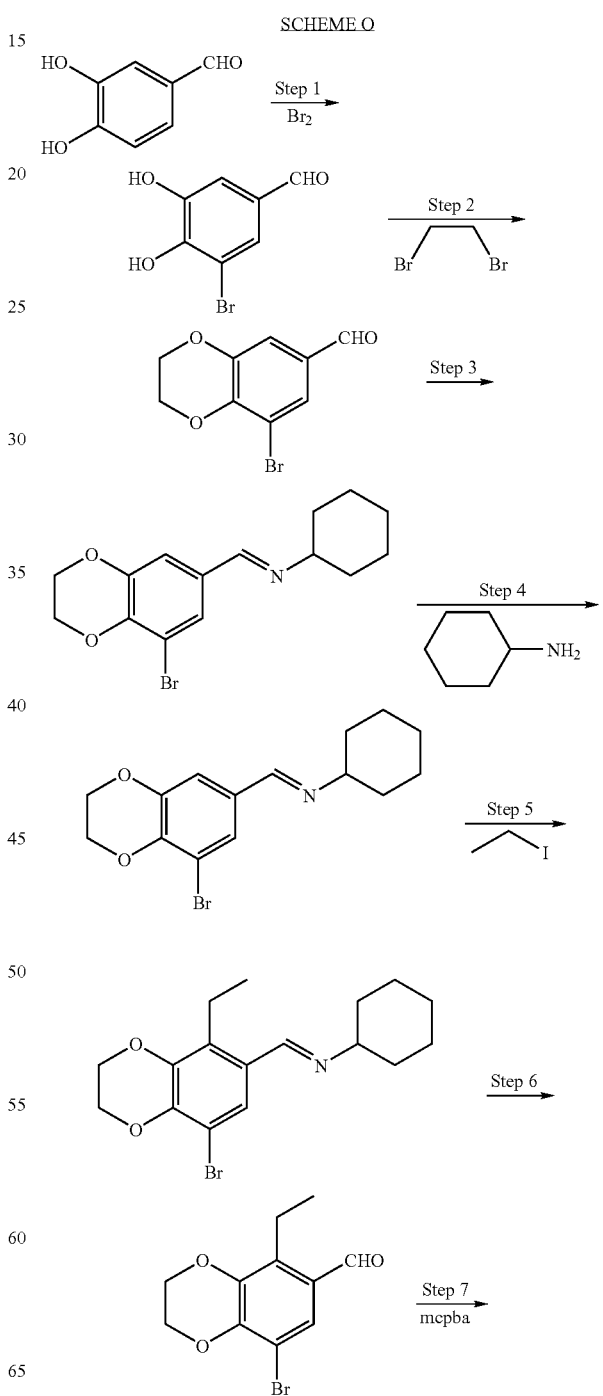

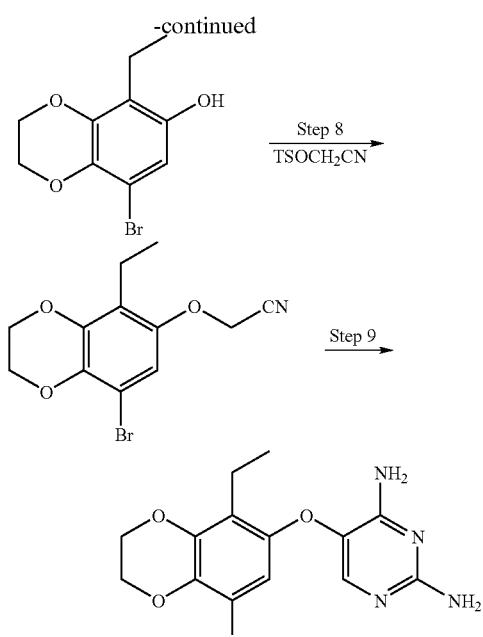

Step 1. 3-Bromo-4,5-dihydroxy-benzaldehyde

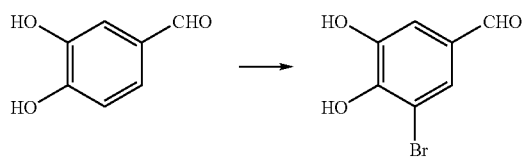

To a solution of 3,4-dihydroxy benzaldehyde (15.48 g, 112 mmol) in 500 ml AcOH was added bromine (6.1 ml, 118 mmol) drop-wise in 50 ml AcOH over 10 min. After 4 h the mixture was poured into cold $H_2O$. The precipitate was filtered, washed with cold $H_2O$ and dried in vacuum to give 3-bromo-4,5-dihydroxy-benzaldehyde (11.64 g, 48%) as a grey solid.

Step 2. 8-Bromo-2,3-dihydro-benzo[1,4]dioxine-6-carboxaldehyde

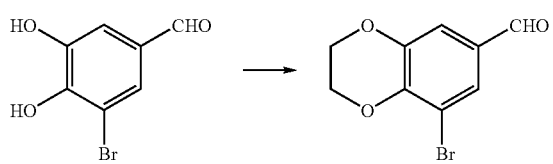

To a solution of 3-bromo-4,5-dihydroxy-benzaldehyde (20.78 g, 95 mmol) in 480 ml DMF was added $K_2CO_3$ (52.95 g, 383 mmol) followed by 1,2-dibromoethane (8.7 ml, 101 mmol). The mixture was warmed to 100° C. After 18 additional 1,2 dibromoethane (1.0 mL) was added. After 2 h the mixture was poured into water and extracted with ethyl acetate. The combined organics were washed with brine, dried over $Na_2SO_4$, filtered and concentrated in vacuo. The crude solid was purified via flash chromatography (9:1 hexane/ethyl acetate) to give 8-bromo-2,3-dihydro-benzo[1,4]dioxine-6-carboxaldehyde (15.82 g, 99%) as a white solid.

Step 3. (8-Bromo-2,3-dihydro-benzo[1,4]dioxine-6-ylmethylene)-cyclohexyl-amine

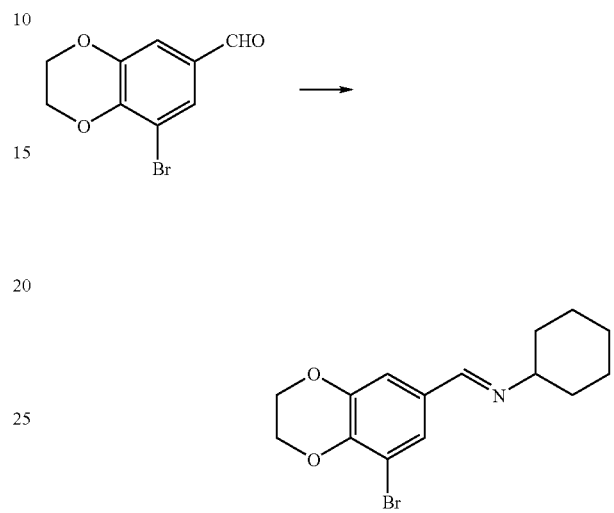

According to the procedure in example 3 (step 1), 8-Bromo-2,3-dihydro-benzo[1,4]dioxine-6-carboxaldehyde (15.63 g, 64 mmol)) and cycolhexylamine (7.02 g, 71 mmol) gave 8-Bromo-2,3-dihydro-benzo[1,4]dioxine-6-ylmethylene)-cyclohexyl-amine (24.2 g) as a viscous oil which was used in the following step without purification.

Step 4. 8-Bromo-5-ethyl-2,3-dihydro-benzo[1,4]dioxine-6-carboxaldehyde

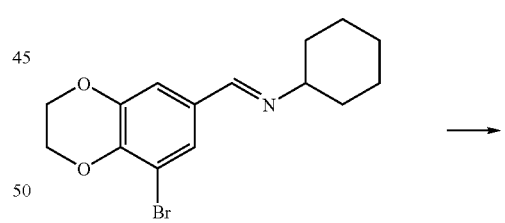

According to the procedure of step 2 of Example 33, 8-Bromo-2,3-dihydro-benzo[1,4]dioxine-6-ylmethylene)- cyclohexyl-amine (23.09 g, 71 mmol) gave 8-Bromo-5-ethyl-2,3-dihydro-benzo[1,4]dioxine-6-carboxaldehyde (3.67 g, 24%).

Step 5.
8-Bromo-5-ethyl-2,3-dihydro-benzo[1,4]dioxin-6-ol

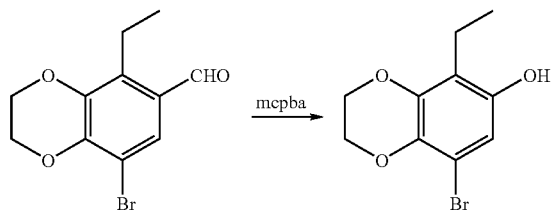

8-Bromo-5-ethyl-2,3-dihydro-benzo[1,4]dioxine-6-carboxaldehyde (3.674 g, 13.5 mmol), using the procedure described in Example 2 (step 4), was converted to 8-Bromo-5-ethyl-2,3-dihydro-benzo[1,4]dioxin-6-ol (3.182 g, 91%) as a white solid.

Step 6. (8-Bromo-5-ethyl-2,3-dihydro-benzo[1,4]dioxin-6-yloxy)-acetonitrile

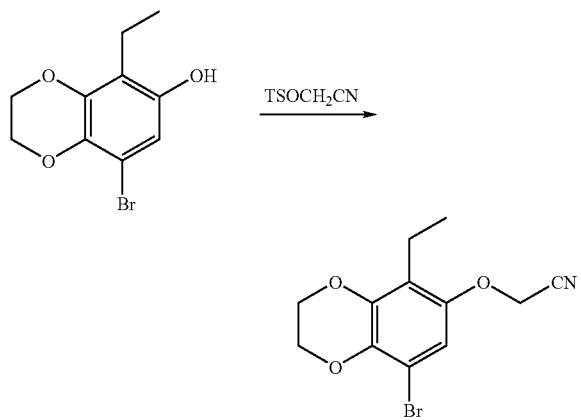

8-Bromo-5-ethyl-2,3-dihydro-benzo[1,4]dioxin-6-ol (3.182 g, 12.3 mmol), as described in the procedure of Step 6 of Example 21, was converted to cyanomethyl ether 8-Bromo-5-ethyl-2,3-dihydro-benzo[1,4]dioxin-6-yloxy)-acetonitrile (2.30 g, 63%).

Step 7. 5-(8-Bromo-5-ethyl-2,3-dihydro-benzo[1,4]dioxin-6-yloxy)-pyrimidine-2,4-diamine

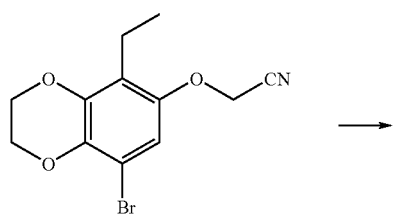

-continued

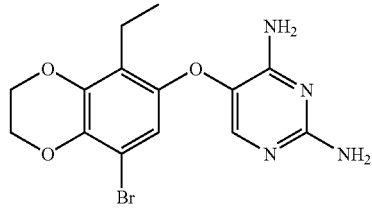

8-Bromo-5-ethyl-2,3-dihydro-benzo[1,4]dioxin-6-yloxy)-acetonitrile (2.30 g, 8.7 mmol), using the procedure of steps 6 and 7 of Example 2, was converted to 5-(8-Bromo-5-ethyl-2,3-dihydro-benzo[1,4]dioxin-6-yloxy)-pyrimidine-2,4-diamine (0.951 g, 32%) as yellow solid; mp=291-293° C.; [MH]$^+$=368.

Example 37

5-(7-Iodo-5-isopropyl-2,3-dihydro-benzo[1,4]dioxin-6-yloxy)-pyrimidine-2,4-diamine The synthetic procedure used in this Example is outlined in Scheme P.

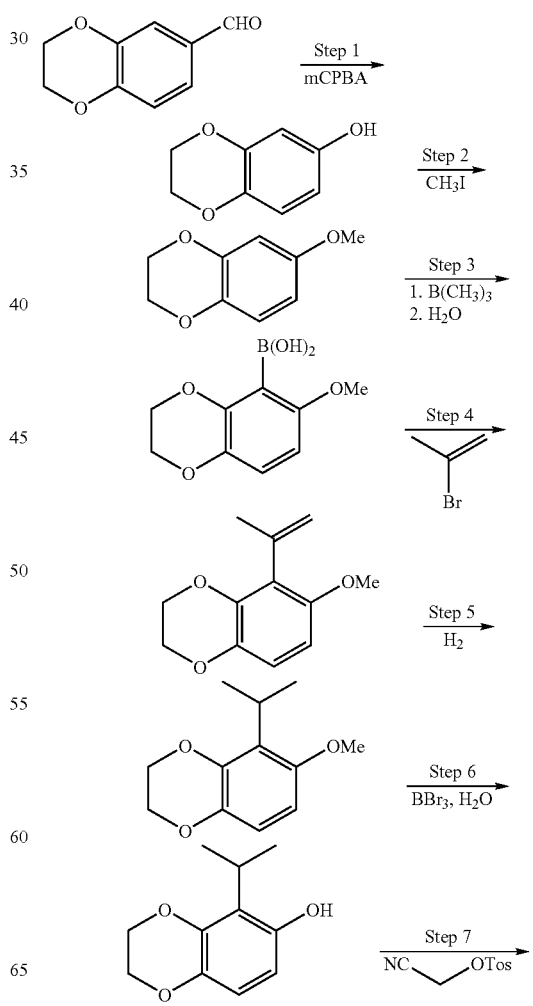

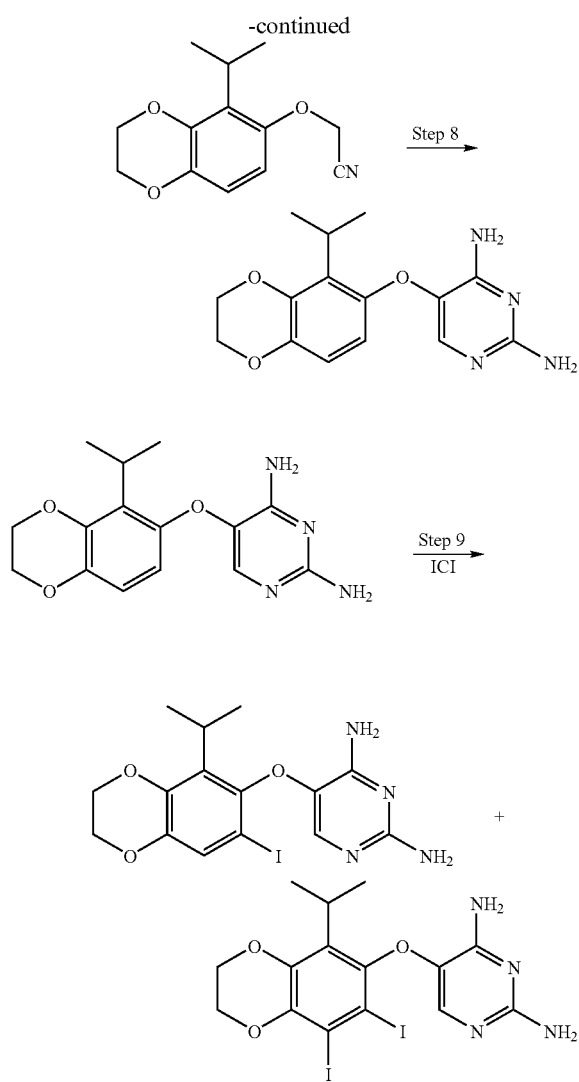

Step 1. 2,3-Dihydro-benzo[1,4]dioxin-6-ol

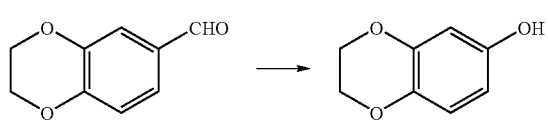

To a solution of 2,3-dihydro-benzo[1,4]dioxin-6-carboxaldehyde (30.0 g, 183 mmol) in 500 ml CH$_2$Cl$_2$ was added mCPBA (37.85 g, 219 mmol). The suspension was heated to 50° C. After 16 h saturated NaHCO$_3$ was added and the mixture was extracted with CH$_2$Cl$_2$ The combined organics were concentrated in vacuo and taken up in MeOH and 200 ml 4M NaOH was added. After 2 h the mixture was acidified with 4M HCl and extracted with ethyl acetate. The combined organics were washed with saturated NaHCO$_3$, washed with brine, concentrated in vacuo, and taken up in CH$_2$Cl$_2$. The solution was filtered to remove the precipitate. The resulting solution was stirred with saturated NaHCO$_3$ for 1 h, separated, dried over MgSO$_4$, filtered and concentrated in vacuo to give 2,3-dihydro-benzo[1,4]dioxin-6-ol (26.92 g, 94%).

Step 2. 6-Methoxy-2,3-dihydro-benzo[1,4]dioxine

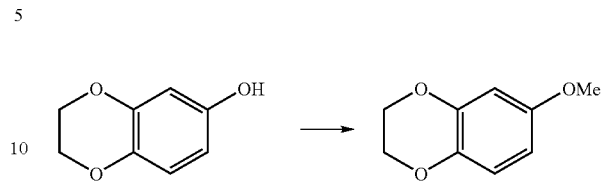

To a mixture of K$_2$CO$_3$ (47.54 g, 344 mmol) and Bu$_4$NI (1.256 g, 3.4 mmol) in DMF was added 2,3-dihydro-benzo[1,4]dioxin-6-ol (26.2 g, 172 mmol) followed by iodomethane (16.1 ml, 258 mmol). After 16 hours the mixture was filtered. The solution was mixed with H$_2$O and extracted with ethyl acetate. The combined organics were washed with brine, dried over MgSO$_4$, filtered and concentrated in vacuo. Purification via flash chromatography (95:5 hexane/ethyl acetate) afforded methyl 6-methoxy-2,3-dihydro-benzo[1,4]dioxine (24.23 g, 85%) as a clear oil.

Step 3. 6-Methoxy-2,3-dihydro-benzo[1,4]dioxin-5-yl-boronic acid

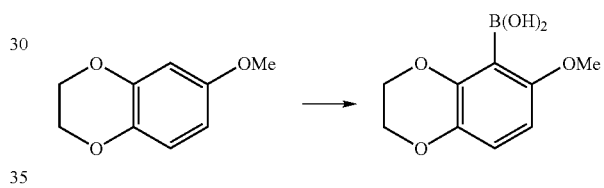

To a solution of methyl ether X (10.0 g, 60 mmol) in 50 ml THF at −78° C. was added n-butyllithium (36 ml, 90 mmol, 2.5 M in hexanes) was added drop-wise. After 1 h the solution was warmed to rt. After 1 h the solution was cooled to −78° C. and trimethyl borate (13.6 ml, 120 mmol) was added. The solution was warmed to rt. After 16 h the mixture was quenched by the addition of water and resulting mixture was acidified with AcOH and extracted with ethyl acetate. The combined organics were washed with saturated NaHCO$_3$, dried with MgSO$_4$, filtered and concentrated in vacuo. The resulting oil was azeotroped with toluene to afford 6-methoxy-2,3-dihydro-benzo[1,4]dioxin-5-yl-boronic acid (13.72 g, 98%) as an oil.

Step 4. 5-Isopropenyl-6-methoxy-2,3-dihydro-benzo[1,4]dioxine

To a solution of 2-bromopropene (5.4 ml, 59 mmol) in 200 mL DME was added Pd(Ph$_3$P)$_4$ (3.116, 2.8 mmol). After 30 min 6-methoxy-2,3-dihydro-benzo[1,4]dioxin-5-yl-boronic acid (13.320 g, 58.6 mmol) and K$_2$CO$_3$ (8.099 g, 58.6 mmol) was added. The mixture was warmed to reflux. After 16 hours the mixture was cooled, filtered through a pad of celite and concentrated in vacuo. The residue was dissolved in H₂O and extracted with ethyl acetate. The combined organics were washed with saturated NaHCO₃, dried over MgSO₄, filtered and concentrated in vacuo. Purification via flash chromatography afforded isoprene 5-isopropenyl-6-methoxy-2,3-dihydro-benzo[1,4]dioxine (5.542 g, as an inseparable mixture of product/sm 1:1) as an oil.

Step 5. 5-Isopropyl-6-methoxy-2,3-dihydro-benzo[1,4]dioxine

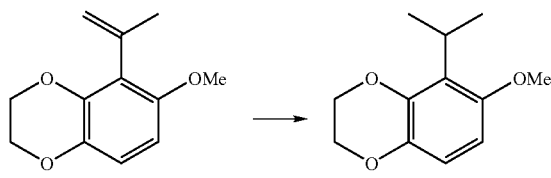

To a solution of 5-isopropenyl-6-methoxy-2,3-dihydro-benzo[1,4]dioxine (5.00 g, x mmol) in 80 ml MeOH was added 10% Pd/C (0.18 g). The mixture was placed under 50 psi of H₂. After 16 hours the mixture was filtered through a pad of celite. The solution was concentrated in vacuo. Purification via flash chromatography (97:3 hexane/ethyl acetate) afforded isopropyl 5-isopropyl-6-methoxy-2,3-dihydro-benzo[1,4]dioxine (2.458 g, 21% from boronic acid) as a clear oil.

Step 6. 5-Isopropyl-6-hydroxy-2,3-dihydro-benzo[1,4]dioxine

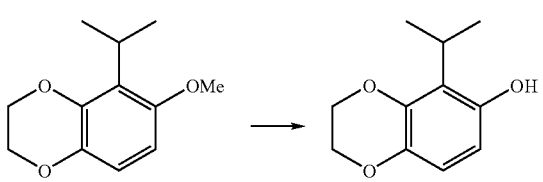

To a solution of 5-isopropyl-6-methoxy-2,3-dihydro-benzo[1,4]dioxine (1.011 g, 4.9 mmol) in 15 ml CH₂Cl₂ at −78° C. was added BBr₃ (7.3 ml, 7.3 mmol). The solution was allowed to warm to room temperature. After 16 hours the solution was cooled to −78° C., quenched with H₂O, warmed to room temperature and extracted with CH₂Cl₂. The combined organics were washed with brine, dried over MgSO₄, filtered and concentrated in vacuo. Purification via flash chromatography (7:3 hexane/ethyl acetate) afforded 5-isopropyl-6hydroxy-2,3-dihydro-benzo[1,4]dioxine (0.622 g, 63%) as a pale yellow oil.

Step 7. 5-Isopropyl-2,3-dihydro-benzo[1,4]dioxin-6-yloxy)acetonitrile

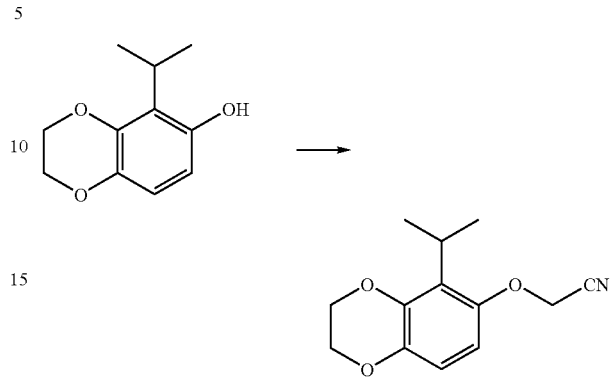

5-Isopropyl-6 hydroxy-2,3-dihydro-benzo[1,4]dioxine (0.622 g, 3.2 mmol) was converted, as describe in Example 2 (step 5), to 5-Isopropyl-2,3-dihydro-benzo[1,4]dioxin-6-yloxy)acetonitrile (0.544 g, 72%) as a clear oil.

Step 8. 5-(5-Isopropyl-2,3-dihydro-benzo[1,4]dioxin-6-yloxy)-pyrimidine-2,4-diamine

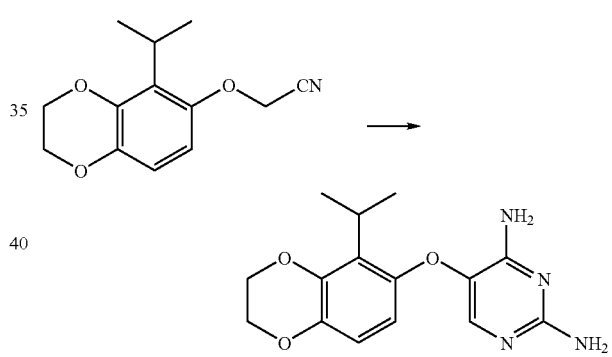

5-Isopropyl-2,3-dihydro-benzo[1,4]dioxin-6-yloxy)acetonitrile (0.544 g, 2.3 mmol) was converted, as described in step 6 of Example 21, to 5-(5-isopropyl-2,3-dihydro-benzo[1,4]dioxin-6-yloxy)-pyrimidine-2,4-diamine (0.560 g, 86%) as a yellow foam.

Step 9. 5-(7-Iodo-5-isopropyl-2,3-dihydro-benzo[1,4]dioxin-6-yloxy)-pyrimidine-2,4-diamine and 5-(7,8-Diiodo-5-isopropyl-2,3-dihydro-benzo[1,4]dioxin-6-yloxy)-pyrimidine-2,4-diamine

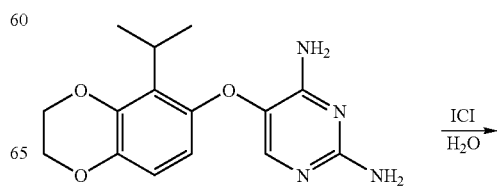

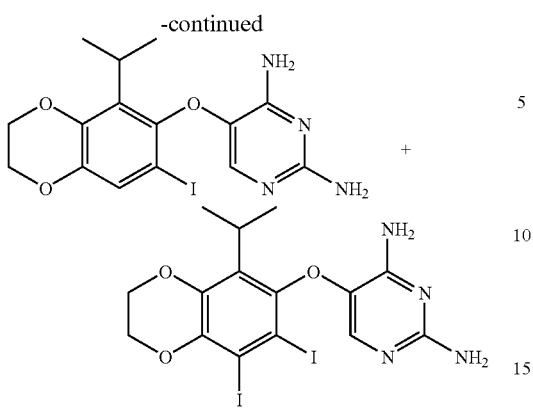

To a solution of 5-(5-isopropyl-2,3-dihydro-benzo[1,4]di-oxin-6-yloxy)-pyrimidine-2,4-diamine (250 mg, 0.83 mmol) in acetic acid (2 ml) was added ICl (0.670 g, 4.13 mmol) in 3 ml AcOH and 2 ml H$_2$O. After 20 h the reaction was neutralized with Na$_2$CO$_3$ and extracted with CH$_2$Cl$_2$. The combined organics were washed with washed 10% NaHSO$_3$, washed with brine, dried over Na$_2$SO$_4$, filtered and concentrated in vacuo. Purification via flash chromatography (97:3 CH$_2$Cl$_2$/MeOH) afforded 5-(7,8-Diiodo-5-isopropyl-2,3-dihydro-benzo[1,4]dioxin-6-yloxy)-pyrimidine-2,4-diamine (0.049 g, 10%) as yellow solid ([MH]$^+$=555) and 5-(7-Iodo-5-isopropyl-2,3-dihydro-benzo[1,4]dioxin-6-yloxy)-pyrimidine-2,4-diamine (0.050 g, 14%) as a foam. [MH]$^+$=429.

Example 38

2-[2-(2,4-Diamino-pyrimidin-5-yloxy)-4-iodo-5-methoxy-phenyl]-propan-1-ol

The synthetic procedure used in this Example is outlined in Scheme Q.

SCHEME Q

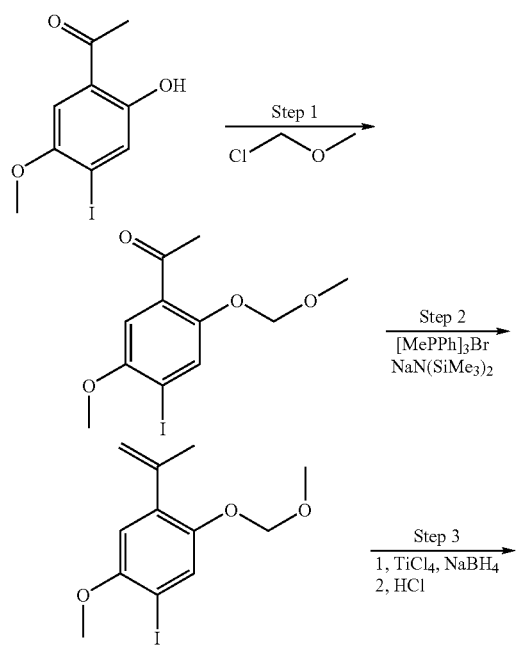

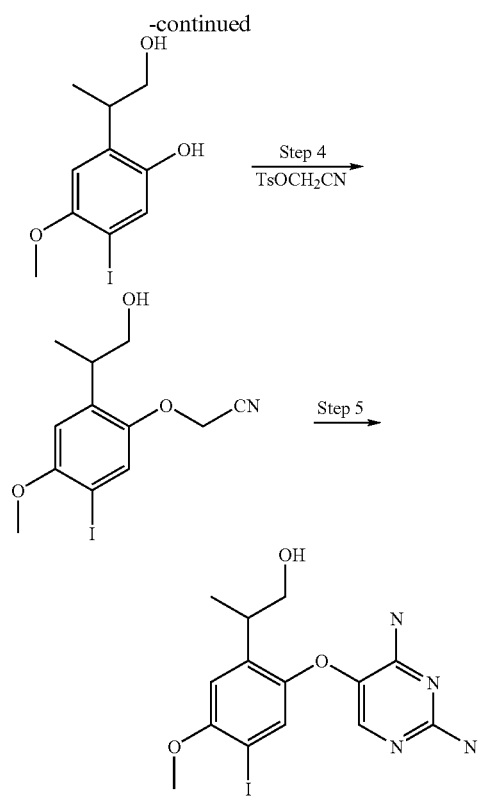

Step 1.
1-(2-Hydroxy-4-iodo-5-methoxy-phenyl)-ethanone

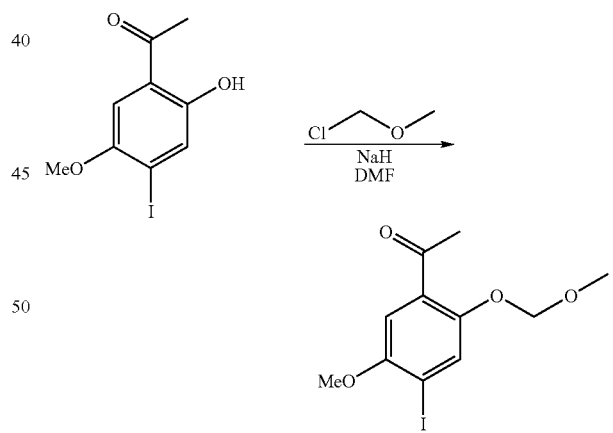

To suspension of sodium hydride (0.044 g, 1.1 mmol, 60% in mineral oil) in 0.5 ml DMF was added sodium 5-iodo-2-acetyl,4-methoxyphenol (0.292 g, 1 mmol, prepared as described in Example 35) as a solution in 1.5 ml DMF. After 10 minutes chloromethoxy methane (0.079 g, 1.0 mmol) was added. After 30 minutes the mixture was extracted with CH$_2$Cl$_2$. The The combined organics were washed with brine, dried over Na$_2$SO$_4$, filtered and concentrated in vacuo. Purification via flash chromatography (88:12=hexane/ethyl acetate) afforded 1-(2-hydroxy-4-iodo-5-methoxy-phenyl)-ethanone (0.314 g, 85%) as yellow solid; [MH]$^+$=337.

Step 2. 1-Iodo-4-iosprenyl-2-methoxy-5-methoxymethoxy-benzene

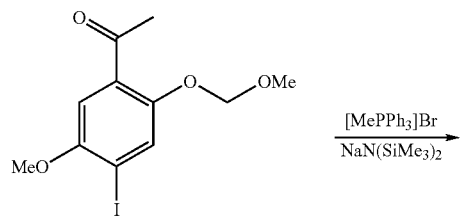

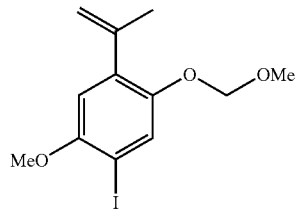

To a suspension of methyl triphenylphosphonium bromide (0.457 g, 1.3 mmol) in 8 ml THF was added sodium hexamethyldisilazide (1.3 ml, 1.29 mmol, 1.0 M in THF). After 1.5 h 1-(2-hydroxy-4-iodo-5-methoxy-phenyl)-ethanone (0.288 g, 0.9 mmol) as a solution in 8 ml THF was added drop-wise. After 20 h the mixture was filtered though a pad of celite and extracted with $CH_2Cl_2$. The combine organics were washed with brine, dried over $Na_2SO_4$ and concentrated in vacuo. Purification via flash chromatography (95:5 hexane/ethyl acetate) afforded 1-iodo-4-iosprenyl-2-methoxy-5-methoxymethoxy-benzene (0.224 g, 78%) as colorless liquid; $[MH]^+=335$.

Step 3. 2-(2-Hydroxy-1-methyl-ethyl)-5-iodo-4-methoxy-phenol

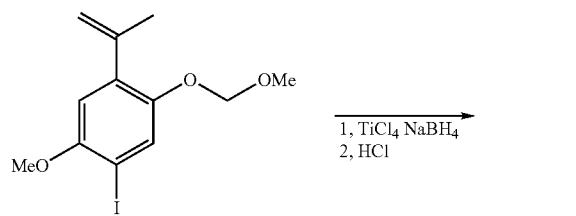

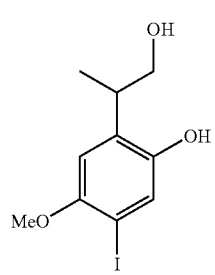

To a mixture of $NaBH_4$ (0.051 g, 1.3 mmol) in 4 ml DME was added $TiCl_4$ (0.67 ml, 0.67 mmol, 1.0 M in $CH_2Cl_2$). After 1 hour, 2-methyl 1-iodo4-iosprenyl-2-methoxy-5-methoxymethoxy-benzene (0.224 g, 0.7 mmol) in 4 ml DME was added. After 20 h the mixture was quenched with $H_2O$ and extracted with ethyl acetate. The combined organics were washed with brine, dried over $Na_2SO_4$, filtered and concentrated in vacuo to give an oil. To a solution of this oil in 3 ml isopropanol was added 3 ml 6M HCl. After 3 h the mixture was neutralized with saturated $NaHCO_3$ and extracted with ethyl acetate. The combined organics were washed with brine, dried over $Na_2SO_4$, filtered and concentrated in vacuo to give an oil. Purification via preparative TLC (70:30 hexane/ethyl acetate) afforded 2-(2-hydroxy-1-methyl-ethyl)-5-iodo4-methoxy-phenol (0.080 g, 30%) as a clear oil; $[MH]^+=309$.

Step 4. [2-(2-Hydroxy-methyl-ethyl)-5-iodo-4-methoxy-phenoxy]-acetonitrile

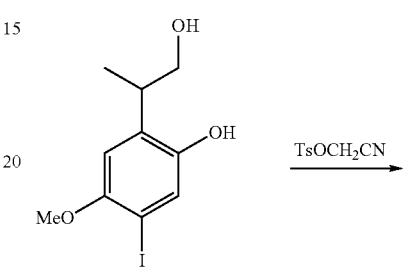

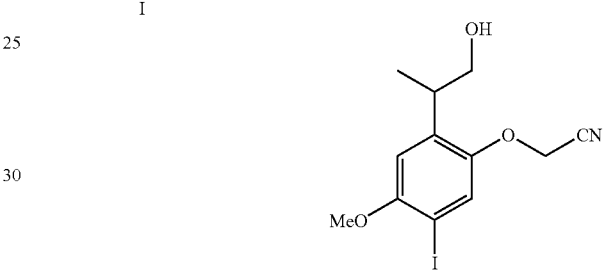

2-(2-Hydroxy-1-methyl-ethyl)-5-iodo-4-methoxy-phenol (0.080 g, 0.3 mmol) was converted, as described in step 6 of Example 21, to [2-(2-hydroxy-methyl-ethyl)-5-iodo-4-methoxy-phenoxy]-acetonitrile (0.076 g, 84%) as white solid; $[MH]^+=348$.

Step 5. 2-[2-(2,4-Diaminopyrimidin-5-yloxy)-4-iodo-5-methoxy-phenyl]-propan-1-ol

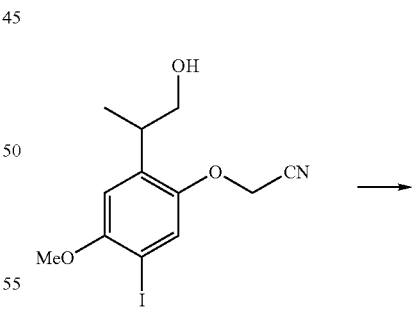

[2-(2-hydroxy-methyl-ethyl)-5-iodo-4-methoxy-phenoxy]-acetonitrile (0.488 g, 1.4 mmol), using the procedure of step 7 of Example 21, was converted to 2-[2-(2,4-diaminopyrimidin-5-yloxy)-4-iodo-5-methoxy-phenyl]-propan-1-ol (0.459 g, 79%) as a white solid; mp (HCl salt)=290.1-292.2° C.; [MH]⁺=417.

Example 39

5-(2,4-Diamino-pyrimidin-5-yloxy)-4-isopropyl-2-methoxy-N-methyl-benzenemethylsulfonamide Step 1. 5-(2,4-Diamino-pyrimidin-5-yloxy)-4-isopropyl-2-methoxy-benzenesulfonyl chloride

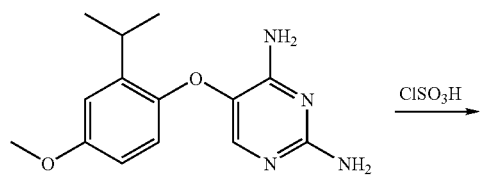

A mixture of pyrimidine (0.400 g, 1.5 mmol) in 2 ml chlorosulfonic acid was allowed to stir 20 min. The mixture was poured over ice. The precipitate was filtered, washed by cold H₂O and dried under vacuum to afford 5-(2,4-diamino-pyrimidin-5-yloxy)-4-isopropyl-2-methoxy-benzenesulfonyl chloride (0.515 g, 95%) as a white solid; [MH]⁺=373.

Step 2. 5-(2,4-Diamino-pyrimidin-5-yloxy)-4-isopropyl-2-methoxy-N-methyl-benzenemethylsulfonamide

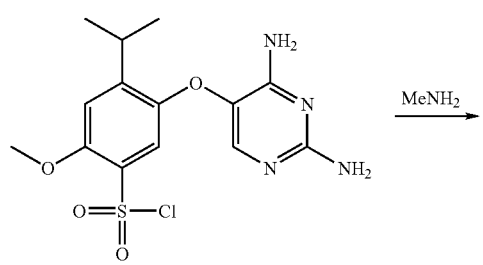

-continued

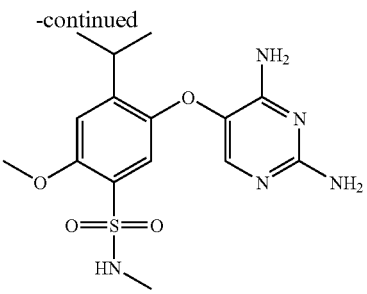

To 10 ml methyl amine −78° C. in a screw-capped tube was added 5-(2,4-diamino-pyrimidin-5-yloxy)-4-isopropyl-2-methoxy-benzenesulfonyl chloride (0.300 g, 0.8 mmol). The mixture was allowed to warm to room temperature. After 20 hours the mixture was evaporated, washed with H₂O, and dried under vacuum to afford 5-(2,4-diamino-pyrimidin-5-yloxy)-4-idopropyl-2-methoxy-N-methyl-benzenemethylsulfonamide (0.170 g, 57%) as a white solid; mp (HCl salt)= 252.3-252.9° C.; [MH]⁺=367.

Similarly prepared, replacing methylamine with ethylamine, was 5-(2,4-Diamino-pyrimidin-5-yloxy)-N-ethyl-4-isopropyl-2-methoxy-benzenesulsonamide (0.186 g, 61%) as a white solid; mp (HCl salt)=260-265° C.; [MH]⁺=382.

Example 40

5-[2-Isopropyl-4-methoxy-5-(1-methyl-1H-imidazol-2-yl)-phenoxy]-3,4-dihydro-pyrimidine-2,4-diamine

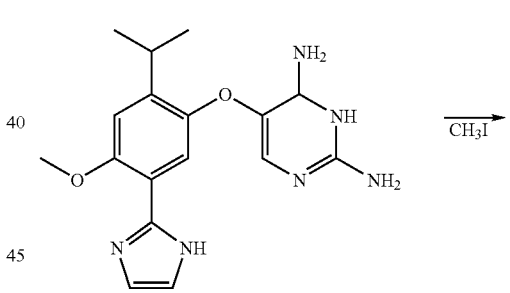

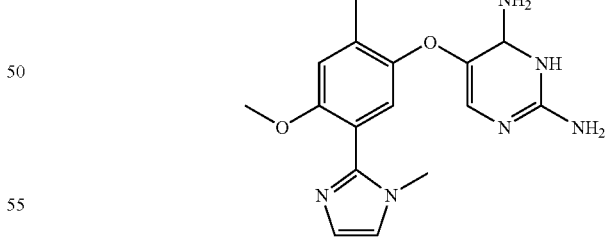

To a solution of 5-[5-(1H-Imidazol-2-yl)-2-isopropyl-4-methoxy-phenoxy]-3,4-dihydro-pyrimidine-2,4-diamine (0.044g, 0.129 mmols) and iodomethane (9 ul, 0.145 mmols) in acetone (5 ml) was added KOH (0.055g, 0.98 mmols), the mixture was heated at 30° C. for 20 minutes, the mixture was filtered through celite, washed with CH₂Cl₂, the combined organic solution was concentrated in vacuo. The residue was purified via preparative TLC silica plates, eluted with 5% MeOH/CH₂Cl₂/NH₄OH four times to give 5-[2-Isopropyl4- methoxy-5-(1-methyl-1H-imidazol-2-yl)-phenoxy]-3,4-di-hydro-pyrimidine-2,4-diamine (0.024g, 52%). Mass Spec: M+H: 355.

Example 41

5-(2,4-Diaminopyrimidin-5-yloxy)-4-isopropyl-2-methoxy-N,N-dimethyl-benzamide

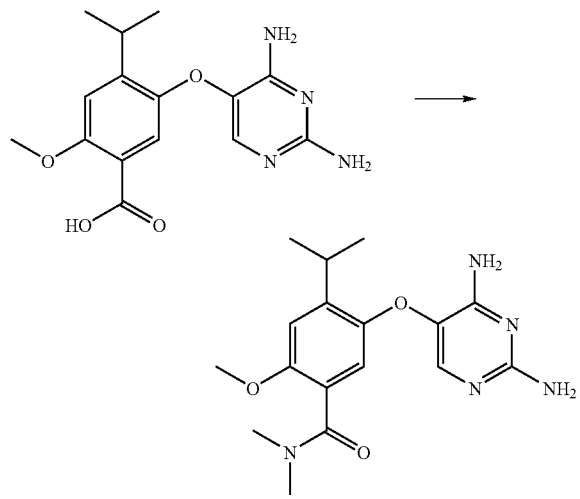

To a suspension of 5-(2,4-Diamino-pyrimidin-5-yloxy)-4-isopropyl-2-methoxy-benzoic acid (180 mg, 0.57 mmol, from Example 17) in anhydrous dichloromethane (5.6 mL) was added trifluoroacetic acid (0.08 mL, 1.14 mmol) and then thionyl chloride (0.36 mL, 5.65 mmol). After 1 hour the reaction was concentrated. To the residue was added anhydrous dichloromethane (4.5 mL) and dimethylamine (2.84 mL of a 2M solution in tetrahydrofuran, 5.65 mmol). After 2 hours stirring at room temperature, the reaction was filtered and concentrated. Purification via silica gel column chromatography eluting with 95/5/0.1 to 93/7/0.1 dichloromethane/methanol/ammonium hydroxide yielded 5-(2,4-diamino-pyrimidin-5-yloxy)-4-isopropyl-2-methoxy-N,N-dimethyl-benzamide (40 mg, 20%) as pale yellow solid, MS (M+H)= 346.

Similarly prepared using methylamine instead of dimethylamine, 5-(2,4-diamino-pyrimidin-5-yloxy)-4-isopropyl-2-methoxy-N-methyl-benzamide (23 mg, 15%) was prepared as pale yellow solid, MS (M+H)=332.

Example 42

4-(2,4-Diamino-pyrimidin-5-yloxy)-2-iodo-5-isopropyl-phenol

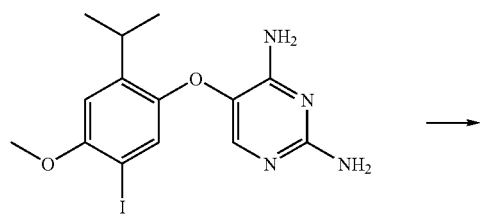

-continued

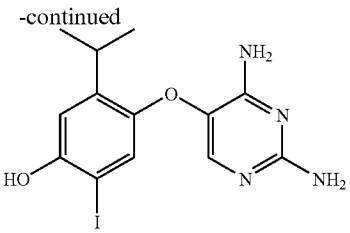

To a cold suspension of 1(0.21 g, 0.52 mmol) in dichloromethane (15 ml) at 0° C. was added BBr3(0.26 g, 1.05 mmol). The reaction mixture was stirred at room temperature for 16 hrs., quenched with water and basified with sat. NaHCO3. The insoluble solid was collected by filtration. The filtrate was washed with water, dried over $Na_2SO_4$, filtered and concentrated in vacuo. The combined residue was purified via flash chromatographed on silica gel (3 to 5% methanol in dichloromethane with 0.1% $NH_4OH$) gave desired product (0.174g, 86%), (M+H)=387.

Example 43

5-(5-Iodo-2-isopropyl-4-prop-2-ynyloxy-phenoxy)-pyrimidine-2,4-diamine

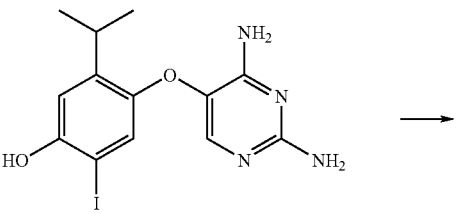

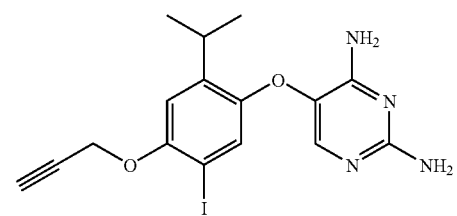

To 4-(2,4-Diamino-pyrimidin-5-yloxy)-2-iodo-5-isopropyl-phenol (200 mg, 0.43 mmol) dissolved in anhydrous N,N-dimethylformamide (2 mL) was added anhydrous potassium carbonate (414 mg, 3.00 mmol) and propargyl chloride (0.03 mL, 0.43 mmol). After stirring at room temperature overnight, the reaction was extracted with dichloromethane, water and brine. The dichloromethane layer was dried using anhydrous magnesium sulfate, concentrated, and purified via silica gel column chromatography (95/5/0.1 dichloromethane/methanol/ammonium hydroxide) to yield 5-(5-iodo-2-isopropyl-4-prop-2-ynyloxy-phenoxy)-pyrimidine-2,4-diamine as white solid (131 mg, 71%), MS (N+H)=425

Example 44

N-[2-Acelylamino-5-(2-isopropyl-4-methoxy-5-methyl-benzol)-pyrimidin-4-yl]-acetamide

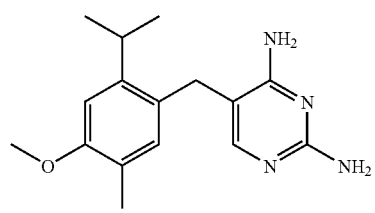

To 5-(2-Isopropyl-4-methoxy-5-methyl-benzyl)-pyrimidine-2,4-diamine (30 mg, 0.10 mmol) dissolved in anhydrous pyridine (1 mL) was added acetyl chloride (0.04 mL, 0.44 mmol). After stirring 30 minutes at room temperature, the reaction was concentrated. The residue was dissolved in dichloromethane, washed with water, and concentrated in vacuo. Purification via preparative TLC (95/5 dichloromethane/methanol) yielded N-[2-acetylamino-5-(2-isopropyl-4-methoxy-5-methyl-benzyl)-pyrimidin-4-yl]-acetamide (7 mg, 18%), MS (M+H)=371.

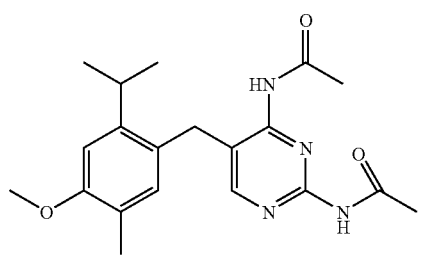

Example 45

5-(2-Isopropyl-5-isoxazol-5-yl-4-methoxy-phenoxy)-pyrimidine-2,4-diamine

The synthetic procedure used in this Example is outlined in Scheme Q.

SCHEME Q

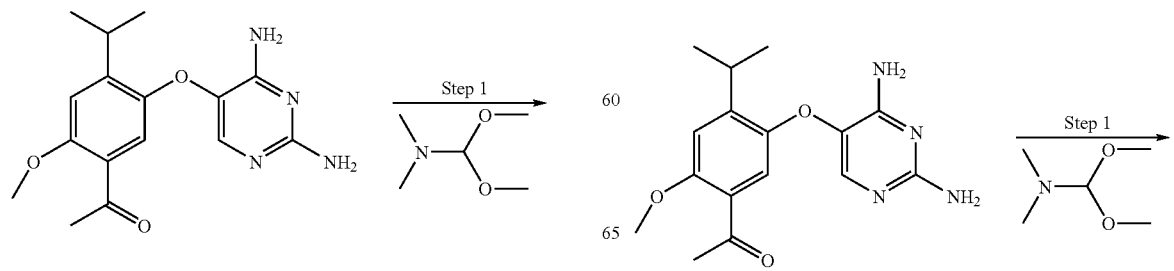

-continued

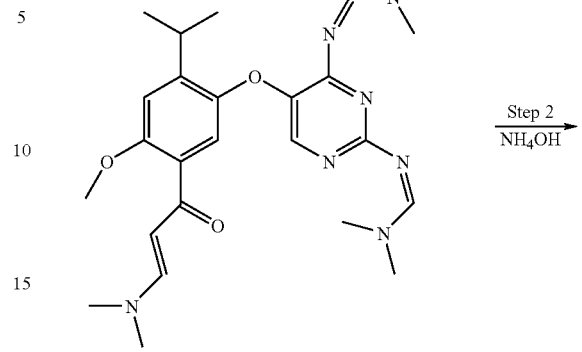

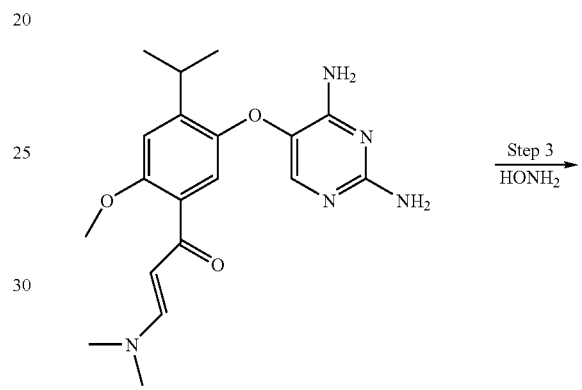

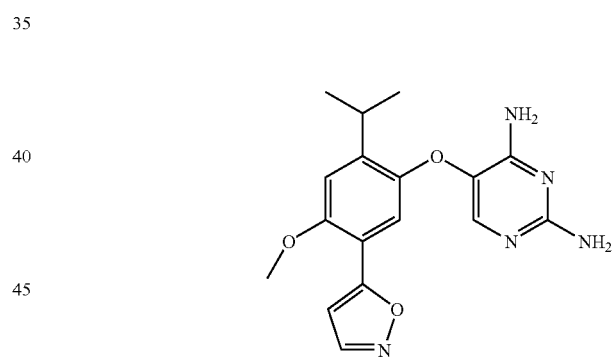

Step 1. N'-[5-[5-(3-Dimethylamino-acryloyl)-2-isopropyl-4-methoxy-phenoxy]-4-(dimethylamino-methyleneamino)-pyrimidin-2-yl]-N,N-dimethyl-formamidine -continued

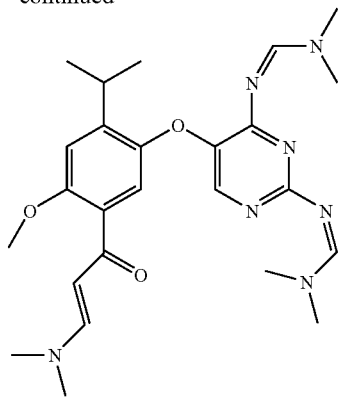

To 1-[5-(2,4-diamino-pyrimidin-5-yloxy)-4-isopropyl-2-methoxy-phenyl]-ethanone (100 mg, 0.32 mmol, from Example 16) dissolved in anhydrous N,N-dimethylformamide (0.6 mL) was added N,N-dimethylformamide dimethyl acetal (0.17 mL, 1.26 mmol) and the reaction was heated at 114° C. overnight. Concentration of the reaction mixture yielded N'-[5-[5-(3-Dimethylamino-acryloyl)-2-isopropyl-4-methoxy-phenoxy]-4-(dimethylamino-methyleneamino)-pyrimidin-2-yl]-N,N-dimethyl-formamidine.

Step 2. 1-[5-(2,4-Diamino-pyrimidin-5-yloxy)-4-isopropyl-2-methoxy-phenyl]-3-dimethylamino-propenone

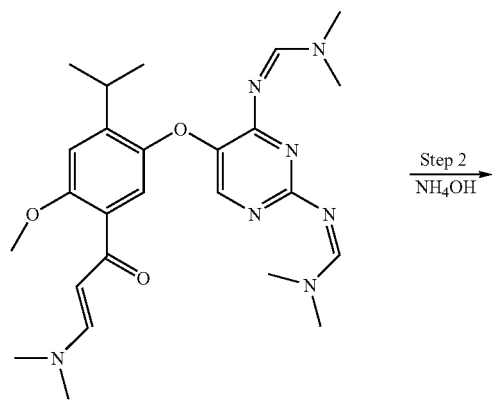

The N'-[5-[5-(3-Dimethylamino-acryloyl)-2-isopropyl-4-methoxy-phenoxy]-4-(dimethylamino-methyleneamino)-pyrimidin-2-yl]-N,N-dimethyl-formamidine from step 1 was dissolved in methanol (1 mL) and ammonium hydroxide (1 mL). After stirring 5 days at room temperature, the reaction was concentrated and purified by preparatory TLC plates (92/8/0.5 dichloromethane/methanol/ammonium hydroxide) to yield 1-[5-(2,4-Diamino-pyrimidin-5-yloxy)-4-isopropyl-2-methoxy-phenyl]-3-dimethylamino-propenone (34 mg, 29%) as white solid.

Step 3. 5-(2-Isopropyl-5-isoxazol-5-yl-4-methoxy-phenoxy)-pyrimidine-2,4-diamine

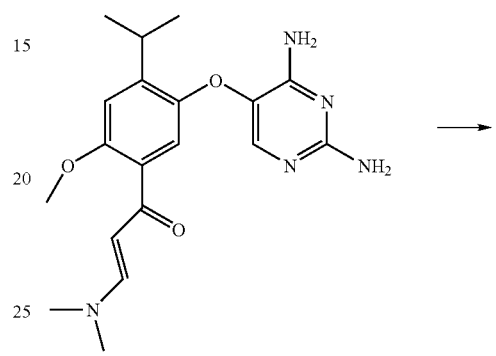

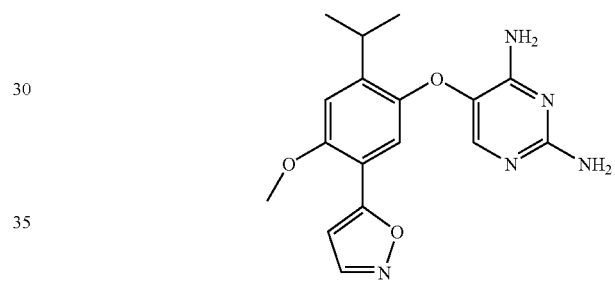

To 1-[5-(2,4-Diamino-pyrimidin-5-yloxy)-4-isopropyl-2-methoxy-phenyl]-3-dimethylamino-propenone (30 mg, 0.08 mmol) dissolved in a mixture of methanol (1.5 mL) and water (0.4 mL) was added hydroxylamine hydrochloride (14 mg, 0.20 mmol) and the reaction was refluxed for 1 hour. Purification by preparatory TLC plates (92/8/0.5 dichloromethane/methanol/ammonium hydroxide) yielded 5-(2-isopropyl-5-isoxazol-5-yl-4-methoxy-phenoxy)-pyrimidine-2,4-diamine (8 mg, 29%) as white solid, MS (M+H)=342.

Example 45

5-(2-Isopropyl-4-methoxy-5-thiazol-5-yl-phenoxy)-pyrimidine-2,4-diamine

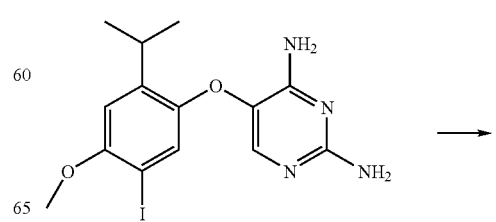

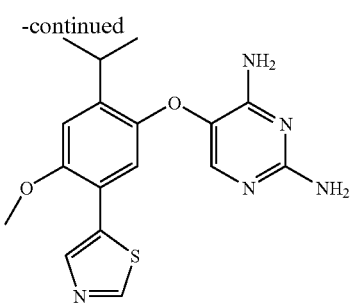

To 5-(5-Iodo-2-isopropyl-4-methoxy-phenoxy)-pyrimidine-2,4-diamine (600 mg, 1.5 mmol, from Example 14, Step 1) dissolved in N,N-dimethylacetamide (4.8 mL) was added potassium acetate (221 mg, 2.24 mmol), thiazole (0.53 mL, 7.5 mmol) and tetrakis(triphenylphosphine)palladium(0) (70 mg, 0.06 mmol). After heating at 115° C. overnight. The cooled reaction was extracted with dichloromethane (100 mL) and water (2×100 mL). The dichloromethane layer was dried using anhydrous sodium sulfate, concentrated and purified by silica gel column chromatography eluting with 95/5/0.1 dichloromethane/methanol/ammonium hydroxide to yield 5-(2-isopropyl-4-methoxy-5-thiazol-5-yl-phenoxy)-pyrimidine-2,4-diamine (49 mg, 9%) as pale yellow solid, MS (M+H)=358.

Example 46

5-(2-Isopropyl-3-methoxy-phenoxy)-pyrimidine-2,4-diamine

The synthetic procedure used in this Example is outlined in Scheme R.

SCHEME R

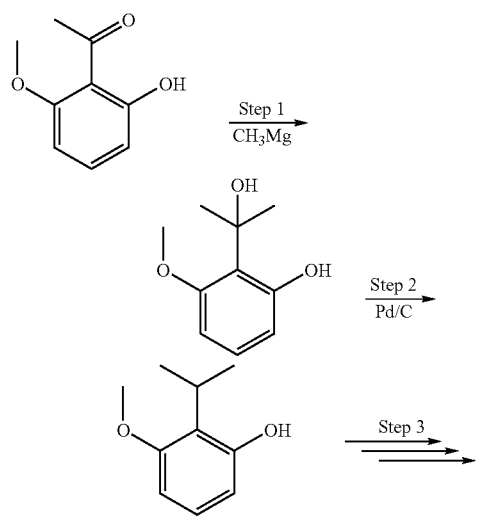

Step 1.
2-(1-Hydroxy-1-methyl-ethyl)-3-methoxy-phenol

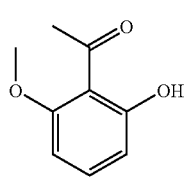 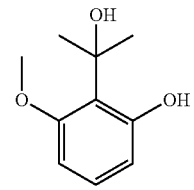

To a solution of methyl magnesium bromide (24 mL of a 3M solution in diethyl ether, 72.2 mmol) in anhydrous tetrahydrofuran (20 mL) at 0° C. was added a solution of 2'-hydroxy-6'-methoxyacetophenone (4 g, 24.1 mmol) in anhydrous tetrahydrofuran (40 mL), maintaining the temperature below 11° C. during the addition. After stirring for 1.5 hours at room temperature, a solution of 10% ammonium chloride (30 mL) was added slowly maintaining the temperature below 22° C. with the use of an ice bath. Water (300 mL) was slowly added and the reaction was extracted twice with ethyl acetate. The combined ethyl acetate layers were washed with water, brine, dried using anhydrous sodium sulfate and concentrated to give 2-(1-Hydroxy-1-methyl-ethyl)-3-methoxy-phenol (4.52 g) as pale yellow solid.

Step 2. 2-Isopropyl-3-methoxy-phenol

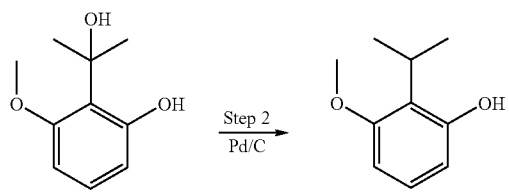

To a solution of 2-(1-Hydroxy-1-methyl-ethyl)-3-methoxy-phenol dissolved in acetic acid (50 mL) was added 10% palladium on charcoal (500 mg), water (6 mL), and ammonium formate (7.82 g, 124 mmol). After refluxing for 1 hour, the reaction was cooled and filtered through celite. The celite pad was washed with ethyl acetate (500 mL). Water (300 mL) was added to the filtrate, and the mixture was basified (pH=8) using solid sodium bicarbonate. The ethyl acetate layer was collected and washed with water, brine, dried using anhydrous sodium sulfate and concentrated to yield 2-Isopropyl-3-methoxy-phenol (3.68 g, 92%) as pale yellow solid.

Step 3. 5-(2-Isopropyl-3-methoxy-phenoxy)-pyrimidine-2,4-diamine

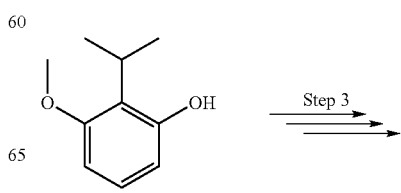

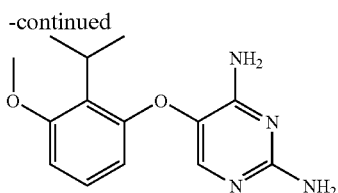

Using the 2-Isopropyl-3-methoxy-phenol of step 3 above, and following the procedure of steps 5-7 of Example 2, 5-(2-isopropyl-3-methoxy-phenoxy)-pyrimidine-2,4-diamine was prepared. MS (M+H)=275.

Similarly prepared was 5-(2-Isopropyl4-methoxy-phenoxy)-pyrimidine-2,4-diamine. MS (M+H)=275.

Example 47

5-(5-Ethanesulfonyl-2-isopropyl4-methoxy-phenoxy)pyrimidine-2,4-diamine

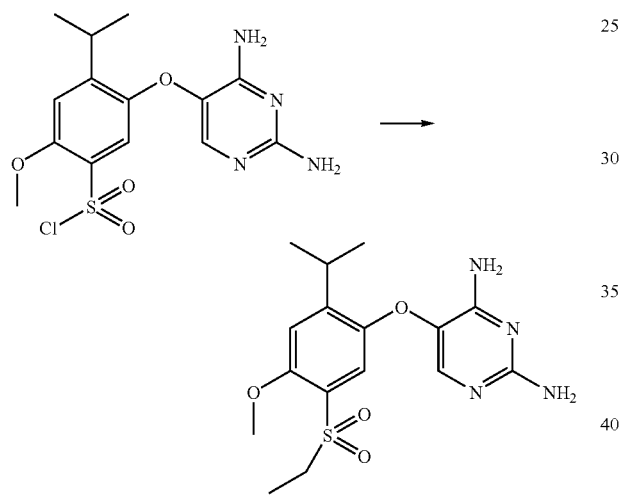

To a solution of sodium sulfite (541 mg, 4.29 mmol) in water (20 mL) was added 5-(2,4-Diamino-pyrimidin-5-yloxy)-4-isopropyl-2-methoxy-benzenesulfonyl chloride (400 mg, 1.07 mmol) and the reaction was heated at 80° C. for 1 hour. Sodium bicarbonate (361 mg, 4.29 mmol-dissolved in 5 mL water), dioxane (20 mL), and ethyl iodide (0.10 mL, 1.29 mmol) were added and the reaction was heated at 80° C. for 2 hours. The reaction was concentrated, extracted with dichoromethane (150 mL) and water (20 mL). The dichloromethane layer was dried using anhydrous sodium sulfate, concentrated, and purified via silica gel column chromatography (95/5/0.1 dichloromethane/methanol/ammonium hydroxide) to yield 5-(5-ethanesulfonyl-2-isopropyl-4-methoxy-phenoxy)-pyrimidine-2,4-diamine (77 mg, 20%) as white solid, MS (M+H)=367.

Example 48

5-(2-Isopropyl-4-methoxy-5-trifluoromethyl-phenoxy)-pyrimidine-2,4-diamine

The synthetic procedure used in this Example is outlined in Scheme S.

SCHEME S

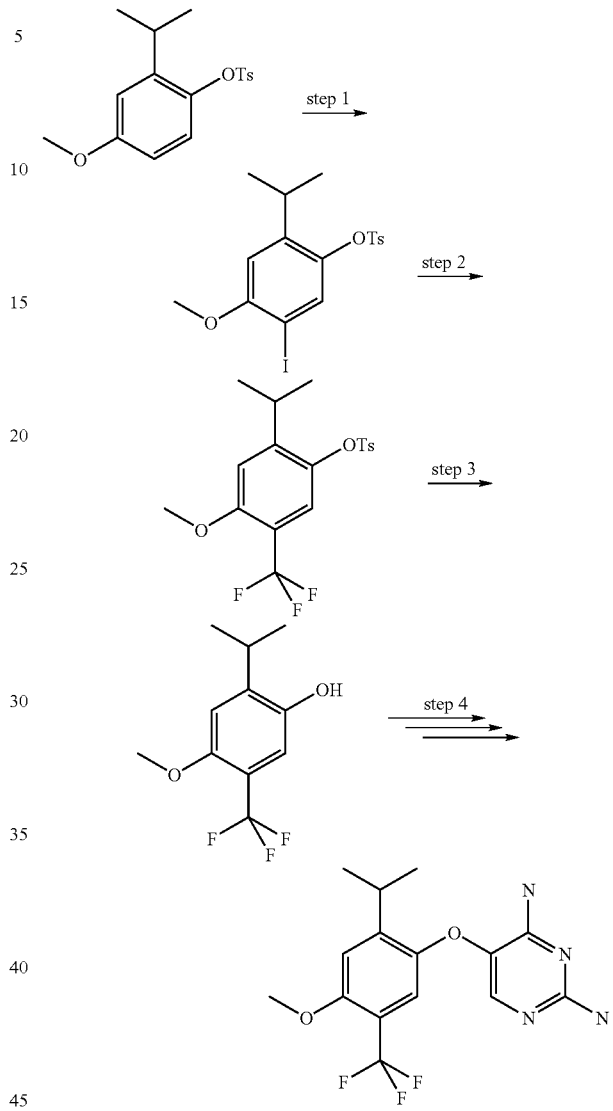

Step 1. 1-Iodo-4-isopropyl-2-methoxy-5-(toluene-4-sulfonyl)-benzene

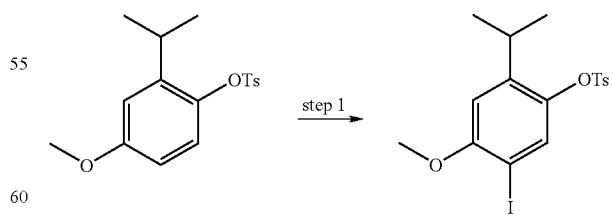

To a solution of 2-Isopropyl4-methoxy-1-(toluene4-sulfonyl)-benzene (10 g, 31.25 mmol) in HOAc (10 ml) was added a solution of ICl (9.6 g, 59.26 mmol) in HOAc (10 ml) and H₂O (5 ml). The reaction mixture was stirred at room temperature for 16 hrs and basified by saturated NaHCO₃ solution. The aqueous solution was extracted into EtOAc which was washed with water, brine, dried over $Na_2SO_4$, filtered and concentrated in vacuo to give 1-Iodo4-isopropyl-2-methoxy-5-(toluene4-sulfonyl)-benzene (12.35 g, 89%).

Step 2. 1-Isopropyl-5-methoxy-2-(toluene4-sulfonyl)
4-trifluoromethyl-benzene

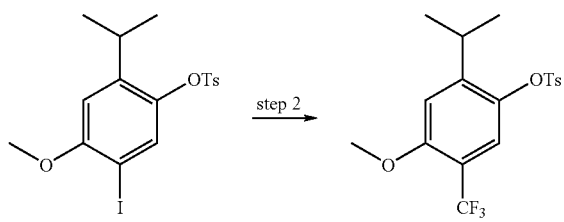

To a hot mixture of 1-Iodo4-isopropyl-2-methoxy-5-(toluene4-sulfonyl)-benzene (0.5 g, 1.12 mmol), CuI, KF in anhydrous DMF (10 ml) at 120° C. oil bath temperature, was added trifluoromethyl iodide (0.64 g, 4.48 mmol) in portions over 30 min. The reaction mixture was heated for 4 hrs and poured into $H_2O$ (100 ml). The insoluble solid, which was collected by filtration was triturated with methylene chloride, filtered and concentrated to give 1-Isopropyl-5-methoxy-2-(toluene4-sulfonyl)4-trifluoromethyl-benzene (0.45 g, 100%) as a solid.

Step 3.
2-Isopropyl4-methoxy-5:-trifluoromethyl-phenol

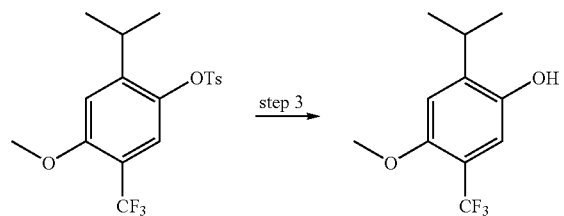

A solution of 1-Isopropyl-5-methoxy-2-(toluene4-sulfonyl)4-trifluoromethyl-benzene (0.40 g, 1.03 mmol) and NaOH (0.5 g, 12.5 mmol) in MeOH(5ml) and $H_2O$ (5ml) was heated at 90° C. for 2 hrs. The cooled reaction mixture was acidified with 3N HCl and extracted into methylene chloride. The combined extracts was dried with $Na_2SO_4$, filtered and concentrated to give desired 2-Isopropyl-4-methoxy-5-trifluoromethyl-phenol (0.194 g, 81%) as an oil.

Step 4. 5-(2-Isopropyl54-methoxy-5-trifluoromethyl-phenoxy):pyrimidine-2,4-diamine

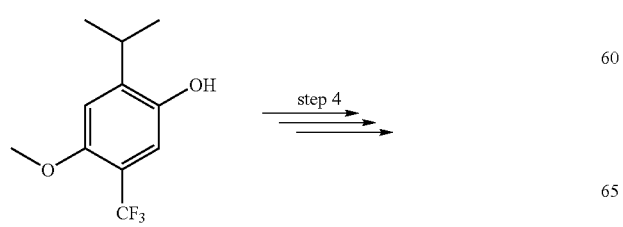

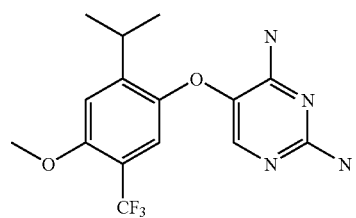

Following the procedure of Example 2 steps 5-7, 2-Isopropyl4-methoxy-5-trifluoromethyl-phenol was converted to 5-(2-Isopropyl4-methoxy-5-trifluoromethyl-phenoxy)-pyrimidine-2,4-diamine. (M+H)=343

Example 49

5-(2-Isopropyl4-methoxy-5-thiazol4-yl-phenoxy-pyrimidine-2,4-diamine

The synthetic procedure used in this Example is outlined in Scheme T.

SCHEME T

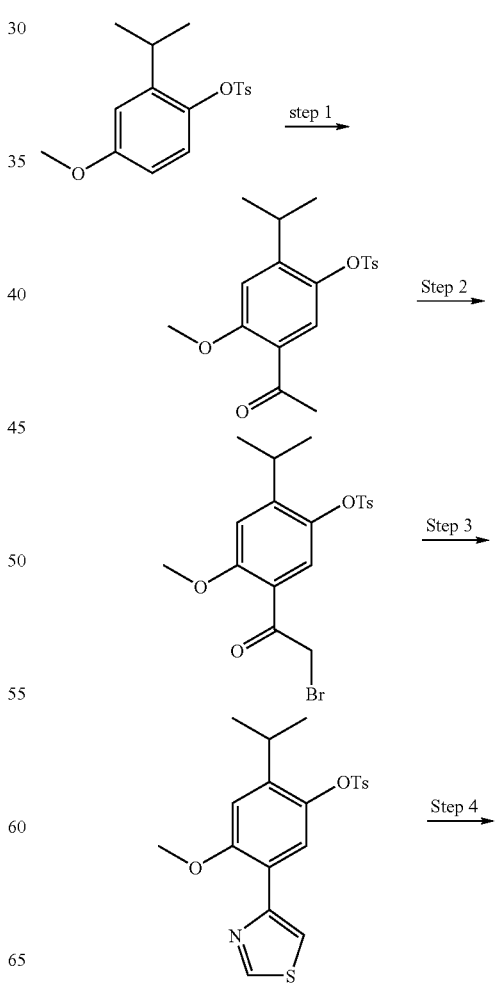

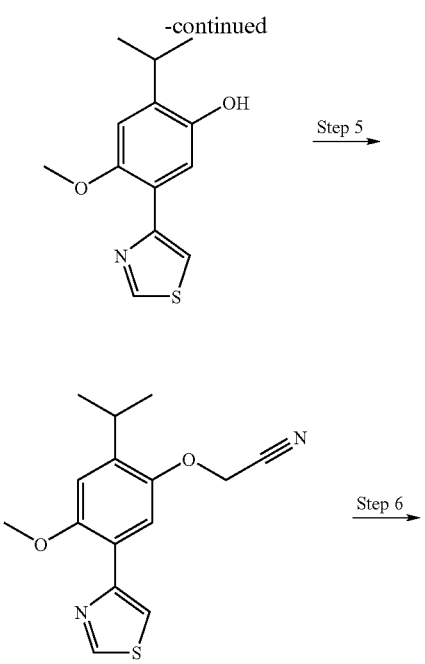

Step 1. 1-[4-Isopropyl-2-methoxy-5-(toluene4-sulfonyl)-phenyl]-ethanone

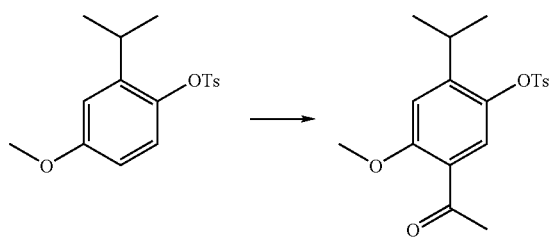

To a clear solution of 2-Isopropyl4-methoxy-1-(toluene-4-sulfonyl)-benzene (5.3 g, 16.56 mmol) in DCE (50 ml) was added acetyl chloride (2.0 g, 24.84 mmol) and AlCl₃ (3.3 g, 24.84 mmol) at room temperature. The reaction mixture was stirred at room temperature for 16 hrs and quenched by H₂O (10 ml). Ten minutes after quenching, the aqueous solution was extracted into CH₂Cl₂. The combined extracts was washed with H₂O, dried wover Na₂SO₄, filtered and concentrated. Flashed chromatography on silica gel (0 to 30% EtOAc in Hex) gave 1-[4-Isopropyl-2-methoxy-5-(toluene4-sulfonyl)-phenyl]-ethanone (4.7 g, 79%) as white solid.

Step 2. 2-Bromo-1-[4-isopropyl-2-methoxy-5-(toluene-4-sulfonyl)-phenyl]-ethanone

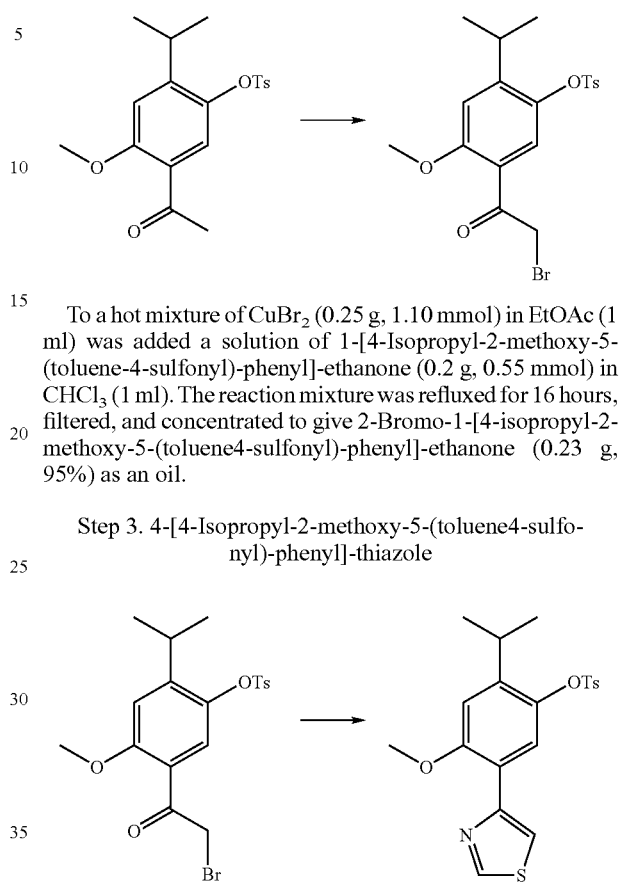

To a hot mixture of CuBr₂ (0.25 g, 1.10 mmol) in EtOAc (1 ml) was added a solution of 1-[4-Isopropyl-2-methoxy-5-(toluene-4-sulfonyl)-phenyl]-ethanone (0.2 g, 0.55 mmol) in CHCl₃ (1 ml). The reaction mixture was refluxed for 16 hours, filtered, and concentrated to give 2-Bromo-1-[4-isopropyl-2-methoxy-5-(toluene4-sulfonyl)-phenyl]-ethanone (0.23 g, 95%) as an oil.

Step 3. 4-[4-Isopropyl-2-methoxy-5-(toluene4-sulfonyl)-phenyl]-thiazole

To a solution of 2-Bromo-1-[4-isopropyl-2-methoxy-5-(toluene4-sulfonyl)-phenyl]-ethanone (0.23 g, 0.51 mmol) in anhydrous dioxane (5 ml) was added Na₂CO₃ (1.1 g, 10.12 mmol) and thioamide (5 ml, 0.31 g, 5.06 mmol). The reaction mixture was refluxed for 3 hrs and partitioned between H₂O and methylene chloride. The combined organic extracts was dried over Na₂SO₄, filtered and concentrated. Flash chromatography on silica (30% EtOAc in Hex) gave 4-[4-Isopropyl-2-methoxy-5-(toluene-4-sulfonyl)-phenyl]-thiazole (0.19 g, 95%)as oil.

Step 4. 2-Isopropyl-4-methoxy-5-thiazol4-yl-phenol

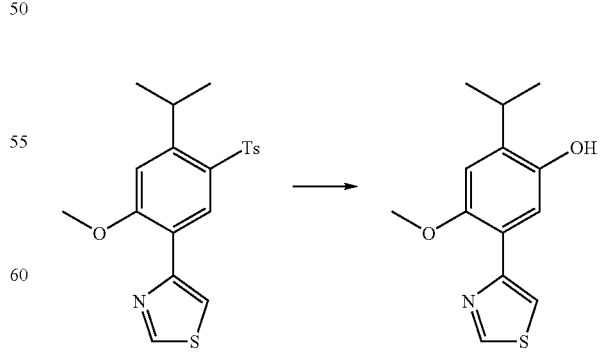

A mixture of 4-[4-Isopropyl-2-methoxy-5-(toluene4-sulfonyl)-phenyl]-thiazole (1.0 g, 2.27 mmol) and K₂CO₃ (1.6 g, 11.34 mmol) in anhydrous MeOH (10 ml) was refluxed for 8 hrs. Solvent was removed in vacuo and the residue was partitioned between methylene chloride and water. The combined organic extract was dried over Na₂SO₄, filtered, and concentrated to give 2-Isopropyl-4-methoxy-5-thiazol-4-yl-phenol.

Step 5. (2-Isopropyl-4-methoxy-5-thiazol-4-yl-phenoxy)-acetonitrile

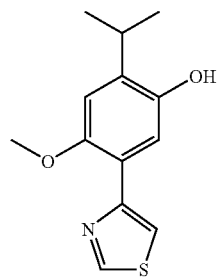

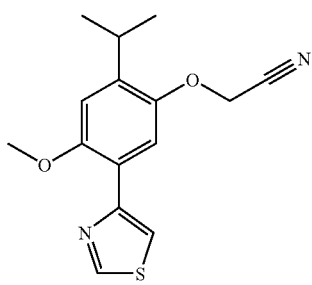

The crude 2-Isopropyl4-methoxy-5-thiazol4-yl-phenol from step 4 and bromoacetonitrile (0.33 g, 2.72 mmol) together with K₂CO₃ (0.94 g, 6.81 mmol) in anhydrous acetonitrile (30 ml) was heated at 60° C. for 3 hrs. The reaction mixture was partitioned between EtOAc and water. The combined organic extract was dried over Na₂SO₄, filtered and concentrated. Flash chromatography on silica (10 to 20%% EtOAc in Hexanes) gave (2-Isopropyl-4-methoxy-5-thiazol4-yl-phenoxy)-acetonitrile (0.47 g, 72%) as an oil.

Step 6. 5-(2-Isopropyl-4-methoxy-5-thiazol-4-yl-phenoxy)-pyrimidine-2,4-diamine

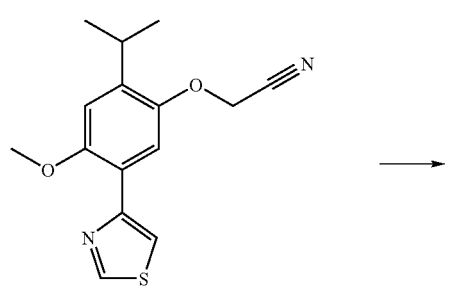

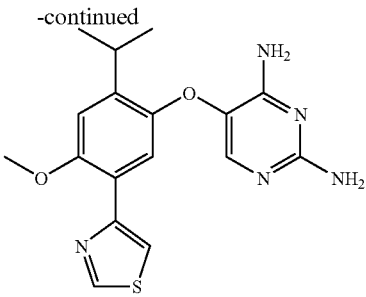

A mixture of (2-Isopropyl-4-methoxy-5-thiazol-4-yl-phenoxy)-acetonitrile (0.27 g, 0.94 mmol) and Brederick's reagent (0.35 g, 2.01 mmol) was heated at 100° C. for 2 hrs. Excess Brederick's reagent was removed under reduced pressure. The residue was dissolved in anhydrous EtOH (10 ml) and aniline HCl (0.38 g, 2.93 mmol) was added. The reaction mixture was heated at 80° C. for 18 hrs and partitioned between EtOAc and water. The combined organic extracts were dried over Na₂SO₄, filtered and concentrated. Guanidine carbonate (0.27 g, 1.49 mmol) and NMP (10 ml) were added and heated to 120° C. for 10 hrs. The reaction mixture was poured into water and extracted into EtOAc. The combined organic extracts were dried over Na₂SO₄, filtered and concentrated. Flash chromatography on silica (3% MeOH in methylene chloride with 0.1% NH₄OH) gave 5-(2-Isopropyl-4-methoxy-5-thiazol-4-yl-phenoxy)-pyrimidine-2,4-diamine (0.15 g, 68%) as a solid. (M+H)=358.

Example 50

5-[5-(N'-Allylidene-hydrazinomethyl)-2-isopropyl-4-methoxy-phenoxy]-pyrimidine-2,4-diamine

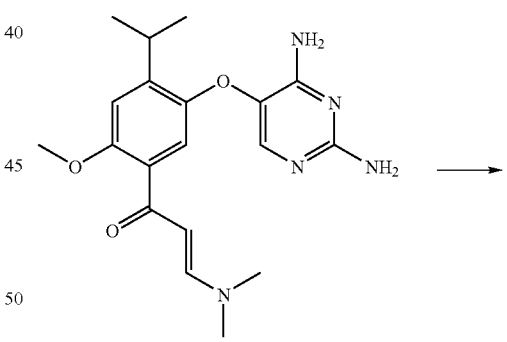

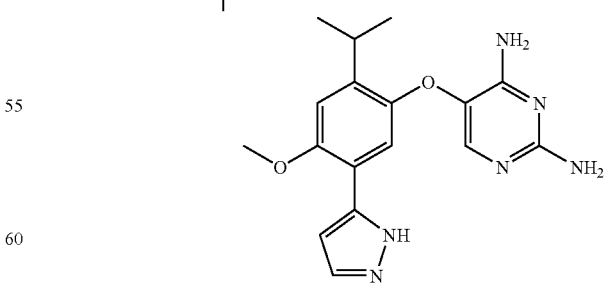

To a solution of 1-[5-(2,4-Diamino-pyrimidin-5-yloxy)4-isopropyl-2-methoxy-phenyl]-3-dimethylamino-propenone (0.25 g, 0.67 mmol) in EtOH (6 ml) was added hydrazine hydrate (0.076 g, 1.2 mmol). The reaction mixture was stirred at room temperature for 16 hrs and concentrated. Recrystallization of the crude residue in EtOH/EtOAc gave 5-[5-(N'-Allylidene-hydrazinomethyl)-2-isopropyl-4-methoxy-phenoxy]-pyrimidine-2,4-diamine (0.228 g, 100%). (M+H)=341.

Example 51

2-[4-(2,4-Diamino-pyrimidin-5-yloxy)-2-iodo-5-isopropyl-phenoxy]-ethanol

Step 1. 5-[5-Iodo-2-isopropyl-4-(2-trimethylsilanyloxy-ethoxy)-phenoxy]pyrimidine-2,4-diamine

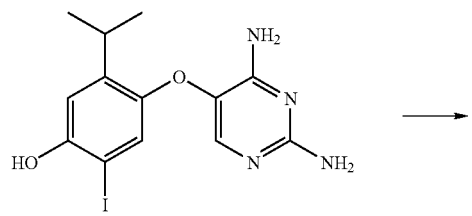

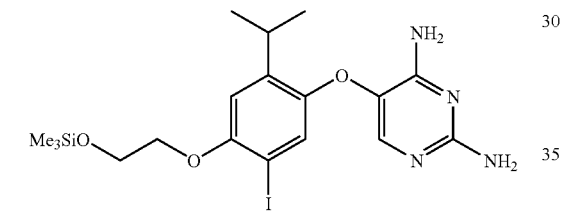

A mixture of 4-(2,4-Diamino-pyrimidin-5-yloxy)-2-iodo-5-isopropyl-phenol (0.3 g, 0.78 mmol), (2-bromoethoxy)-tert-butyl-dimethyl silane (0.28 g, 1.17 mmol), and $K_2CO_3$ (0.22 g, 1.56 mmol) in anhydrous DMF (5 ml) was heated at 50° C. for 16 hrs. Solvent was removed in vacuo. The residue was partitioned between methylene chloride and water. The combined organic extracts was washed with water, dried over $Na_2SO_4$, filtered and concentrated. Flash chromatography on silica (3% MeOH in methylene chloride with 0.1% $NH_4OH$) gave 5-[5-Iodo-2-isopropyl-4-(2-trimethylsilanyloxy-ethoxy)-phenoxy]-pyrimidine-2,4-diamine (0.38 g, 90%) as a solid.

Step 2. 2-[4-(2,4-Diamino-pyrimidin-5-yloxy)-2-iodo-5-isopropyl-phenoxy]-ethanol

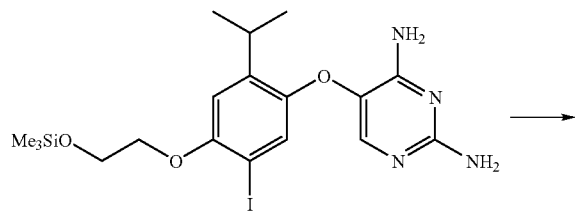

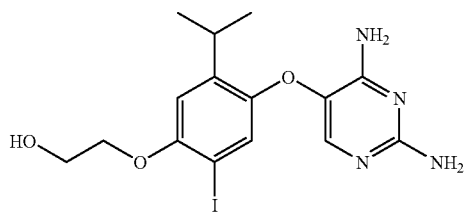

5-[5-Iodo-2-isopropyl-4-(2-trimethylsilanyloxy-ethoxy)-phenoxy]-pyrimidine-2,4-diamine (0.38 g, 0.69 mmol) in a solution of HOAc/THF/$H_2O$ in a ratio of 3:1:1.95 ml) was heated at 65° C. for 16 hrs. The pH of the reaction mixture was adjusted to pH=9 and extracted into methylene chloride. The combined eatracts was dried over $Na_2SO_4$, filtered and concentrated. Flash chromatography on silica (5% MeOH in methylene chloride with 0.1% NH40H) gave 2-[4-(2,4-Diamino-pyrimidin-5-yloxy)-2-iodo-5-isopropyl-phenoxy]-ethanol (0.25 g, 86%) as a white solid. (M+H)=431

Example 52

5-(4-Amino-2-ethylamino-pyrimidin-5-yloxy)-4-isopropyl-2-methoxy-benzamide

Step 1. 5-(4-Amino-2-ethylamino-pyrimidin-5-yloxy)-4-isopropyl-2-methoxy-benzonitrile

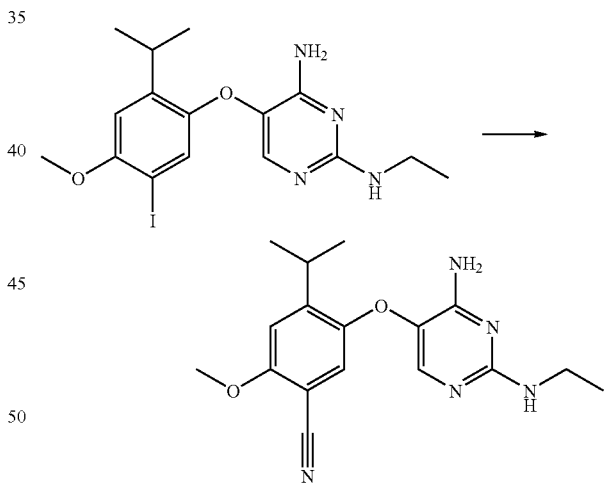

To a solution of N*2*-Ethyl-5-(5-iodo-2-isopropyl-4-methoxy-phenoxy)-pyrimidine-2,4-diamine (1.65 g, 4.12 mmol) in anhydrous DMF (10 ml) was added CuCN, and the reaction mixture was heated to 120° C. for 3 hrs. The reaction mixture was poured into water (200 ml) and the insoluble portion was collected by filtration. The solid was triturated with 10% MeOH/methylene chloride/0.1% $NH_4OH$ solution (100 ml) and filtered again. The filtrate was concentrated and flash chromatographed on silica (3% MeOH in methylene chloride with 0.1% $NH_4OH$) to give 5-(4-Amino-2-ethylamino-pyrimidin-5-yloxy)-4-isopropyl-2-methoxy-benzonitrile (0.87 g, 71%) as a white solid.

Step 2. 5-(4-Amino-2-ethylamino-pyrimidin-5-yloxy)-4-isopropyl-2-methoxy-benzamide

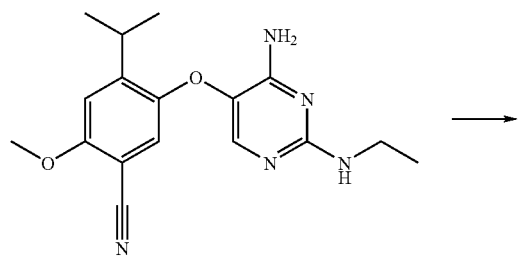

To a solution of 5-(4-Amino-2-ethylamino-pyrimidin-5-yloxy)-4-isopropyl-2-methoxy-benzonitrile (0.3 g, 0.92 mmol) in EtOH/H$_2$O (1:1,10 ml) was added a solution of NaOH (0.37 g, 9.17 mmol) in H$_2$O (1 ml). The reaction mixture was heated at 100° C. for 24 hrs and neutralized with 3N HCl. Ethanol was removed in vacuo and the remaining aqueous solution was extracted into methylene chloride. The combined extract was washed with water, dried over Na$_2$SO$_4$, filtered and concentrated. Flash chromatography on silica gel (3 to 8% EtOAc in Hexanes) gave 5-(4-Amino-2-ethylamino-pyrimidin-5-yloxy)-4-isopropyl-2-methoxy-benzamide (0.086 g, 27% ) as a white solid. (M+H)=346.

Example 53

N*2*-Ethyl-5-(2-isopropyl-5-methanesulfonyl-4-methoxy-phenoxy)-pyrimidine-2,4-diamine

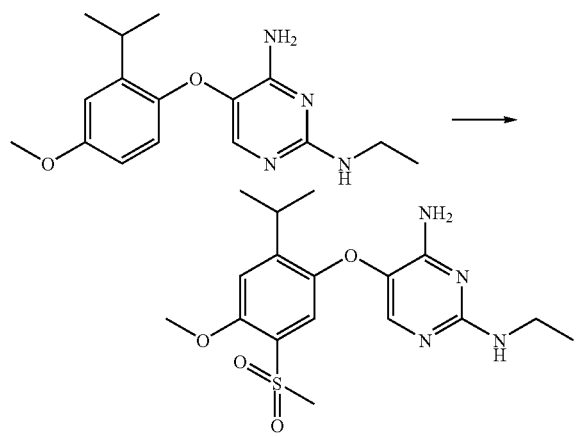

A mixture of N*2*-Ethyl-5-(2-isopropyl-4-methoxy-phenoxy)-pyrimidine-2,4-diamine (0.30 g, 0.99 mmol), methanesulfonic anhydride (1.0 g, 5.96 mmol) and trifluoromethanesulfonic acid (0.37 g, 2.48 mmol) was heated at 70° C. for two hrs. The hot reaction mixture was poured into ice water and basified with sat. NaHCO$_3$ solution. The aqueous solution was then extracted into methylene chloride. The combined organic extracts was washed with H$_2$O, dried over Na$_2$SO$_4$, filtered and concentrated. Flash chromatography on silica (1% MeOH in methylene chloride with 1% NH$_4$OH) gave N*2*-Ethyl-5-(2-isopropyl-5-methanesulfonyl-4-methoxy-phenoxy)-pyrimidine-2,4-diamine (87 mg, 23% ) as a solid. (M+H)=381.

Example 54

5-(2-Isopropyl-4-methoxy-5-oxazol-4-yl-phenoxy)-pyrimidine-2,4-diamine

Step 1. Toluene4-sulfonic acid 5-(2-formyloxy-acetyl)-2-isopropyl-4-methoxy-phenyl ester

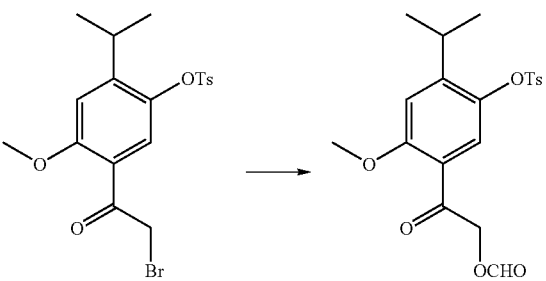

A mixture of 2-Bromo-1-[4-isopropyl-2-methoxy-5-(toluene4-sulfonyl)-phenyl]-ethanone (0.2 g, 0.45 mmol) and sodium formate (0.040 g, 0.60 mmol) in anhydrous DMF (3 ml) was stirred at room temperature for 16 hours. The reaction mixture was poured into H$_2$O and extracted into EtOAc. The combined organic extract was dried over Na$_2$SO$_4$, filtered and concentrated to yield toluene4-sulfonic acid 5-(2-formyloxy-acetyl)-2-isopropyl-4-methoxy-phenyl ester.

Step 2. 4-[4-Isopropyl-2-methoxy-5-(toluene-4-sulfonyl)-phenyl]-oxazole

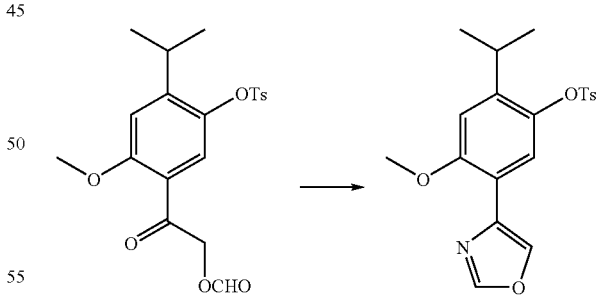

A solution of the crude toluene-4-sulfonic acid 5-(2-formyloxy-acetyl)-2-isopropyl-4-methoxy-phenyl ester from above and ammonium acetate (0.17 g, 2.25 mmol) in HOAc (5 ml) was heated at 100° C. for 2 hrs. The reaction mixture was partitioned between methylene chloride and sat. NaHCO$_3$ solution. The combined organic extract was dried over Na$_2$SO$_4$, filtered and concentrated. Flash chromatography on silica (30 to 50% EtOAc in Hexanes) gave 4-[4-Isopropyl-2-methoxy-5-(toluene-4-sulfonyl)-phenyl]-oxazole (25 mg, 14% ) as a white solid.

Step 3. 5-(2-Isopropyl-4-methoxy-5-oxazol-4-yl-phenoxy)-pyrimidine-2,4-diamine

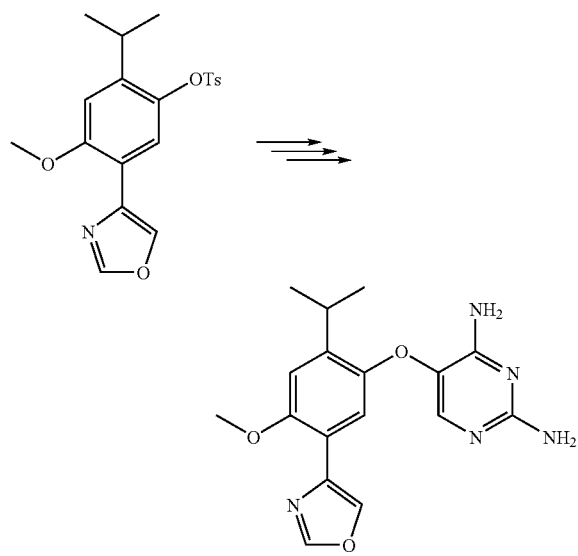

4-[4-Isopropyl-2-methoxy-5-(toluene-4-sulfonyl)-phenyl]-oxazole was converted, using the procedure of steps 4-6 of Example 49, to 5-(2-Isopropyl-4-methoxy-5-oxazol-4-yl-phenoxy)-pyrimidine-2,4-diamine. (M+H)=342.

Example 55

5-(2-Isopropyl-4-methoxy-5-thiazol-2-yl-phenoxy)-pyrimidine-2,4-diamine

Step 1. 5-(2,4-Diamino-pyrimidin-5-yloxy)-4-isopropyl-2-methoxy-thiobenzamide

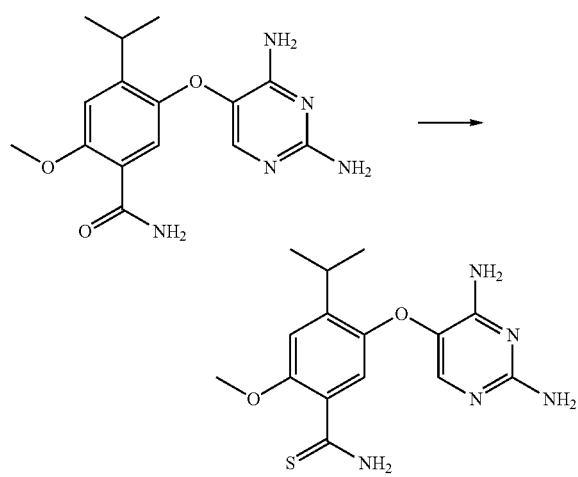

A mixture of 5-(2,4-Diamino-pyrimidin-5-yloxy)-4-isopropyl-2-methoxy-benzamide (0.25 g, 0.79 mmol, prepared according to the procedure of Example 52) and Lawesson's reagent (0.96 g, 2.37 mmol) in anhydrous THF (20 ml) was stirred at room temperature for 16 hrs and concentrated in vacuo. Flash chromatography on silica (5% $CH_3OH$ in methylene chloride with 1% $NH_4OH$) gave 5-(2,4-Diamino-pyrimidin-5-yloxy)-4-isopropyl-2-methoxy-thiobenzamide (0.201 g, 76%) as a yellow solid.

Step 2. 5-(2-Isopropyl-4-methoxy-5-thiazol-2-yl-phenoxy)-pyrimidine-2,4-diamine

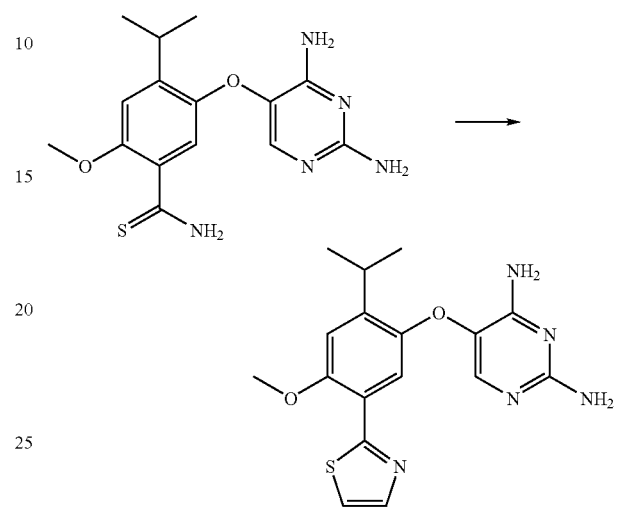

To a solution of 5-(2,4-Diamino-pyrimidin-5-yloxy)-4-isopropyl-2-methoxy-thiobenzamide (0.23 g, 0.69 mmol) in HOAc (5 ml) was added bromoactaldehyde diethylacetal (0.18 g, 0.9 mmol) and TsOH (5 mg) as a catalyst. The reaction mixture was heated at 110° C. for 16 hrs and basified with sat. $NaHCO_3$ solution. The aqueous solution was extracted into methylene chloride. The combined organic extract was dried over $Na_2SO_4$, filtered and concentrated. Flash chromatography on silica (5% MeOH in methylene chloride with 1% $NH_4OH$) gave 5-(2-Isopropyl-4-methoxy-5-thiazol-2-yl-phenoxy)-pyrimidine-2,4-diamine (0.070 g, 28%) as a yellow solid. (M+H)=358

Example 56

5-(4-Ethoxy-5-iodo-2-isopropyl-phenoxy)-pyrimidine-2,4-diamine

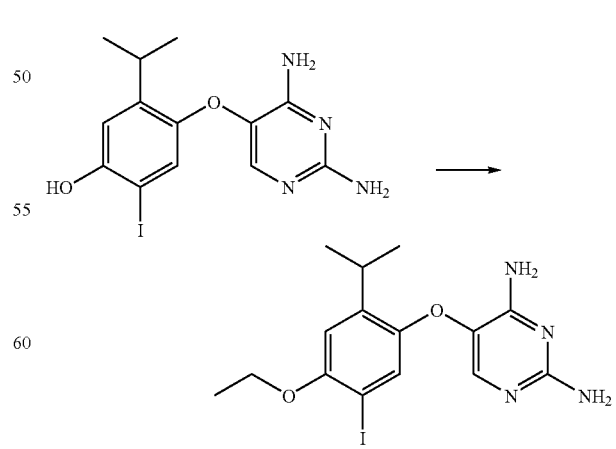

To a solution of 4-(2,4-Diamino-pyrimidin-5-yloxy)-2-iodo-5-isopropyl-phenol (0.2 g, 0.52 mmol) in anhydrous DMF (2 ml) was added EtBr (57 mg, 0.52 mmol) in portions. The reaction mixture was partitioned between EtOAc and H₂O. The organic extract was dried over Na₂SO₄, filtered and aconcentrated. Flash chromatography on silica (3% MeOH in methylene chloride with 1% NH₄OH) gave 5-(4-Ethoxy-5-iodo-2-isopropyl-phenoxy)-pyrimidine-2,4-diamine (0.17 g, 28%) as a yellow solid. (M+H)=415.

Example 57

5-(2-Isopropyl-4-methoxy-5-[1,2,4]oxadiazol-3-yl-phenoxy)-pyrimidine-2,4-diamine The synthetic procedure used in this Example is outlined in Scheme U.

SCHEME U

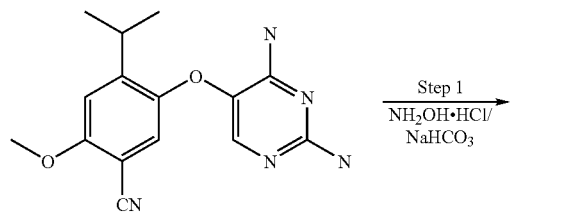

Step 1
NH₂OH·HCl/
NaHCO₃

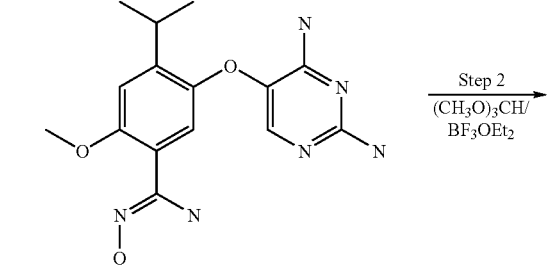

Step 2
(CH₃O)₃CH/
BF₃OEt₂

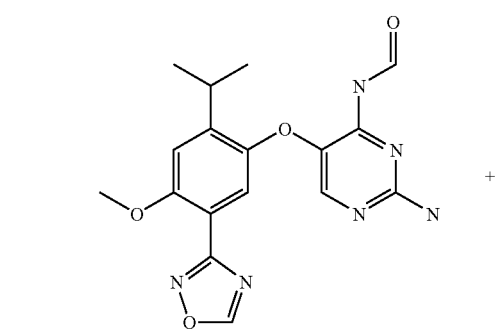

+

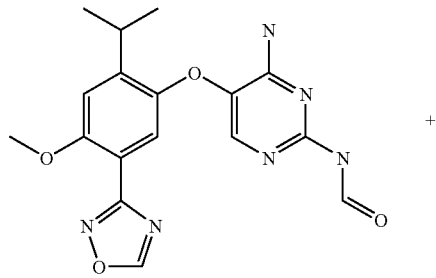

-continued

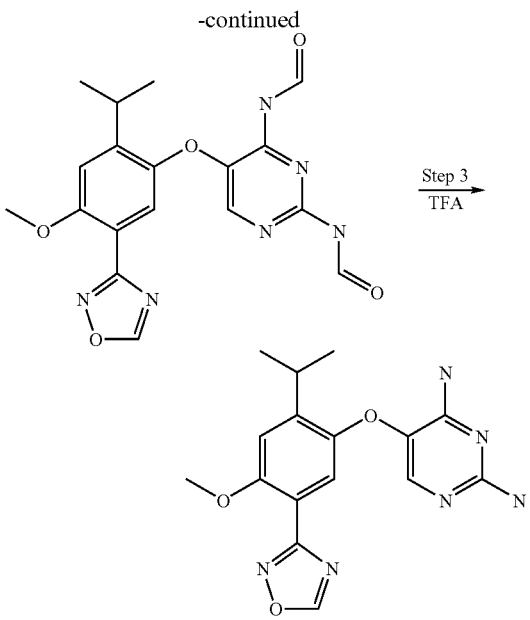

Step 3
TFA

The 5-(2,4-Diamino-pyrimidin-5-yloxy)-4-isopropyl-2-methoxy-benzonitrile utilized in step 1 of this Example was prepared as described in Scheme 1.

Step 1

5-(2,4-Diamino-pyrimidin-5-yloxy)-N-hydroxy-4-isopropyl-2-methoxy-benzamidine

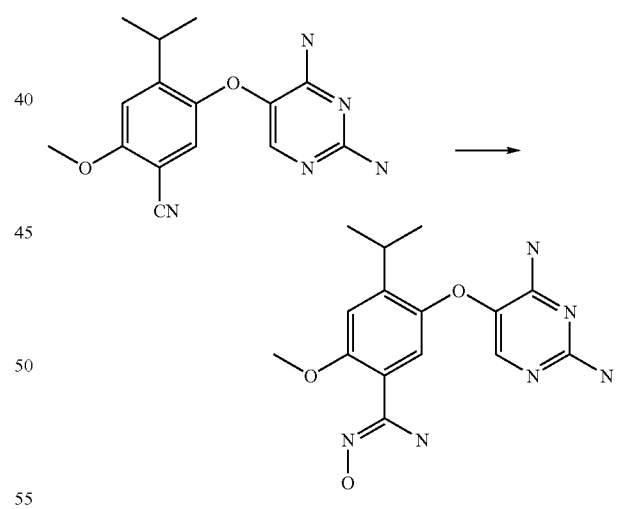

The benzamidination carried out in this step follows the procedure reported by Meyer et al., *Synthesis* 2003, 6, pp. 899-905. To a stirred mixture of hydroxylamine hydrochloride (0.099 g, 1.43 mmol) and sodium hydrogen carbonate (0.119 g, 1.42 mmol) in ethanol (1.4 ml) and water (0.3 ml) was added 5-(2,4-diamino-pyrimidin-5-yloxy)-4-isopropyl-2-methoxy-benzonitrile (0.385 g, 1.29 mmol) and the mixture heated at reflux for 5 hours. A second portion of hydroxylamine hydrochloride (0.049 g, 0.71 mmol) and sodium hydrogen carbonate (0.060 g, 0.71 mmol) was added. After a further 2 hours the mixture was cooled, concentrated in vacuo, then diluted with water (10 ml) and extracted with ethyl acetate. The combined organic extracts were washed with brine then dried (MgSO₄), filtered and concentrated in vacuo to yield 5-(2,4-diamino-pyrimidin-5-yloxy)-N-hydroxy4-isopropyl-2-methoxy-benzamidine (355 mg) as a yellow foam. This material was used directly without further purification.

Step 2

N-[2-Amino-5-(2-isopropyl-4-methoxy-5-[1,2,4]oxadiazol-3-yl-phenoxy)-pyrimidin-4-yl]formamide, N-[4-amino-5-(2-isopropyl-4-methoxy-5-[1,2,4]oxadiazol-3-yl-phenoxy)-pyrimidin-2-yl]formamide and N-[4-formylamino-5-(2-isopropyl-4-methoxy-5-[1,2,4]oxadiazol-3-yl-phenoxy)-pyrimidin-2-yl]-formamide The formylation carried out in this step follows the procedure reported by Kitamura et al. *Chem. Pharm. Bull.* 2001, 49, pp. 268-277. To a suspension of 5-(2,4-diamino-pyrimidin-5-yloxy)-N-hydroxy-4-isopropyl-2-methoxy-benzamidine (0.350 g, 1.05 mmol) in trimethylorthoformate (1.12 g, 10.5 mmol) at ambient temperature and under nitrogen was added boron trifluoride diethyl etherate (1 drop) then the mixture heated at reflux for 1 ½ hours. The resultant mixture was cooled, diluted with dichloromethane (60 ml), then washed with water (20 ml), brine (20 ml) and then dried (MgSO₄) filtered and concentrated in vacuo to provide a mixture of N-[2-amino-5-(2-isopropyl-4-methoxy-5-[1,2,4]oxadiazol-3-yl-phenoxy)-pyrimidin-4-yl]formamide, N-[4-amino-5-(2-isopropyl-4-methoxy-5-[1,2,4]oxadiazol-3-yl-phenoxy)-pyrimidin-2-yl]formamide and N-[4-formylamino-5-(2-isopropyl-4-methoxy-5-[1,2,4]oxadiazol-3-yl-phenoxy)-pyrimidin-2-yl]-formamide as a yellow solid (260 mg). This material was used directly without further purification.

Step 3

5-(2-Isopropyl-4-methoxy-5-[1,2,4]oxadiazol-3-yl-phenoxy)-pyrimidine-2,4-diamine

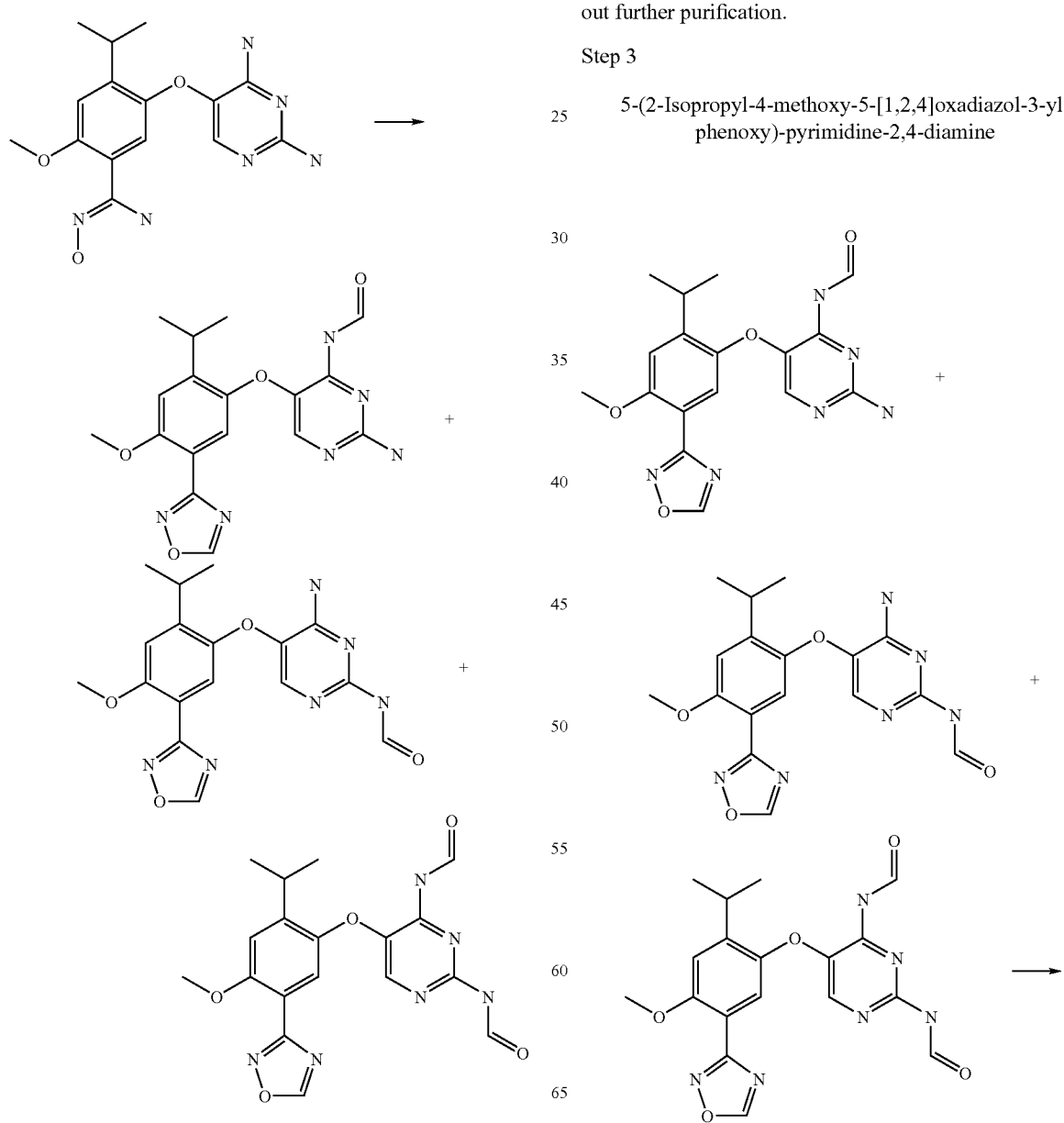

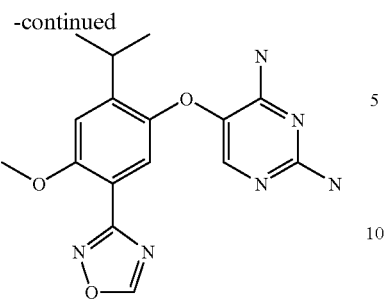

A mixture of N-[2-amino-5-(2-isopropyl-4-methoxy-5-[1,2,4]oxadiazol-3-yl-phenoxy)-pyrimidin-4-yl]formamide, N-[4-amino-5-(2-isopropyl-4-methoxy-5-[1,2,4]oxadiazol-3-yl-phenoxy)-pyrimidin-2-yl]formamide and N-[4-formylamino-5-(2-isopropyl-4-methoxy-5-[1,2,4]oxadiazol-3-yl-phenoxy)-pyrimidin-2-yl]-formamide (0.164 g) in trifluoroacetic acid (10 mL) was heated at reflux for 24 h. The mixture was then cooled and concentrated in vacuo. The residue was purified by flash chromatography (0-5% methanol in dichloromethane) to yield 76 mg of 5-(2-isopropyl-4-methoxy-5-[1,2,4]oxadiazol-3-yl-phenoxy)-pyrimidine-2,4-diamine as its trifluoroacetic acid salt. (M+H)+=343; MP 135-138.5° C.

Example 58

5-(6-Isopropyl-4-methyl-3,4-dihydro-2H-benzo[1,4]oxazin-7-yloxy)-pyrimidine-2,4-diamine The synthetic procedure used in this Example is outlined in Scheme V.

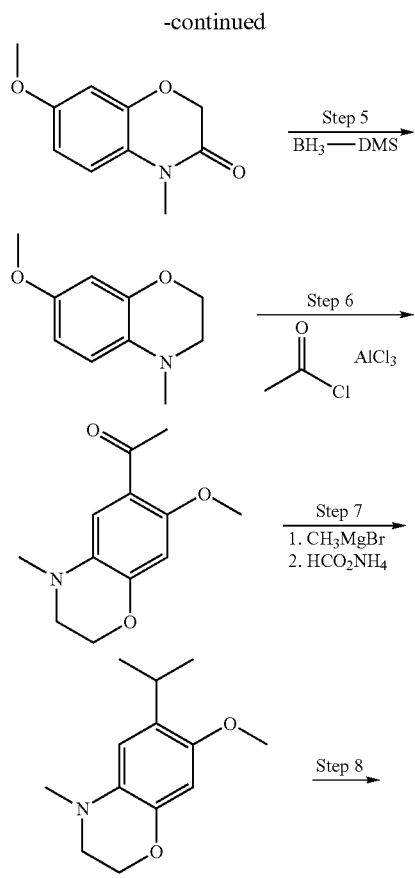

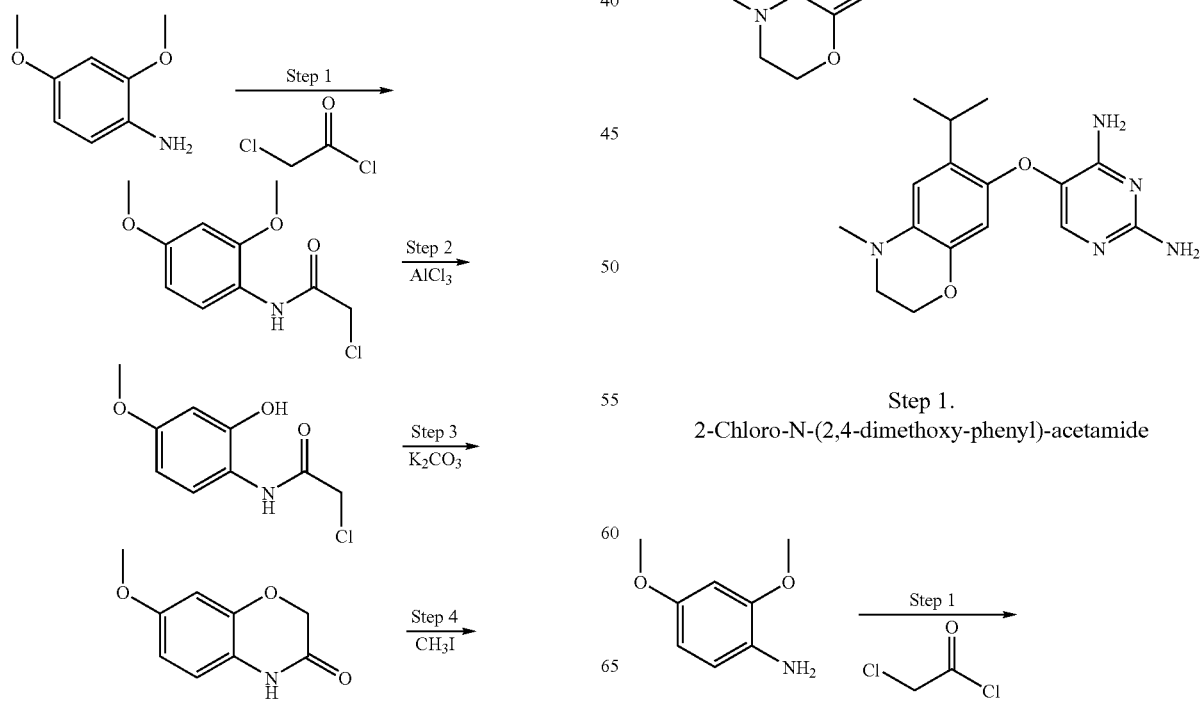

Step 1.
2-Chloro-N-(2,4-dimethoxy-phenyl)-acetamide

-continued

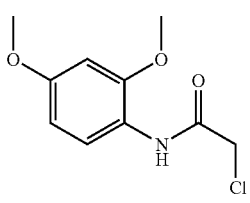

A mixture of 2,4-dimethoxy aniline (30.6 g, 0.2 mol), triethylamine (27.9 mL, 0.2 mol) in 600 mL methylene choride was stirred at 0° C. under nitrogen. Chloroacetyl chloride (16 mL, 0.2 mol) was added dropwise, and the reaction mixture was stirred for 15 minutes at 0° C., and then stirred for an additional two hours during which time the reaction mixture was allowed to warm to room temperature. The reaction was quenched by addition of 1N HCl, followed by saturated aqueous sodium bicarbonate. The aqueous mixture was partitioned with EtOAc, and the organic phase was separated, dried (MgSO$_4$), filtered, and evaporated under reduced pressure to give 45.58 g of crude 2-Chloro-N-(2,4-dimethoxy-phenyl)-acetamide. MS (M+H)=230.

Step 2.
2-Chloro-N-(2-hydroxy-4-methoxy-phenyl)-acetamide

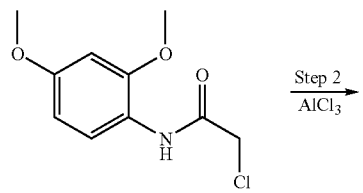

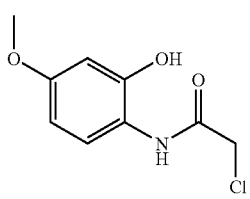

2-Chloro-N-(2,4-dimethoxy-phenyl)-acetamide (45.8 g, 0.2 mol) was dissolved in 1000 mL methylene chloride, and the reaction mixture was stirred at 0° C. under nitrogen. Aluminum trichloride (78.9 g, 0.6 mol) was added in portions over 30 minutes, and the reaction mixture was allowed to stir for 17 hours at room temperature. The reaction mixture was concentrated to 200 mL volume under reduced pressure, and then poured onto ice. Solids were removed by filtration, and the liquid was taken up in EtOAc, washed with brine, dried (MgSO$_4$), filtered, and evaporated under reduced pressure to yield 39.67 g of 2-Chloro-N-(2-hydroxy4-methoxy-phenyl)-acetamide. MS (M+H)=216.

Step 3. 7-Methoxy-4H-benzo[1,4]oxazin-3-one

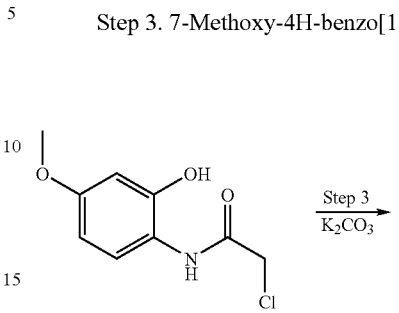

2-Chloro-N-(2-hydroxy4-methoxy-phenyl)-acetamide (390.0 g, 0.18 mol) and powdered potassium carbonate (27.6 g, 0.2 mol) were added to 1000 mL acetone, and the reaction mixture was refluxed under nitrogen for eight hours. The reaction mixture was cooled, solids were removed by filtration, and the liquid was concentrated under reduced pressure to give 32.56 g of crude 7-Methoxy-4H-benzo[1,4]oxazin-3-one. (M+H)=180.

Step 4.
7-Methoxy-4-methyl-4H-benzo[1,4]oxazin-3-one

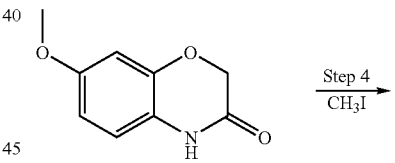

7-Methoxy-4H-benzo[1,4]oxazin-3-one (11.61 g, 0.065 mol) in 100 mL dry DMF was stirred at 0° C. under nitrogen. Sodium hydride (60% , 2.85 g, 0.072 mol) was added in portions over 30 minutes, after which methyl iodide (4.44 mL, 0.071 mol) was added dropwise. The reaction mixture was stirred at 0° C. for 2.5 hours, then poured into 1400 mL water. The resulting aqueous mixture was extracted four times with 400 mL EtOAc, and the combined organic layers were washed with water, then brine, dried (MgSO$_4$), filtered, and evaporated under reduced pressure to provide 13.07 g of 7-Methoxy-4-methyl-4H-benzo[1,4]oxazin-3-one. (M+H)= 194.

Step 5. 7-Methoxy-4-methyl-3,4-dihydro-2H-benzo[1,4]oxazine

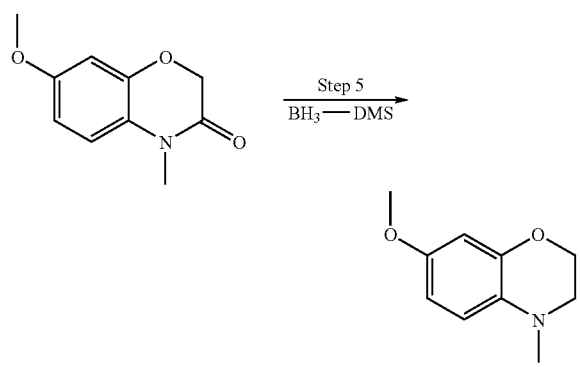

7-Methoxy-4-methyl-4H-benzo[1,4]oxazin-3-one (13.07 g, 0.68 mol) was added to 100 mL dry THF, and the reaction mixture was refluxed under nitrogen. Borane-dimethyl sulfide (13.6 mL, 0.136 mol) was added dropwise over one hour, and the reaction mixture was allowed to reflux for two hours. The reaction mixture was cooled and then quenched by addition of 50 mL of 10% aqueous HCl. Precipitate was removed by filtration, and the liquid was concentrated under reduced pressure to give 11.17 g of 7-Methoxy-4-methyl-3,4-dihydro-2H-benzo[1,4]oxazine. (M+H)=180.

Step 6. 1-(7-Methoxy-4-methyl-3,4-dihydro-2H-benzo[1,4]oxazin-6-yl)-ethanone

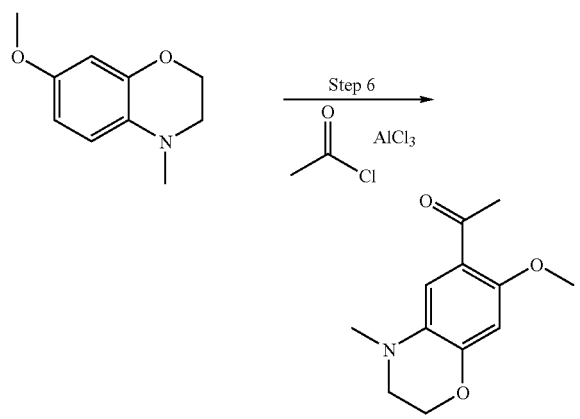

7-Methoxy-4-methyl-3,4-dihydro-2H-benzo[1,4]oxazine (11.17 g, 0.625 mol) in 400 mL of 1,2-dichloroethane was stirred at 0° C. under nitrogen. Aluminum trichloride (8.3 g, 0.625 mol) was added in portions, followed by dropwise addition of acetyl chloride (4.9 mL, 0.678 mol). The reaction mixture was stirred at 0° C. for 2.5 hours. Aluminum trichloride (3 g) was added, and the reaction mixture was stirred at room temperature for 24 hours. The reaction mixture was pourd into ice and 550 mL 3N HCl was added. The aqueous mixture was extracted with methylene chloride, and the combined organic layers were dried (MgSO$_4$), filtered, and evaporated under reduced pressure to yield 10.48 g of 1-(7-Methoxy-4-methyl-3,4-dihydro-2H-benzo[1,4]oxazin-6-yl)-ethanone. (M+H)=222.

Step 7. 6-Isopropyl-7-methoxy-4-methyl-3,4-dihydro-2H-benzo[1,4]oxazine

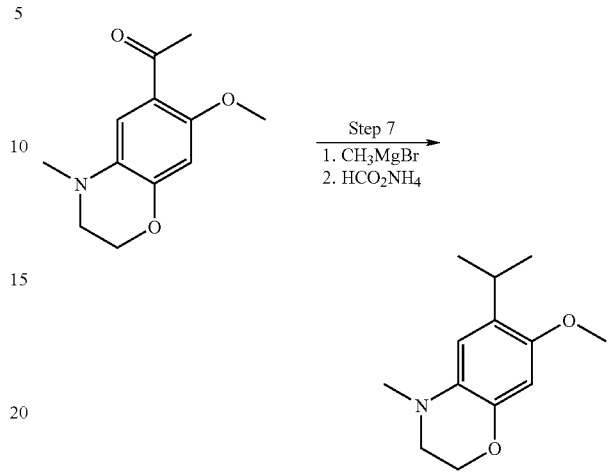

1-(7-Methoxy-4-methyl-3,4-dihydro-2H-benzo[1,4]oxazin-6-yl)-ethanone (10.48 g, 0.473 mol) was dissolved in 25 mL dry THF and the reaction mixture was stirred at 0° C. under nitrogen. Methyl magnesium bromide (22 mL of 3M solution in Et$_2$O, 0.15 mol) was added dropwise, and the reaction mixture was stirred at 0° C. for two hours. The reaction was quenched by dropwise addition of 50 mL 10% aqueous ammonium chloride, followed by water. The aqueous mixture was extracted with EtOAc, and the combined organic layers were dried (MgSO$_4$), filtered, and evaporated under reduced pressure. The residue was taken up in 95 mL acetic acid, and the reaction mixture was stirred at room temperature under nitrogen. Ammonium formate (14.92 g) and 10% Palladium on activated carbon (1.0 g) were added, and the reaction mixture was heated to 120° C. for three hours. The reaction mixture was cooled, solids were removed by filtration, and the filtrate was diluted with water, and made neutral by addition of solid sodium bicarbonate. The resulting aqueous solution was extracted with EtOAc, and the combined organic layers were dried (MgSO$_4$), filtered, and evaporated under reduced pressure to yield 9.97 g of 6-Isopropyl-7-methoxy-4-methyl-3,4-dihydro-2H-benzo[1,4]oxazine.

Step 8. 5-(6-Isopropyl-4-methyl-3,4-dihydro-2H-benzo[1,4]oxazin-7-yloxy)-pyrimidine-2,4-diamine

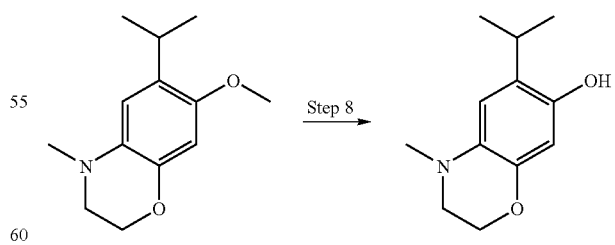

6-Isopropyl-7-methoxy-4-methyl-3,4-dihydro-2H-benzo[1,4]oxazine (2.21 g, 0.01 mol) was dissolved in 20 mL methylene chloride, and the reaction mixture was cooled to −65° C. Boron tribromide (12 mL of 1M solution in methylene chloride, 0.012 mol) was added dropwise over 15 minutes, and the reaction mixture was stirred for 5.5 hours, during which time the reaction mixture was allowed to warm to 0° C. The reaction mixture was then stirred for 24 hours at room temperature. The reaction mixture was cooled to 0° C., and methanol was slowly added until exotherm stopped. The reaction mixture was partitioned between water and methylene chloride, and the organic phase was dried (MgSO$_4$), filtered, and evaporated under reduced pressure to yield 1.38 g of 5-(6-Isopropyl-4-methyl-3,4-dihydro-2H-benzo[1,4]oxazin-7-yloxy)-pyrimidine-2,4-diamine. (M+H)=208.

Step 9. 5-(6-Isopropyl-4-methyl-3,4-dihydro-2H-benzo[1,4]oxazin-7-yloxy)-pyrimidine-2,4-diamine

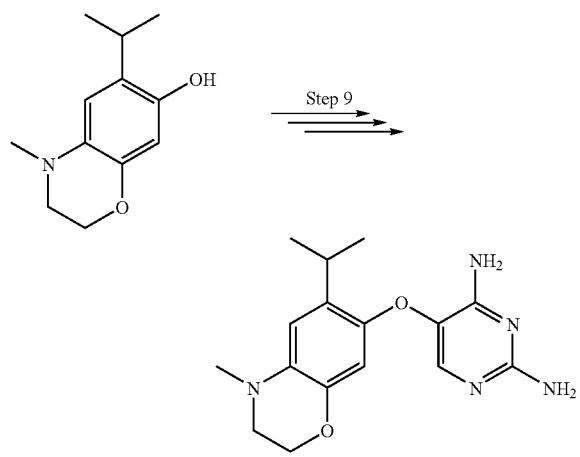

5-(6-Isopropyl-4-methyl-3,4-dihydro-2H-benzo[1,4]oxazin-7-yloxy)-pyrimidine-2,4-diamine was converted, using the procedure of steps 4-6 of Example 49, to 5-(6-Isopropyl-4-methyl-3,4-dihydro-2H-benzo[1,4]oxazin-7-yloxy)-pyrimidine-2,4-diamine. (M+H)=316. Mp=167.3-170.1° C.

Example 59

5-(5-Furan-2-yl-2-isopropyl-4-methoxy-phenoxy)-pyrimidine-2,4-diamine

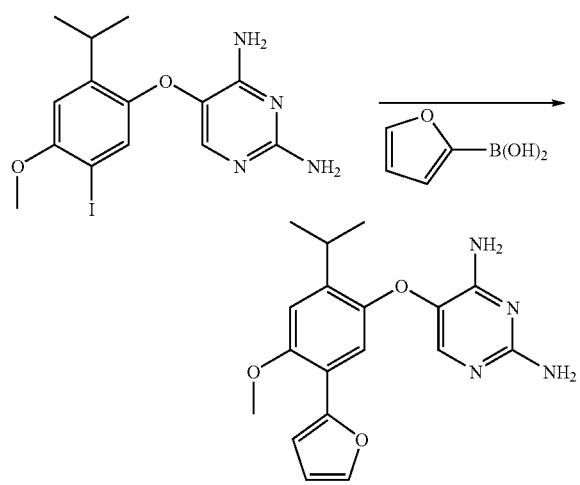

5-(5-Iodo-2-isopropyl-4-methoxy-phenoxy)-pyrimidine-2,4-diamine (400 mg, 1 mmol), furan 2-boronic acid (285 mg, 1.5 mmol) and Pd(Ph$_3$)$_2$Cl$_2$ (50 mg) were taken up in 13 mL of degassed dioxane in a screw cap pressure flask. Sodium bicarbonate (2 mL of 2M aqueous solution) was added, and the reaction mixture was heated to 105° C. for 40 hours. The reaction mixture was cooled and partitioned between water and ethyl acetate. The organic phase was separated, dried (MgSO$_4$), filtered, and evaporated under reduced pressure. The residue was purified by flash chromatography (3% to 5% MeOH in methylene chloride with 1% ammonium hydroxide) to yield 53 mg of 5-(5-Furan-2-yl-2-isopropyl-4-methoxy-phenoxy)-pyrimidine-2,4-diamine. (M+H)=339. Mp=253.7-254.6° C.

Example 60

5-(5-Furan-2-yl-2-isopropyl-4-methoxy-phenoxy)-pyrimidine-2,4-diamine

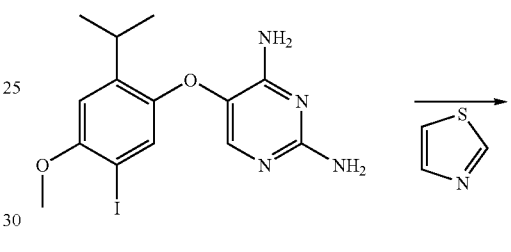

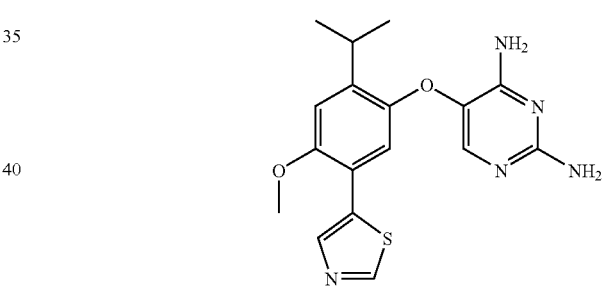

5-(5-Iodo-2-isopropyl-4-methoxy-phenoxy)-pyrimidine-2,4-diamine (400 mg, 1.0 mmol), potassium acetate ((147 mg), Pd(Ph$_3$)$_2$Cl$_2$ (40 mg in 2 mL dimethyl acetamide) and thiazole were added to a screw cap pressure vial and heated to 155° C. for 40 hours. The reaction mixture was cooled and partitioned between water and ethyl acetate. The organic phase was separated, dried (MgSO$_4$), filtered, and evaporated under reduced pressure. The residue was purified by flash chromatography (3% to 5% MeOH in methylene chloride with 1% ammonium hydroxide) to yield 61 mg of 5-(5-Furan-2-yl-2-isopropyl-4-methoxy-phenoxy)-pyrimidine-2,4-diamine. (M+H)=356. Mp=199.1-203.3° C.

Example 61

5:-[2-Isopropyl-5-(4-methanesulfonyl-piperazin-1-yl)-4-methoxy-phenoxy]-pyrimidine-2,4-diamine The synthetic procedure used in this Example is outlined in Scheme W.

SCHEME W

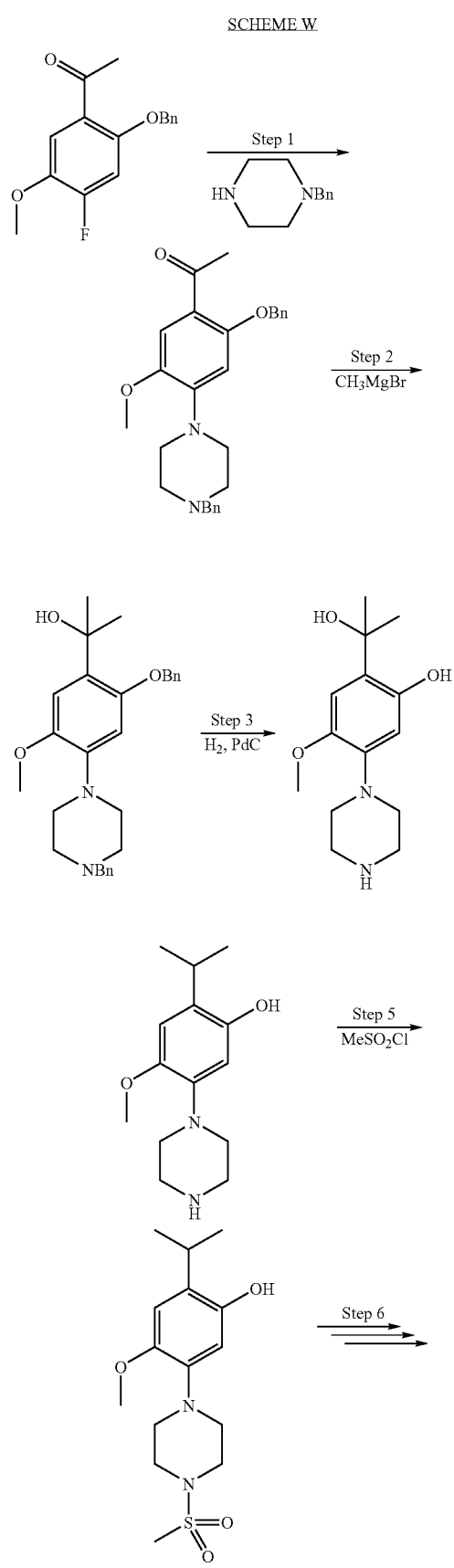

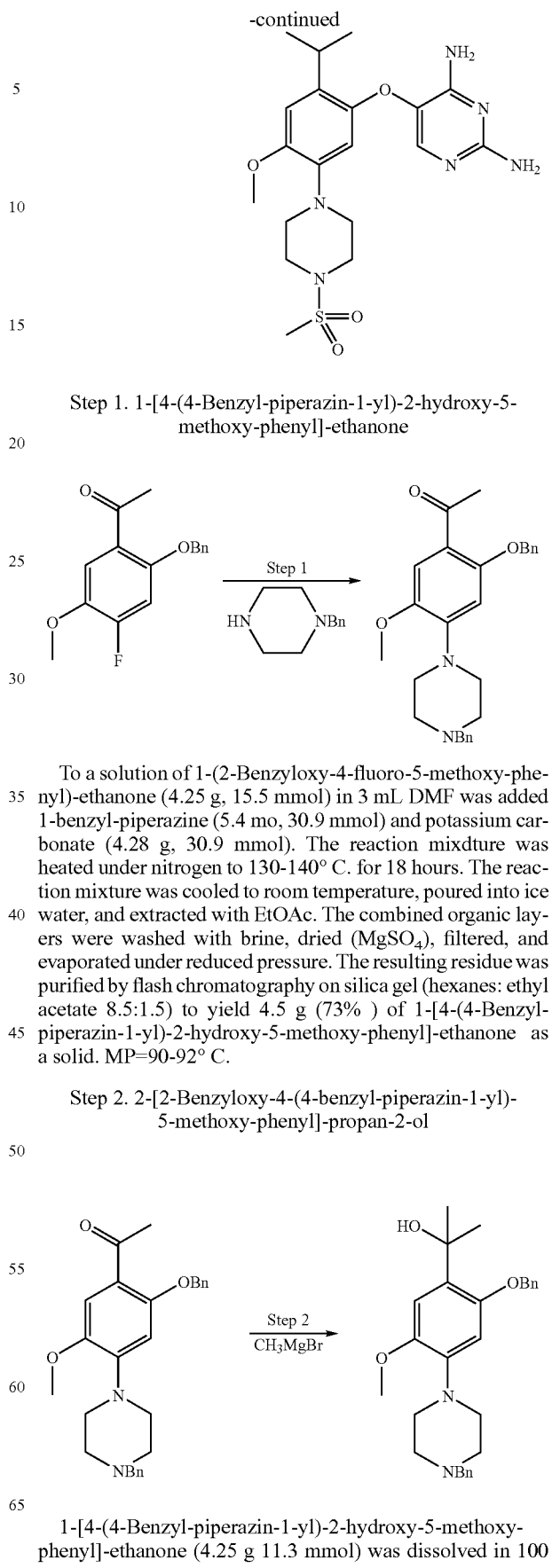

Step 1. 1-[4-(4-Benzyl-piperazin-1-yl)-2-hydroxy-5-methoxy-phenyl]-ethanone

To a solution of 1-(2-Benzyloxy-4-fluoro-5-methoxy-phenyl)-ethanone (4.25 g, 15.5 mmol) in 3 mL DMF was added 1-benzyl-piperazine (5.4 mo, 30.9 mmol) and potassium carbonate (4.28 g, 30.9 mmol). The reaction mixdture was heated under nitrogen to 130-140° C. for 18 hours. The reaction mixture was cooled to room temperature, poured into ice water, and extracted with EtOAc. The combined organic layers were washed with brine, dried (MgSO$_4$), filtered, and evaporated under reduced pressure. The resulting residue was purified by flash chromatography on silica gel (hexanes: ethyl acetate 8.5:1.5) to yield 4.5 g (73% ) of 1-[4-(4-Benzyl-piperazin-1-yl)-2-hydroxy-5-methoxy-phenyl]-ethanone as a solid. MP=90-92° C.

Step 2. 2-[2-Benzyloxy-4-(4-benzyl-piperazin-1-yl)-5-methoxy-phenyl]-propan-2-ol 1-[4-(4-Benzyl-piperazin-1-yl)-2-hydroxy-5-methoxy-phenyl]-ethanone (4.25 g 11.3 mmol) was dissolved in 100 mL dry THF, and the resulting solution was cooled to 0° C. and stirred under nitrogen. Methyl magnesium bromide (5.6 mL, 16.9 mmol) was added dropwise, and the reaction miture was stirred for 30 minutes at 0° C. The reaction mixture was stirred for an additional 12 hours at room temperature, then poured into ice water and extracted with EtOAc. The combined organic layers were washed with saturated aqueous ammonium chloride, dried (MgSO$_4$), filtered, and evaporated under reduced pressure. The resulting residue was purified by flash chromatography on silica gel (hexanes: ethyl acetate 8:2) to yield 4.73 g (94% ) of 2-[2-Benzyloxy-4-(4-benzyl-piperazin-1-yl)-5-methoxy-phenyl]-propan-2-ol as a solid. MP=94-96° C.

Step 3. 2-(1-Hydroxy-1-methyl-ethyl)-4-methoxy-5-piperazin-1-yl-phenol

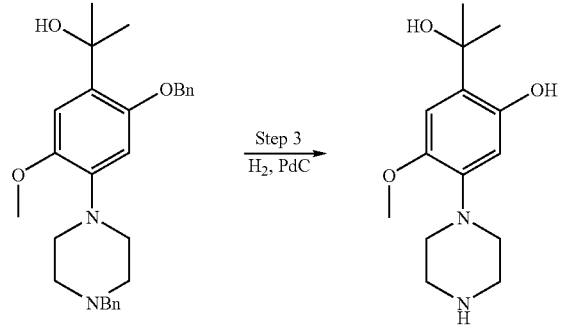

A mixture of 2-[2-Benzyloxy-4-(4-benzyl-piperazin-1-yl)-5-methoxy-phenyl]-propan-2-ol (2.01 g, 4.5 mmol) 10% Pd/C (0.28 g) in EtOH (60 mL) was hydrogenated at 50 psi at room temperature for 12 hours. The reaction mixture was filtered to remove the catalyst, and the filtrate was concentrated uner reduced pressure to yield 1.1 g (92% ) of 2-(1-Hydroxy-1-methyl-ethyl)-4-methoxy-5-piperazin-1-yl-phenol.

Step 4.
2-Isopropyl-4-methoxy-5-piperazin-1-yl-phenol

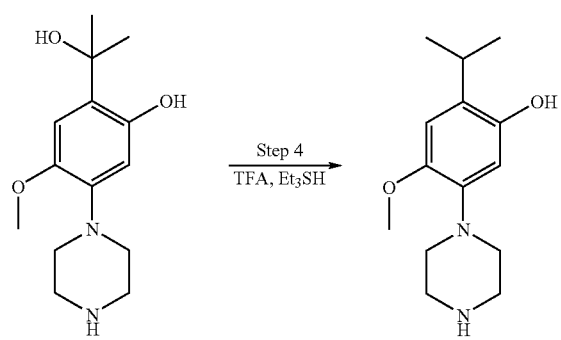

To a stirred suspension of 2-(1-Hydroxy-1-methyl-ethyl) 4-methoxy-5-piperazin-1-yl-phenol (0.5 g, 1.9 mmol) in dichloromethane under nitrogen at room temperature was aded trifluoroacetic acid (7.2 mL, 93.86 mmol) followed by triethyl silane (3.0 mL, 18.8 mmol). The reaction mixture was stirred for 18 hours at room temperature, and then was evaporated under reduced pressure. The residue was partitioned between dichloromethane and saturated aqueous potassium carbonate. The organic layer was separated, washed with water, dried (MgSO$_4$), filtered, and evaporated under reduced pressure to afford 0.47 g (99% ) of 2-Isopropyl-4-methoxy-5-piperazin-1-yl-phenol as an oil.

Step 5. 2-Isopropyl-5-(4-methanesulfonyl-piperazin-1-yl)-4-methoxy-phenol

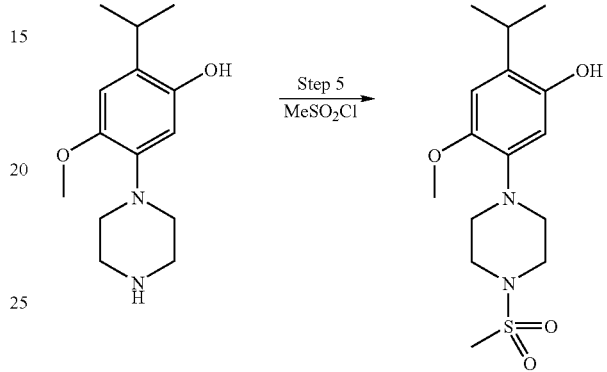

To a stirring solution of 2-Isopropyl-4-methoxy-5-piperazin-1-yl-phenol (0.47 g, 1.88 mmol) in dichloromethane at 0° C. under nitrogen was added triethylamine (0.26 mL, 1.89 mmol), followed by methanesulfonyl chloride (0.15 mL, 1.89 mmol). The reaction mixture was stirred at 0° C. for five minutes, and then allowed to warm to room temperature. The reaction mixture was partitioned between dichloromethane and water, and the organic layer was separated, washed with water, dried (MgSO$_4$), filtered, and evaporated under reduced pressure. The residue was purified via flash chromatography (hexanes:EtOAc 3:2) to afford 0.1 g (16% ) of 2-Isopropyl-5-(4-methanesulfonyl-piperazin-1-yl)-4-methoxy-phenol as an oil.

Step 6. 5-[2-Isopropyl-5-(4-methanesulfonyl-piperazin-1-yl)4-methoxy-phenoxy]-pyrimidine-2,4-diamine

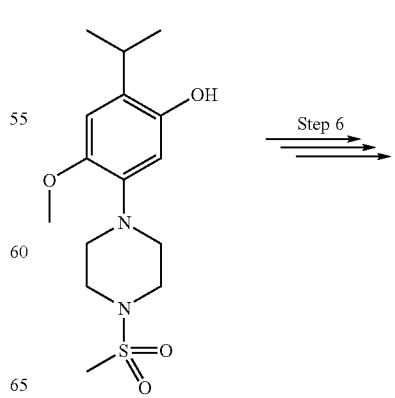

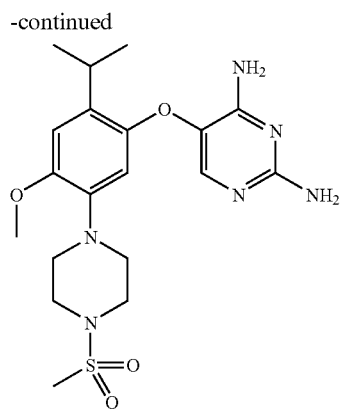

2-Isopropyl-5-(4-methanesulfonyl-piperazin-1-yl)-4-methoxy-phenol was converted, using the procedure of steps 4-6 of Example 49, to 5-[2-Isopropyl-5-(4-methanesulfonyl-piperazin-1-yl)-4-methoxy-phenoxy]-pyrimidine-2,4-diamine. (M+H)=437. Mp=115-117° C.

Example 62

5-(4-Ethel-7-methyl-benzo[b]thiophen-5-yloxy)-pyrimidine-2,4-diamine

The synthetic procedure used in this Example is outlined in Scheme X.

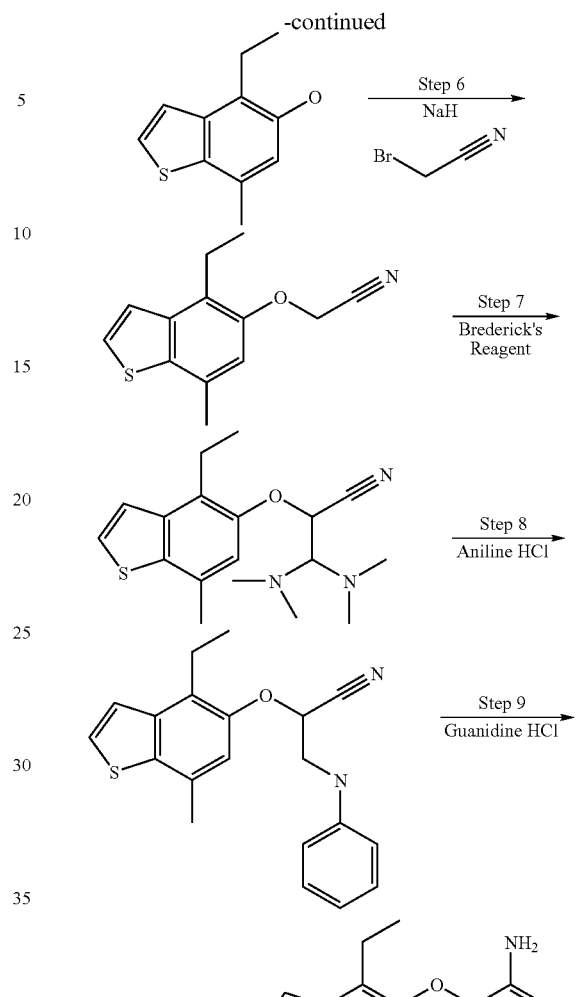

SCHEME X

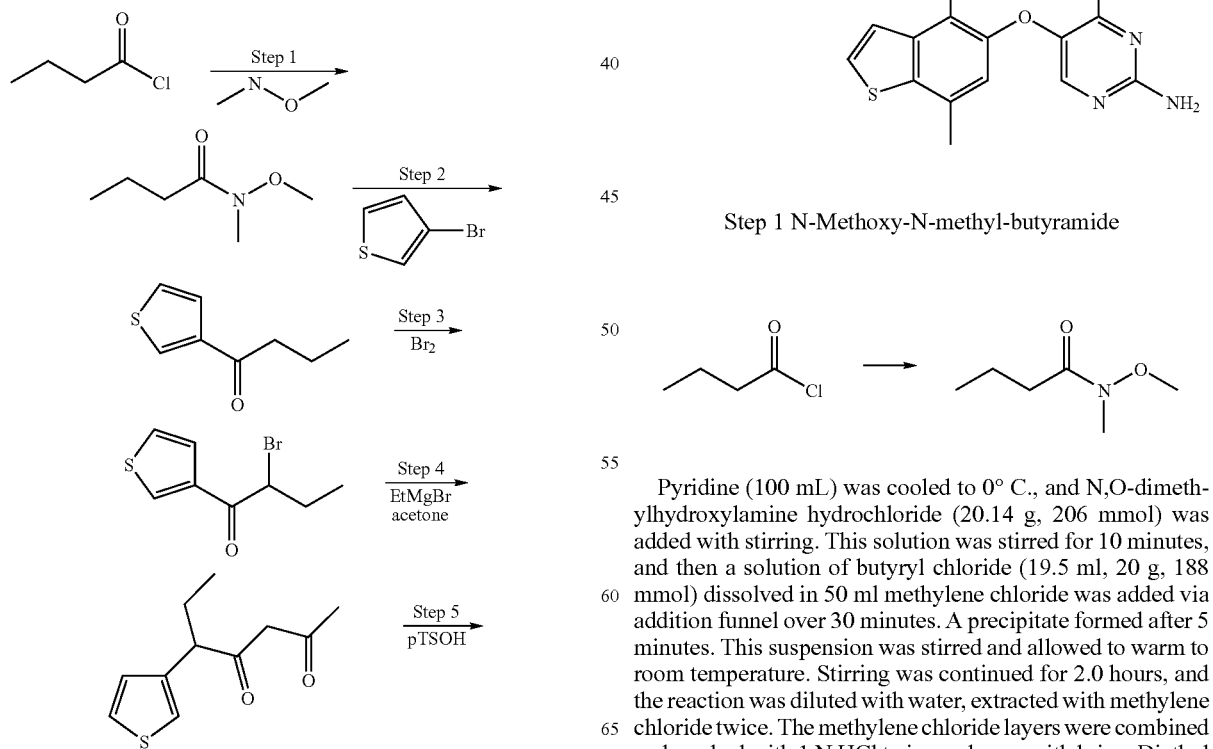

Step 1 N-Methoxy-N-methyl-butyramide

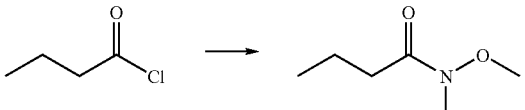

Pyridine (100 mL) was cooled to 0° C., and N,O-dimethylhydroxylamine hydrochloride (20.14 g, 206 mmol) was added with stirring. This solution was stirred for 10 minutes, and then a solution of butyryl chloride (19.5 ml, 20 g, 188 mmol) dissolved in 50 ml methylene chloride was added via addition funnel over 30 minutes. A precipitate formed after 5 minutes. This suspension was stirred and allowed to warm to room temperature. Stirring was continued for 2.0 hours, and the reaction was diluted with water, extracted with methylene chloride twice. The methylene chloride layers were combined and washed with 1 N HCl twice and once with brine. Diethyl ether (100 mL) was added to facilitate emulsion separation, and the organic layer was separated and washed with saturated bicarbonate solution, brine, and dried over magnesium sulfate. The solution was filtered and the solvent removed in vacuo to give N-Methoxy-N-methyl-butyramide as an oil (22.1 g, 89%).

Step 2. 1-Thiophen-3-yl-butan-1-one

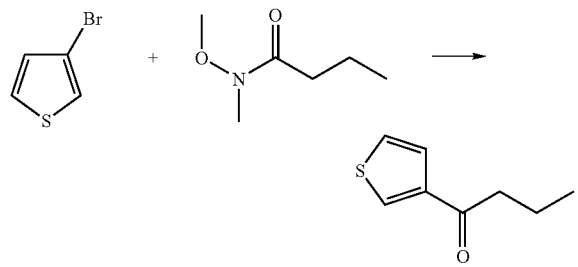

3-Bromothiophene (11 g, 67 mmol) dissolved in hexanes (110 ml) was cooled to –20 C in acetone/water bath, and n-Bu Li (28 ml, 71 mmol, 2.5 N solution in hexanes)was added slowly, over 10 min, then stirred 10 min at –20 C. THF was added (10 ml) over 5 min with rapid stirring. Precipitate formed after about ⅔ of addition. After adding all of the THF, the reaction mixture was stirred 20 min at –20 C, then 20 ml hexanes was added and the reaction mixture was allowed to warm to zero degrees C. N-Methoxy-N-methyl-butyramide (9.29 g, 71 mmol) dissolved in 20 ml hexanes was added via cannula over 5 minutes, and the reaction mixture was stirred at zero degrees C for 1.5 hours. The reaction mixture was quenched with water, then 1 N HCl (75 ml), extracted twice with ether, washed 1 N HCl, brine, and dried over magnesium sulfate. Solvent was removed under reduced pressure to give an oil, which was chromatographed by flash chromatography (5% EtOAc/hexanes) to give 6.7 g, 64% of 1-Thiophen-3-yl-butan-1-one as an oil.

Step 3. 2-Bromo-1-thiophen-3-yl-butan-1-one

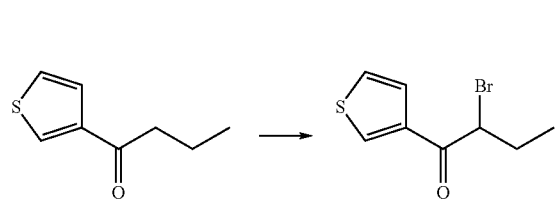

1-Thiophen-3-yl-butan-1-one (6.7 g. 43 mmol) in 210 mL diethyl ether was cooled to zero degrees C, and 0.6 ml glacial acetic acid was added dropwise, followed by bromine (2.26 ml, 46 mmol) dropwise. The reaction mixture was allowed to warm to room temperature over hours. The reaction mixture was washed the with water, 1 N sodium thiosulfate, brine, and then dried over magnesium sulfate. Solvent was removed under reduced pressure to give an oil which was chromatographed (5% EtOAc/Hexanes) to give 6.1 g 2-Bromo-1-thiophen-3-yl-butan-1-one, 79%, as an oil.

Step 4. 5-Thiophen-3-yl-heptane-2,4-dione

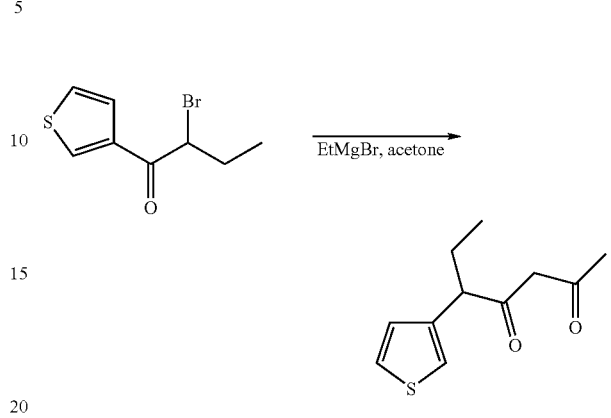

EtMgBr (6.69 ml, 13 mmol, 2 M in ethyl ether) in benzene (10 ml) was cooled to zero degrees C, and tBuOH (1.28 ml, 13 mmol) was slowly added. The reaction mixture was stirred at zero degrees C for 5 minutes, then acetone (530 ul, 7 mmol) was added, followed by a solution of 2-Bromo-1-thiophen-3-yl-butan-1-one (1.3 g, 6 mmol) in 3 ml benzene via cannula. The reaction mixture was heated to reflux for 1 hour, and acetone (250 ul) was added. The reaction mixture was heated 2 hours more at reflux. The reaction was cooled, quenched with 1 N HCl (10 ml), extracted three times with diethyl ether, washed brine, and dried over magnesium sulfate. The solvent was removed in vacuo and the residue chromatographed (5% ethyl acetate/hexanes) to give 247 mg of 2-Bromo-1-thiophen-3-yl-butan-1-one starting material and 520 mg of 5-Thiophen-3-yl-heptane-2,4-dione, 44%.

Step 5. 4-Ethyl-7-methyl-benzo[b]thiophen-5-ol

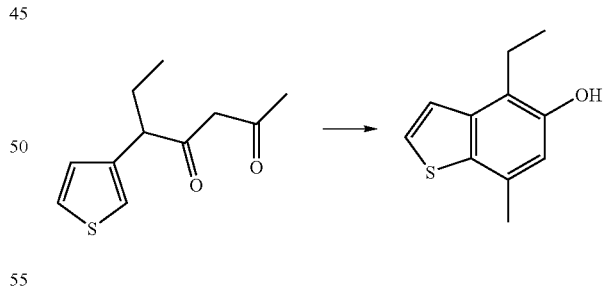

5-Thiophen-3-yl-heptane-2,4-dione (410 mg, 2 mmol) was dissolved inin 15 ml benzene, and p-toluene sulfonic acid monohydrate (408 mg, 2 mmol) was added. The reaction mixture was heated to reflux for 30 min, cooled, diluted with diethy ether, washed with saturated sodium bicarbonate, water, brine, and dried over magnesium sulfate. Concentration in vacuo 370 mg of 4-Ethyl-7-methyl-benzo[b]thiophen-5-ol, 98%, as a white solid.

Step 6. (4-Ethyl-7-methyl-benzo[b]thiophen-5-yloxy)-acetonitrile

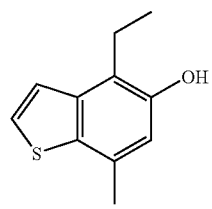
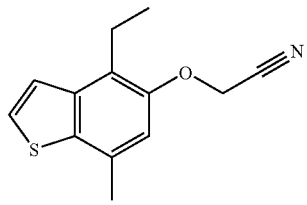

4-Ethyl-7-methyl-benzo[b]thiophen-5-ol (438 mg, 2 mmol) was dissolved in 10 ml DMF, and the reaction mixture was cooled to zero degrees C. Sodium hydride (66 mg, 3 mmol) was added and the reaction mixture was stirred 30 minutes at zero C. Bromoacetonitrile (170 ul, 3 mmol) was addeed, and the reaction mixture was stirred 10 minutes at zero degrees C, then allowed to warm to room temperature. The reaction was quenched after 1 hour at room temperature with water, diluted with ethyl acetate, washed with water, brine, and dried over magnesium sulfate. Solvent was removed in vacuo, and the residue chromatographed (10% ethyl acetate in hexanes) to give 422 mg of (4-Ethyl-7-methyl-benzo[b]thiophen-5-yloxy)-acetonitrile as an oil, 80%.

Step 7. 3,3-Bis-dimethylamino-2-(4-ethyl-7-methyl-benzo[b]thiophen-5-yloxy)-propionitrile

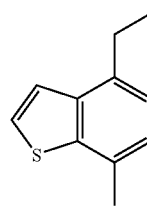
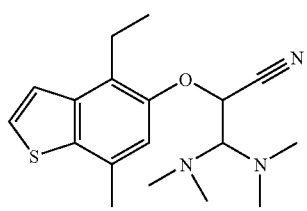

3,3-Bis-dimethylamino-2-(4-ethyl-7-methyl-benzo[b]thiophen-5-yloxy)-propionitrile (422 mg, 2 mmol) was dissolved in 2.5 ml tert-ButoxyBis (dimethylamino)methane, and the reaction mixture was heated to 100 C for 1 hour. The reaction was cooled to room temperature and the volume reduced under 1 mm vacuum while heating at 60° C. The residue was then placed on a high vacuum pump for 1 hour to give 3,3-Bis-dimethylamino-2-(4-ethyl-7-methyl-benzo[b]thiophen-5-yloxy)-propionitrile, 595 mg, 98%, as an oil.

Step 8. 2-(4-Ethyl-7-methyl-benzo[b]thiophen-5-yloxy)-3-phenylamino-acrylonitrile

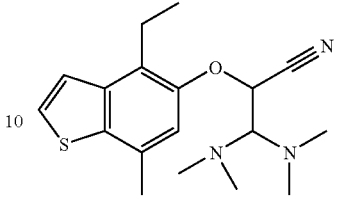
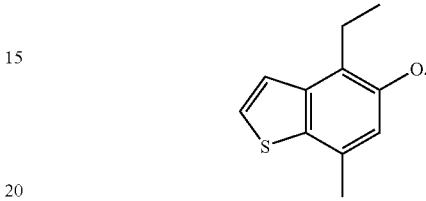

3,3-Bis-dimethylamino-2-(4-ethyl-7-methyl-benzo[b]thiophen-5-yloxy)-propionitrile (590 mg, 2 mmol) and aniline HCl (1.1 g, 9 mmol) in 5 mL absolute ethanol were heated at reflux for 2.0 hours. In a separate flask, guanidine HCl (0.850 mg., 9 mmol) and sodium methoxide solution (1.83 ml, 9 mmol, 4.9 molar solution in methanol) were mixed in 1 ml Ethanol. The guanidine solution was added to the reaction mixture via pipette, and the reaction mixture was heated to reflux for 5 hours, then cooled. Solvent was removed in vacuo, and the residue was, chromatographed (5% MeOH/methylene chloride/1% $NH_4OH$) to give 368 mg 2-(4-Ethyl-7-methyl-benzo[b]thiophen-5-yloxy)-3-phenylamino-acrylonitrile, 61%. Also present was 50 mg of 5-(4-Ethyl-7-methyl-benzo[b]thiophen-5-yloxy)-pyrimidine-2,4-diamine, 9%.

Step 9. 5-(4-Ethyl-7-methyl-benzo[b]thiophen-5-yloxy)-pyrimidine-2,4-diamine

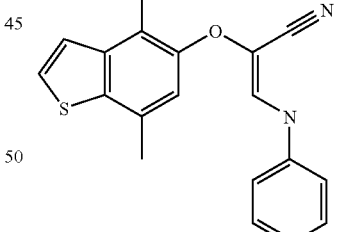
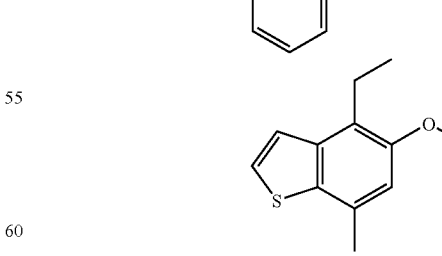

2-(4-Ethyl-7-methyl-benzo[b]thiophen-5-yloxy)-3-phenylamino-acrylonitrile (360 mg, 1 mmol), guanidine HCl (411 mg, 4 mmol) and sodium methoxide (880 ul, 4 mmol, 4.9 M solution in methanol) in 5 mL absolute ethanol were heated to reflux in 5 ml absolute ethanol for 2 hours. Premixed guanidine HCl (411 mg, 4 mmol) and sodium methoxide (880 ul, 4 mmol, 4.9 M solution in methanol) in 1 ml EtOH was added via pipette, and the reaction mixture was heated to reflux for 2 hours. The reaction mixture was cooled, diluted with water, extracted twice with EtOAc, washed with brine, and dried over magnesium sulfate. Solvent was removed in vacuo to give 241 mg of 5-(4-Ethyl-7-methyl-benzo[b]thiophen-5-yloxy)-pyrimidine-2,4-diamine as a white solid (74%). Mass Spec M+H=301, M.P.=181 OC. Recrystallization of 175 mg of this product from MeOH and HCl/diethyl ether afforded 98 mg of the corresponding HCl salt 49%., Mass Spec M+H=301, M.P.>300 C.

Example 63

5-(1,3-Dimethyl-6-trifluoromethyl-1H-indol-5-yloxy)-pyrimidine-2,4-diamine

The synthetic procedure used in this Example is outlined in Scheme Y.

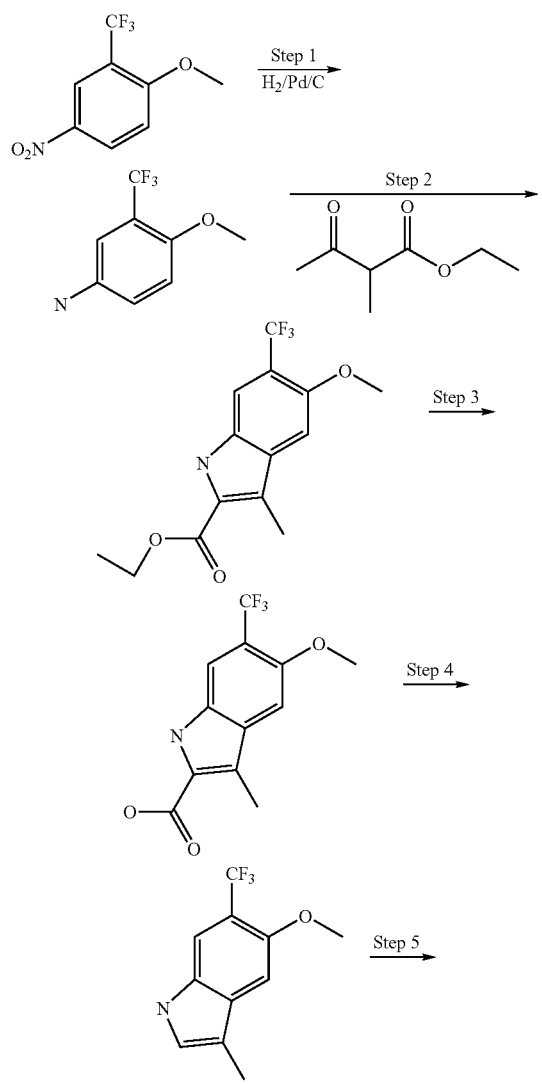

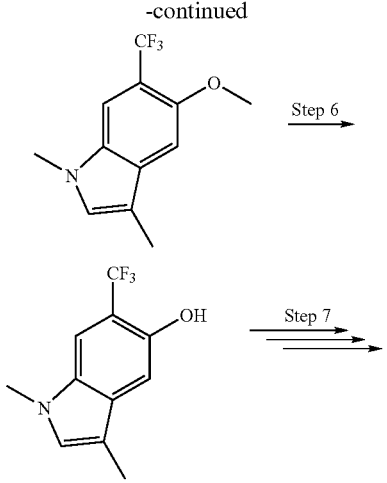

Step 1. 4-Methoxy-3-trifluoromethyl-phenylamine

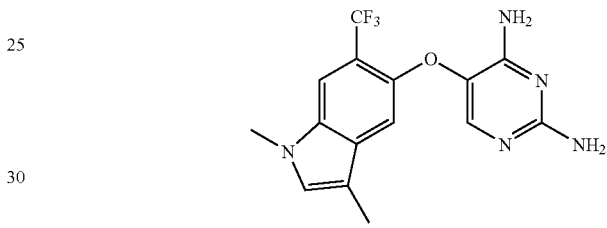

1-Methoxy-4-nitro-2-trifluoromethyl-benzene (10 g, 45 mmol) was hydrogenated in a Paar apparatus with shaking at 50 psi for 4 hours, with 1 g 10 wt % Pd/C. The reaction mixture was filtered through celite, and the filtrate was evaporated in vacuo to give 8.6 g 4-Methoxy-3-trifluoromethyl-phenylamine, 99%, as a solid.

Step 2. 5-Methoxy-3-methyl-6-trifluoromethyl-1H-indole-2-carboxylic acid ethyl ester

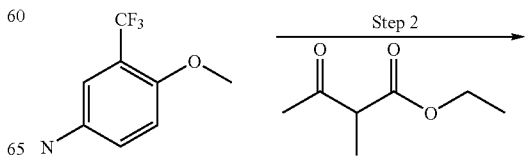

-continued

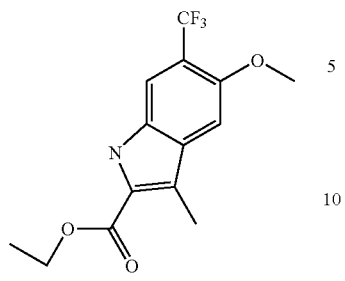

-continued

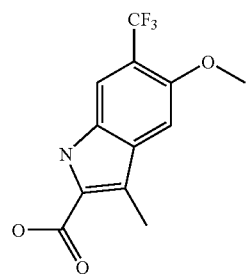

4-Methoxy-3-trifluoromethyl-phenylamine (5 g, 26 mmol) in 12 mL water was cooled to −5 degrees C (Ice/Methanol bath). Conc. HCl was added dropwise (7 ml), and the reaction mixture was stirred for five minutes. A solution of NaNO$_2$ (2.0 g, 29 mmol) dissolved in 3 ml water was added dropwise over 10 minutes, and the reaction mixture was tirred for 30 min. Sodium acetate (1.8 g, 22 mmol) was then added, and stirring was continued at −5 degrees C. In a separate flask, ethyl alpha-acetoacetate (4.55 g, 29 mmol) in 20 ml absolute ethanol was stirred, and KOH (1.6 g, 29 mmol) dissolved in 3 ml water was added, followed by ice (30 g). The resulting diazonium salt was added quickly to the reaction mixture, rinsing in with 5 ml EtOH, and the reaction mixture was stirred at zero degrees C for 3.5 hours, then stored at −10 C) for 16 hours. The reaction mixture was warmed to room temperature and extracted with ethyl acetate, washed with brine, and dried over magnesium sulfate. Solvent was removed under reduced pressure to leave a liquid residue. In a separate flask 100 ml EtOH and 21 ml acetyl chloride were mixed, with cooling in an ice bath, then heated to 70 degrees C. The liquid residue was added via pipette over 15 minutes to the acetyl chloride solution. This reaction mixture was heated to reflux for 2.5 hours, cooled, evaporated under reduced pressure. The residue was purified by colunm chromatography (10% ethyl acetate/hexane) to give 3.0 g 5-Methoxy-3-methyl-6-trifluoromethyl-1H-indole-2-carboxylic acid ethyl ester, 38% as a white solid. and triturated with diethyl ether to give 5-Methoxy-3-methyl-6-trifluoromethyl-1H-indole-2-carboxylic acid ethyl ester (1.0 g) as a white solid, and 5-Methoxy-3-methyl-4-trifluoromethyl-1H-indole-2-carboxylic acid ethyl ester (14%) as a white solid.

Step 3. 5-Methoxy-3-methyl-6-trifluoromethyl-1H-indole-2-carboxylic acid.

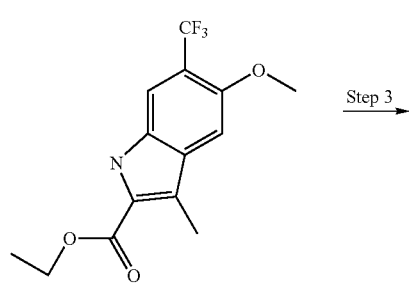

5-Methoxy-3-methyl-6-trifluoromethyl-1H-indole-2-carboxylic acid ethyl ester (3.0 g, 10 mmol) was dissolved in 10 ml absolute ethanol, and a solution of KOH (1.7 g, 30 mmol) in 7 ml water was added. The reaction mixture was heated to reflux for 2.5 hours, then cooled, acidified slowly with 6 N HCl to pH=2, and extracted with ethyl acetate. The combined organic layers were washed with brine, dried over magnesium sulfate, filtered, and concentrated under reduced pressure to give 2.0 g, (73%) 5-Methoxy-3-methyl-6-trifluoromethyl-1H-indole-2-carboxylic acid.

Step 4.5-Methoxy-3-methyl-6-trifluoromethyl-1H-indole

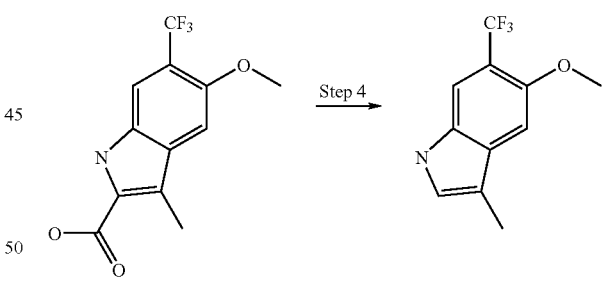

To a solution of 5-Methoxy-3-methyl-6-trifluoromethyl-1H-indole-2-carboxylic acid (2.0 g, 7 mmol) in 5 ml quinoline was added copper powder (50 mg), and the reaction mixture was heated to reflux for 1.5 hours. Copper powder (50 mg) was added, and the reaction mixture was refluxed for 1 hour. The reaction mixture was cooled, diluted with EtOAc, poured into 50 ml 6 N HCl, and extracted with EtOAc. The combined organic layers were washed with brine, dried over magnesium sulfate, filtered, and concentrated under reduced pressure. The residue was chromatographed (10% EtOAc/

Hexanes) to give 5-Methoxy-3-methyl-6-trifluoromethyl-1H-indole (850 mg, 51%) as a solid.

Step 5.
5-Methoxy-1,3-dimethyl-6-trifluoromethyl-1H-indole

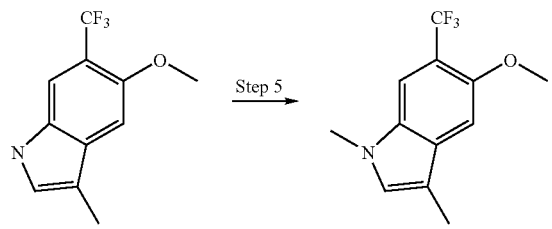

A solution of 5-Methoxy-3-methyl-6-trifluoromethyl-1H-indole (900 mg, 4 mmol) in 7 ml DMF was cooled to zero degrees C, and sodium hydride (104 mg, 4 mmol, 95% powder) was added. The reaction mixture was stirred 15 minutes at zero degrees C, and then iodomethane (270 ul, 4 mmol) was added. The reaction mixture was stirred for 1 hour and allowed to warm to room temperature. The reaction mixture was then cooled to 0° C., quenched by adddition of 1 N NH$_4$Cl, diluted with water, and extracted with EtOAc. The combined organic layers were washed with water, brine, dried over magnesium sulfate, filtered, and concentrated under reduced pressure to give 5-Methoxy-1,3-dimethyl-6-trifluoromethyl-1H-indole (725 mg, 75%) as a solid.

Step 6

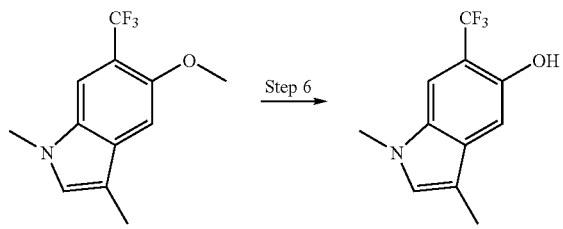

5-Methoxy-1,3-dimethyl-6-trifluoromethyl-1H-indole (725 mg, 3 mmol) in methylene chloride (15 ml) was cooled to zero degrees C, and BBr$_3$ (14.9 ml of a 1 N solution in methylene chloride) was slowly added via syringe. The reaction mixture was stirred 15 minutes at zero degrees C, then allowed to warm to room temperature with stirring for one hour. The reaction mixture was quenched slowly with 75 mL 1 N NaOH. The mixture was acidified to pH 5 with 1 N HCl, extracted with methylene chloride, and the combined organic layers were washed with water, brine, and dried over magnesium sulfate. Solvent was removed under reduced pressure, and the residue was chromatographed (20% EtOAc/Hexanes) to give 235 mg (75%) 1,3-Dimethyl-6-trifluoromethyl-1H-indol-5-ol.

Step 7.
1,3-Dimethyl-6-trifluoromethyl-1H-indol-5-ol

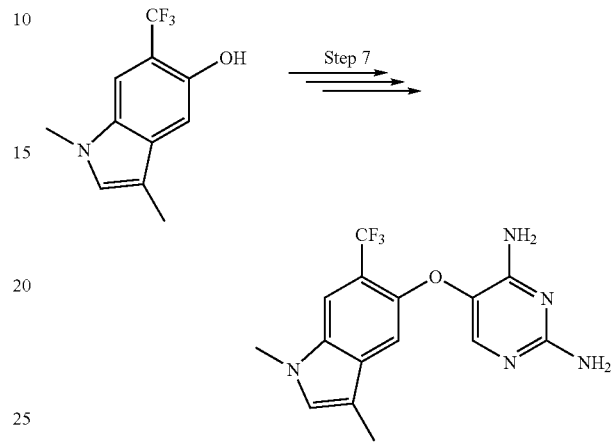

1,3-Dimethyl-6-trifluoromethyl-1H-indol-5-ol was converted to 5-(1,3-Dimethyl-6-trifluoromethyl-1H-indol-5-yloxy)-pyrimidine-2,4-diamine using the procedure of steps 6-9 of Example 62 (70 mg). The corresponding hydrochloride salt was recrystallized from MeOH/diethyl ether. (M+H)= 338, M.P. 256° C.

Example 64

6-(2,4-Diamino-pyrimidin-5-yloxy)-5-isopropyl-3-methyl-1H-indole-2-carboxylic acid The synthetic procedure used in this Example is outlined in Scheme Z.

SCHEME Z

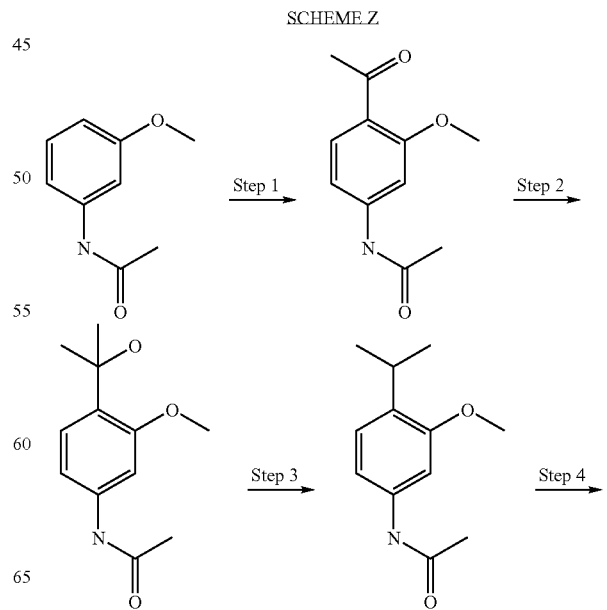

-continued

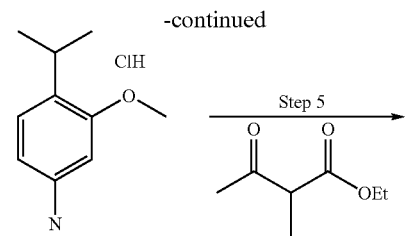

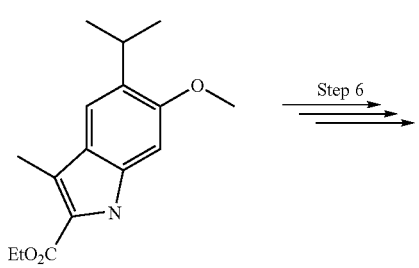

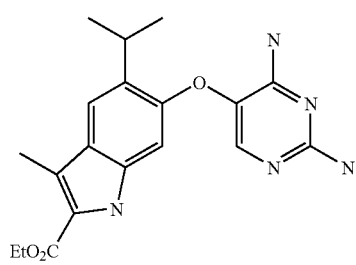

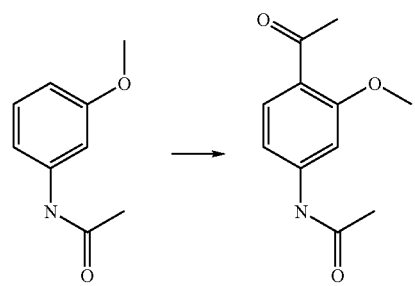

Step 1. N-(4-Acetyl-3-methoxy-phenyl)-acetamide

Step 2. N-[4-(1-Hydroxy-1-methyl-ethyl)-3-methoxy-phenyl]-acetamide

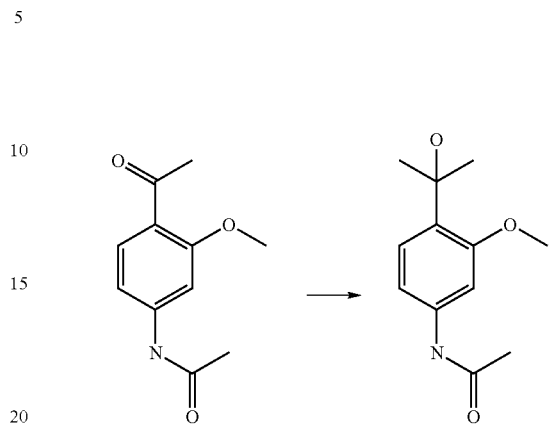

Methyl magnesium chloride (49.9 ml, 150 mmol, 3 M solution in THF) in 100 ml THF was cooled to zero degrees C, and N-(4-Acetyl-3-methoxy-phenyl)-acetamide (14.1 g, 68 mmol) in 200 ml THF was added via cannula to over 25 minutes. The reaction mixture was stirred and allowed to warm to room temperature over 2.5 hours. The reaction was quenched by addition of 1 N NH$_4$Cl and extracted with EtOAc. The combined organic layers were washed with 1 N ammonium chloride, brine, dried over MgSO$_4$, and concentrated under reduced pressure to afford N-[4-(1-Hydroxy-1-methyl-ethyl)-3-methoxy-phenyl]-acetamide (16.4 g, 100%).

Step 3 N-(4-Isopropyl-3-methoxy-phenyl)-acetamide

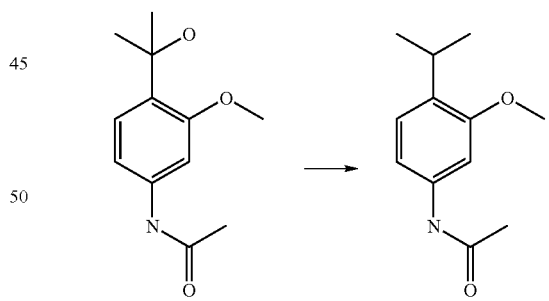

N-(3-Methoxy-phenyl)-acetamide (17.7 g, 107 mmol) in methylene chloride was cooled to zero degrees C, and acetyl chloride (19.0 ml, 268 mmol) was slowly added, followed by aluminum chloride (35.7 g, 268 mmol) in small portions over 15 min. The reaction mixture was stirred 15 minutes at zero degrees, then allowed to warm to room temperature with stirring. The reaction mixture was poured into ice, stirred 35 minutes, and filtered. The solid was washed with water. The filtrate was extracted with EtOAc and solvent was removed under reduced pressure. The combined solids gave N-(4-Acetyl-3-methoxy-phenyl)-acetamide (16.5 g., 74%) as a solid.

N-[4-(1-Hydroxy-1-methyl-ethyl)-3-methoxy-phenyl]-acetamide (16.4 g) in 100 ml glacial acetic acid was stirred at room temperature under N$_2$, and palladium on activated carbon (3 g 10 wt %) was added, followed by 5 g of ammonium formate. The reaction mixture was heated to reflux. After 30 minutes 5 g ammonium formate was added, and after 45 minutes another 8.5 g ammonium formate was added. Reflux was continued for another hour, then the reaction mixture was cooled, and filtered through Celite. The filtrate was diluted with water, extracted with EtOAc, and the combined organic layers were washed with brine and dried over magnesium sulfate. Evaporation under reduced pressure gave N-(4-Isopropyl-3-methoxy-phenyl)-acetamide (15.1 g, 99%).

Step 4. 4-Isopropyl-3-methoxy-phenylamine

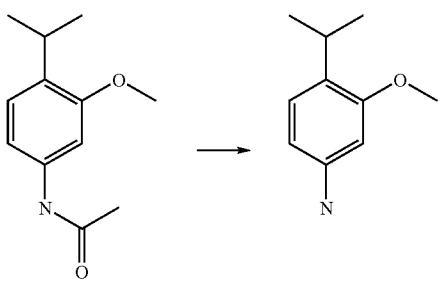

N-(4-Isopropyl-3-methoxy-phenyl)-acetamide (14.5 g, 69.9 mmol) in 200 ml 6 N HCl was heated to 95° C. for 3.0 hours. The reaction mixture was cooled to room temperature, and allowed to sit for 72 hours at room temperature, during which time crystals formed. The reaction mixture was filtered, and the crystals were washed 1 N HCl and dried under vacuum to give 4-Isopropyl-3-methoxy-phenylamine as an HCl salt (7.6 g, 60%).

Step 5. 5-Isopropyl-6-methoxy-3-methyl-1H-indole-2-carboxylic acid ethyl ester

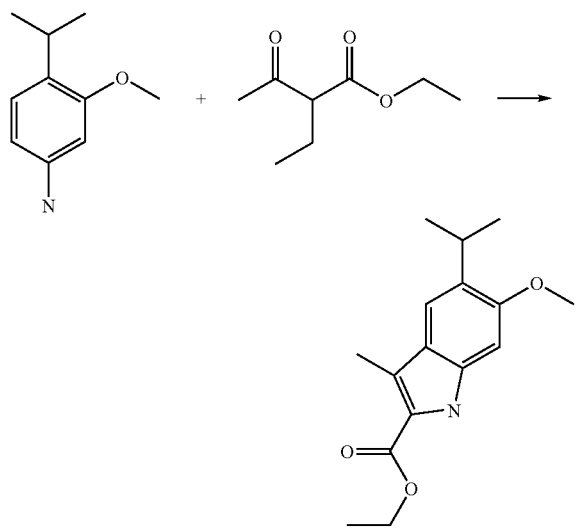

4-Isopropyl-3-methoxy-phenylamine HCl salt (3.1 g, 19 mmol) was cooled to −5 C (Ice/Methanol bath), and a mixture of 8 ml water and 5 ml concentrated. HCl was added dropwise. The reaction mixture was stirred for five minutes, and sodium nitrite (1.42 g, 21 mmol) disolved in 3 ml water was added dropwise over 10 minutes. The reaction mixture was stirred for 45 min, then sodium acetate (1.3 g, 16 mmol) was added. In a separate flask, to a stirring mixture of ethyl alpha-acetoacetate (3.26 g, 21 mmol) in 15 ml absolute ethanol was added KOH (1.2 g, 21 mmol) dissolved in 3 ml water and then added ice (10 g). This mixture was added to the diazonium salt, and the reaction mixture was stirred at zero degrees C for 3.5 hours. The reaction mixture was stored at −10 C for 16 hours, then extracted with EtOAC. The combined organic layers were washed with brine, dried over magnesium sulfate, and concentrated under reduced pressure to a liquid residue. In a separate flask, mixed 100 ml EtOH was mixed slowly with 22 ml acetyl chloride, with cooling in an ice bath. The EtOH/acetyl chloride solution was heated to 70 degrees C, and added the residue was added via pipette over 10 min. The reaction mixture was heated to reflux for 2.5 hours, cooled, evaporated under reduced pressure to give a slurry; diluted with water (100 ml) and filtered. The solid was washed with water. The solid was triturated with hexanes to give 5-Isopropyl-6-methoxy-3-methyl-1H-indole-2-carboxylic acid ethyl ester (1.7 g, 34%) as a solid.

Step 6. 6-(2,4-Diamino-pyrimidin-5-yloxy)-5-isopropyl-3-methyl-1H-indole-2-carboxylic acid ethyl ester

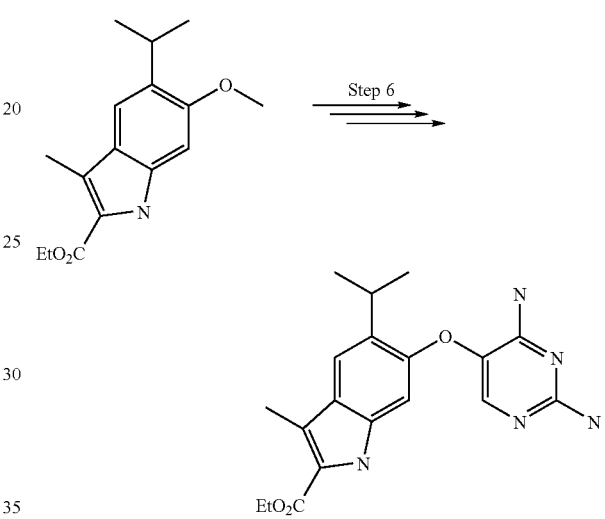

5-Isopropyl-6-methoxy-3-methyl-1H-indole-2-carboxylic acid ethyl ester was converted to 6-(2,4-Diamino-pyrimidin-5-yloxy)-5-isopropyl-3-methyl-1H-indole-2-carboxylic acid ethyl ester using the procedure of steps 5-9 of Example 62. Mass Spec M+H=370, M.P. 188.2 C 6-(2,4-Diamino-pyrimidin-5-yloxy)-5-isopropyl-3-methyl-1H-indole-2-carboxylic acid ethyl ester was converted to 6-(2,4-diamino-pyrimidin5-yloxy)-5-isopropyl-3-methyl-1H-indole-2-carboxylic acid by treatment with ethanolic potassium hydroxide. (91 mg, 76%). Mass Spec M+H=342 M.P.>300 C Example 65

5-(7-Isopropyl-4-methyl-benzooxazol-6-yloxy)-pyrimidine-2,4-diamine

Step 1. 7-Isopropyl-4-methyl-benzooxazol-6-ol

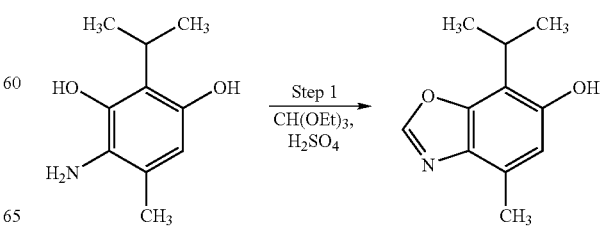

To a flask charged with 4-amino-2-isopropyl-5-methyl-benzene-1,3-diol (450 mg, 2.5 mmol) (Treibs and Albrecht, "The dihydroxycymenes. IV. Isocymorcin (3,5-dihydroxycymene) from 3,5-menthanedione by dehydrogenation and total synthesis," *Journal fuer Praktische Chemie* (1961), 13, 291-305), purged with argon, and cooled to 0° C. was sequentially added triethylorthoformate (0.7 mL, 4.2 mmol), EtOH (4 mL), and a 10% v/v solution of H$_2$SO$_4$ in EtOH (40 μL). The reaction was allowed to warm to room temperature slowly, stirred overnight, quenched with saturated NaHCO$_3$, and concentrated. The residue was partitioned between water and methylene chloride. The combined organic phases were dried with Na$_2$SO$_4$ and concentrated to provide 510 mg of 7-isopropyl-4-methyl-benzooxazol-6-ol.

Step 2. 5-(7-Isopropyl-4-methyl-benzooxazol-6-yloxy)-pyrimidine-2.4-diamine

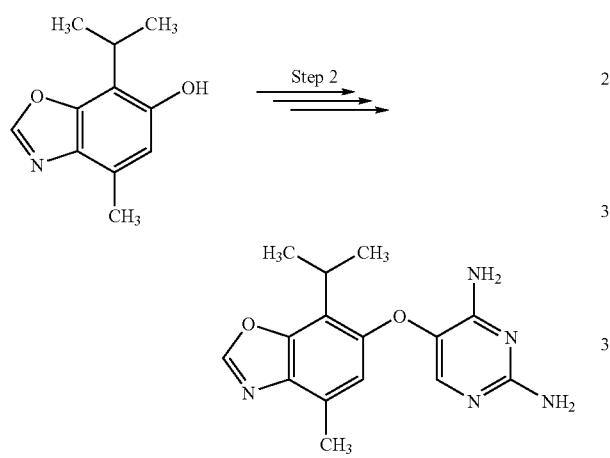

Using the procedure of steps 5-7 of Example 2, 7-isopropyl-4-methyl-benzooxazol-6-ol was converted to 5-(7-isopropyl-4-methyl-benzooxazol-6-yloxy)-pyrimidine-2,4-diamine. The hydrochloride salt was recrystallized from EtOH/diethyl ether. MS (M+H): 300.

Example 66

5-(7-Isopropyl-2,4-dimethyl-benzooxazol-6-yloxy)-pyrimidine-2,4-diamine

Step 1. 7-Isopropyl-2,4-dimethyl-benzooxazol-6-ol

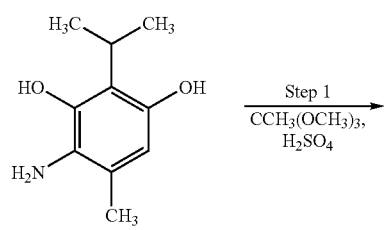

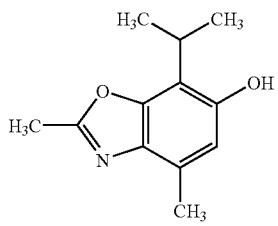

To a flask charged with 4-amino-2-isopropyl-5-methyl-benzene-1,3-diol (250 mg, 1.4 mmol) (Treibs and Albrecht, "The dihydroxycymenes. IV. Isocymorcin (3,5-dihydroxycymene) from 3,5-menthanedione by dehydrogenation and total synthesis," *Journal fuer Praktische Chemie* (1961), 13, 291-305), purged with argon, and cooled to 0° C., was sequentially added triethylorthoformate (0.53 mL, 4.2 mmol), MeOH (2.5 mL), and a 10% v/v solution of H$_2$SO$_4$ in MeOH (25 μL). The reaction was allowed to warm to room temperature slowly, stirred overnight, quenched with saturated NaHCO$_3$, and concentrated. The residue was partitioned between water and methylene chloride. The combined organic phases were dried with Na$_2$SO$_4$ and concentrated. Purification via flash chromatography afforded 175 mg of 7-isopropyl-2,4-dimethyl-benzooxazol-6-ol.

Step 2. 5-(7-Isopropyl-2,4-dimethyl-benzooxazol-6-yloxy)-pyrimidine-2,4-diamine

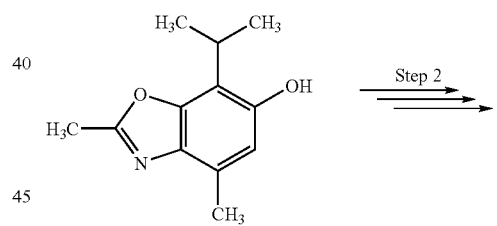

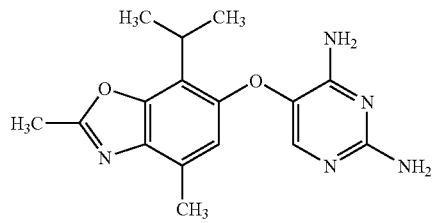

Using the procedure of steps 5-7 of Example 2, 7-isopropyl-2,4-dimethyl-benzooxazol-6-ol was converted to 5-(7-Isopropyl-2,4-dimethyl-benzooxazol-6-yloxy)-pyrimidine-2,4-diamine. The hydrochloride salt was recrystallized from EtOH/diethyl ether. MS (M+H): 314, MP>300°

Example 67

5-(5-Iodo-2-isopropyl-4-methoxy-phenoxy)-1-oxy-pyrimidine-2,4-diamine

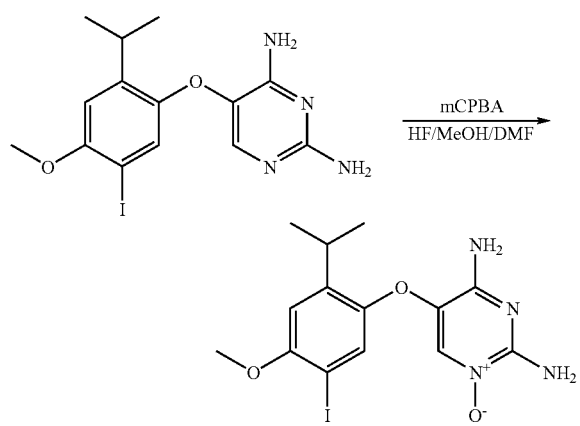

To a solution of compound 5-(5-Iodo-2-isopropyl-4-methoxy-phenoxy)-pyrimidine-2,4-diamine (1.6 g, 4.0 mmol) in DMF/MeOH(30 ml/10 ml) was added HF (48% aqueous solution, 0.3 ml, 8.3 mmol). After 3 minutes, m-chloroperoxybenzoic acid (80% , 2.16 g, 10.0 mmol) was added, the mixture was stirred at room temperature for one hour. Cold 1N NaOH aqueous solution was added, and the reaction mixture was partitioned between ethyl acetate and water. The organic phase was washed with brine, dried over anhydrous sodium sulfate, filtered, concentrated in vacuo. The residue was purified by silica gel chromatography (gradient: 2% , 5% , 6%, 8% MeOH in $CH_2Cl_2$ with 0.1% $NH_4OH$) to give 5-(5-Iodo-2-isopropyl-4-methoxy-phenoxy)-1-oxy-pyrimidine-2,4-diamine (0.2 g, 12% ) as a yellow solid. (M+H)= 417.

Example 68

5-(2,5-Diiodo-4-methoxy-phenoxy)-pyrimidine-2,4-diamine

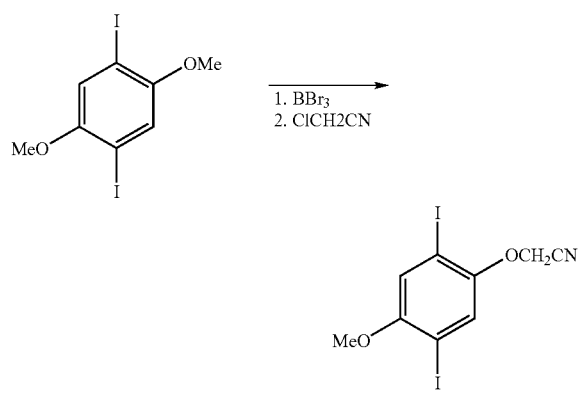

Step 1. (2,5-Diiodo4-methoxy-phenoxy)-acetonitrile

Diiododimethoxybenzene (10 mmol) was dissolved in 75 ml $CH_2Cl_2$ and cooled to 0°. BBr3 (1M in $CH_2Cl_2$, 1.1 equivalents) was added. After 30 minutes the reaction was partitioned between $CH_2Cl_2$ and water. The organic layer was dried and evaporated. The resulting crude phenol was dissolved in 60 ml acetone and treated with 1.1 equivalents of $ClCH_2CN$ and excess $K_2CO_3$. After refluxing overnight the reaction mixture was was partitioned between ether and water. Purification by preparative thin layer chromatography (1:5 EtOAc/hexane) gave (2,5-Diiodo-4-methoxy-phenoxy)-acetonitrile, MS (M+H)=416.

Step 2. 5-(2,5-Diiodo-4-methoxy-phenoxy)-pyrimidine-2,4-diamine

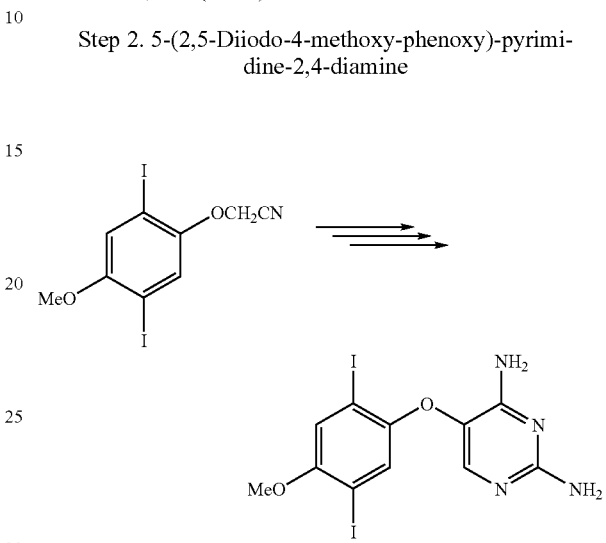

Using the procedure of step 7 of Example 21, (2,5-Diiodo-4-methoxy-phenoxy)-acetonitrile was converted to 240 mg of 5-(2,5-Diiodo-4-methoxy-phenoxy)-pyrimidine-2,4-diamine. MS (m+H)=484.9.

Example 69

Formulations

Pharmaceutical preparations for delivery by various routes are formulated as shown in the following Tables. "Active ingredient" or "Active compound" as used in the Tables means one or more of the Compounds of Formula I.

| Composition for Oral Administration | |
|---|---|
| Ingredient | % wt./wt. |
| Active ingredient | 20.0% |
| Lactose | 79.5% |
| Magnesium stearate | 0.5% |

The ingredients are mixed and dispensed into capsules containing about 100 mg each; one capsule would approximate a total daily dosage.

| Composition for Oral Administration | |
|---|---|
| Ingredient | % wt./wt. |
| Active ingredient | 20.0% |
| Magnesium stearate | 0.5% |
| Crosscarmellose sodium | 2.0% |
| Lactose | 76.5% |
| PVP (polyvinylpyrrolidine) | 1.0% |

The ingredients are combined and granulated using a solvent such as methanol. The formulation is then dried and formed into tablets (containing about 20 mg of active compound) with an appropriate tablet machine.

| Composition for Oral Administration | |
|---|---|
| Ingredient | Amount |
| Active compound | 1.0 g |
| Fumaric acid | 0.5 g |
| Sodium chloride | 2.0 g |
| Methyl paraben | 0.15 g |
| Propyl paraben | 0.05 g |
| Granulated sugar | 25.5 g |
| Sorbitol (70% solution) | 12.85 g |
| Veegum K (Vanderbilt Co.) | 1.0 g |
| Flavoring | 0.035 ml |
| Colorings | 0.5 mg |
| Distilled water | q.s. to 100 ml |

The ingredients are mixed to form a suspension for oral administration.

| Parenteral Formulation | |
|---|---|
| Ingredient | % wt./wt. |
| Active ingredient | 0.25 g |
| Sodium Chloride | qs to make isotonic |
| Water for injection | 100 ml |

The active ingredient is dissolved in a portion of the water for injection. A sufficient quantity of sodium chloride is then added with stirring to make the solution isotonic. The solution is made up to weight with the remainder of the water for injection, filtered through a 0.2 micron membrane filter and packaged under sterile conditions.

| Suppository Formulation | |
|---|---|
| Ingredient | % wt./wt. |
| Active ingredient | 1.0% |
| Polyethylene glycol 1000 | 74.5% |
| Polyethylene glycol 4000 | 24.5% |

The ingredients are melted together and mixed on a steam bath, and poured into molds containing 2.5 g total weight.

| Topical Formulation | |
|---|---|
| Ingredients | Grams |
| Active compound | 0.2-2 |
| Span 60 | 2 |
| Tween 60 | 2 |
| Mineral oil | 5 |
| Petrolatum | 10 |
| Methyl paraben | 0.15 |
| Propyl paraben | 0.05 |
| BHA (butylated hydroxy anisole) | 0.01 |
| Water | q.s. 100 |

All of the ingredients, except water, are combined and heated to about 60° C. with stirring. A sufficient quantity of water at about 60° C. is then added with vigorous stirring to emulsify the ingredients, and water then added q.s. about 100 g.

Nasal Spray Formulations

Several aqueous suspensions containing from about 0.025-0.5 percent active compound are prepared as nasal spray formulations. The formulations optionally contain inactive ingredients such as, for example, microcrystalline cellulose, sodium carboxymethylcellulose, dextrose, and the like. Hydrochloric acid may be added to adjust pH. The nasal spray formulations may be delivered via a nasal spray metered pump typically delivering about 50-100 microliters of formulation per actuation. A typical dosing schedule is 2-4 sprays every 4-12 hours.

Example 70

$P2X_3/P2X_{2/3}$ FLIPR (Fluorometric Imaging Plate Reader) Assay

CHO-K1 cells were transfected with cloned rat $P2X_3$ or human $P2X_{2/3}$ receptor subunits and passaged in flasks. 18-24 hours before the FLIPR experiment, cells were released from their flasks, centrifuged, and resuspended in nutrient medium at $2.5 \times 10^5$ cells/ml. The cells were aliquoted into black-walled 96-well plates at a density of 50,000 cells/well and incubated overnight in 5% $CO_2$ at 37° C. On the day of the experiment, cells were washed in FLIPR buffer (calcium- and magnesium-free Hank's balanced salt solution, 10 mM HEPES, 2 mM $CaCl_2$, 2.5 mM probenecid; FB). Each well received 100 µl FB and 100 µl of the fluorescent dye Fluo-3 AM [2 µM final conc.]. After a 1 hour dye loading incubation at 37° C., the cells were washed 4 times with FB, and a final 75 µl/well FB was left in each well.

Test compounds (dissolved in DMSO at 10 mM and serially diluted with FB) or vehicle were added to each well (25 µl of a 4× solution) and allowed to equilibrate for 20 minutes at room temperature. The plates were then placed in the FLIPR and a baseline fluorescence measurement (excitation at 488 nm and emission at 510-570 nm) was obtained for 10 seconds before a 100 µl/well agonist or vehicle addition. The agonist was a 2× solution of α,β-meATP producing a final concentration of 1 µM ($P2X_3$) or 5 µM ($P2X_{2/3}$). Fluorescence was measured for an additional 2 minutes at 1 second intervals after agonist addition. A final addition of ionomycin (5 µM, final concentration) was made to each well of the FLIPR test plate to establish cell viability and maximum fluorescence of dye-bound cytosolic calcium. Peak fluorescence in response to the addition of α,β-meATP (in the absence and presence of test compounds) was measured and inhibition curves generated using nonlinear regression. PPADS, a standard P2X antagonist, was used as a positive control.

Using the above procedure, compounds of the invention exhibited activity for the $P2X_3$ receptor. The compound 4-(2,4-Diamino-pyrimidin-5-yloxy)-2-iodo-5-isopropyl-phenol, for example, exhibited a $pIC_{50}$ of approximately 8.3 using the above assay.

Surprisingly and unexpectedly, compounds of formulas (I-IV) wherein $R^1$ is isopropyl exhibit better affinity for $P2X_3$ than compounds wherein $R^1$ is any other alkyl or other substituent. Table 3 below provides comparison $pIC_{50}$ data for various compounds of different $R^1$ substituents.

TABLE 3

| Compound | $R^1$ | $pIC_{50}$ |
|---|---|---|
| 5-(2-tert-Butyl-4,5-dimethoxy-benzyl)-pyrimidine-2,4-diamine | -tert-butyl | <5.00 |
| 5-(4,5-Dimethoxy-2-propyl-benzyl)-pyrimidine-2,4-diamine | -n-propyl | <5.00 |
| 5-(2-Isopropyl-4,5-dimethoxy-benzyl)-pyrimidine-2,4-diamine | -isopropyl | 6.94 |
| 5-(2-Ethyl-4,5-dimethoxy-benzyl)-pyrimidine-2,4-diamine | -ethyl | 5.85 |
| 5-(4,5-Dimethoxy-2-methyl-benzyl)-pyrimidine-2,4-diamine | -methyl | <5.00 |

As can be seen from Table 3, compounds of the invention $R^1$ is isopropyl exhibit better affinity for the $P2X_3$ receptor than analogous compounds having other alkyl substituents as $R^1$.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective spirit and scope of the present invention. All such modifications are intended to be within the scope of the claims appended hereto.

What is claimed is:

1. A compound of the formula (II):

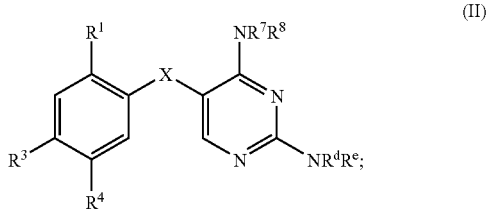

(II)

or a pharmaceutical salt thereof;
wherein:
X is —O—;
$R^1$ is: isopropyl;
$R^3$ and $R^4$ each independently is: alkenyl; amino; halo; amido; haloalkyl; alkoxy; hydroxy; haloalkoxy; nitro; hydroxyalkyl; alkoxyalkyl; hydroxyalkoxy; alkynylalkoxy; alkylsulfonyl; arylsulfonyl; cyano; aryl; heteroaryl; heterocyclyl; heterocyclylalkoxy; aryloxy; heteroaryloxy; aralkyloxy; heteroaralkyloxy; optionally substituted phenoxy; —$(CH_2)_m$-$(Z)_n$-(CO)—$R^f$ or —$(CH_2)_m$-$(Z)_n$-$SO_2$—$(NR^g)_n$—$R^f$ where m and n each independently is 0 or 1, Z is O or $NR^g$, $R^f$ is hydrogen, alkyl, hydroxy, alkoxy, amino, hydroxyalkyl or alkoxyalkyl, and each $R^g$ is independently hydrogen or alkyl; or $R^3$ and $R^4$ may together form an alkylene dioxy; or $R^3$ and $R^4$ together with the atoms to which they are attached may form a five or six-membered ring that optionally includes one or two heteroatoms selected from O, S and N;
one of $R^7$ and $R^8$ is hydrogen, and the other is: hydrogen; alkyl; cycloalkyl; cycloalkylalkyl; haloalkyl; haloalkoxy; hydroxyalkyl; alkoxyalkyl; acetyl; alkylsulfonyl; alkylsulfonylalkyl; aminocarbonyloxyalkyl; hydroxycarbonylalkyl; hydroxyalkyloxycarbonylalkyl; aryl; aralkyl; arylsulfonyl; heteroaryl; heteroarylalkyl; heteroarylsulfonyl; heterocyclyl; or heterocyclylalkyl; and
one of $R^d$ and $R^e$ is hydrogen, and the other is: hydrogen; alkyl; cycloalkyl; cycloalkylalkyl; haloalkyl; haloalkoxy; hydroxyalkyl; alkoxyalkyl; acetyl; alkylsulfonyl; alkylsulfonylalkyl; aminocarbonyloxyalkyl; hydroxycarbonylalkyl; hydroxyalkyloxycarbonylalkyl; aryl; aralkyl; arylsulfonyl; heteroaryl; heteroarylalkyl; heteroarylsulfonyl; heterocyclyl; or heterocyclylalkyl.

2. The compound of claim 1, wherein one of $R^7$ and $R^8$ is hydrogen and the other is alkyl, hydroxyalkyl or haloalkyl.

3. The compound of claim 1, wherein one of $R^d$ and $R^e$ is hydrogen and the other is alkyl, hydroxyalkyl or haloalkyl.

4. The compound of claim 1, wherein $R^7$, $R^8$, $R^d$ and $R^e$ are hydrogen.

5. The compound of claim 1, wherein $R^4$ is heteroaryl.

6. The compound of claim 1, wherein $R^3$ is halo, alkoxy, haloalkoxy or hydroxy.

7. The compound of claim 1, wherein $R^4$ is halo, alkoxy, alkylsulfonyl or heteroaryl.

8. The compound of claim 1, wherein said compound is of the formula (VI):

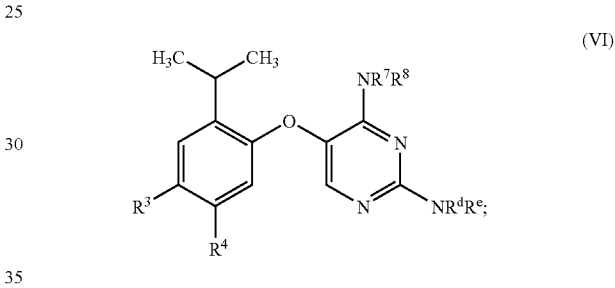

(VI)

wherein:
$R^3$ is halo, alkoxy, haloalkoxy or hydroxy;
$R^4$ halo, alkoxy, alkylsulfonyl or heteroaryl; and
$R^7$, $R^8$, $R^d$ and $R^e$ are as recited in claim 1.

9. The compound of claim 4, wherein $R^3$ is methoxy, fluoro, or chloro.

10. The compound of claim 9, wherein $R^4$ is methoxy, iodo, methanesulfonyl or heteroaryl.

11. The compound of claim 10, wherein $R^3$ is methoxy.

12. The compound of claim 10, wherein $R^4$ methoxy.

13. The compound of claim 10, wherein $R^4$ is iodo.

14. The compound of claim 10, wherein $R^4$ methanesulfonyl.

15. The compound of claim 9, wherein $R^4$ sulfonamido.

16. The compound of claim 9, wherein $R^4$ heteroaryl selected from tetrazolyl, pyrazolyl, oxazolyl, imidazolyl, thiazolyl, thiophenyl, triazolyl, furanyl, isoxazolyl, oxadiazolyl, benzothiophenyl, pyridinyl, or pyrrolyl.

17. The compound of claim 10, wherein $R^4$ is heteroaryl selected from tetrazol-5-yl, pyrazol-1-yl, 3-methylpyrazol-1-yl, oxazol-2-yl, oxazol-5-yl, imidazol-2-yl, thiazol-2-yl, thiazol-4-yl, thiophen-3-yl, 5-chloro-thiophen-2-yl, 1-methyl-imidazol-2-yl, imidazol-1-yl, pyrazol-3-yl, 2-methyl-thiazol-4-yl, furan-2-yl, 3,5-dimethyl-pyrazol-1-yl, 4,5-dihydrooxazol-2-yl, isoxazol-5-yl, [1,2,4]-oxadiazol-3-yl, benzo[b]thioplien-3-yl, oxazol-4-yl, furan-3-yl, 4-methyl-thiophen-2-yl, thiazol-5-yl, tetrazol-1-yl, [1,2,4]triazol-1-yl, 2-methyl-thiazol-5-yl, 1-methyl-pyrazol-4-yl, 2-thiolyl-imidazol-1-yl, pyridin-2-yl, or 2,5-dimethyl-pyrrol-1-yl).

18. The compound of claim 1, wherein said compound is selected from the group consisting of:

5-(2-Isopropyl-4,5-dimethoxy-phenoxy)-pyrimidine-2,4-diamine;
5-(5-Bromo-2-isopropyl-4-methoxy-phenoxy)-pyrimidine-2,4-diamine;
5-(5-Chloro-2-isopropyl-4-methoxy-phenoxy)-pyrimidine-2,4-diamine;
N*2* Benzyl5(5chloro2isopropyl4-methoxy-phenoxy)-pyrimidine-2,4-diamine;
5-(5-Chloro-2-isopropyl-4-methoxy-phenoxy)-N*2*-(tetrahydro-pyran-4-yl)-pyrimidine-2,4-diamine;
5-(5-Chloro-2-isopropyl-4-methoxy-phenoxy)-N*2*-isopropyl-pyrimidine-2,4-diamine;
N*2*-Isopropyl-5(2-isopropyl-4,5-dimethoxy-phenoxy)-pyrimidine-2,4-diamine;
5-(2-Isopropyl-4,5-dimethoxy-phenoxy)-N*2*-phenyl-pyrimidine-2,4-diamine;
N*2*-Benzyl-5-(2-isopropyl-4,5-dimethoxy-phenoxy)-pyrimidine-2,4-diamine;
N-[4-Amino-5-(2-isopropyl-4,5-dimethoxy-phenoxy)-pyrimidin-2-yl]-acetamide;
5-(2-Isopropyl-4,5,-dimethoxy-phenoxy)-N*2*-(2,2,2-trifluoro-ethyl)-pyrimidine-2,4-diamine;
5-(2-Isopropyl-4,5-dimethoxy-phenoxy)-N*2*-(2-methoxy-ethyl)-pyrimidine-2,4-diamine;
3-[4-Amino-5-(5-chloro-2-isopropyl-4-methoxy-phenoxy)-pyrimidin-2-ylamino]-pentane-1,5-diol;
2-[4-Amino-5-(5-chloro-2-isopropyl-4-methoxy-phenoxy)-pyrimidin-2-ylamino]-butan-1-ol;
1-[5-(2,4-Diamino-pyrimidin-5-yloxy)-4-isopropyl-2-methoxy-phenyl]-ethanone; 5-[5-(1 H-Imidazol-2-yl)-2-isopropyl-4-methoxy-phenoxy]-pyrimidine-2,4-diamine;
5-(5-Chloro-2-isopropyl-4-methoxy-phenoxy)-N*2*-(3-ethanesulfonyl-1-methyl-propyl)-pyrimidine-2,4-diamine;
5-(2,4-Diamino-pyrimidin-5-yloxy)-4-isopropyl-2-methoxy-benzamide;
5-(2,4-Diamino-pyrimidin-5-yloxy)-4-isopropyl-2-methoxy-benzoic acid;
5-[2-Isopropyl-4-methoxy-5-(1H-tetrazol-5-yl)-phenoxy]-pyrimidine-2,4-diamine;
5-(2,4-Diamino-pyrimidin-5-yloxy)-4-isopropyl-2-methoxy-benzonitrile;
4-[4-Amino-5-(5-chloro-2-isopropyl-4-methoxy-phenoxy)-pyrimidin-2-ylamino]-piperidine-1-carboxylic acid ethyl ester;
[5-(2,4-Diamino-pyrimidin-5-yloxy)-4-isopropyl-2-methoxy-phenyl]-urea;
5-(5-Chloro-2-isopropyl-4-methoxy-phenoxy)-N*2*-(1-cyclopropyl-ethyl)-pyrimidine-2,4-diamine;
5-(5-Chloro-4-difluoromethoxy-2-isopropyl-phenoxy)-pyrimidine-2,4-diamine;
5-(5-Amino-2-isopropyl-4-methoxy-phenoxy)-pyrimidine-2,4-diamine;
N-[5-(2,4-Diamino-pyrimidin-5-yloxy)-4-isopropyl-2-methoxy-phenyl]-acetamide;
5-(2-isopropyl-4-methoxy-5-tetrazol-1-yl-phenoxy)-pyrimidine-2,4-diamine;
5-(2-Isopropyl-5-methanesulfonyl-4-methoxy-phenoxy)-pyrimidine-2,4-diamine;
5-(5-Chloro-2-isopropyl-4-methoxy-phenoxy)-N*2*-(1,1-dioxo-hexahydro-1lambda* 6*-thiopyran-4-yl)-pyrimidine-2,4-diamine;
Methyl-carbamic acid 2-[4-amino-5-(5-chloro-2-isopropyl-4-methoxy-phenoxy)-pyrimidin-2-ylamino]-propyl ester;
5-(2-Isopropyl-4,5-dimethoxy-phenoxy)-6-methyl-pyrimidine-2,4-diamine;
1-(4-{2-[4-Amino-5-(5-chloro-2-isopropyl-4-methoxy-phenoxy)-pyrimidin-2-ylamino]-propyl)}-piperazin-1-yl)-ethanone;
5-(5-Chloro-2-isopropyl-4-methoxy-phenoxy)-N*2*-(1-methanesulfonyl-piperidin-4-yl)-pyrimidine-2,4-diamine;
2-[4-Amino-5-(5-chloro-2-isopropyl-4-methoxy-phenoxy)-pyrimidin-2-ylamino]-(R)-propan-1-ol;
5-(2-Isopropyl-5-methanesulfonyl-4-methoxy-phenoxy)-$N^2$-(tetrahydro-thiopyran-4-yl)-pyrimidine-2,4-diamine;
5-(5-Chloro-2-isopropyl-4-methoxy-phenoxy)-$N^2$-( 1,1-dioxo-hexahydro-1$\lambda^6$-thiopyran-4-yl)-pyrimidine-2,4-diamine;
1-[5-(2,4-Diamino-pyrimidin-5-yloxy)-2-hydroxy-4-isopropyl-phenyl]-ethanone;
5-(5-Iodo-2-isopropyl-4-methoxy-phenoxy)-pyrimidine-2,4-diamine;
5-(2,4-Diamino-pyrimidin-5-yloxy)-4-isopropyl-2-methoxy-benzenesulfonamide;
4-(2,4-Diamino-pyrimidin-5-yloxy)-2-iodo-5-isopropyl-phenol;
3-[4-Amino-5-(5-bromo-2-isopropyl-4-methoxy-phenoxy)-pyrimidin-2-ylamino]-pentane-1,5-diol;
5-(2-Isopropyl-4methoxy-5-vinyl-phenoxy)-pyrimidine-2,4-diamine;
5-(2-Isopropyl-4-methoxy-5-pyrazol-1-yl-phenoxy)-pyrimidine-2,4-diamine;
5-[2-Isopropyl-4-methoxy-5-(3-methyl-pyrazol-1-yl)-phenoxy]-pyrimidine-2,4-diamine;
5-(2-Isopropyl-4-methoxy-5-oxazol-2-yl-phenoxy)-pyrimidine-2,4-diamine;
(S)-2-[4-Amino-5-(5-bromo-2-isopropyl-4-methoxy-phenoxy)-pyrimidin-2-ylamino]-butan-1-ol;
5-4-Iodo-2-isopropyl-5-methoxy-phenoxy)-pyrimidine-2,4-diamine;
5-(4-Bromo-2-isopropyl-5-methoxy-phenoxy)-pyrimidine-2,4-diamine;
5-(2-Isopropyl-4-methoxy-5-trifluoromethyl-phenoxy)-pyrimidine-2,4-diamine;
5-(2-Isopropyl-4-methoxy-5-thiazol-4-yl-phenoxy)-pyrimidine-2,4-diamine;
[4-(2,4-Diamino-pyrimidin-5-yloxy)-2-iodo-5-isopropyl -phenoxy]-acetonitrile;
5-(2-Isopropyl-4-methoxy-5-thiophen-3-yl-phenoxy)-pyrimidine-2,4-diamine;
(R)-2-[4-Amino-5-(2-isopropyl-5-methanesulfonyl-4-methoxy-phenoxy)-pyrimidin-2-ylamino]-butan-1-ol;
(S)-2-[4-Amino-5-(5-chloro-2-isopropyl-4-methoxy-phenoxy)-pyrimidin-2-ylamino]-propionic acid;
5-[5-(4,5-Dihydro-oxazol-2-yl)-2-isopropyl-4-methoxy-phenoxy]-pyrimidine-2,4-diamine;
5-(2-Isopropyl-5-methanesulfonyl-4-methoxy-phenoxy)-N2-(2,2,2-trifluoro-ethyl)-pyrimidine-2,4-diamine;
(S)-2-[4-Amino-5-(5-chloro-2-isopropyl-4-methoxy-phenoxy)-pyrimidin-2-ylamino]-propionic acid 3-hydroxy-2-hydroxymethyl-2-methyl-propyl ester;
5-[5-(5-Chloro-thiophen-2-yl)-2-isopropyl-4-methoxy-phenoxy]-pyrimidine-2,4-diamine;
5-[2-Isopropyl-4-methoxy-5-(1-methyl-1H-imidazol-2-yl)-phenoxy]-pyrimidine-2,4-diamine;
5-[2-Isopropyl-4-methoxy-5-(2H-pyrazol-3-yl)-phenoxy]-pyrimidine-2,4-diamine;
5-(5-Imidazol-1-yl-2-isopropyl-4-methoxy-phenoxy)-pyrimidine-2,4-diamine;

N2-Isopropyl-5-(2-isopropyl-5-methanesulfonyl-4-methoxy-phenoxy)-pyrimidine-2,4-diamine;
2-[4-(2,4-Diamino-pyrimidin-5-yloxy)-2-iodo-5-isopropyl-phenoxy]-ethanol;
5-(2-Isopropyl-5-methanesulfonyl-4-methoxy-phenoxy)-N2-phenyl-pyrimidine-2,4-diamine;
5-(4-Amino-2-ethylamino-pyrimidin-5-yloxy)-4-isopropyl-2-methoxy-benzarnide;
2-[4-Amino-5-(2-isopropyl-5-methanesulfonyl-4-methoxyphenoxy)-pyrimidin-2-ylamino]-ethanol;
5-[2-Isopropyl-4-methoxy-5-(2-methyl-thiazol-4-yl)-phenoxy]-pyrimidine-2,4-diamine;
5-[5-Iodo-2-isopropyl-4-(pyrazin-2-ylmethoxy)-phenoxy]-pyrimidine-2,4-diamine;
5-(2-Isopropyl-5-methanesulfonyl-4-methoxy-phenoxy)-N2-(2-methoxy-ethyl)-pyrimidine-2,4-diamine;
5-(2-Isopropyl-4-methoxy-5-[1,2,3]triazol-1-yl-phenoxy)-pyrimidine-2,4-diamine;
5-(5-Furan-2-yl-2-isopropyl-4-methoxy-phenoxy)-pyrimidine-2,4-diamine;
1-[5-(2,4-Diamino-pyrimidin-5-yloxy)-4-isopropyl-2-methoxy-phenyl]-3-ethyl-urea;
N2-Cyclopropyl-5-(2-isopropyl-5-methanesulfonyl-4-methoxy-phenoxy)-pyrimidine-2,4-diamine;
2-[4-(2,4-Diamino-pyrimidin-5-yloxy)-2-iodo-5-isopropyl-phenoxy]-acetamide;
5-[5-(3,5-Dimethyl-pyrazol-1-yl)-2-isopropyl-4-methoxy-phenoxy]-pyrimidine-2,4-diamine;
N2-Benzyl-5-(2-isopropyl-5-methanesulfonyl-4-methoxy-phenoxy)-pyrimidine-2,4-diamine;
N2-Ethyl-5-(2-isopropyl-5-methanesulfonyl-4-methoxy-phenoxy)-pyrimidine-2,4-diamine;
5-(2-Isopropyl-5-methanesulfonyl-4-methoxy-phenoxy)-N2-(1-methanesulfonyl-piperidin-4-yl)-pyrimidine-2,4-diamine;
N2-Isobutyl-5-(2-isopropyl-5-methanesulfonyl-4-methoxy-phenoxy)-pyrimidine-2,4-diamine;
5-(2,4-Diamino-pyrimidin-5-yloxy)-4-isopropyl-2-methoxy-N-methyl-benzamide;
5-(2-Isopropyl-5-isoxazol-5-yl-4-methoxy-phenoxy)-pyrimidine-2,4-diamine;
N2-(4-Fluoro-phenyl)-5-(2-isopropyl-5-methanesulfonyl-4-methoxy-phenoxy)-pyrimidine-2,4-diamine;
5-(2-Isopropyl-4-methoxy-5-[1,2,4]oxadiazol-3-yl-phenoxy)-pyrimidine-2,4-diamine;
5-(2-Isopropyl-5-methanesulfonyl-4-methoxy-phenoxy)-N2-(tetrahydro-pyran-4-yl)-pyrimidine-2,4-diamine;
1-[5(2,4-Diamino-pyrimidin-5-yloxy)-4-isopropyl-2-methoxy-phenyl]-ethanol;
5-(6-Isopropyl-4-methyl-3,4-dihydro-2H-benzo[1,4]oxazin-7-yloxy)-pyrimidine-2,4-diamine;
5-(5-Benzo[b]thiophen-3-yl-2-isopropyl-4-methoxy-phenoxy)-pyrimidine-2,4-diamine;
5-[2-Isopropyl-4-methoxy-5-(1-methoxy-ethyl)-phenoxy]-pyrimidine-2,4-diamine;
5-(2-Isopropyl-4-methoxy-5-oxazol-4-yl-phenoxy)-pyrimidine-2,4-diamine;
5-(2-Isopropyl-4-methoxy-5-thiazol-2-yl-phenoxy)-pyrimidine-2,4-diamine;
5-(5-Furan-3-yl-2-isopropyl-4-methoxy-phenoxy)-pyrimidine-2,4-diamine;
5-[5-Iodo-2-isopropyl-4-(pyrimidin-2-ylmethoxy)-phenoxy]-pyrimidine-2,4-diamine;
5-(2-Isopropyl-4-methoxy-5-thiophen-2-yl-phenoxy)-pyrimidine-2,4-diamine;
1-[5-(2,4-Diamino-pyrimidin-5-yloxy)-4-isopropyl-2-methoxy-phenyl]-3-phenyl-urea;
5-(2,4-Diamino-pyrimidin-5-yloxy)-4-isopropyl-2-methoxy-N-methyl-benzenesulfonamide;
5-(2-Isopropyl-5-methanesulfonyl-4-methoxy-phenoxy)-N2-methyl-pyrimidine-2,4-diamine;
5-[5-Iodo-2-isopropyl-4-(pyridin-2-ylmethoxy)-phenoxy]-pyrimidine-2,4-diamine;
5-[4-(2-Fluoro-benzyloxy)-5-iodo-2-isopropyl-phenoxy]-pyrimidine-2,4-diamine;
5-(2-Isopropyl-4-methoxy-5-pyrrol-1-yl-phenoxy)-pyrimidine-2,4-diamine;
5-(2-Isopropyl-4-methoxy-5-trifluoromethoxy-phenoxy)-pyrimidine-2,4-diamine;
2-[4-(2,4-Diamino-pyrimidin-5-ylmethyl)-2-iodo-5-isopropyl-phenoxy]-ethanol;
5'-(2,4-Diamino-pyrimidin-5-yloxy)-4'-isopropyl-2'-methoxy-biphenyl-3'-carbonitrile;
5-[2-Isopropyl-4-methoxy-5-(4-methyl-thiophen-2-yl)-phenoxy]-pyrimidine-2,4-diamine;
5-(5-Chloro-2-isopropyl-4-methoxy-phenoxy)-N$^2$-[(S)-1-(4-methyl-2,6,7-trioxa-bicyclo[2.2.2]oct-1-yl)-ethyl]-pyrimidine-2,4-diamine;
5-(5-Iodo-2-isopropyl-4-prop-2-ynyloxy-phenoxy)-pyrimidine-2,4-diamine;
5-(2-Isopropyl-4-methoxy-5-nitro-phenoxy)-pyrimidine-2,4-diamin;
5-(4-Ethoxy-5-iodo-2-isopropyl-phenoxy)-pyrimidine-2,4-diamine;
5-[5-Iodo-2-isopropyl-4-(pyridin-3-ylmethoxy)-phenoxy]-pyrimidine-2,4-diamine;
5-(4-Benzyloxy-5-iodo-2-isopropyl-phenoxy)-pyrimidine-2,4-diamine;
5-(4-Isopropyl-6-methoxy-biphenyl-3-yloxy)-pyrimidine-2,4-diamine;
5-(2-Isopropyl-4-methoxy-5-thiazol-5-yl-phenoxy)-pyrimidine-2,4-diamine;
1-[5-(2,4-Diamino-pyrimidin-5-yloxy)-4-isopropyl-2-methoxy-phenyl]-pyrrolidin-2-one;
5-[5-Iodo-2-isopropyl-4-(2-methoxy-ethoxy)-phenoxy]-pyrimidine-2,4-diamine;
5-(2-Isopropyl-4-methoxy-5-oxazol-5-yl-phenoxy)-pyrimidine-2,4-diamine;
5-[5-Iodo-2-isopropyl-4-(2-methoxy-benzyloxy)-phenoxy]-pyrimidine-2,4-diamine;
5-[5-Iodo-2-isopropyl-4-(2,2,2-trifluoro-ethoxy)-phenoxy]-pyrimidine-2,4-diamine;
5-[5-Iodo-2-isopropyl-4-(3,4,5-trimethoxy-benzyloxy)-phenoxy]-pyrimidine-2,4-diamine;
5-[2-Isopropyl-4-methoxy-5-(4-methyl-thiophen-3-yl)-phenoxy]-pyrimidine-2,4-diamine;
5-(2-Isopropyl-4-methoxy-5-nitro-phenoxy)-pyrimidine-2,4-diamine;
5-[5-Iodo-2-isopropyl-4-(1-methyl-piperidin-2-ylmethoxy)-phenoxy]-pyrimidine-2,4-diamine;
5-[5-Iodo-2-isopropyl-4-(tetrahydro-pyran-2-ylmethoxy)-phenoxy]-pyrimidine-2,4-diamine;
5-(2-Isopropyl-4-methoxy-5-[1,2,4]triazol-1-yl-phenoxy)-pyrimidine-2,4-diamine;
5-(2-Isopropyl-4,5-dimethoxy-phenoxy)-N$^2$-(2-methoxy-ethyl)-pyrimidine-2,4-diamine;
5-(4'-Fluoro-4-isopropyl-6-methoxy-biphenyl-3-yloxy)-pyrimidine-2,4-diamine;
5-(5-Chloro-2-isopropyl-4-methoxy-phenoxy)-N$^2$-(2,2,2-trifluoro-ethyl)-pyrimidine-2,4-diamine;
5-[2-Isopropyl-4-methoxy-5-(2-methyl-thiazol-5-yl)-phenoxy]-pyrimidine-2,4-diamine;
5-(5-Ethanesulfonyl-2-isopropyl-4-methoxy-phenoxy)-pyrimidine-2,4-diamine;

1-[5-(2,4-Diamino-pyrimidin-5-yloxy)-4-isopropyl-2-methoxy-phenyl]-1 H-imidazole-2-thiol;
5-[2-Isopropyl-4-methoxy-5-(1-methyl-1H-pyrazol-4-yl)-phenoxy]-pyrimidine-2,4-diamine;
5-[5-Iodo-2-isopropyl-4-(pyridin-4-ylmethoxy)-phenoxy]-pyrimidine-2,4-diamine;
5-(5-Fluoro-2-isopropyl-4-methoxy-phenoxy)-pyrimidine-2,4-diamine;
5-(4'-Fluoro-5-isopropyl-2-methoxy-biphenyl-4-yloxy)-pyrimidine-2,4-diamine;
5-[4-(3-Fluoro-benzyloxy)-5-iodo-2-isopropyl-phenoxy]-pyrimidine-2,4-diamine;
5-(4-Furan-2-yl-2-isopropyl-5-methoxy-phenoxy)-pyrimidine-2,4-diamine;
2-[5-(2,4-Diamino-pyrimidin-5-yloxy)-4-isopropyl-2-methoxy-phenyl]-propan-2-ol;
5-[4-(2,6Difluoro-benzyloxy)-5-iodo-2-isopropyl-phenoxy]-pyrimidine-2,4-diamine;
5-(5-Iodo-2-isopropyl-4-phenethyloxy-phenoxy)-pyrimidine-2,4-diamine;
5-(2-Isopropyl-4-methoxy-5-pyridin-4-yl-phenoxy)-pyrimidine-2,4-diamine;
5-(2,4-Diamino-pyrimidin-5-yloxy)-N-ethyl-4-isopropyl-2-methoxy-benzenesulfonamide;
5-[2-Isopropyl-5-(4-methanesulfonyl-piperazin-1-yl)-4-methoxy-phenoxy]-pyrimidine-2,4-diamine;
5-(2-Isopropyl-4-methoxy-5-pyridin-3-yl-phenoxy)-pyrimidine-2,4-diamine;
5-(2,4-Diamino-pyrimidin-5-yloxy)-4-isopropyl-2-methoxy-N,N-dimethyl-benzamide; and
5-[5-(2,5-Dimethyl-pyrrol-1-yl)-2-isopropyl-4-methoxy-phenoxy]-pyrimidine-2,4-diamine.

19. The compound of claim 1, wherein said compound is selected from the group consisting of:
5-(2-Isopropyl-4,5-dimethoxy-phenoxy)-pyrimidine-2,4-diamine;
5-(5-Bromo-2-isopropyl-4-methoxy-phenoxy)-pyrimidine-2,4-diamine;
5-(5-Chloro-2-isopropyl-4-methoxy-phenoxy)-pyrimidine-2,4-diamine;
N*2*-Benzy5-(5-chloro-2-isopropyl-4-methoxy-phenoxy)-pyrimidine-2,4-diamine;
5-(5-Chloro-2-isopropyl-4-methoxy-phenoxy)-N*2*-(tetrahydro-pyran-4-yl)- pyrimidine-2,4-diamine;
5-(5-Chloro-2-isopropyl-4-methoxy-phenoxy)-N*2*-isopropyl -pyrimidine-2,4-diamine;
N*2*-Isopropyl-5-(2-isopropyl-4,5-dimethoxy-phenoxy)-pyrimidine-2,4-diamine;
5-(2-Isopropyl-4,5-dimethoxy-phenoxy)-N*2*-phenyl-pyridimine-2,4-diamine;
N*2*-Benzyl-5-(2-isopropyl-4,5-dimethoxy-phenoxy)-pyrimidine-2,4-diamine;
N-[4-Amino-5-(2-isopropyl-4,5-dimethoxy-phenoxy)-pyrimidin-2-yl]-acetamide;
5-(2-Isopropyl-4,5dimethoxy-phenoxy)-N*2*-(2,2,2-trifluoro-ethyl)-pyrimidine-2,4-diamine;
5-(2Isopropyl-4,5-dimethoxy-phenoxy)-pyrimidin-2,4-diamine;
3-[4-Amino-5-(5-chloro-2-isopropyl-4-methoxy-phenoxy)-pyrimidin-2-ylamino]-pentane-1,5-diol;
2-[4-Amino-5-(5-chloro-2-isopropyl-4-methoxy-phenoxy)-pyrimidin-2-ylamino]-butan-1-ol;
5-[5-(1H-Imidazol-2-yl)-2-isopropyl-4-methoxy-phenoxy]-pyrimidine-2,4-diamine;
5-(5-Chloro-2-isopropyl-4-methoxy-phenoxy)-N*2*-(3-ethanesulfonyl-1-methyl-propyl)-pyrimidine-2,4-diamine;
5-[2-Isopropyl-4-methoxy-5-(1H-tetrazol-5-yl)-phenoxy]-pyrimidine-2,4-diamine;
4-[4-Amino-5-(5-chloro-2-isopropyl-4-methoxy-phenoxy)-pyrimidin-2-ylaminol]-piperidine-1-carboxylic acid ethyl ester;
5-(5-Chloro-2-isopropyl-4methoxy-phenoxy)-N*2*-( 1-cyclopropyl-ethyl)-pyrimidine-2,4-diamine;
5-(5-Chloro-4-difluoromethoxy-2-isopropyl-phenoxy)-pyrimidine-2,4-diamine;
5-(2-Isopropyl-4-methoxy-5-tetrazol-1-yl-phenoxy)-pyrimidine-2,4-diamine;
5-(2-Isopropyl-5-methanesulfonyl-4-methoxy-phenoxy)-pyrimidine-2,4-diamine;
5(5-Chloro-2isoproyl-4-methoxy-phenoxy)-N*2*-( 1,1-dioxo-hexahydro-1lambda*6*-thiopyran-4-yl)-pyrimidine-2,4-diamine;
Methyl-carbamic acid 2-[4-amino-5-(5-chloro-2-isopropyl-4-methoxy-phenoxy)-pyrimidin-2-ylamino]-propyl ester;
5-(2-Isopropyl-4,5-dimethoxy-phenoxy)-6-methyl-pyrimidine-2,4-diamine;
1-(4-{2-[4-Amino-5-(5-chloro-2-isopropyl-4-methoxy-phenoxy)-pyrimidin-2-ylamino]-propyl}-piperazin-1-yl)-ethanone;
5-(5-Chloro-2-isopropyl-4-methoxy-phenoxy)-N*2*-(1-methanesulfonyl-piperdin-4-yl)-pyrimidine-2,4-diamine;
2-[4-Amino-5-(5-chloro-2-isopropyl-4-methoxy-phenoxy)-pyrimidin-2-ylamino]-(R)-propan-1-ol;
5-(2-Isopropyl-5-methanesulfonyl-4-methoxy-phenoxy)-$N^2$-(tetrahydro-thiopyran-4-yl)-pyrimidine-2,4-diamine;
5-(5-Chloro-2-isopropyl-4-methoxy-phenoxy)-$N^2$-( 1,1-dioxo-hexahydro-1$\lambda^6$-thiopyran-4-yl)-pyrimidine-2,4-diamine;
5-(5-Iodo-2-isopropyl-4-methoxy-phenoxy)-pyrimidine-2,4-diamine;
4-(2,4-Diamino-pyrimidin-5-yloxy)-2-iodo-5-isopropyl-phenol;
3-[4-Amino-5-(5-bromo-2-isopropyl-4-methoxy-phenoxy)-pyrimidin-2-ylamino]-pentane-1,5-diol;
5-(2-Isopropyl-4-methoxy-5-pyrazol-1-yl-phenoxy)-pyrimidine-2,4-diamine;
5-[2-Isopropyl-4-methoxy-5-(3-methyl-pyrazol-1-yl)-phenoxy]-pyrimidine-2,4-diamine;
5-(2-Isopropyl-4-methoxy-5-oxazol-2-yl-phenoxy)-pyrimidine-2,4-diamine;
(S)-2-[4-Amino-5-(5-bromo-2-isopropyl-4-methoxy-phenoxy)-pyrimidin-2-ylamino]-butan-1-ol;
5-(4-Iodo-2-isopropyl-5-methoxy-phenoxy)-pyrimidine-2,4-diamine;
5-(4-Bromo-2-isopropyl-5-methoxy-phenoxy)-pyrimidine-2,4-diamine;
5-(2-Isopropyl-4-methoxy-5-thiazol-4-yl-phenoxy)-pyrimidine-2,4-diamine;
5-(2-Isopropyl-4-methoxy-5-thiophen-3-yl-phenoxy)-pyrimidine-2,4-diamine
(R)-2-[4-Amino-5-(2-isopropyl-5-methanesulfonyl-4-methoxy-phenoxy)-pyrimidin-2-ylamino]-butan-1-ol;
(S)-2-[4-Amino-5-(5-chloro-2-isopropyl-4-methoxy-phenoxy)-pyrimidin-2-ylamino]-propionic acid;
5-[5-(4,5-Dihydro-oxazol-2-yl)-2-isopropyl-4-methoxy-phenoxy]-pyrimidine-2,4-diamine;
5-(2-Isopropyl-5-methanesulfonyl-4-methoxy-phenoxy)-N2-(2,2,2-trifluoro-ethyl)-pyrimidine-2,4-diamine;

(S)-2-[4-Amino-5-(5-chloro-2-isopropyl-4-methoxy-phenoxy)-pyrimidin-2-ylamino]-propionic acid 3-hydroxy-2-hydroxymethyl-2-methyl-propyl ester;
5-[5-(5-Chloro-thiophen-2-yl)-2-isopropyl-4-methoxy-phenoxy]-pyrimidine-2,4-diamine;
5-[2-Isopropyl-4-methoxy-5-(1-methyl-1H-imidazol-2-yl)-phenoxy]-pyrimidine-2,4-diamine;
5-[2-Isopropyl-4-methoxy-5-(2H-pyrazol-3-yl)-phenoxy]-pyrimidine-2,4-diamine;
5-(5-Imidazol-1-yl-2-isopropyl-4-methoxy-phenoxy)-pyrimidine-2,4-diamine;
N2-Isopropyl-5-(2-isopropyl-5-methanesulfonyl-4-methoxy-phenoxy)-pyrimidine-2,4-diamine;
5-(2-Isopropyl-5-methanesulfonyl-4-methoxy-phenoxy)-N2-phenyl-pyrimidine-2,4-diamine;
2-[4-Amino-5-(2-isopropyl-5-methanesulfonyl-4-methoxy-phenoxy)-pyrimidin-2ylamino]-ethanol;
5-[2-Isopropyl-4-methoxy-5-(2-methyl-thiazol-4-yl)-phenoxy]-pyrimidine-2,4-diamine;
5-(2-Isopropyl-5-methanesulfonyl-4-methoxy-phenoxy)-N2-(2-methoxy-ethyl)-pyrimidine-2,4-diamine;
5-(2-Isopropyl-4-methoxy-5-[1,2,3]triazol-1-yl-phenoxy)-pyrimidine-2,4-diamine;
5-(5-Furan-2-yl-2-isopropyl-4-methoxy-phenoxy)-pyrimidine-2,4-diamine;
N2-Cyclopropyl-5-(2-isopropyl-5-methanesulfonyl-4-methoxy-phenoxy)-pyrimidine-2,4-diamine;
5-5-(3,5-Dimethyl-pyrazol-1-yl)-2-isopropyl-4-methoxy-phenoxy]-pyrimidine-2,4-diamine;
N2-Benzyl-5-(2-isopropyl-5-methanesulfonyl-4-methoxy-phenoxy)-pyrimidine-2,4-diamine;
N2-Ethyl-5-(2-isopropyl-5-methanesulfonyl-4-methoxy-phenoxy)-pyrimidine-2,4-diamine;
5-(2-Isopropyl-5-methanesulfonyl-4-methoxy-phenoxy)-N2-( 1-methanesulfonyl-piperidin-4-yl)-pyrimidine-2,4-diamine;
N2-Isobutyl-5-(2-isopropyl-5-methanesulfonyl-4-methoxy-phenoxy)-pyrimidine-2,4-diamine;
5-(2-Isopropyl-5-isoxazol-5-yl-4-methoxy-phenoxy)-pyrimidine-2,4-diamine;
N2-(4-Fluoro-phenyl)-5-(2-isopropyl-5-methanesulfonyl-4-methoxy-phenoxy)-pyrimidine-2,4-diamine;
5-(2-Isopropyl-4-methoxy-5-[1,2,4]oxadiazol-3-yl-phenoxy)-pyrimidine-2,4-diamine;
5-(2-Isopropyl-5-methanesulfonyl-4-methoxy-phenoxy)-N2-(tetrahydro-pyran-4-yl)-pyrimidine-2,4-diamine;
5-(5-Benzo[b]thiophen-3-yl-2-isopropyl-4-methoxy-phenoxy)-pyrimidine-2,4-diamine;
5-(2-Isopropyl-4-methoxy-5-oxazol-4-yl-phenoxy)-pyrimidine-2,4-diamine;
5-(2-Isopropyl-4-methoxy-5-thiazol-2-yl-phenoxy)-pyrimidine-2,4-diamine;
5-(5-Furan-3-yl-2-isopropyl-4-methoxy-phenoxy)-pyrimidine-2,4-diamine;
5-(2-Isopropyl-4-methoxy-5-thiophen-2-yl-phenoxy)-pyrimidine-2,4-diamine;
5-(2-Isopropyl-5-methanesulfonyl-4-methoxy-phenoxy)-N2-methyl-pyrimidine-2,4-diamine;
5-(2-Isopropyl-4-methoxy-5-pyrrol-1-yl-phenoxy)-pyrimidine-2,4-diamine;
5-[2-Isopropyl-4-methoxy-5-(4-methyl-thiophen-2-yl)-phenoxy]-pyrimidine-2,4-diamine;
5-(5-Chloro-2-isopropyl-4-methoxy-phenoxy)-N$^2$-[(S)-1-(4-methyl-2,6,7-trioxa-bicyclo[2.2.2]oct-1-yl)-ethyl]-pyrimidine-2,4-diamine;
5-(2-Isopropyl-4-methoxy-5-thiazol-5-yl-phenoxy)-pyrimidine-2,4-diamine;
5-(2-Isopropyl-4-methoxy-5-oxazol-5-yl-phenoxy)-pyrimidine-2,4-diamine;
5-[2-Isopropyl-4-methoxy-5-(4-methyl-thiophen-3-yl)-phenoxy]-pyrimidine-2,4-diamine;
5-(2-Isopropyl-4-methoxy-5-[1,2,4]triazol-1-yl-phenoxy)-pyrimidine-2,4-diamine;
5-(2-Isopropyl-4,5-dimethoxy-phenoxy)-N$^2$-(2-methoxy-ethyl)-pyrimidine-2,4-diamine;
5-(5-Chloro-2-isopropyl-4-methoxy-phenoxy)-N$^2$-(2,2,2-trifluoro-ethyl)-pyrimidine-2,4-diamine;
5-[2-Isopropyl-4-methoxy-5-(2-methyl-thiazol-5-yl)-phenoxy]-pyrimidine-2,4-diamine;
5-(5-Ethanesulfonyl-2-isopropyl-4-methoxy-phenoxy)-pyrimidine-2,4-diamine;
1-[5-(2,4-Diamino-pyrimidin-5-yloxy)-4-isopropyl-2-methoxy-phenyl]-1H-imidazole-2-thiol;
5-[2-Isopropyl-4-methoxy-5-( 1-methyl-1H-pyrazol-4-yl)-phenoxy]-pyrimidine-2,4-diamine;
5-(5-Fluoro-2-isopropyl-4-methoxy-phenoxy)-pyrimidine-2,4-diamine;
5-[5-(2,5-Dimethyl-pyrrol-1-yl)-2-isopropyl-4-methoxy-phenoxy]-pyrimidine-2,4-diamine.

20. The compound of claim 1, wherein said compound is selected from the group consisting of:
5-(2-Isopropyl-4,5-dimethoxy-phenoxy)-pyrimidine-2,4-diamine;
5-(5-Bromo-2-isopropyl-4-methoxy-phenoxy)-pyrimidine-2,4-diamine;
5-(5-Chloro-2-isopropyl-4-methoxy-phenoxy)-pyrimidine-2,4-diamine;
5-[5-( 1H-Imidazol-2-yl)-2-isopropyl-4-methoxy-phenoxy]-pyrimidine-2,4-diamine;
5-[2-Isopropyl-4-methoxy-5-( 1H-tetrazol-5-yl)-phenoxy]-pyrimidine-2,4-diamine;
5-(5-Chloro-4-difluoromethoxy-2-isopropyl-phenoxy)-pyrimidine-2,4-diamine;
5-(2-Isopropyl-4-methoxy-5-tetrazol-1-yl-phenoxy)-pyrimidine-2,4-diamine;
5-(2-Isopropyl-5-methanesulfonyl-4-methoxy-phenoxy)-pyrimidine-2,4-diamine;
5-(2-Isopropyl-4,5-dimethoxy-phenoxy)-6-methyl-pyrimidine-2,4-diamine;
5-(5-Iodo-2-isopropyl-4-methoxy-phenoxy)-pyrimidine-2,4-diamine;
4-(2,4-Diamino-pyrimidin-5-yloxy)-2-iodo-5-isopropyl-phenol;
5-(2-Isopropyl-4-methoxy-5-pyrazol-1yl-phenoxy)-pyrimidine-2,4-diamine;
5-[2-Isopropyl-4-methoxy-5-(3-methyl-pyrazol-1-yl)-phenoxy]-pyrimidine-2,4-diamine;
5-(2-Isopropyl-4-methoxy-5-oxazol-2-yl-phenoxy)-pyrimidine-2,4-diamine;
5-(4-Iodo-2-isopropyl-5-methoxy-phenoxy)-pyrimidine-2,4-diamine;
5-(4-Bromo-2-isopropyl-5-methoxy-phenoxy)-pyrimidine-2,4-diamine;
5-(2-Isopropyl-4-methoxy-5-thiazol-4-yl-phenoxy)-pyrimidine-2,4-diamine;
5-(2-Isopropyl-4-methoxy-5-thiophen-3-yl-phenoxy)-pyrimidine-2,4-diamine;
5-[5-(4,5-Dihydro-oxazol-2-y1)-2-isopropy1-4-methoxy-phenoxy]-pyrimidine-2,4-diamine;
5-[5-(5-Chloro-thiophen-2-yl)-2-isopropyl-4-methoxy-phenoxy]-pyrimidine-2,4-diamine;
5-[2-Isopropyl-4-methoxy-5-( 1-methyl-1H-imidazol-2-yl)-phenoxy]-pyrimidine-2,4-diamine;

5-[2-Isopropyl-4-methoxy-5-(2H-pyrazol-3-yl)-phenoxy]-pyrimidine-2,4-diamine;
5-(5-Imidazol-1-yl-2-isopropyl-4-methoxy-phenoxy)-pyrimidine-2,4-diamine;
5-[2-Isopropyl-4-methoxy-5-(2-methyl-thiazol-4-yl)-phenoxy]-pyrimidine-2,4-diamine;
5-(2-Isopropyl-4-methoxy-5-[1,2,3 ]triazol-1-yl-phenoxy)-pyrimidine-2,4-diamine;
5-(5-Furan-2-yl-2-isopropyl-4-methoxy-phenoxy)-pyrimidine-2,4-diamine;
5-[5-(3,5-Dimethyl-pyrazol-1-yl)-2-isopropyl-4-methoxy-phenoxy]-pyrimidine-2,4-diamine;
5-(2-Isopropyl-5-isoxazol-5-yl-4-methoxy-phenoxy)-pyrimidine-2,4-diamine;
5-(2-Isopropyl-4-methoxy-5-[1,2,4]oxadiazol-3yl-phenoxy)-pyrimidine-2,4-diamine;
5-(5-Benzo[b]thiophen-3-yl-2-isopropyl-4-methoxy-phenoxy)-pyrimidine-2,4-diamine;
5-(2-Isopropyl-4-methoxy-5-oxazol-4-yl-phenoxy)-pyrimidine-2,4-diamine;
5-(2-Isopropyl-4-methoxy-5-thiazol-2-yl-phenoxy)-pyrimidine-2,4-diamine;
5-(5-Furan-3-yl-2-isopropyl-4-methoxy-phenoxy)-pyrimidine-2,4-diamine;
5-(2-Isopropyl-4-methoxy-5-thiophen-2-yl-phenoxy)-pyrimidine-2,4-diamine;
5-(2-Isopropyl-4-methoxy-5-pyrrol-1-yl-phenoxy)-pyrimidine-2,4-diamine;
5-[2-Isopropyl1-4-methoxy-5-(4-methyl-thiophen-2-yl)-phenoxy]-pyrimidine-2,4-diamine;
5-(2-Isopropyl-4-methoxy-5-thiazol-5-yl-phenoxy)-pyrimidine-2,4-diamine;
5-(2-Isopropyl-4-methoxy-5-oxazol-5-yl-phenoxy)-pyrimidine-2,4-diamine;
5-[2-Isopropyl-4-methoxy-5-(4-methyl-thiophen-3-yl)-phenoxy]-pyrimidine-2,4-diamine;
5-(2-Isopropyl-4-methoxy-5-[1,2,4]triazol-1-yl-phenoxy)-pyrimidine-2,4-diamine;
5-[2-Isopropyl-4-methoxy-5-(2-methyl-thiazol-5-yl)-phenoxy]-pyrimidine-2,4-diamine;
5-(5-Ethanesulfonyl-2-isopropyl-4-methoxy-phenoxy)-pyrimidine-2,4-diamine;
1-[5-(2,4-Diamino-pyrimidin-5-yloxy)-4-isopropyl-2-methoxy-phenyl]-1H-imidazole-2-thiol;
5-[2-Isopropyl-4-methoxy-5-(1-methyl-1H-pyrazol-4-yl)-phenoxy]-pyrimidine-2,4-diamine;
5-(5-Fluoro-2-isopropyl-4-methoxy-phenoxy)-pyrimidine-2,4-diamine;
5-[5-(2,5-Dimethyl-pyrrol-1-yl)-2-isopropyl-4-methoxy-phenoxy]-pyrimidine-2,4-diamine.

21. The compound of claim 1, wherein said compound is selected from the group consisting of:
5-(5-Iodo-2-isopropyl-4-methoxy-phenoxy)-pyrimidine-2,4-diamine;
4-(2,4-Diamino-pyrimidin-5-yloxy)-2-iodo-5-isopropyl-phenol;
[4-(2,4-Diamino-pyrimidin-5-yloxy)-2-iodo-5-isopropyl-phenoxy]-acetonitrile;
2-[4-(2,4-Diamino-pyrimidin-5-yloxy)-2-iodo-5-isopropyl-phenoxy]-ethanol; 5-[5-Iodo-2-isopropyl-4-(pyrazin-2-ylmethoxy)-phenoxy]-pyrimidine-2,4-diamine;
5-[5-Iodo-2-isopropyl-4-(pyrimidin-2-ylmethoxy)-phenoxy]-pyrimidine-2,4-diamine;
5-[5-Iodo-2-isopropyl-4-(pyridin-2-ylmethoxy)-phenoxy]-pyrimidine-2,4-diamine;
5-[4-2-Fluoro-benzyloxy)5-iodo-2-isopropyl-phenoxy]-pyrimidine-2,4-diamine;
2-[4-(2,4-Diamino-pyrimidin-5-ylmethyl)-2-iodo-5-isopropyl-phenoxy]-ethanol;
5-(5-Iodo-2-isopropyl-4-prop-2-ynyloxy-phenoxy)-pyrimidine-2,4-diamine;
5-(4-Ethoxy-5-iodo-2-isopropyl-phenoxy)-pyrimidine-2,4-diamine;
5-[5-Iodo-2-isopropyl-4-(pyridin-3-ylmethoxy)-phenoxy]-pyrimidine-2,4-diamine;
5-(4-Benzyloxy-5-iodo-2-isopropyl-phenoxy)-pyrimidine-2,4-diamine;
5-[5-Iodo-2-isopropyl-4-(2-methoxy-ethoxy)-phenoxy]-pyrimidine-2,4-diamine;
5-[5-Iodo-2-isopropyl-4-(2-methoxy-benzyloxy)-phenoxy]-pyrimidine-2,4-diamine;
5-[5-Iodo-2-isopropyl-4-(2,2,2-trifluoro-ethoxy)-phenoxy]-pyrimidine-2,4-diamine
5-[5-Iodo-2-isopropyl-4-(3,4,5-trimethoxy-benzyloxy)-phenoxy]-pyrimidine-2,4-diamine;
5-[5-Iodo-2-isopropyl-4-( 1-methyl-piperidin-2-ylmethoxy)-phenoxy]-pyrimidine-2,4-diamine;
5-[5-Iodo-2-isopropyl-4-(tetrahydro-pyran-2-ylmethoxy)-phenoxy]-pyrimidine-2,4-diamine;
5-[4-(3-Fluoro-benzyloxy)-5-iodo-2-isopropyl-phenoxy]-pyrimidine-2,4-diamine;
5-[4-(2,6-Difluoro-benzyloxy)-5-iodo-2-isopropyl-phenoxy]-pyrimidine-2,4-diamine; and
5-(5-Iodo-2-isopropyl-4-phenethyloxy-phenoxy)-pyrimidine-2,4-diamine.

22. The compound of claim 18, wherein said compound is selected from the group consisting of:
5-(2-Isopropyl-5-methanesulfonyl-4-methoxy-phenoxy)-pyrimidine-2,4-diamine;
5-(2Isopropyl-5-methanesulfonyl-4-methoxy-phenoxy)-N²-(tetrahydro-thiopyran-4-yl)-pyrimidine-2,4-diamine;
(R)-2-[4-Amino-5-(2-isopropyl-5-methanesulfonyl-4-methoxy-phenoxy)-pyrimidin-2-ylamino]-butan-1-ol;
5-(2-Isopropyl-5-methanesulfonyl-4-methoxy-phenoxy)-N2-(2,2,2-trifluoro-ethyl)-pyrimidine-2,4-diamine;
N2-Isopropyl-5-(2-isopropyl-5-methanesulfonyl-4-methoxy-phenoxy)-pyrimidine-2,4-diamine;
5-(2-Isopropyl-5-methanesulfonyl-4-methoxy-phenoxy)-N2-phenyl-pyrimidine-2,4-diamine;
2-4-Amino-5-(2-isopropyl-5-methanesulfonyl-4-methoxy-phenoxy)-pyrimidin-2-ylamino]-ethanol;
5-(2-Isopropyl-5-methanesulfonyl-4-methoxy-phenoxy)-N2-(2-methoxy-ethyl)-pyrimidine-2,4-diamine;
N2-Cyclopropyl-5-(2-isopropyl-5-methanesulfonyl-4-methoxy-phenoxy)-pyrimidine-2,4-diamine;
N2-Benzyl-5-(2-isopropyl-5-methanesulfonyl-4-methoxy-phenoxy)-pyrimidine-2,4diamine;
N2-Ethyl-5-(2-isopropyl-5-methanesulfonyl-4-methoxy-phenoxy)-pyrimidine-2,4-diamine;
5-(2-Isopropyl-5-methanesulfonyl-4-methoxy-phenoxy)-N2-( 1-methanesulfonyl-piperidin-4-yl)-pyrimidine-2,4-diamine;
N2-Isobutyl-5-(2-isopropyl-5-methanesulfonyl-4-methoxy-phenoxy)-pyrimidine-2,4-diamine;
N2-(4-Fluoro-phenyl)-5-(2-isopropyl-5-methanesulfonyl-4-methoxy-phenoxy)-pyrimidine-2,4diamine;
5-(2-Isopropyl-5-methanesulfonyl-4-methoxy-phenoxy)-N2-(tetrahydro-pyran-4-yl)-pyrimidine-2,4-diamine; and
5-(2-Isopropyl-5-methanesulfonyl-4-methoxy-phenoxy)-N2-methyl-pyrimidine-2,4-diamine.

23. The compound of claim 18, wherein said compound is selected from the group consisting of:
- 5-(2,4-Diamino-pyrimidin-5-yloxy)-4-isopropyl-2methoxy-benzenesulfonamide;
- 5-(2,4-Diamino-pyrimidin-5-yloxy)-4-isopropyl-2-methoxy-N-methyl-benzenesulfonamide; and
- 5-(2,4-Diamino-pyrimidin-5-yloxy)-N-ethyl-4-isopropyl-2-methoxy-benzenesulfonamide.

24. The compound of claim 18, wherein said compound is selected from the group consisting of:
- 5-[5-(1H-Imidazol-2-yl)-2-isopropyl-4-methoxy-phenoxy]-pyrimidine-2,4-diamine;
- 5-[2-Isopropyl-4-methoxy-5-(1H-tetrazol-5-yl)-phenoxy]-pyrimidine-2,4-diamine
- 5-(2-Isopropyl-4-methoxy-5-pyrazol-1-yl-phenoxy)-pyrimidine-2,4-diamine;
- 5-[2-Isopropyl-4-methoxy-5-(3-methyl-pyrazol-1-yl)-phenoxy]-pyrimidine-2,4-diamine;
- 5-(2-Isopropyl-4-methoxy-5-oxazol-2-yl-phenoxy)-pyrimidine-2,4-diamine;
- 5-(2-Isopropyl-4-methoxy-5-thiazol-4-yl-phenoxy)-pyrimidine-2,4-diamine;
- 5-(2-Isopropyl-4-methoxy-5-thiophen-3-yl-phenoxy)-pyrimidine-2,4-diamine;
- 5-[5-(4,5-Dihydro-oxazol2-yl)-2-isopropyl-4-methoxy-phenoxy]-pyrimidine-2,4diamine;
- 5-[5-(5-Chloro-thiophen-2-yl)-2-isopropyl-4-methoxy-phenoxy]-pyrimidine-2,4-diamine;
- 5-[2-Isopropyl-4-methoxy-5-(1-methyl-1H-imidazol-2-yl)-phenoxy]-pyrimidine-2,4-diamine;
- 5-[2-Isopropyl-4-methoxy-5-(2H-pyrazol-3-yl)-phenoxy]-pyrimidine-2,4-diamine;
- 5-(5-Imidazol-1-yl-2-isopropyl-4-methoxy-phenoxy)-pyrimidine-2,4-diamine;
- 5-[2-Isopropyl-4-methoxy-5-(2-methyl-thiazol-4-yl)-phenoxy]-pyrimidine-2,4-diamine;
- 5-(2-Isopropyl-4-methoxy-5-[1,2,3]triazol-1-yl-phenoxy)-pyrimidine-2,4-diamine;
- 5-(5-Furan-2-yl-2-isopropyl-4-methoxy-phenoxy)-pyrimidine-2,4-diamine;
- 5-[5-(3,5-Dimethyl-pyrazol-1-yl)-2-isopropyl-4-methoxy-phenoxy]-pyrimidine-2,4-diamine;
- 5-(2-Isopropyl-5-isoxazol-5-yl-4-methoxy-phenoxy)-pyrimidine-2,4-diamine;
- 5-(2-Isopropyl-4-methoxy-5-[1,2,4]oxadiazol-3-yl-phenoxy)-pyrimidine-2,4-diamine;
- 5-(5-Benzo[b]thiophen-3-yl-2-isopropyl-4-methoxy-phenoxy)-pyrimidine-2,4-diamine;
- 5-(2-Isopropyl-4-methoxy-5-oxazol-4-yl-phenoxy)-pyrimidine-2,4-diamine
- 5-(2-Isopropyl-4-methoxy-5-thiazol-2-yl-phenoxy)-pyrimidine-2,4-diamine;
- 5-(5-Furan-3-yl-2-isopropyl-4-methoxy-phenoxy)-pyrimidine-2,4-diamine;
- 5-(2-Isopropyl-4-methoxy-5-thiophen-2-yl-phenoxy)-pyrimidine-2,4-diamine;
- 5-(2-Isopropyl-4-methoxy-5-pyrrol-1-yl-phenoxy)-pyrimidine-2,4-diamine;
- 5-2-Isopropyl-4-methoxy-5-(4-methyl-thiophen-2-yl)-phenoxy]-pyrimidine-2,4-diamine;
- 5-(2-Isopropyl-4-methoxy-5-thiazol-5-yl-phenoxy)-pyrimidine-2,4-diamine;
- 5-(2-Isopropyl-4-methoxy-5-oxazol-5-yl-phenoxy)-pyrimidine-2,4-diamine;
- 5-[2-Isopropyl-4-methoxy-5-(4-methyl-thiophen-3-yl)-phenoxy]-pyrimidine-2,4-diamine;
- 5-(2-Isopropyl-4-methoxy-5-[1,2,4]triazol-1-yl-phenoxy)-pyrimidine-2,4-diamine;
- 5-[2-Isopropyl-4-methoxy-5-(2-methyl-thiazol-5-yl)-phenoxy]-pyrimidine-2,4-diamine;
- 1-[5-(2,4-Diamino-pyrimidin-5-yloxy)-4-isopropyl-2-methoxy-phenyl]-1H-imidazole-2-thiol;
- 5-[2-Isopropyl-4-methoxy-5-(1-methyl-1H-pyrazol-4-yl)-phenoxy]-pyrimidine-2,4-diamine;
- 5-(2-Isopropyl-4-methoxy-5-pyridin-4-yl-phenoxy)-pyrimidine-2,4-diamine;
- 5-[5-(2,5-Dimethyl-pyrrol-1-yl)-2-isopropyl-4-methoxy-phenoxy]-pyrimidine-2,4-diamine.

25. The compound 5-(2-isopropyl-5-methanesulfonyl-4-methoxy-phenoxy)-pyrimidine-2,4-diamine, or a pharmaceutically acceptable salt thereof.

26. The compound 5-(2,4-diamino-pyrimidin-5-yloxy)-4-isopropyl-2-methoxy-benzenesulfonamide, or a pharmaceutically acceptable salt thereof.

27. The compound 5-(5-iodo-2-isopropyl-4-methoxy-phenoxy)-pyrimidine-2,4-diamine, or a pharmaceutically acceptable salt thereof.

28. The compound 5-(2-isopropyl-4,5-dimethoxy-phenoxy)-pyrimidine-2,4-diamine, or a pharmaceutically acceptable salt thereof 29. The compound 4-(2,4-diamino-pyrimidin-5-yloxy)-2-iodo-5-isopropyl-phenol, or a pharmaceutically acceptable salt thereof.

30. A pharmaceutical composition comprising:
(a) a pharmaceutically acceptable excipient; and
(b) a compound of claim 1.

* * * * *